(12) United States Patent
Holtzman et al.

(10) Patent No.: US 11,407,771 B2
(45) Date of Patent: Aug. 9, 2022

(54) MITOGEN-ACTIVATED PROTEIN KINASE INHIBITORS, METHODS OF MAKING, AND METHODS OF USE THEREOF

(71) Applicant: Washington University, Saint Louis, MO (US)

(72) Inventors: Michael J. Holtzman, St. Louis, MO (US); Arthur G. Romero, Chesterfield, MO (US); Benjamin J. Gerovac, St. Louis, MO (US); Zhenfu Han, St. Louis, MO (US); Shamus P. Keeler, University City, MO (US); Kangyun Wu, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/059,251

(22) PCT Filed: May 30, 2019

(86) PCT No.: PCT/US2019/034751
§ 371 (c)(1),
(2) Date: Nov. 26, 2020

(87) PCT Pub. No.: WO2019/232275
PCT Pub. Date: Dec. 5, 2019

(65) Prior Publication Data
US 2021/0214378 A1 Jul. 15, 2021

Related U.S. Application Data

(60) Provisional application No. 62/677,741, filed on May 30, 2018.

(51) Int. Cl.
*C07D 417/06* (2006.01)
*C07F 7/08* (2006.01)
*C07D 213/75* (2006.01)

(52) U.S. Cl.
CPC .......... *C07F 7/0812* (2013.01); *C07D 213/75* (2013.01)

(58) Field of Classification Search
CPC .................................................. C07D 417/06
USPC .......................................................... 514/63
See application file for complete search history.

(56) References Cited

U.S. PATENT DOCUMENTS

| | | | |
|---|---|---|---|
| 6,605,623 B1 * | 8/2003 | Ko | C07D 207/08 514/236.8 |
| 9,187,470 B2 | 11/2015 | Holtzman et al. | |
| 2005/0038080 A1 | 2/2005 | Boyer et al. | |
| 2006/0035893 A1 | 2/2006 | Jung et al. | |
| 2006/0063796 A1 | 3/2006 | Borcherding et al. | |
| 2007/0244120 A1 | 10/2007 | Dumas et al. | |
| 2011/0269800 A1 | 11/2011 | Ito et al. | |
| 2011/0312963 A1 | 12/2011 | Ito et al. | |
| 2012/0046290 A1 | 2/2012 | Dumas et al. | |
| 2012/0136031 A1 | 5/2012 | Ito et al. | |
| 2013/0143914 A1 | 6/2013 | Woo et al. | |
| 2015/0183777 A1 | 7/2015 | Holtzman et al. | |

FOREIGN PATENT DOCUMENTS

| | | |
|---|---|---|
| AU | 2008252068 B2 | 1/2009 |
| WO | 2005/002673 A1 | 1/2005 |

OTHER PUBLICATIONS

Alevy et al., "IL-13-induced airway mucus production is attenuated by MAPK13 inhibition", The Journal of Clinical Investigation vol. 122 No. 12, URL: https://doi.org/10.1172/JCI64896, Dec. 2012, pp. 4555-4568.
Aspord et al., "Breast cancer instructs dendritic cells to prime interleukin 13-secreting CD4+T cells that facilitate tumor development", The Journal of Experimental Medicine vol. 204, No. 5, URL: www.jem.org/cgi/doi/10.1084/jem.20061120, May 14, 2007, pp. 1037-1047.
Banerjee et al., "p38 MAPK inhibitors, IKK2 inhibitors, and TNFα inhibitors in COPD", Curr Opin Pharmacol vol. 12 No. 3, DOI: 10.1016/j.coph.2012.01.016, Jun. 2012, pp. 287-292.
Byers et al., "Long-term IL-33-producing epithelial progenitor cells in chronic obstructive lung disease", The Journal of Clinical Investigation, vol. 123, No. 9, URL: https://doi.org/10.1172/JCI65570, Dec. 2013, pp. 3967-3982.
Chen et al., "Inhibition of the p38 Kinase Suppresses the Proliferation of Human ER-Negative Breast Cancer Cells", Cancer Res vol. 69, No. 23, DOI: 10.1158/0008-5472.CAN-09-1636, Dec. 1, 2009, pp. 8853-8861.
Dumas et al., "Synthesis and Pharmacological Characterization of a Potent, Orally Active p38 Kinase Inhibitor", Bioorganic & Medicinal Chemistry Letters, vol. 12, Jun. 17, 2002, pp. 1559-1562.
Igea et al., "The Stress Kinase p38a as a Target for Cancer Therapy", American Association for Cancer Research, DOI: 10.1158/0008-5472.CAN-15-0173, Sep. 16, 2015, pp. 3997-4002.
Fairbairn et al., "Comparative Analysis of Monocyte Subsets in the Pig", The Journal of Immunology, Doi: 10.4049/jimmunol.1300365, May 2013, pp. 6389-6396.
Gaggianesi et al., "IL4 Primes the Dynamics of Breast Cancer Progression via DUSP4 Inhibition", Cancer Research vol. 77 No. 12, DOI: 10.1158/0008-5472.CAN-16-3126, Apr. 11, 2017, pp. 3268-3279.
Groneberg et al., Expression of respiratory mucins in fatal status asthmaticus and mild asthma, Blackwell Science Limited, Histopathology, 2002, pp. 367-373.
Ha et al., "Novel Therapies to Inhibit Mucus Synthesis and Secretion in Airway Hypersecretory Diseases", Pharmacology, DOI: 10.1159/000442794, Dec. 17, 2015, pp. 84-100.
Hogg et al., "The Nature of Small-Airway Obstruction in Chronic Obstructive Pulmonary Disease", The New England Journal of Medicine, vol. 350, No. 26, Jun. 24, 2004, pp. 2645-2653.

(Continued)

*Primary Examiner* — Niloofar Rahmani
(74) *Attorney, Agent, or Firm* — Stinson LLP

(57) ABSTRACT

Compounds that inhibit mitogen-activated protein kinases (MAPKs) are disclosed. Some inhibitor compounds specifically target a single MAPK such as MAPK13, while others target multiple MAPKs such as MAPK13 and MAPK12. The compounds can be used therapeutically for a variety of diseases, including cancer and respiratory diseases. Methods of synthesis of the compounds are also disclosed.

6 Claims, 11 Drawing Sheets

(56) References Cited

OTHER PUBLICATIONS

Hogg et al., "Survival after Lung Volume Reduction in Chronic Obstructive Pulmonary Disease", Insights from Small Mrway Pathology, DOI: 10.1164/rccm.200612-1772OC vol. 176, Jun. 7, 2007, pp. 454-459.

Holtzman et al., "The role of airway epithelial cells and innate immune cells in chronic respiratory disease", Nat Rev Immunol. vol. 14, No. 10, DOI: 10.1038/nri3739, 2014, pp. 686-698.

Irwin et al., "ZINC—A Free Database of Commercially Available Compounds for Virtual Screening", J Chem Inf Mode vol. 45, No. 1, 2005, pp. 177-182.

Kim et al., "Persistent activation of an innate immune axis translates respiratory viral infection into chronic lung disease", Nat Med. vol. 14 No. 6, DOI: 10.1038/nm1770, Jun. 2008, pp. 633-640.

Kuyper, "Characterization of Airway Plugging in Fatal Asthma", The American Journal of Medicine, vol. 115, DOI: 10.1016/S0002-9343(03)00241-9, Jul. 2003, 06 pages.

Lipinski, Christopher A., "Drug-like properties and the causes of poor solubility and poor permeability", Journal of Pharmacological and Toxicological Methods, vol. 44, Sep. 21, 2000, pp. 235-249.

Miska, "Initiation of inflammatory tumorigenesis by CTLA4 insufficiency due to type 2 cytokines", J. Exp. Med., vol. 215 No. 3, DOI: https://doi.org/10.1084/jem.20171971, 2018, pp. 841-858.

Norman, Peter, "Investigational p38 inhibitors for the treatment of chronic obstructive pulmonary disease", Norman Consulting Expert Opin. Investig. Drugs, vol. 24, No. 5, 2015, 10 Pages.

Ou et al., "Loss-of-function RNAi screens in breast cancer cells identify AURKB, PLK1, PIK3R1, MAPK12, PRKD2, and PTK6 as sensitizing targets of rapamycin activity", Cancer Lett. vol. 354, No. 2, DOI: 10.1016/j.canlet.2014.08.043, Nov. 28, 2014, pp. 336-347.

Park et al., "Elevated Interleukin-13 Receptor Alpha 1 Expression in Tumor Cells Is Associated with Poor Prognosis in Patients with Invasive Breast Cancer", Annals of Surgical Oncology, DOI: 10.1245/s10434-017-5907-2, Jun. 20, 2017, 08 Pages.

Patel et al., "Genetic segregation of airway disease traits despite redundancy of calcium-activated chloride channel family members", Physiol Genomics, DOI: 10.1152/physiolgenomics.00321. 2005, Mar. 28, 2006, pp. 502-513.

Patel et al., "High Throughput Screening for Small Molecule Enhancers of the Interferon Signaling Pathway to Drive Next-Generation Antiviral Drug Discovery", Plos one, vol. 7, Issue 5, May 2012, 12 pages.

Renukaradhya et al., "Functional Invariant NKT Cells in Pig Lungs Regulate the Airway Hyperreactivity: A Potential Animal Model", J Clin Immunol, vol. 31, No. 2, DOI: 10.1007/S10875-010-9476-4, Apr. 2011, pp. 228-239.

Suzuki et al., "Targeting of IL-4 and IL-13 receptors for cancer therapy", Cytokine, vol. 75, No. 1, DOI: 10.1016/j.cyto.2015.05. 026, Sep. 2015, 10 Pages.

Tyner et al., "Blocking airway mucous cell metaplasia by inhibiting EGFR antiapoptosis and IL-13 transdifferentiation signals", The Journal of Clinical Investigation, vol. 116, No. 2, Feb. 2006, pp. 309-321.

Van Nunen et al., "Experimental infection with Sendai virus in mice", vol. 22, No. 3, DOI: 10.1007/BF01242959, Jun. 26, 1967, 10 pages.

Venmar et al., "IL4 Receptor ILR4a Regulates Metastatic Colonization by Mammary Tumors through Multiple Signaling Pathways", Cancer Research vol. 74, No. 16, DOI: 10.1158/0008-5472.CAN-14-0093, Jun. 19, 2014, pp. 4329-4340.

Wada et al., "P38 delta MAPK promotes breast cancer progression and lung metastasis by enhancing cell proliferation and cell detachment", Oncogene vol. 36, No. 47, DOI: 10.1038/onc.2017.274, Nov. 23, 2017, pp. 6649-6657.

Wu et al., "TREM-2 promotes macrophage survival and lung disease after respiratory viral infection", The Journal of Experimental Medicine, vol. 212, No. 5, 2015, pp. 681-697.

Zhang et al., "Respiratory Enterovirus (like Parainfluenza Virus) Can Cause Chronic Lung Disease if Protection by Airway Epithelial STAT1 Is Lost", The Journal of Immunology, DOI: 10.4049/jimmunol.1801491, Feb. 25, 2019, pp. 2332-2347.

International Search Report and Written Opinion received for PCT Application Serial No. PCT/US2019/034751 dated Sep. 22, 2019, 15 pages.

Huang et al., "An acoustofluidic sputum liquefier", Lab Chip, vol. 15, 2015, pp. 3125-3131.

\* cited by examiner

MITOGEN-ACTIVATED PROTEIN KINASE INHIBITORS, METHODS OF MAKING, AND METHODS OF USE THEREOF

CROSS-REFERENCE TO RELATED APPLICATIONS

This application is the 371 national stage of International PCT Application No. PCT/US2019/034751 filed 30 May 2019, which claims priority to U.S. Provisional Application No. 62/677,741 filed 30 May 2018, the contents of which are incorporated by reference herein.

STATEMENT REGARDING FEDERALLY SPONSORED RESEARCH OR DEVELOPMENT

This invention was made with government support under HL123429, HL145252, and HL149523 awarded by the National Institutes of Health and W81XWH-20-1-0603 awarded by the ARMY/MRMC. The government has certain rights in the invention.

INTRODUCTION

The present disclosure relates to inhibitors of mitogen-activated protein kinases (MAPKs), including inhibitors which target individual kinases such as MAPK13 with high specificity, and inhibitors with broader specificity, i.e., inhibit multiple MAPKs, such as inhibitors which target a combination of MAPK13 and MAPK14, MAPK13 AND MAPK12, and inhibitors which target a combination of MAPK 11, MAPK12, MAPK13 and MAPK14.

U.S. Pat. No. 9,187,470 to Holtzman et al. discloses inhibitors of MAPK13. However, the compounds do not always have the desired effectiveness or selectivity.

SUMMARY

The present inventors disclose compounds that inhibit mitogen-activated protein kinases (MAPKs). In some embodiments, a compound can exhibit high specificity for an individual MAPK, such as, for example, an inhibitor can specifically target MAPK13. In some embodiments, a compound can target multiple MAPKs, such as, for example, MAPK11. MAPK12, MAPK13 and MAPK14, or a combined inhibitor targeting MAPK13 and MAPK14 or MAPK13 and MAPK12. Inhibitors of the present teachings are disclosed in Table 1; some inhibitory properties are disclosed in Table 2.

In various embodiments, the present inventors disclose compounds having a structure of Formula I as set forth below, as well as pharmaceutically acceptable salts thereof, solvates thereof, polymorphs thereof, tautomers thereof, stereoisomers thereof, and prodrugs thereof.

In some embodiments, Compounds of Formula I can have a structure

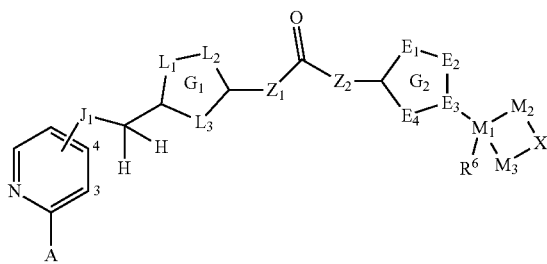

(I)

wherein A can be selected from the group consisting of H and $-NH(CO)R^2$;

$R^2$ can be selected from the group consisting of H, alkyl, cycloalkyl, cycloalkylalkyl, heterocyclyl, heterocycylalkyl, aryl, heteroaryl, $OR^3$ and $NR^4R^4$;

$R^3$ can be selected from the group consisting of alkyl, cycloakyl, cycloalkyalkyl, heterocyclyl and heterocycylalkyl;

each $R^4$ can be independently selected from the group consisting of H, alkyl, cycloalkyl, cycloalkylalkyl, heterocyclyl and heterocyclylalkyl, or the two $R^4$ can be taken together to form a 5- or 6-membered heterocyclic ring with the nitrogen;

$J_1$ can be selected from the group consisting of $-O-$ and $-CH_2-$ and can be substituted at position 3 or 4 on the pyridine;

$G_1$ can be a 5-member heteroaromatic ring wherein each of $L_1$, $L_2$ and $L_3$ can be independently selected from the group consisting of CH, N, O and S;

$Z_1$ and $Z_2$ can each be independently selected from the group consisting of NH, O and $CH_2$, with the proviso that at least one of $Z_1$ and $Z_2$ can be NH;

$G_2$ can be an aromatic or heteroaromatic ring selected from the group consisting of (i) a 5-membered heteroaromatic ring selected from the group consisting of pyrazole, oxazole, isoxazole, imidazole and oxadiazole; and (ii) a 6-membered aromatic or heteroaromatic ring selected from the group consisting of benzene, pyridine and pyrimidine:

$E_1$ can be selected from the group consisting of CH, $CR^1$, N and $NR^1$ when $G_2$ is a 6-membered aromatic or heteroaromatic ring, or $E_1$ can be selected from the group consisting of CH, $CR^1$, N, $NR^1$, and O when $G_2$ is a 5-membered heteroaromatic ring;

E2 can be selected from the group consisting of CH, N and O when $G_2$ is a 5-membered heteroaromatic ring, or $E_2$ can be selected from the group consisting of CH—CH and CH—N when $G_2$ is a 6-membered aromatic or heteroaromatic ring;

$E_3$ can be selected from the group consisting of C and N;

$E_4$ can be selected from the group consisting of CH, N and O when $G_2$ is a 5-membered heteroaromatic ring, or $E_4$ can be selected from CH and N when $G_2$ is a 6-membered aromatic or heteroaromatic ring;

$M_1$ can be selected from the group consisting of C and Si, provided that when $M_1$ is Si, each of $M_2$ and $M_3$ can be methyl and X can be absent;

each of $M_2$ and $M_3$ can be selected from the group consisting of $CH_3$, $CH_2$ and H;

X can be selected from the group consisting of $CH_2$, O and S, or is absent, wherein if each of $M_1$, $M_2$ and $M_3$ is C, and X is $CH_2$, O or S then $M_1$, $M_2$, $M_3$ and X together form a 4-member ring, or if each of $M_1$, $M_2$ and $M_3$ is C, and X absent, then $M_1$, $M_2$, $M_3$ together form a 3-member ring;

$R^1$ can be selected from the group consisting of H, $C_{1-8}$ alkyl, cycloalkyl, cycloalkylalkyl, aryl and heteroaryl;

$R^6$ can be selected from the group consisting of H and $C_{1-8}$ alkyl, provided that when $M_1$ is Si, $R^6$ is methyl.

In various aspects of formula I, ring $G_1$ can be selected from the group consisting of a thiazole, a pyrazole, an oxazole, an isoxazole, and an imidazole.

In various aspects of formula I, $R^1$ can be selected from the group consisting of H, phenyl, 4-tolyl, halophenyl, 2-cyclopropylmethyl and $C_{1-8}$ alkyl.

In various aspects of formula I, the $C_{1-8}$ alkyl of $R^6$ can be methyl.

In various aspects of formula I, $M_1$ can be CH, $M_2$ can be $CH_3$, $M_3$ can be $CH_3$, and $R^6$ can be absent.

In various aspects of formula I, if $G_2$ is a benzene ring and $E_1$ is a halogen, then the combination of $G_2$ and $E_1$ can be selected from the group consisting of 3-chlorophenyl, 4-chlorophenyl, 3-fluorophenyl and 4-fluorophenyl.

In various aspects of formula I, ring $G_2$ can be a pyrazole.

In various aspects, some non-limiting examples of compounds of formula I comprising a pyrazole moiety include:

270

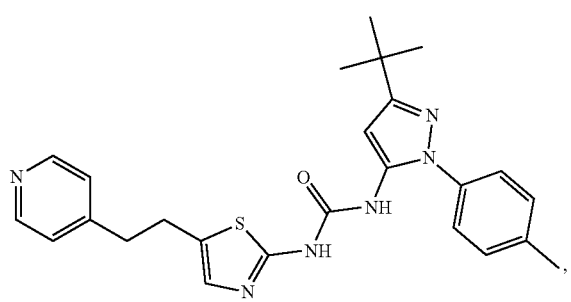

271

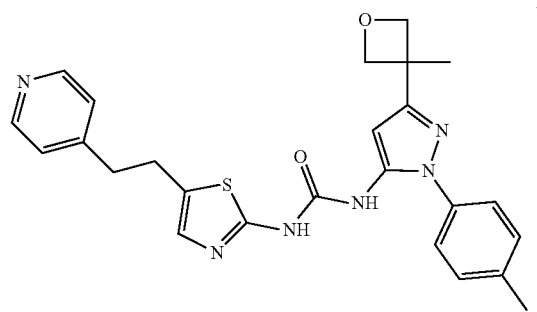

272

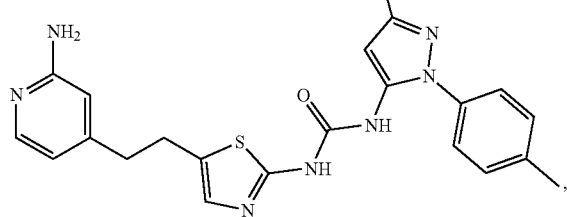

273

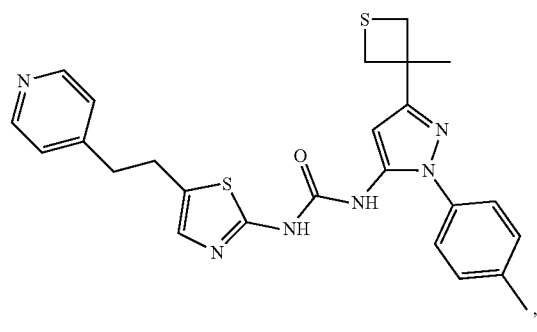

-continued

277

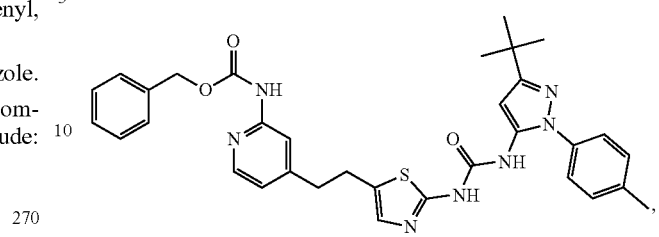

281

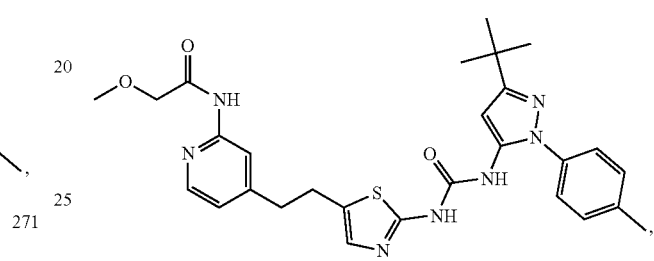

282

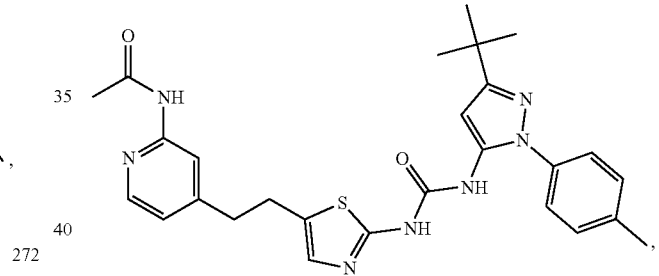

283

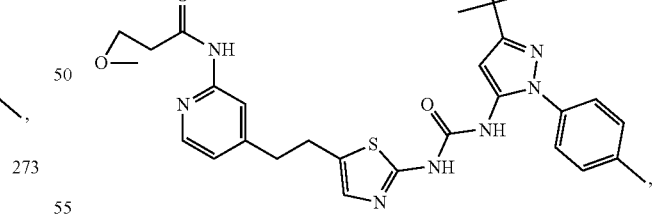

284

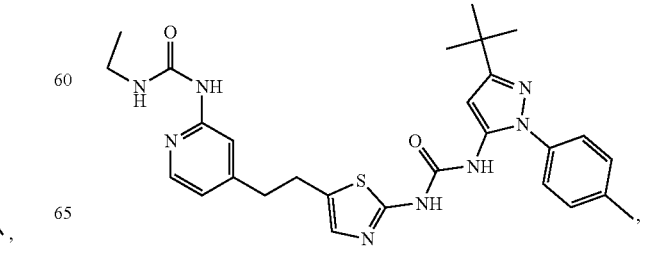

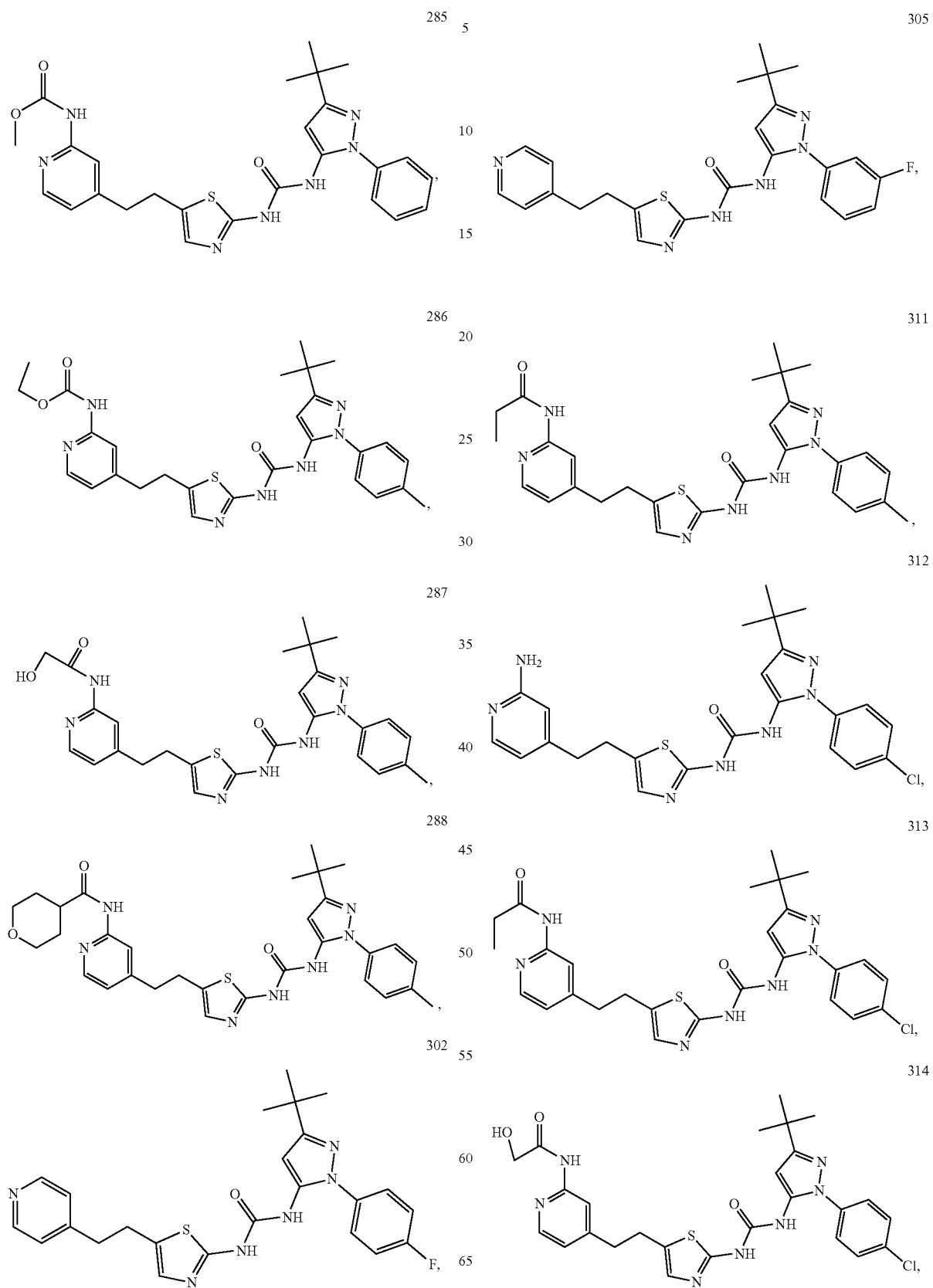

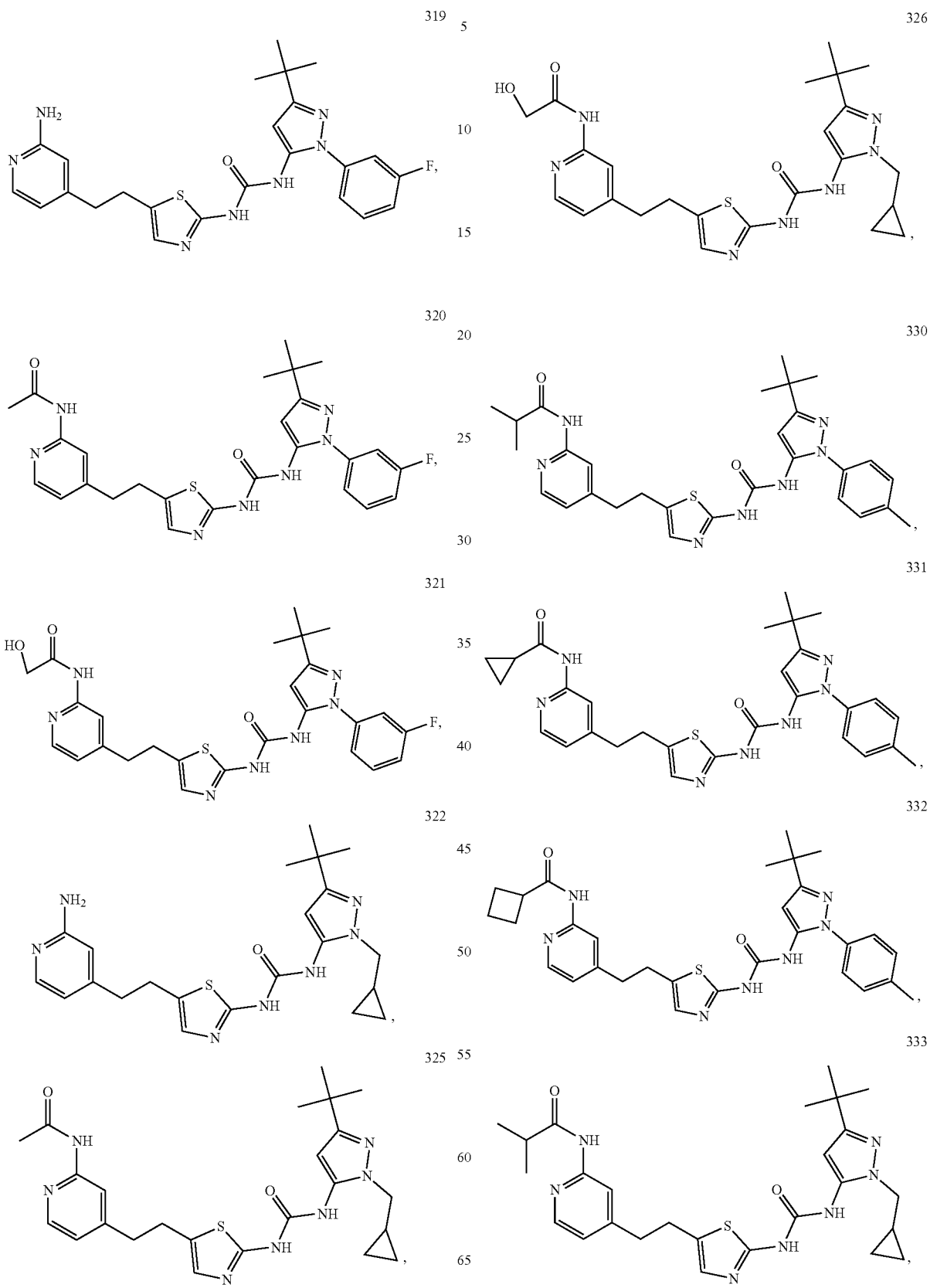

334
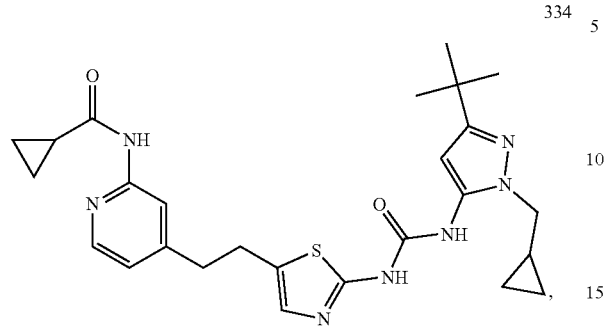
335
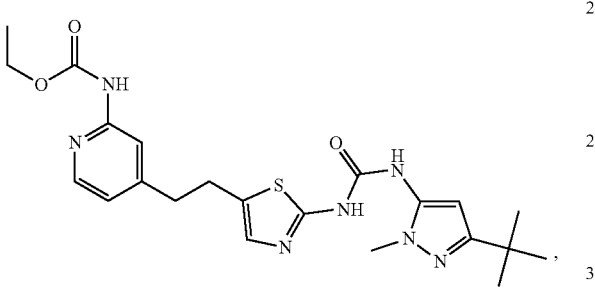
336
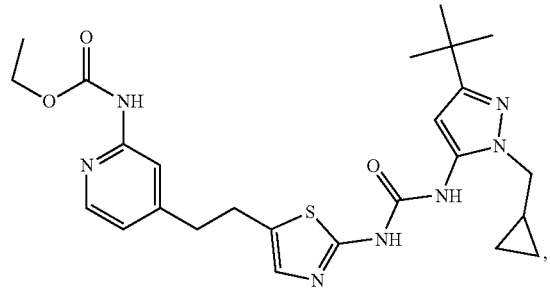
337
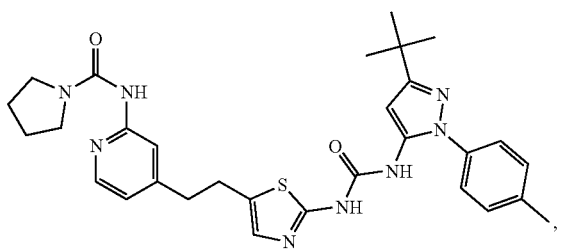
339
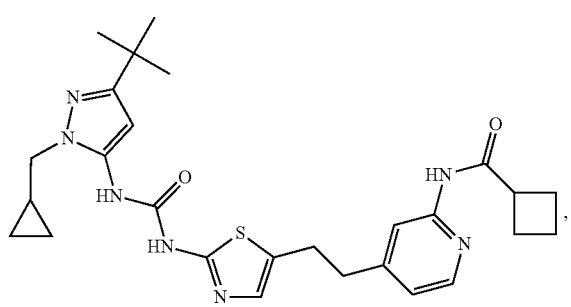
340
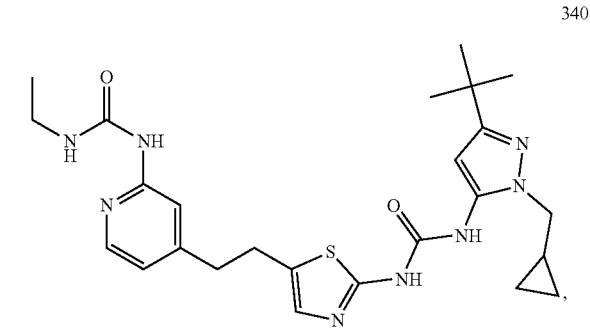
341
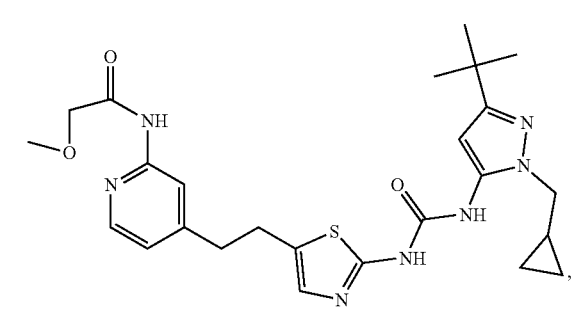
342
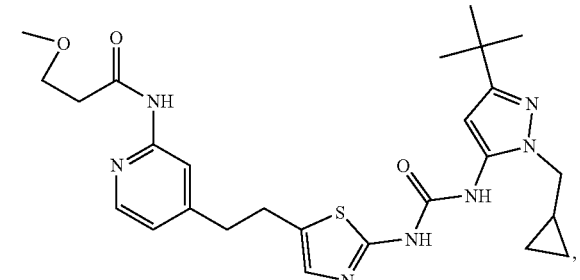
343
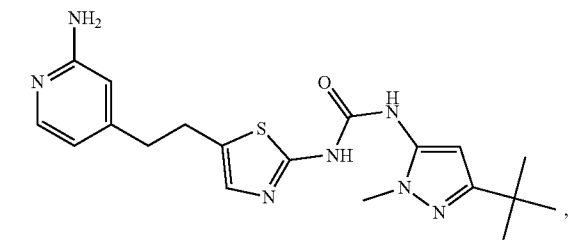
344
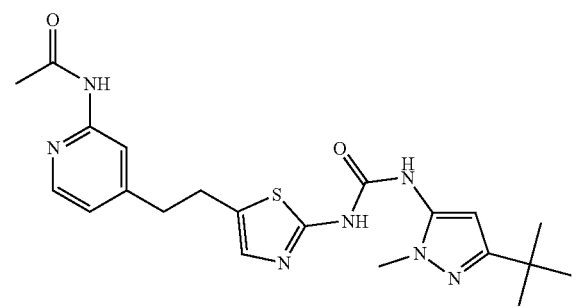

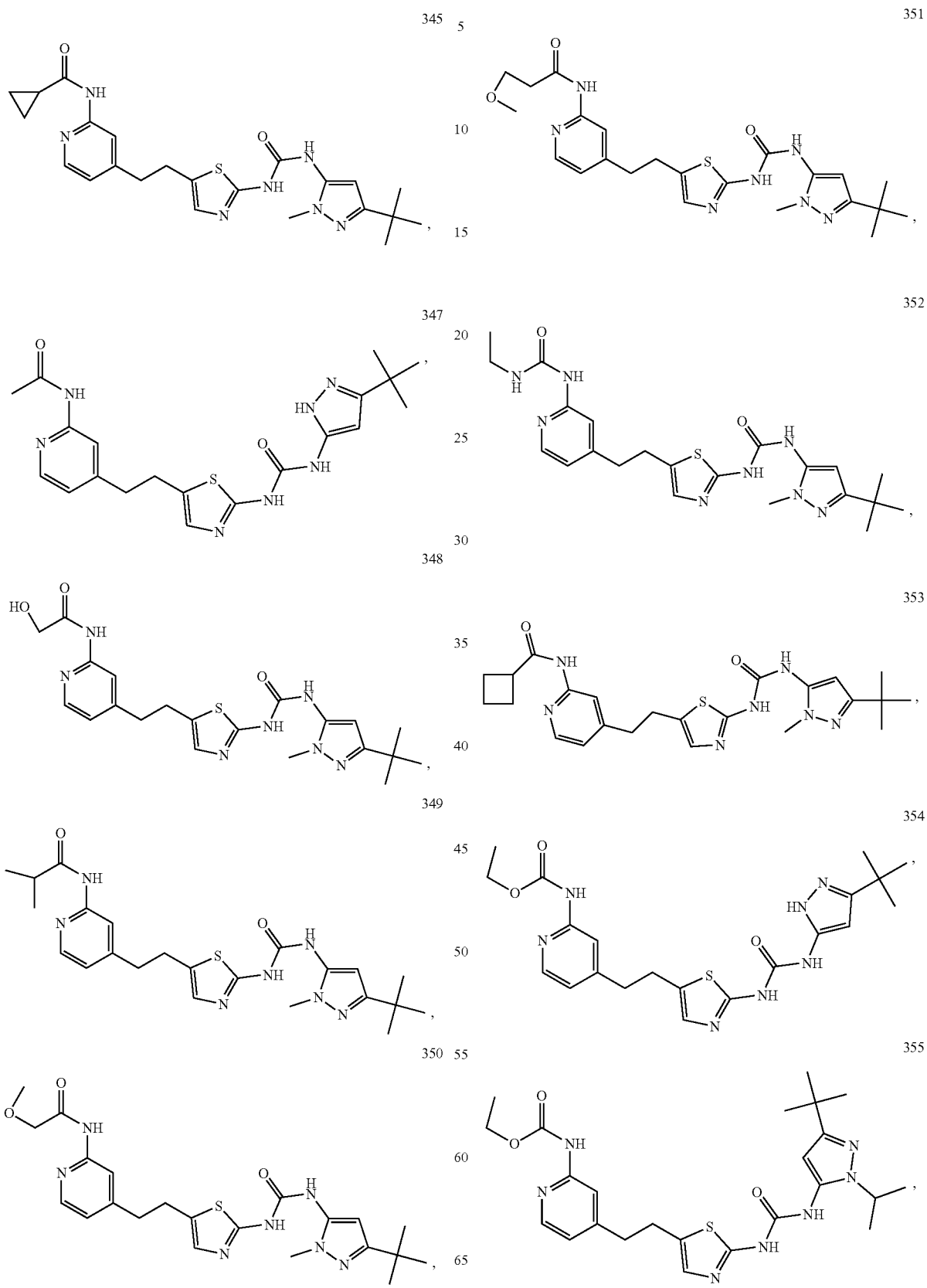

367
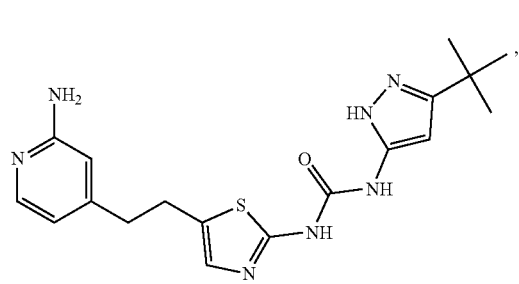
368
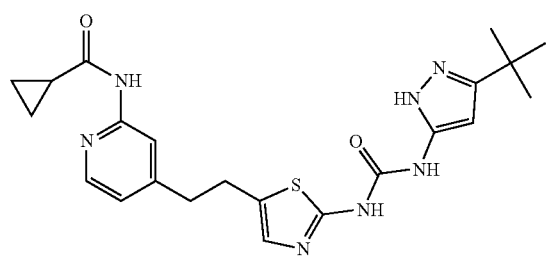
381
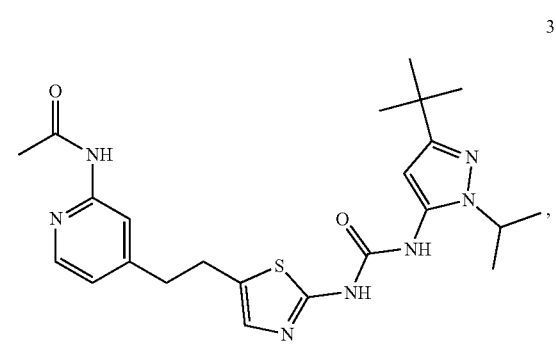
384
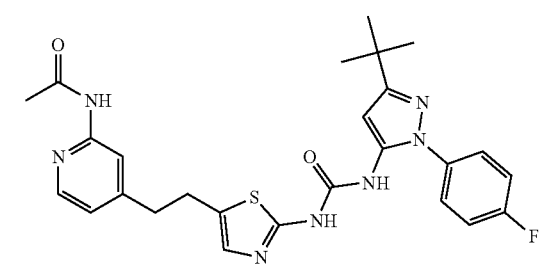
385
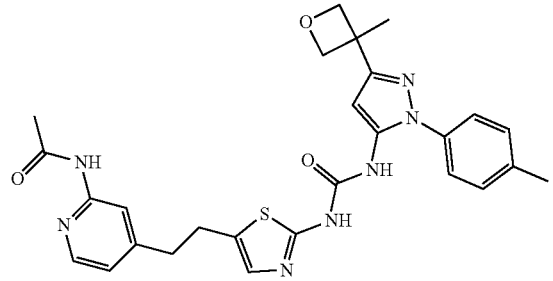
389
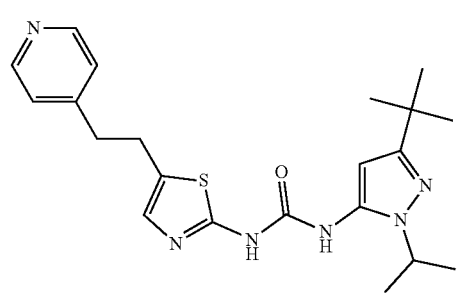
and
390
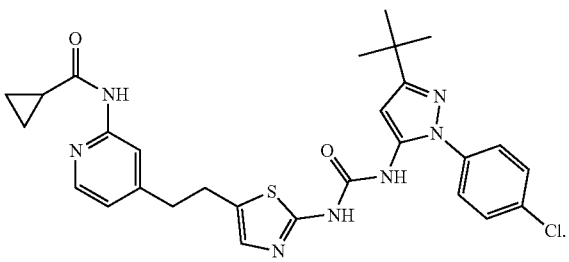
In various aspects of formula I, some non-limiting examples of compounds comprising a pyrazole moiety include
282
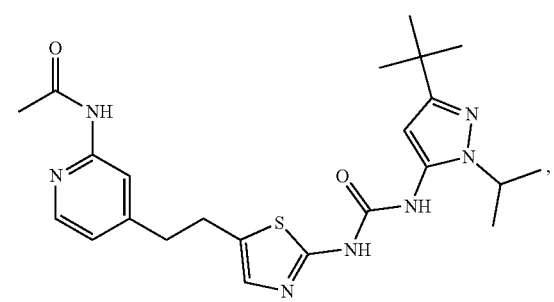
,
284
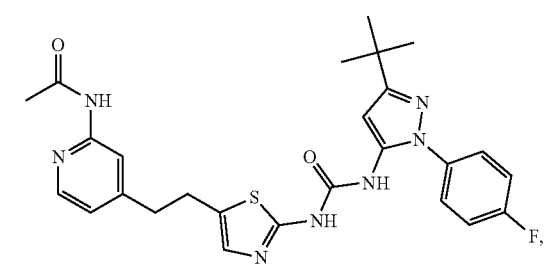
and
354
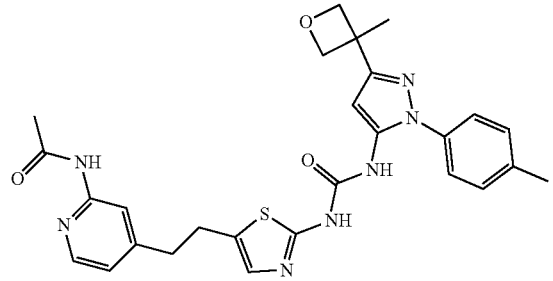

In various aspects of formula I, ring $G_2$ can be an oxazole.

In some configurations, a compound of formula I can be

396

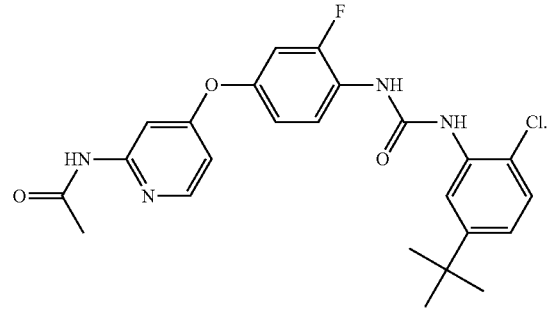

In various aspects, non-limiting examples of compounds of formula I comprising an oxazole moiety include:

364

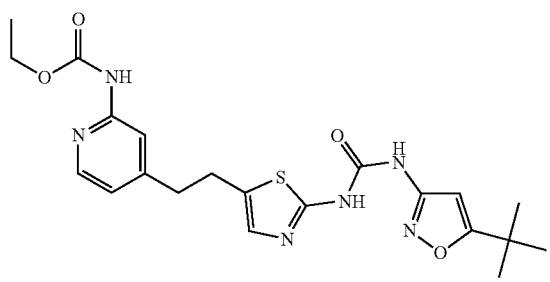

365

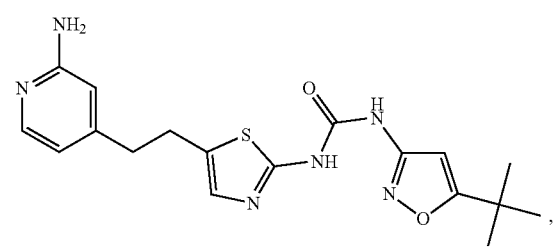

366

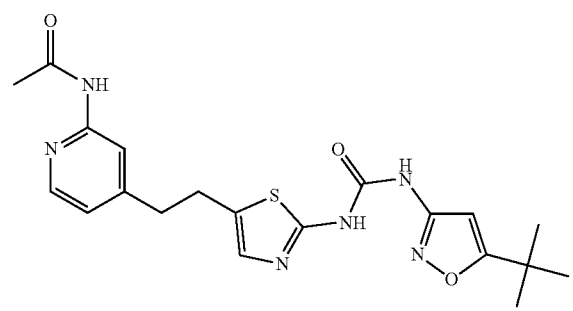

369

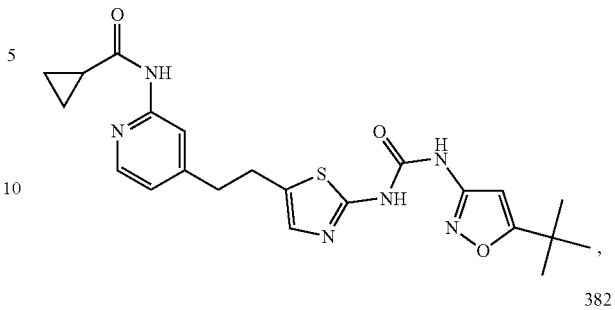

382

386

387

In various aspects of formula I, ring $G_2$ can be a 6-membered aromatic ring.

In various aspects, non-limiting examples of compounds of formula I comprising a 6-member aromatic ring for $G_2$ include:

356

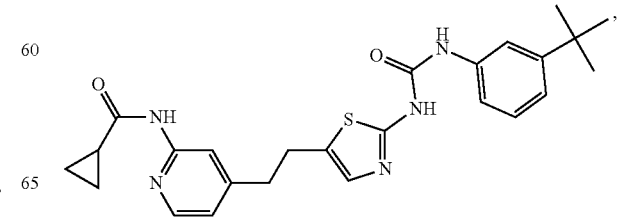

357
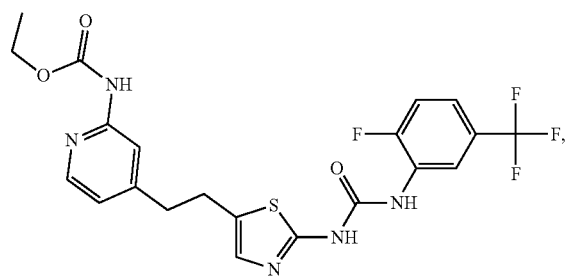
363
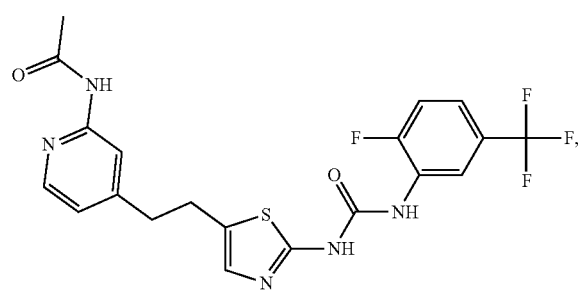
380
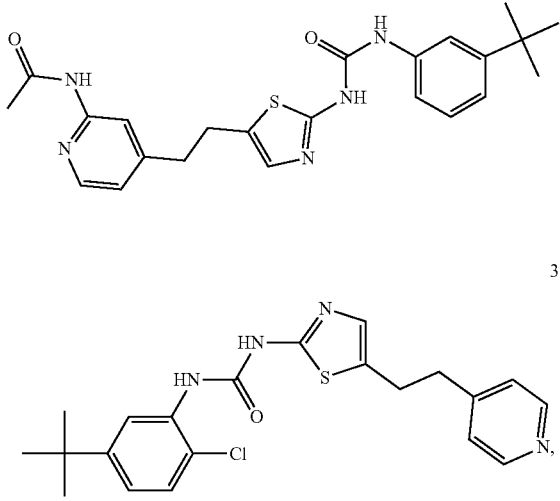
383
388
398
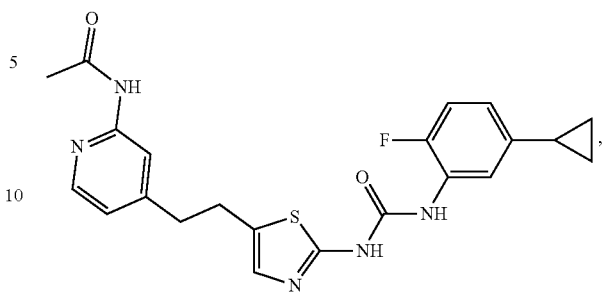
400
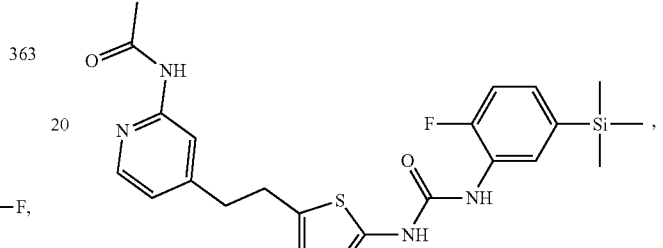
409
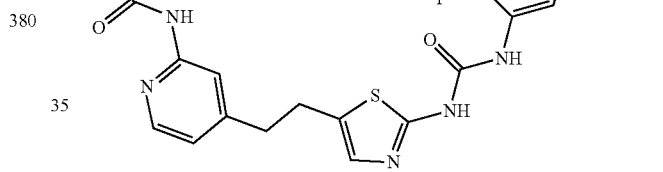
410
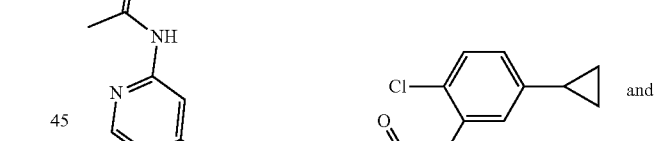
and
411
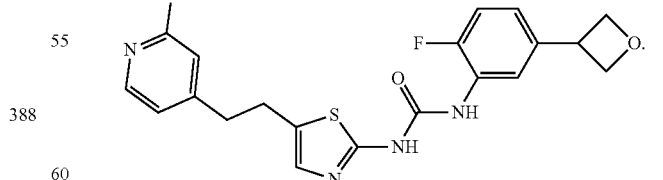
In various embodiments, the present inventors disclose compounds having a structure of Formula II as set forth below, as well as pharmaceutically acceptable salts thereof, solvates thereof, polymorphs thereof, tautomers thereof, stereoisomers thereof, and prodrugs thereof.

In some embodiments, Compounds of Formula I can have a structure

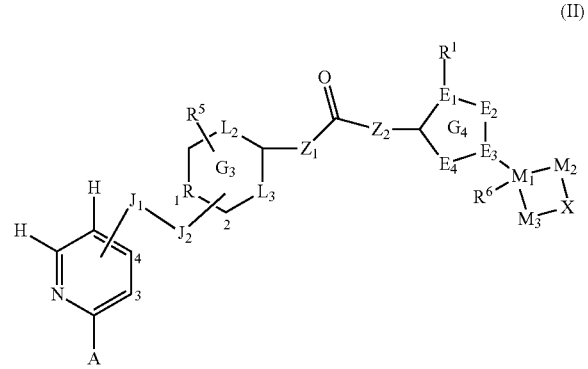

(II)

wherein A can be selected from the group consisting of H and —NH(CO)R²;

R² can be selected from the group consisting of H, alkyl, cycloalkyl, cycloalkylalkyl, heterocyclyl, heterocycylalkyl, aryl, heteroaryl, OR³ and NR⁴R⁴;

R³ can be selected from the group consisting of alkyl, cycloakyl, cycloalkyalkyl, heterocyclyl and heterocycylalkyl;

each R⁴ can be independently selected from the group consisting of H, alkyl, cycloalkyl, cycloalkylalkyl, heterocyclyl and heterocyclylalkyl, or the two R⁴ can be taken together to form a 5- or 6-membered heterocyclic ring with the nitrogen;

J₁ and J₂ together can be selected from the group consisting of —CH₂—CH₂—, —CH₂—O— and —O—CH₂—, wherein J₁ can be substituted at position 3 or 4 on the pyridine and J₂ can be substituted on ring G₃ at position 1 or 2;

G₃ can be a 6-member aromatic or heteroaromatic ring;

each of R, L₂ and L₃ can be independently selected from the group consisting of carbon and nitrogen;

R⁵ can be selected from the group consisting of H, halogen, C₁₋₈ alkyl, and cyclopropyl;

G₄ can be an aromatic or heteroaromatic ring selected from the group consisting of (i) a 5-membered heteroaromatic ring selected from the group consisting of pyrazole, oxazole, isoxazole, imidazole and oxadiazole, and (ii) a 6-membered aromatic or heteroaromatic ring selected from the group consisting of benzene, pyridine and pyrimidine;

E₁ can be selected from the group consisting of C, N and O when G₄ is a 5-membered heteroaromatic ring, or E₁ can be selected from the group consisting of C and N when G₄ is a 6-membered aromatic or heteroaromatic ring;

E₂ can be selected from the group consisting of CH, N and O when G₄ is a 5-membered heteroaromatic ring, or E₂ can be selected from the group consisting of CH—CH and CH—N when G₄ is a 6-membered aromatic or heteroaromatic ring;

E₃ can be selected from the group consisting of C and N;

E₄ can be selected from the group consisting of CH, N and O when G₄ is a 5-membered heteroaromatic ring, or E₄ can be selected from the group consisting of CH and N when G₄ is a 6-membered aromatic or heteroaromatic ring;

R¹ can be selected from the group consisting of H, C₁₋₈ alkyl, cycloalkyl, cycloalkylalkyl, aryl, heteroaryl and halogen, or can be absent, with provisos that when E₁ is O then R¹ is absent and when R¹ is a halogen then E₁ is C;

Z₁ and Z₂ can each be independently selected from the group consisting of NH, O and CH₂, with the proviso that at least one of Z₁ and Z₂ is NH;

M₁ can be selected from the group consisting of C and Si, provided that when M₁ is Si, each of M₂ and M₃ is methyl and X is absent;

each of M₂ and M₃ can be selected from the group consisting of CH₃, CH₂ and H;

X can be selected from the group consisting of CH₂, O and S, or can be absent, wherein if each of M₁, M₂ and M₃ is C, and X is CH₂, O or S, then M₁, M₂, M₃ and X together form a 4-member ring, or if each of M₁, M₂ and M₃ is C, and X absent, then M₁, M₂, M₃ together form a 3-member ring;

R³ can be selected from the group consisting of H, phenyl, 4-tolyl, halophenyl, 2-cyclopropylmethyl, C₁₋₈ alkyl R⁶ can be selected from the group consisting of H and C₁₋₈ alkyl, provided that when M₁ is Si, R⁶ is methyl.

In various aspects of Formula II, ring G₃ can be selected from the group consisting of benzene, pyridine and pyrimidine.

In various aspects of Formula I, each of Z₁ and Z₂ can be NH.

In various aspects of Formula II, R₅ can be F.

In various aspects of Formula II, a halogen can be ortho- to Z₁.

In various aspects, non-limiting examples of compounds of formula II include

315

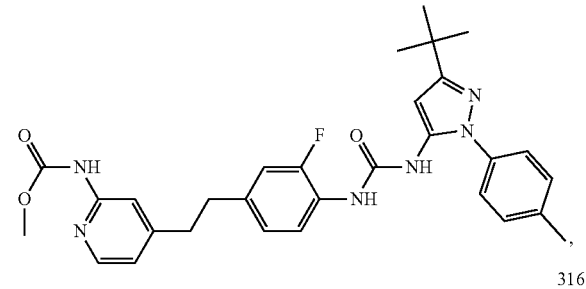

316

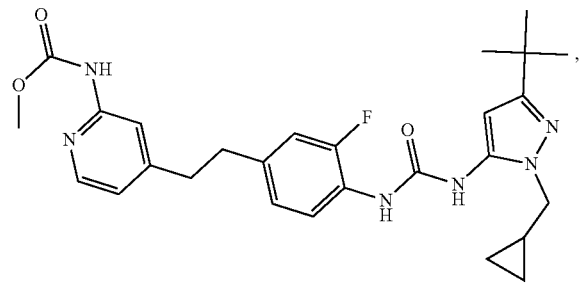

317

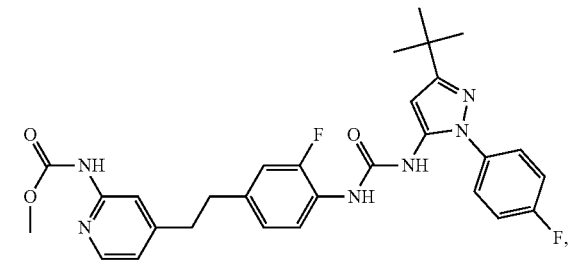

318
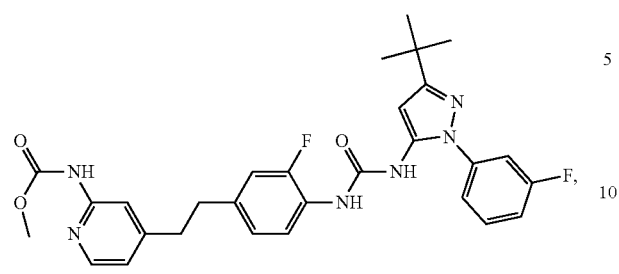
329
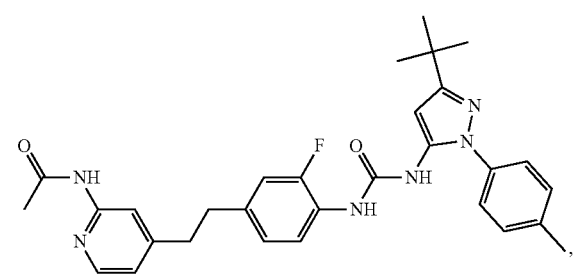
358
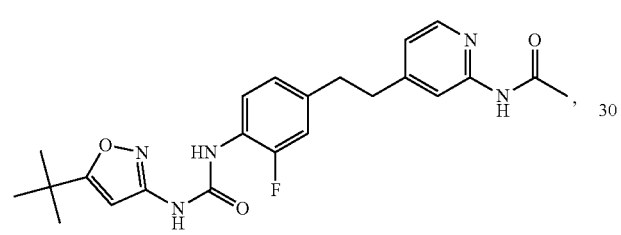
359
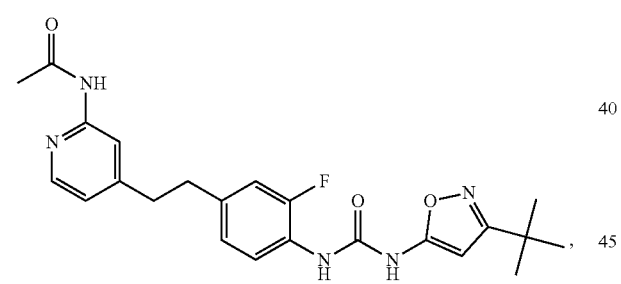
360
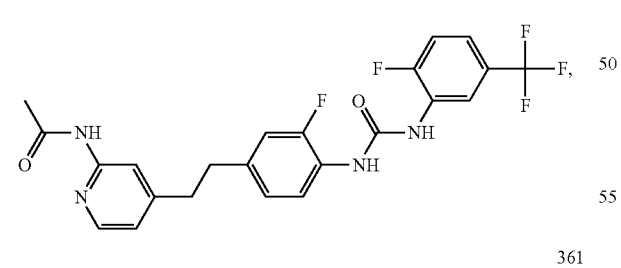
361
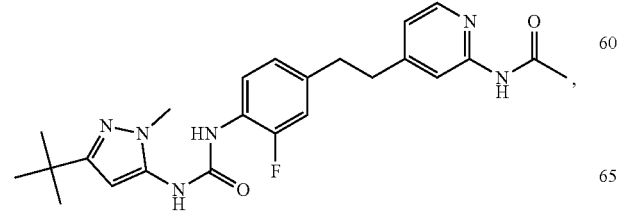
370
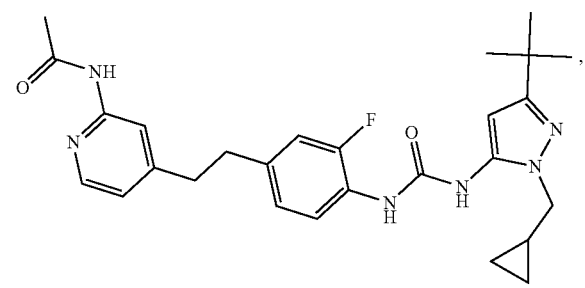
371
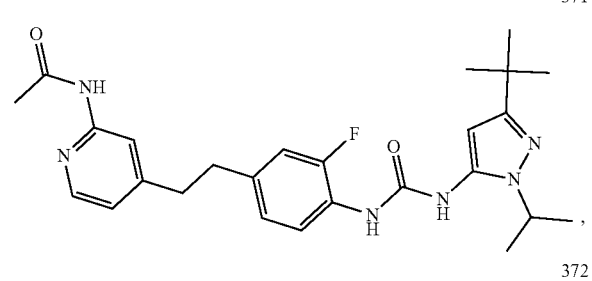
372
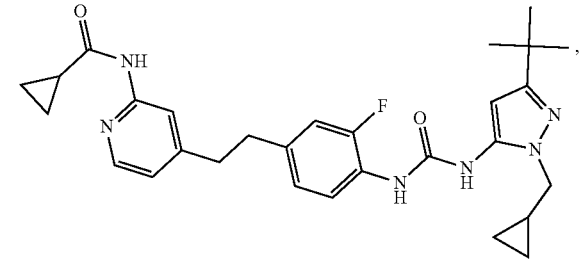
373
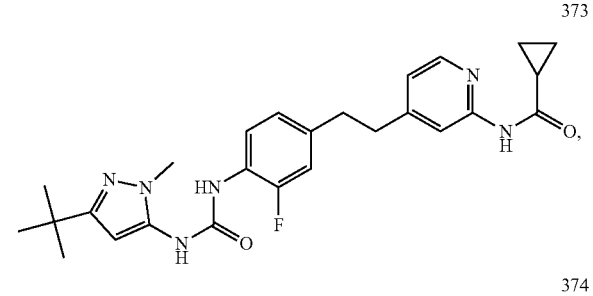
374
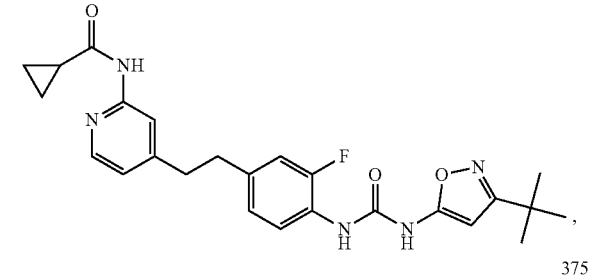
375
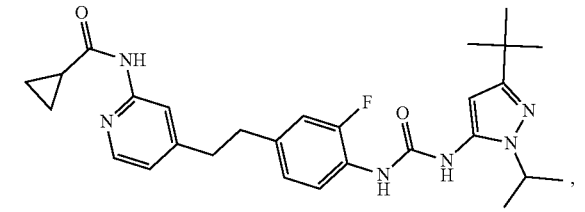

376
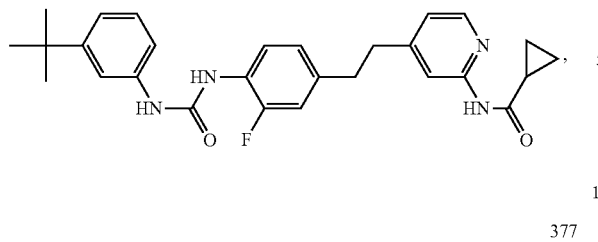
377
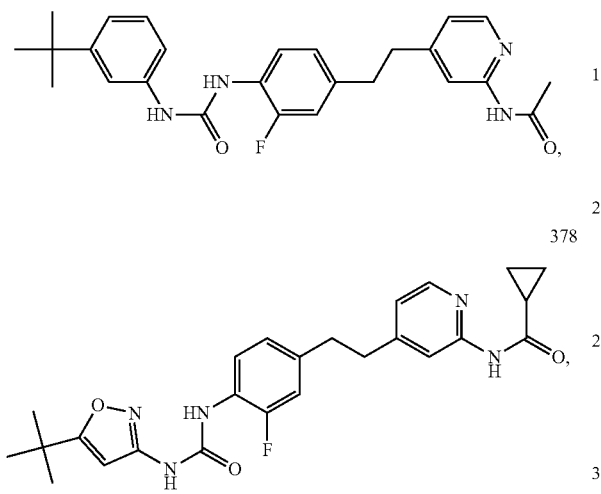
378
379
402
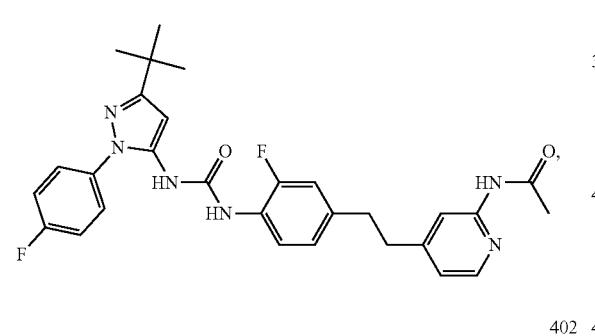
403
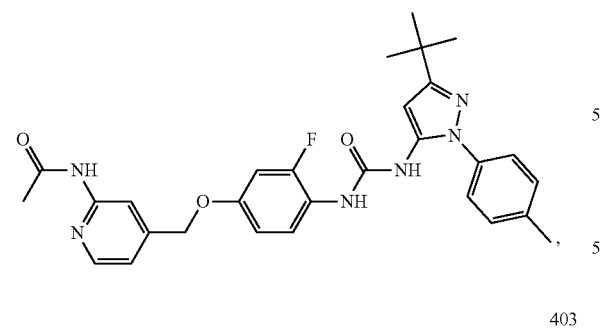
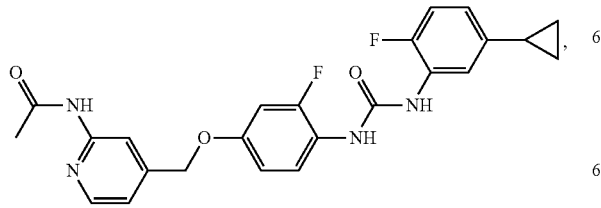
404
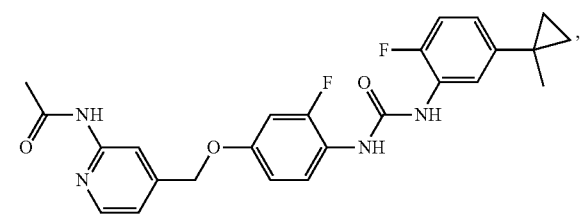
405
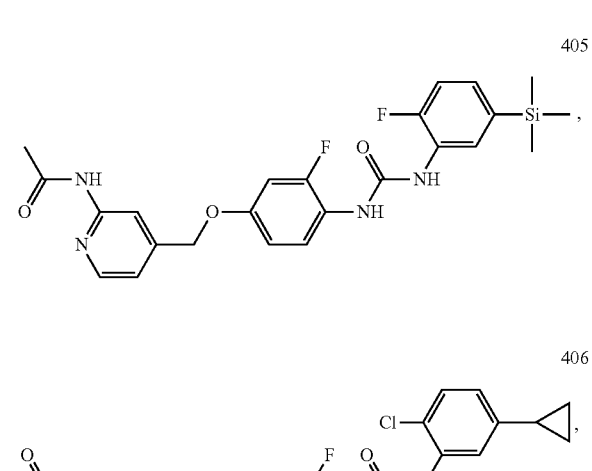
406
413
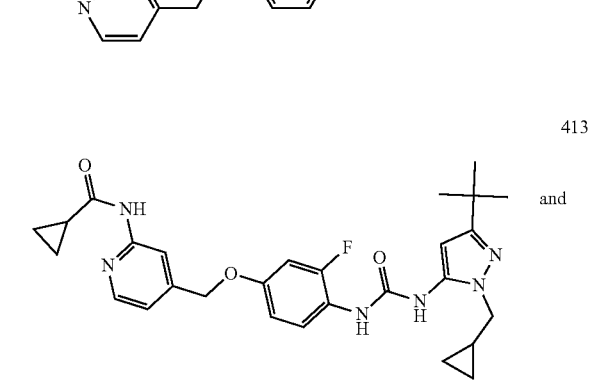
and
414
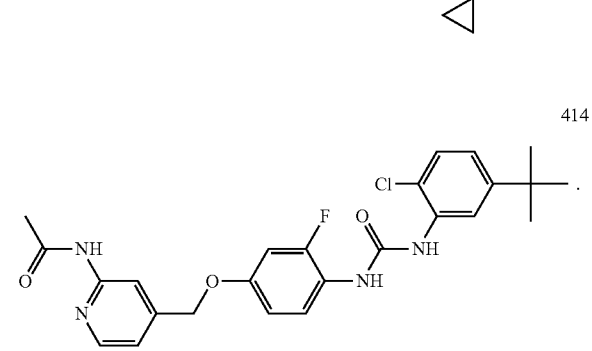
In various embodiments, the present inventors disclose compounds having a structure of Formula III as set forth below, as well as pharmaceutically acceptable salts thereof, solvates thereof, polymorphs thereof, tautomers thereof, stereoisomers thereof, and prodrugs thereof.
In some embodiments, Compounds of Formula III can have a structure

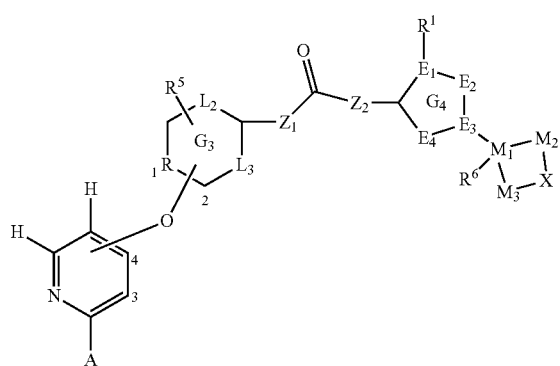

(III)

wherein A can be selected from the group consisting of H and N—(CO)R²;

R² can be selected from the group consisting of H, alkyl, cycloalkyl, cycloalkylalkyl, heterocyclyl, heterocycylalkyl, aryl, heteroaryl, OR³ and NR⁴R⁴;

R³ can be selected from the group consisting of alkyl, cycloalkyl, cycloalkylalkyl, heterocyclyl and heterocycylalkyl;

each R⁴ can be independently selected from the group consisting of H, alkyl, cycloalkyl, cycloalkylalkyl, heterocyclyl and heterocyclylalkyl, or the two R⁴ are taken together to form a 5- or 6-membered heterocyclic ring with the nitrogen;

the oxygen linker can be substituted on the pyridine at position 3 or 4 and on ring $G_3$ at position 1 or 2;

$G_3$ can be a 6-member aromatic or heteroaromatic ring;

each of R, $L_2$ and $L_3$ can be independently selected from the group consisting of carbon and nitrogen;

$R^5$ can be selected from the group consisting of H, halogen, $C_{1-8}$ alkyl, and cyclopropyl;

$Z_1$ and $Z_2$ can each be independently selected from the group consisting of NH, O and $CH_2$, with the proviso that at least one of $Z_1$ and $Z_2$ is NH;

$G_4$ can be an aromatic or heteroaromatic ring selected from the group consisting of (i) a 5-membered heteroaromatic ring selected from the group consisting of pyrazole, oxazole, isoxazole, imidazole and oxadiazole, and (ii) a 6-membered aromatic or heteroaromatic ring selected from the group consisting of benzene, pyridine and pyrimidine;

$E_1$ can be selected from the group consisting of C, N and O when $G_4$ is a 5-membered heteroaromatic ring, or $E_1$ can be selected from the group consisting of C and N when $G_4$ is a 6-membered aromatic or heteroaromatic ring;

$E_2$ can be selected from the group consisting of CH, N and O when $G_4$ is a 5-membered heteroaromatic ring, or $E_2$ can be selected from the group consisting of CH—CH and CH—N when $G_4$ is a 6-membered aromatic or heteroaromatic ring;

$E_3$ can be selected from the group consisting of C and N:

$E_4$ can be selected from the group consisting of CH, N and O when $G_4$ is a 5-membered heteroaromatic ring, or $E_4$ can be selected from CH and N when $G_2$ is a 6-membered aromatic or heteroaromatic ring:

$R^1$ can be selected from the group consisting of H, $C_{1-8}$ alkyl, cycloalkyl, cycloalkylalkyl, aryl, heteroaryl and halogen, or can be absent, with provisos that when $E_1$ is O then $R^1$ is absent and when $R^1$ is a halogen then $E_1$ is C;

$M_1$ can be selected from the group consisting of C and Si, provided that when $M_1$ is Si, each of $M_2$ and $M_3$ is methyl and X is absent;

each of $M_2$ and $M_3$ can be selected from the group consisting of $CH_3$, $CH_2$ and H;

X can be selected from the group consisting of $CH_2$, O and S, or can be absent, wherein if each of $M_1$, $M_2$ and $M_3$ is C, and X is $CH_2$, O or S, then $M_1$, $M_2$, $M_3$ and X together form a 4-member ring, or if each of $M_1$, $M_2$ and $M_3$ is C, and X absent, then $M_1$, $M_2$, $M_3$ together form a 3-member ring;

$R^6$ can be selected from the group consisting of H and $C_{1-8}$ alkyl, provided that when $M_1$ is Si, $R^6$ is methyl.

In various aspects of Formula III, ring $G_3$ can be selected from the group consisting of benzene, pyridine and pyrimidine.

In various aspects of Formula III, $R^1$ can be selected from the group consisting of H, phenyl, 4-tolyl, halophenyl, 2-cyclopropylmethyl and $C_{1-8}$ alkyl.

In various aspects of Formula III, each of $Z_1$ and $Z_2$ can be NH.

In various aspects of Formula III, $R^5$ can be fluorine.

In various aspects of Formula III, a halogen can be ortho- to $Z_1$.

In various aspects, non-limiting examples of compounds of formula III include

259

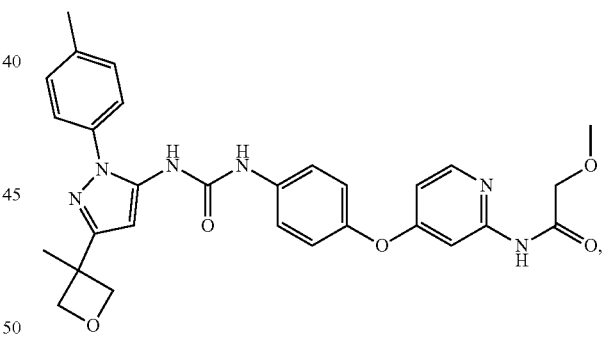

260

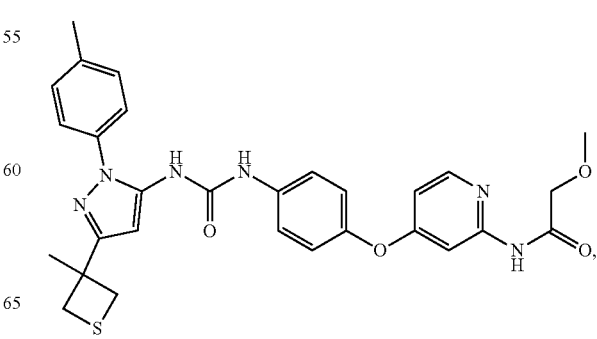

261 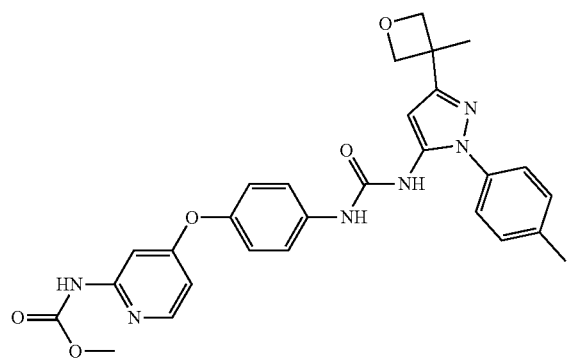
262 
267 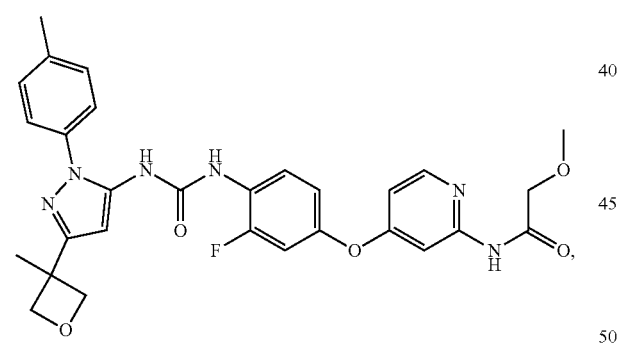
268 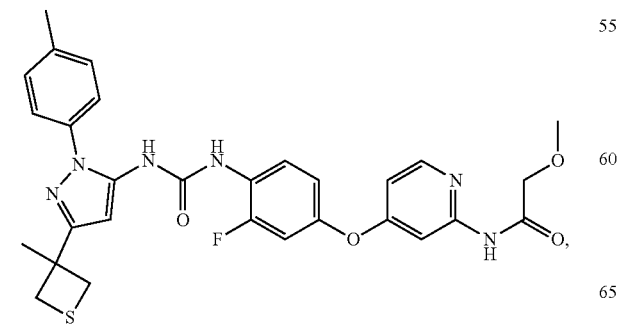
279 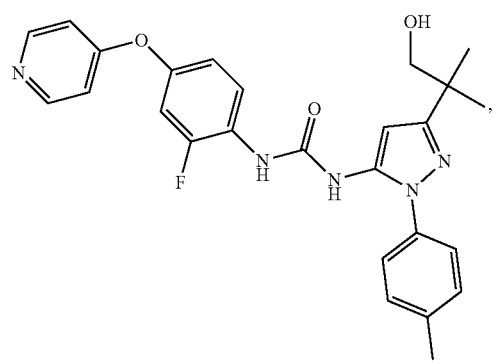
280 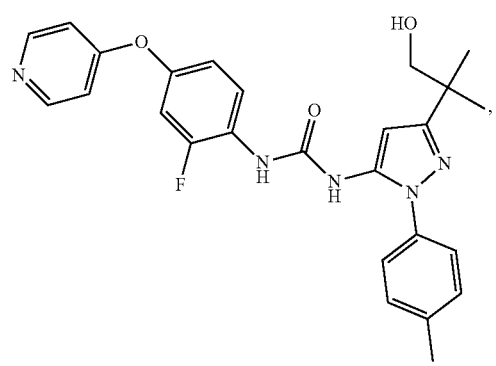
300 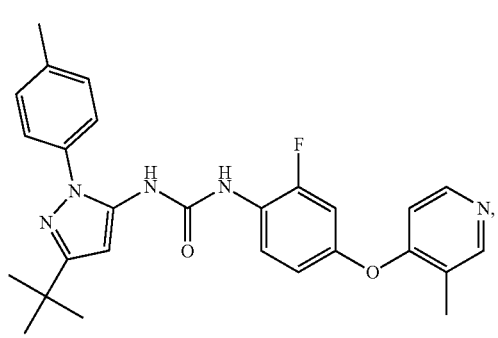
303 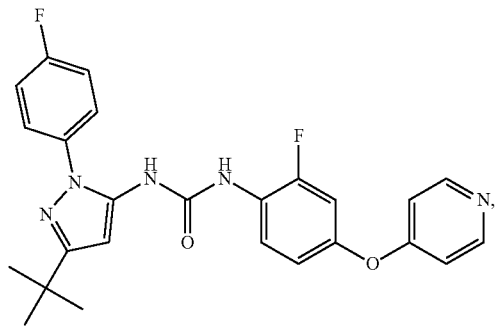

304
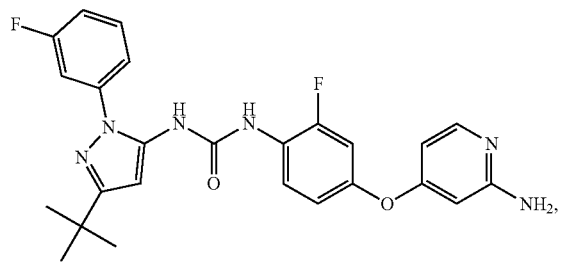
306
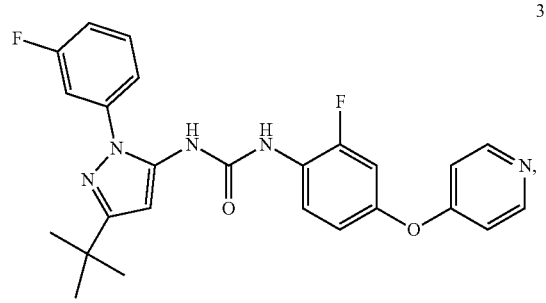
310
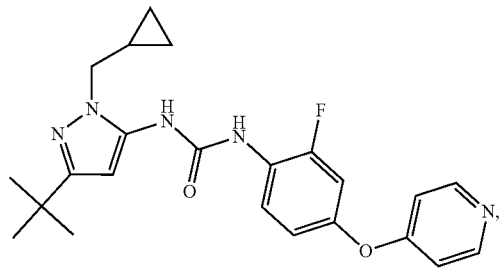
391
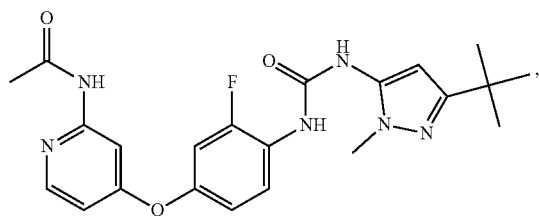
392
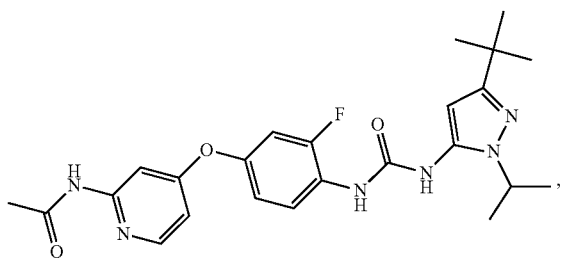
393
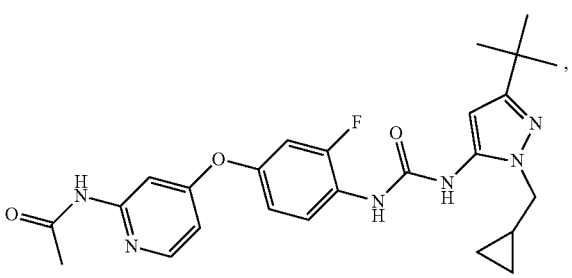
394
395
396
397
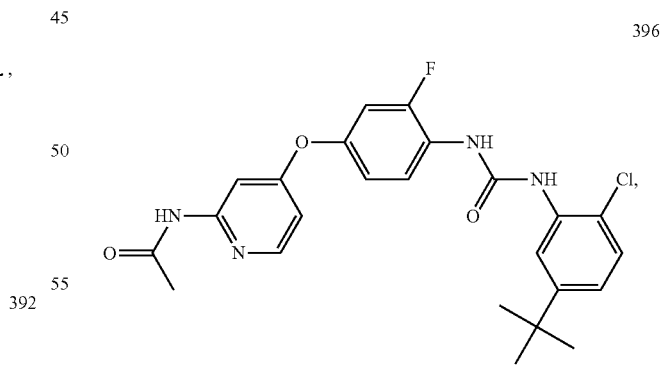
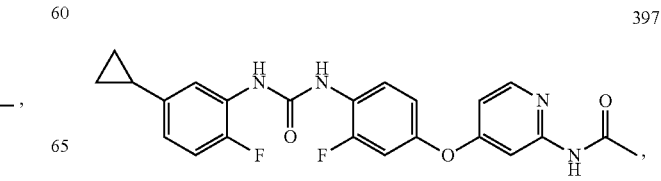

399

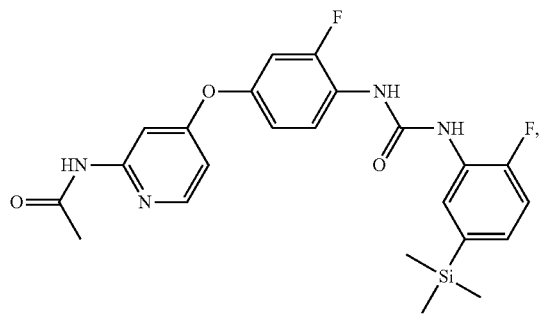

426

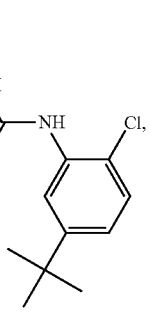

407

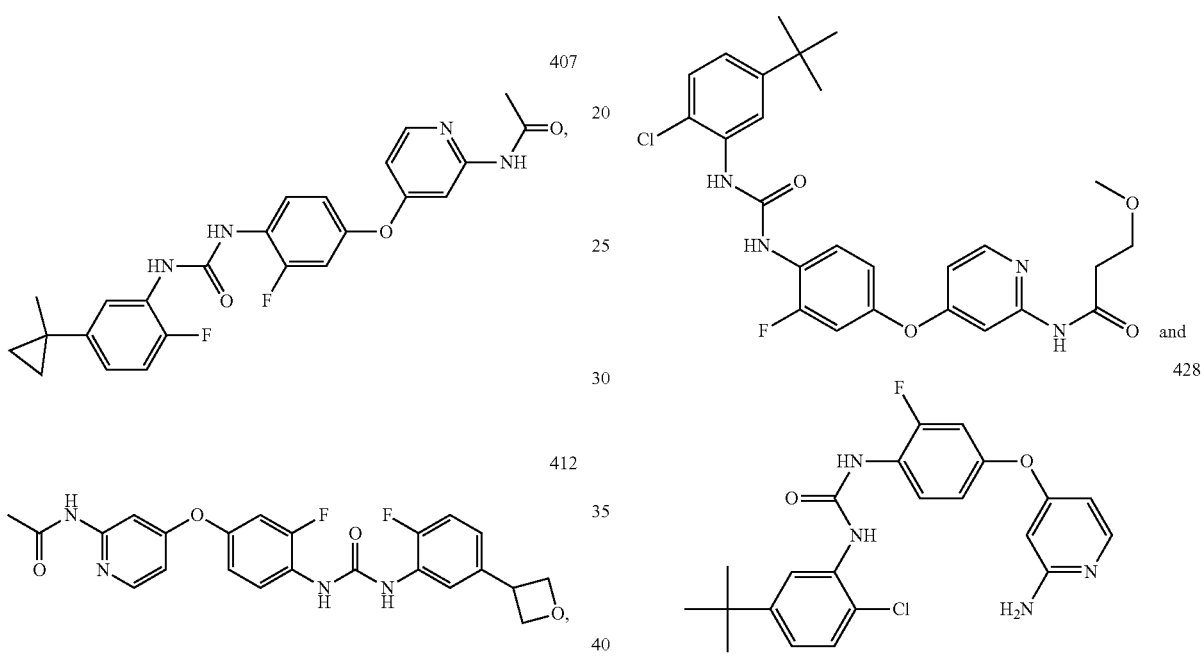

412

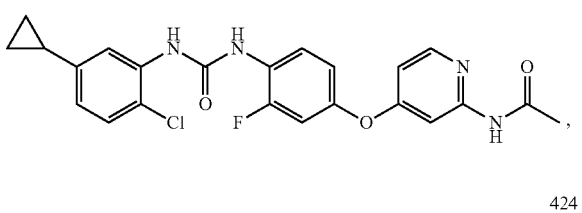

423

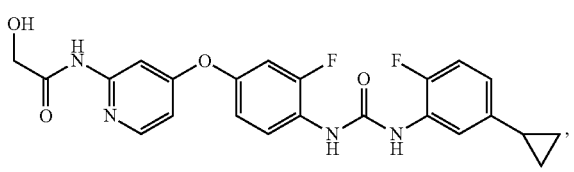

424

425

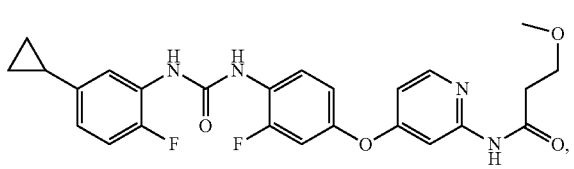

In various aspects, a compound of the present teachings can include, without limitation, 1-(5-tert-Butyl-2-p-tolyl-2H-pyrazol-3-yl)-3-[5-(2-pyridin-4-yl-ethyl)-thiazol-2-yl]-urea, 1-[5-(3-Methyl-oxetan-3-yl)-2-p-tolyl-2H-pyrazol-3-yl]-3-[5-(2-pyridin-4-yl-ethyl)-thiazol-2-yl]-urea, 1-{5-[2-(2-Amino-pyridin-4-yl)-ethyl]-thiazol-2-yl}-3-(5-tert-butyl-2-p-tolyl-2H-pyrazol-3-yl)-urea, 1-[5-(3-Methyl-thietan-3-yl)-2-p-tolyl-2H-pyrazol-3-yl]-3-[5-(2-pyridin-4-yl-ethyl)-thiazol-2-yl]-urea. [4-(2-{2-[3-(5-tert-Butyl-2-p-tolyl-2H-pyrazol-3-yl)-ureido]-thiazol-5-yl}-ethyl)-pyridin-2-yl]-carbamic acid benzyl ester, N-[4-[2-[2-[[5-tert-butyl-2-(p-tolyl)pyrazol-3-yl]carbamoylamino]thiazol-5-yl]ethyl]-2-pyridyl]-2-methoxy-acetamide, N-[4-[2-[2-[[5-tert-butyl-2-(p-tolyl)pyrazol-3-yl]carbamoylamino]thiazol-5-yl]ethyl]-2-pyridyl]acetamide, N-[4-[2-[2-[[5-tert-butyl-2-(p-tolyl)pyrazol-3-yl]carbamoylamino]thiazol-5-yl]ethyl]-2-pyridyl]-3-methoxy-propanamide, 1-[4-(2-{2-[3-(5-tert-Butyl-2-p-tolyl-2H-pyrazol-3-yl)-ureido]-thiazol-5-yl}-ethyl)-pyridin-2-yl]-3-ethyl-urea, [4-(2-{2-[3-(5-tert-Butyl-2-p-tolyl-2H-pyrazol-3-yl)-ureido]-thiazol-5-yl}-ethyl)-pyridin-2-yl]-carbamic acid methyl ester, [4-(2-{2-[3-(5-tert-Butyl-2-p-tolyl-2H-pyrazol-3-yl)-ureido]-thiazol-5-yl}-ethyl)-pyridin-2-yl]-carbamic acid ethyl ester, N-[4-(2-{2-[3-(5-tert-Butyl-2-p-tolyl-2H-pyrazol-3-yl)-ureido]-thiazol-5-yl}-ethyl)-pyridin-2-yl]-2-hydroxy-acetamide, Tetrahydro-pyran-4-carboxylic acid [4-(2-{2-[3-(5-tert-butyl-2-p-tolyl-2H-pyrazol-3-yl)-ureido]-thiazol-5-yl}-ethyl)-pyridin-2-yl-amide, 1-[5-tert-Butyl-2-(4-fluoro-phenyl)-2H-pyrazol-3-yl]-3-[5-(2-pyridin-4-yl-ethyl)-thiazol-2-yl]-urea, 1-[5-tert-Butyl-2-(3-fluoro-phenyl)-2H-pyrazol-3-yl]-3-[5-(2-pyridin-4-yl-ethyl)-thiazol-2-yl]-urea, N-[4-(2-{2-[3-(5-tert-Butyl-2-p-tolyl-2H-pyrazol-3-yl)-ureido]-thiazol-5-yl}-ethyl)-pyridin-2-yl]-propionamide, 1-{(5-[2-(2-Amino-pyridin-4-yl)-ethyl]-thiazol-2-yl}-3-[5-tert-butyl-2-(4-chloro-phenyl)-2H-pyrazol-3-yl]-urea, N-{4-[2-(2-{3-[5-tert-Butyl-2-(4-chloro-phenyl)-2H-pyrazol-3-yl]-ureido}-thiazol-5-yl)-ethyl]-pyridin-2-yl}-acetamide, N-[4-(3-{3-[5-tert-Butyl-2-(4-chloro-phenyl)-2H-pyrazol-3-yl]-ureidomethylsulfanyl}-propyl)-pyridin-2-yl]-2-hydroxy-acetamide, 1-{5-[2-(2-Amino-pyridin-4-yl)-ethyl]-thiazol-2-yl}-3-[5-tert-butyl-2-(3-fluoro-phenyl)-2H-pyrazol-3-yl]-urea, N-{4-[2-(2-{3-[5-tert-Butyl-2-(3-fluoro-phenyl)-2H-pyrazol-3-yl]-ureido}-thiazol-5-yl)-ethyl]-pyridin-2-yl}-acetamide, N-[4-[2-[2-[[5-tert-butyl-2-(3-fluorophenyl)pyrazol-3-yl]carbamoylamino]thiazol-5-yl]ethyl]-2-pyridyl]-2-hydroxy-acetamide, 1-{5-[2-(2-Amino-pyridin-4-yl)-ethyl]-thiazol-2-yl}-3-(5-tert-butyl-2-cyclopropylmethyl-2H-pyrazol-3-yl)-urea, N-[4-(2-{2-[3-(5-tert-Butyl-2-cyclopropylmethyl-2H-pyrazol-3-yl)-ureido]-thiazol-5-yl}-ethyl-pyridin-2-yl]-acetamide, N-[4-(2-{2-[3-(5-tert-Butyl-2-cyclopropylmethyl-2H-pyrazol-3-yl)-ureido]-thiazol-5-yl}-ethyl)-pyridin-2-yl]-2-hydroxy-acetamide, N-[4-(2-{2-[3-(5-tert-Butyl-2-p-tolyl-2H-pyrazol-3-yl)-ureido]-thiazol-5-yl}-ethyl)-pyridin-2-yl]-isobutyramide, Cyclopropanecarboxylic acid [4-(2-{2-[3-(5-tert-butyl-2-p-tolyl-2H-pyrazol-3-yl)-ureido]-thiazol-5-yl}-ethyl)-pyridin-2-yl]-amide, Cyclobutanecarboxylic acid [4-(2-{2-[3-(5-tert-butyl-2-p-tolyl-2H-pyrazol-3-yl)-ureido]-thiazol-5-yl}-ethyl)-pyridin-2-yl]-amide, N-[4-(2-{2-[3-(5-tert-Butyl-2-cyclopropylmethyl-2H-pyrazol-3-yl)-ureido]-thiazol-5-yl}-ethyl-pyridin-2-yl]-isobutyramide, Cyclopropanecarboxylic acid [4-(2-{2-[3-(5-tert-butyl-2-cyclopropylmethyl-2H-pyrazol-3-yl)-ureido]-thiazol-5-yl}-ethyl)-pyridin-2-yl]-amide, [4-(2-{2-[3-(5-tert-Butyl-2-methyl-2H-pyrazol-3-yl)-ureido]-thiazol-5-yl}-ethyl)-pyridin-2-yl]-carbamic acid ethyl ester, [4-(2-{2-[3-(5-tert-Butyl-2-cyclopropylmethyl-2H-pyrazol-3-yl)-ureido]-thiazol-5-yl}-ethyl)-pyridin-2-yl]-carbamic acid ethyl ester. Pyrrolidine-1-carboxylic acid [4-(2-{2-[3-(5-tert-butyl-2-p-tolyl-2H-pyrazol-3-yl)-ureido]-thiazol-5-yl}-ethyl)-pyridin-2-yl]-amide, Cyclobutanecarboxylic acid [4-(2-{2-[3-(5-tert-butyl-2-cyclopropylmethyl-2H-pyrazol-3-yl)-ureido]-thiazol-5-yl}-ethyl)-pyridin-2-yl]-amide, 1-[4-(2-{2-[3-(5-tert-Butyl-2-cyclopropylmethyl-2H-pyrazol-3-yl)-ureido]-thiazol-5-yl}-ethyl)-pyridin-2-yl]-3-ethyl-urea, N-[4-(2-{2-[3-(5-tert-Butyl-2-cyclopropylmethyl-2H-pyrazol-3-yl)-ureido]-thiazol-5-yl}-ethyl)-pyridin-2-yl]-2-methoxy-acetamide, N-[4-(2-{2-[3-(5-tert-Butyl-2-cyclopropylmethyl-2H-pyrazol-3-yl)-ureido]-thiazol-5-yl}-ethyl)-pyridin-2-yl]-3-methoxy-propionamide, 1-{5-[2-(2-Amino-pyridin-4-yl)-ethyl]-thiazol-2-yl}-3-(5-tert-butyl-2-methyl-2H-pyrazol-3-yl)-urea, N-[4-(2-{2-[3-(5-tert-Butyl-2-methyl-2H-pyrazol-3-yl)-ureido]-thiazol-5-yl}-ethyl)-pyridin-2-yl]-acetamide, Cyclopropanecarboxylic acid [4-(2-{2-[3-(5-tert-butyl-2-methyl-2H-pyrazol-3-yl)-ureido]-thiazol-5-yl}-ethyl)-pyridin-2-yl]-amide, N-[4-(2-{2-[3-(5-tert-butyl-2H-pyrazol-3-yl)-ureido]-thiazol-5-yl}-ethyl)-pyridin-2-yl]-acetamide, N-[4-(2-{2-[3-(S-tert-Butyl-2-methyl-2H-pyrazol-3-yl)-ureido]-thiazol-5-yl}-ethyl)-pyridin-2-yl]-2-hydroxy-acetamide, N-[4-(2-{2-[3-(5-tert-Butyl-2-methyl-2H-pyrazol-3-yl)-ureido]-thiazol-5-yl}-ethyl)-pyridin-2-yl]-isobutyramide, N-[4-(2-{2-[3-(5-tert-Butyl-2-methyl-2H-pyrazol-3-yl)-ureido]-thiazol-5-yl}-ethyl)-pyridin-2-yl]-2-methoxy-acetamide. N-[4-(2-{2-[3-(5-tert-Butyl-2-methyl-2H-pyrazol-3-yl)-ureido]-thiazol-5-yl}-ethyl)-pyridin-2-yl]-3-methoxy-propionamide, 1-[4-(2-{2-[3-(5-tert-Butyl-2-methyl-2H-pyrazol-3-yl)-ureido]-thiazol-5-yl}-ethyl)-pyridin-2-yl]-3-ethyl-urea, Cyclobutanecarboxylic acid [4-(2-{2-[3-(5-tert-butyl-2-methyl-2H-pyrazol-3-yl)-ureido]-thiazol-5-yl}-ethyl)-pyridin-2-yl]-amide, [4-(2-{2-[3-(5-tert-Butyl-2H-pyrazol-3-yl)-ureido]-thiazol-5-yl}-ethyl)-pyridin-2-yl]-carbamic acid ethyl ester, [4-(2-{2-[3-(5-tert-Butyl-2-isopropyl-2H-pyrazol-3-yl)-ureido]-thiazol-5-yl}-ethyl)-pyridin-2-yl]-carbamic acid ethyl ester. Cyclopropanecarboxylic acid [4-(2-{2-[3-(3-tert-butyl-phenyl)-ureido]-thiazol-5-yl}-ethyl)-pyridin-2-yl]-amide, [4-(2-{2-[3-(2-Fluoro-5-trifluoromethyl-phenyl)-ureido]-thiazol-5-yl}-ethyl)-pyridin-2-yl]-carbamic acid ethyl ester, N-[4-(2-{2-[3-(2-Fluoro-5-trifluoromethyl-phenyl)-ureido]-thiazol-5-yl}-ethyl)-pyridin-2-yl]-acetamide, [4-(2-{2-[3-(5-tert-Butyl-isoxazol-3-yl)-ureido]-thiazol-5-yl}-ethyl)-pyridin-2-yl]-carbamic acid ethyl ester, 1-{5-[2-(2-Amino-pyridin-4-yl)-ethyl]-thiazol-2-yl}-3-(5-tert-butyl-isoxazol-3-yl)-urea, N-[4-(2-{2-[3-(5-tert-Butyl-isoxazol-3-yl)-ureido]-thiazol-5-yl}-ethyl)-pyridin-2-yl]-acetamide, 1-{5-[2-(2-Amino-pyridin-4-yl)-ethyl]-thiazol-2-yl}-3-(5-tert-butyl-2H-pyrazol-3-yl)-urea, Cyclopropanecarboxylic acid [4-(2-{2-[3-(5-tert-butyl-2H-pyrazol-3-yl)-ureido]-thiazol-5-yl}-ethyl)-pyridin-2-yl]-amide, Cyclopropanecarboxylic acid [4-(2-{2-[3-(5-tert-butyl-isoxazol-3-yl)-ureido]-thiazol-5-yl}-ethyl)-pyridin-2-yl]-amide, N-[[4-(2-{2-[3-(5-tert-Butyl-2-chlorophenyl)-ureido]-thiazol-5-yl}-ethyl)-pyridin-2-yl]-acetamide, N-[4-(2-{2-[3-(5-tert-Butyl-2-isopropyl-2H-pyrazol-3-yl)-ureido]-thiazol-5-yl}-ethyl)-pyridin-2-yl]-acetamide, N-[4-(2-{2-[3-(3-tert-Butyl-isoxazol-5-yl)-ureido]-thiazol-5-yl}-ethyl)-pyridin-2-yl]-acetamide, N-[4-(2-{2-[3-(3-tert-Butyl-phenyl)-ureido]-thiazol-5-yl}-ethyl)-pyridin-2-yl]-acetamide, N-{4-[2-(2-{3-[5-tert-Butyl-2-(4-fluoro-phenyl)-2H-pyrazol-3-yl]-ureido}-thiazol-5-yl)-ethyl]-pyridin-2-yl}-acetamide, N-{4-[2-(2-{3-[5-(3-Methyl-oxetan-3-yl)-2-p-tolyl-2H-pyrazol-3-yl]-ureido}-thiazol-5-yl)-ethyl]-pyridin-2-yl}-acetamide, 1-(3-tert-Butyl-isoxazol-5-yl)-3-[5-(2-pyridin-4-yl-ethyl)-thiazol-2-yl]-urea, 1-(5-tert-Butyl-isoxazol-3-yl)-3-[5-(2-pyridin-4-yl-ethyl)-thiazol-2-yl]-urea, 1-(5-tert-Butyl-2-chlorophenyl)-3-[5-(2-pyridin-4-yl-ethyl)-thiazol-2-yl]-urea, 1-(5-tert-Butyl-2-isopropyl-2H-pyrazol-3-yl)-3-[5-(2-pyridin-4-yl-ethyl)-thiazol-2-yl]-urea, N-[4-[2-[2-[[5-tert-butyl-2-(4-chlorophenyl)pyrazol-3-yl]carbamoylamino]thiazol-5-yl]ethyl]-2-pyridyl]cyclopropanecarboxamide, N-[4-(2-{2-[3-(5-Cyclopropyl-2-fluoro-phenyl)-ureido]-thiazol-5-yl}-ethyl)-pyridin-2-yl]-acetamide, N-[4-(2-{2-[3-(2-Fluoro-5-trimethylsilanyl-phenyl)-ureido]-thiazol-5-yl}-ethyl)-pyridin-2-yl]-acetamide, N-{4-[2-(2-{3-[2-Fluoro-5-(1-methyl-cyclopropyl)-phenyl]-ureido}-thiazol-5-yl)-ethyl]-pyridin-2-yl}-acetamide, N-[4-(2-{2-[3-(2-Chloro-5- cyclopropyl-phenyl)-ureido]-thiazol-5-yl}-ethyl)-pyridin-2-yl]-acetamide, N-[4-(2-{2-[3-(2-Fluoro-5-oxetan-3-yl-phenyl)-ureido]-thiazol-5-yl}-ethyl)-pyridin-2-yl]-acetamide, [4-(2-{4-[3-(5-tert-Butyl-2-p-tolyl-2H-pyrazol-3-yl)-ureido]-3-fluoro-phenyl)}-ethyl)-pyridin-2-yl]-carbamic acid methyl ester, [4-(2-{4-[3-(5-tert-Butyl-2-cyclopropylmethyl-2H-pyrazol-3-yl)-ureido]-3-fluoro-phenyl}-ethyl)-pyridin-2-yl]-carbamic acid methyl ester, {4-[2-(4-{3-[5-tert-Buty-2-(4-fluoro-phenyl)-2H-pyrazol-3-yl]-ureido}-3-fluoro-phenyl)-ethyl]-pyridin-2-yl}-carbamic acid methyl ester, {4-[2-(4-{3-[5-tert-Butyl-2-(3-fluoro-phenyl)-2H-pyrazol-3-yl]-ureido}-3-fluoro-phenyl)-ethyl]-pyridin-2-yl}-carbamic acid methyl ester, N-[4-(2-{4-[3-(5-tert-Butyl-2-p-tolyl-2H-pyrazol-3-yl)-ureido]-3-fluoro-phenyl}-ethyl)-pyridin-2-yl]-acetamide, N-[4-(2-{4-[3-(5-tert-Butyl-isoxazol-3-yl)-ureido]-3-fluoro-phenyl}-ethyl)-pyridin-2-yl]-acetamide, N-[4-(2-{4-[3-(3-tert-Butyl-isoxazol-5-yl)-ureido]-3-fluoro-phenyl}-ethyl)-pyridin-2-yl]-acetamide. N-[4-(2-{3-Fluoro-4-[3-(2-fluoro-5-trifluoromethyl-phenyl)-ureido]-phenyl}-ethyl)-pyridin-2-yl]-acetamide, N-[4-(2-{4-[3-(5-tert-Butyl-2-methyl-2H-pyrazol-3-yl)-ureido]-3-fluoro-phenyl}-ethyl)-pyridin-2-yl]-acetamide, N-[4-(2-{4-[3-(5-tert-Butyl-2-cyclopropylmethyl-2H-pyrazol-3-yl)-ureido]-3-fluoro-phenyl}-ethyl)-pyridin-2-yl]-acetamide, N-[4-(2-{4-[3-(5-tert-Butyl-2-isopropyl-2H-pyrazol-3-yl)-ureido]-3-fluoro-phenyl}-ethyl)-pyridin-2-yl]-acetamide, Cyclopropanecarboxylic acid [4-(2-{4-[3-(5-tert-butyl-2-cyclopropylmethyl-2H-pyrazol-3-yl)-ureido]-3-fluoro-phenyl}-ethyl)-pyridin-2-yl]-amide, Cyclopropanecarboxylic acid [4-(2-{4-[3-(5-tert-buty-2-methyl-2H-pyrazol-3-yl)-ureido]-3-fluoro-phenyl}-ethyl)-pyridin-2-yl]-amide, Cyclopropanecarboxylic acid [4-(2-{4-[3-(3-tert-buty-isoxazol-5-yl)-ureido]-3-fluoro-phenyl}-ethyl)-pyridin-2-yl]-amide, Cyclopropanecarboxylic acid [4-(2-{4-[3-(5-tert-butyl-2-isopropyl-2H-pyrazol-3-yl)-ureido]-3-fluoro-phenyl}-ethyl)-pyridin-2-yl]-amide, Cyclopropanecarboxylic acid [4-(2-{4-[3-(3-tert-butyl-phenyl)-ureido]-3-fluoro-phenyl}-ethyl)-pyridin-2-yl]-amide, N-[4-(2-{4-[3-(3-tert-Butyl-phenyl)-ureido]-3-fluoro-phenyl}-ethyl)-pyridin-2-yl]-acetamide, Cyclopropanecarboxylic acid [4-(2-{4-[3-(5-tert-butyl-isoxazol-3-yl)-ureido]-3-fluoro-phenyl}-ethyl)-pyridin-2-yl]-amide, N-{4-[2-(4-{3-[5-tert-Butyl-2-(4-fluoro-phenyl)-2H-pyrazol-3-yl]-ureido}-3-fluoro-phenyl)-ethyl]-pyridin-2-yl}-acetamide, N-(4-{4-[3-(5-tert-Butyl-2-p-tolyl-2H-pyrazol-3-yl)-ureido]-3-fluoro-phenoxymethyl}-pyridin-2-yl)-acetamide, N-(4-{4-[3-(5-Cyclopropyl-2-fluoro-phenyl)-ureido]-3-fluoro-phenoxymethyl}-pyridin-2-yl)-acetamide, N-[4-(3-Fluoro-4-{3-[2-fluoro-5-(1-methyl-cyclopropyl)-phenyl]-ureido}-phenoxymethyl)-pyridin-2-yl]-acetamide, N-(4-{3-Fluoro-4-[3-(2-fluoro-5-trimethylsilanyl-phenyl)-ureido]-phenoxymethyl}-pyridin-2-yl)-acetamide, N-(4-{4-[3-(2-Chloro-5-cyclopropyl-phenyl)-ureido]-3-fluoro-phenoxymethyl}-pyridin-2-yl)-acetamide, N-(4-{4-[3-(5-tert-Butyl-2-cyclopropylmethyl-2H-pyrazol-3-yl)-ureido]-3-fluoro-phenoxymethyl}-pyridin-2-yl)-acetamide, N-(4-{4-[3-(5-tert-Butyl-2-chloro-phenyl)-ureido]-3-fluoro-phenoxymethyl}-pyridin-2-yl)-acetamide, 2-Methoxy-N-[4-(4-{3-[5-(3-methyl-oxetan-3-yl)-2-p-tolyl-2H-pyrazol-3-yl]-ureido}-phenoxy)-pyridin-2-yl]-acetamide, 2-Methoxy-N-[4-(4-{3-[5-(3-methyl-thietan-3-yl)-2-p-tolyl-2H-pyrazol-3-yl]-ureido}-phenoxy)-pyridin-2-yl]-acetamide, [4-(4-{3-[5-(3-Methyl-oxetan-3-yl)-2-p-tolyl-2H-pyrazol-3-yl]-ureido}-phenoxy)-pyridin-2-yl]-carbamic acid methyl ester, [4-(4-{3-[5-(3-Methyl-thietan-3-yl)-2-p-tolyl-2H-pyrazol-3-yl]-ureido}-phenoxy)-pyridin-2-yl]-carbamic acid methyl ester, N-[4-[3-fluoro-4-[[5-(3-methyloxetan-3-yl)-2-(p-tolyl)pyrazol-3-yl]carbamoylamino]phenoxy]-2-pyridyl]-2-methoxy-acetamide, N-[4-(3-Fluoro-4-{3-[5-(3-methyl-thietan-3-yl)-2-p-tolyl-2H-pyrazol-3-yl]-ureido}-phenoxy)-pyridin-2-yl]-2-methoxy-acetamide, 1-[2-Fluoro-4-(pyridin-4-yloxy)-phenyl]-3-[5-(2-hydroxy-1,1-dimethyl-ethyl)-2-p-tolyl-2H-pyrazol-3-yl]-urea, 1-[5-(2-Hydroxy-1,1-dimethyl-ethyl)-2-p-tolyl-2H-pyrazol-3-yl]-3-[4-(pyridin-4-yloxy)-phenyl]-urea, 1-(5-tert-Butyl-2-p-tolyl-2H-pyrazol-3-yl)-3-[2-fluoro-4-(3-methyl-pyridin-4-yloxy)-phenyl]-urea, 1-[5-tert-Butyl-2-(4-fluoro-phenyl)-2H-pyrazol-3-yl]-3-[2-fluoro-4-(pyridin-4-yloxy)-phenyl]-urea, 1-[4-(2-Amino-pyridin-4-yloxy)-2-fluoro-phenyl]-3-[5-tert-butyl-2-(3-fluoro-phenyl)-2H-pyrazol-3-yl]-urea, 1-[5-tert-butyl-2-(3-fluorophenyl)pyrazol-3-yl]-3-[2-fluoro-4-(4-pyridyloxy)phenyl]urea, 1-(5-tert-Butyl-2-cyclopropylmethyl-2H-pyrazol-3-yl)-3-[2-fluoro-4-(pyridin-4-yloxy)-phenyl]-urea, N-(4-{4-[3-(5-tert-Butyl-2-methy-2H-pyrazol-3-yl)-ureido]-3-fluoro-phenoxy}-pyridin-2-yl)-acetamide, N-(4-{4-[3-(5-tert-Butyl-2-isopropyl-2H-pyrazol-3-yl)-ureido]-3-fluoro-phenoxy}-pyridin-2-yl)-acetamide, N-(4-{4-[3-(5-tert-Butyl-2-cyclopropylmethyl-2H-pyrazol-3-yl)-ureido]-3-fluoro-phenoxy}-pyridin-2-yl)-acetamide, N-(4-{4-[3-(5-tert-Butyl-isoxazol-3-yl)-ureido]-3-fluoro-phenoxy}-pyridin-2-yl)-acetamide, N-(4-{4-[3-(3-tert-Butyl-isoxazol-5-yl)-ureido]-3-fluoro-phenoxy}-pyridin-2-yl)-acetamide, N-(4-{4-[3-(5-tert-Butyl-2-chloro-phenyl)-ureido]-3-fluoro-phenoxy}-pyridin-2-yl)-acetamide, N-(4-{4-[3-(5-Cyclopropyl-2-fluoro-phenyl)-ureido]-3-fluoro-phenoxy}-pyridin-2-yl)-acetamide, N-(4-{3-Fluoro-4-[3-(2-fluoro-5-trimethylsilanyl-phenyl)-ureido]-phenoxy}-pyridin-2-yl)-acetamide, N-[4-(3-Fluoro-4-{3-[2-fluoro-5-(I-methyl-cyclopropyl)-phenyl]-ureido}-phenoxy)-pyridin-2-yl]-acetamide, N-(4-{3-Fluoro-4-[3-(2-fluoro-5-oxetan-3-yl-phenyl)-ureido]-phenoxy}-pyridin-2-yl)-acetamide, N-(4-{4-[3-(2-Chloro-5-cyclopropyl-phenyl)-ureido]-3-fluoro-phenoxy}-pyridin-2-yl)-acetamide, N-(4-{4-[3-(5-Cyclopropyl-2-fluoro-phenyl)-ureido]-3-fluoro-phenoxy}-pyridin-2-yl)-2-hydroxy-acetamide, N-(4-{4-[3-(5-Cyclopropyl-2-fluoro-phenyl)-ureido]-3-fluoro-phenoxy}-pyridin-2-yl)-3-methoxy-propionamide, N-(4-{4-[3-(5-tert-Butyl-2-chloro-phenyl)-ureido]-3-fluoro-phenoxy}-pyridin-2-yl)-2-hydroxy-acetamide, N-(4-{4-[3-(5-tert-Butyl-2-chloro-phenyl)-ureido]-3-fluoro-phenoxy}-pyridin-2-yl)-3-methoxy-propionamide, 1-[4-(2-Amino-pyridin-4-yloxy)-2-fluoro-phenyl]-3-(5-tert-butyl-2-chloro-phenyl)-urea and 1-[4-(4-{3-[2-Chloro-5-(tert-butyl)phenyl]ureido}-3-fluoro-phenoxy)-2-pyridylamino]-1-ethanone.

In various configurations, a compound of the present teachings can have a structure as set forth in Table 1. In case of a discrepancy between a compound structure and its IUPAC name, the IUPAC name will be considered definitive.

TABLE 1
| Analog # | IUPAC Chemical Name | Chemical Structure |
|---|---|---|
| 270 | 1-(5-tert-Butyl-2-p-tolyl-2H-pyrazol-3-yl)-3-[5-(2-pyridin-4-yl-ethyl)-thiazol-2-yl]-urea | 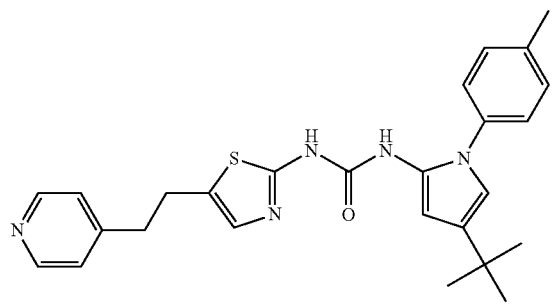 [SMILES: Cc1ccc(-n2cc(C(C)(C)C)cc2NC(=O)Nc2ncc(CCc3ccncc3)s2)cc1] |
| 271 | 1-[5-(3-Methyl-oxetan-2-p-tolyl-2H-pyrazol-3-yl]-3-[5-(2-pyridin-4-yl-ethyl)-thiazol-2-yl]-urea | 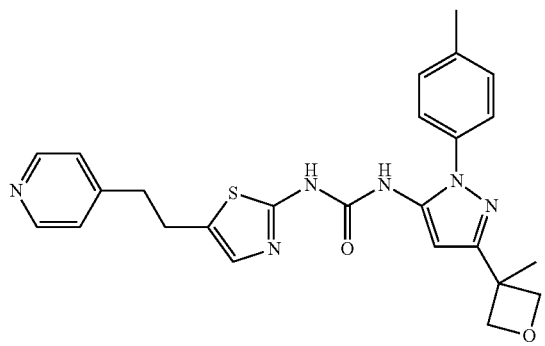 [SMILES: Cc1ccc(-n2nc(C3(C)COC3)cc2NC(=O)Nc2ncc(CCc3ccncc3)s2)cc1] |
| 272 | 1-{5-[2-(2-Amino-pyridin-4-yl)-ethyl]-thiazol-2-yl}-3-[5-tert-butyl-2-p-tolyl-2H-pyrazol-3-yl)-urea | 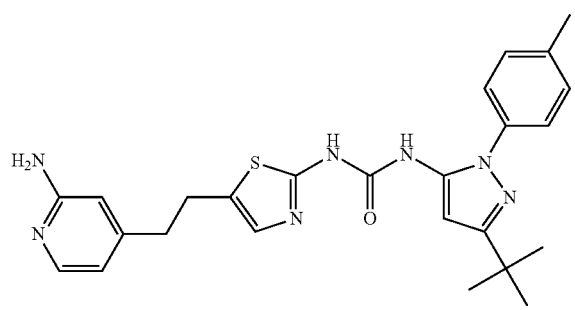 [SMILES: Cc1ccc(-n2nc(C(C)(C)C)cc2NC(=O)Nc2ncc(CCc3ccnc(N)c3)s2)cc1] |
| 273 | 1-[5-(3-Methyl-thietan-3-yl)-2-p-tolyl-2H-pyrazol-3-yl]-3-[5-(2-pyridin-4-yl-ethyl)-thiazol-2-yl]-urea | 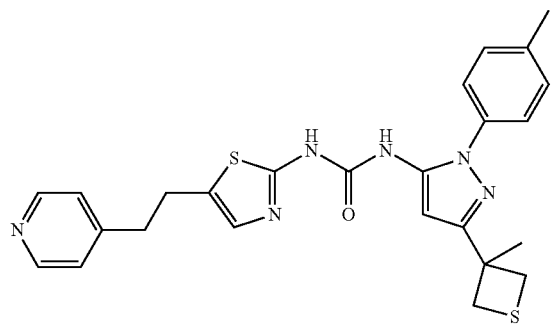 [SMILES: Cc1ccc(-n2nc(C3(C)CSC3)cc2NC(=O)Nc2ncc(CCc3ccncc3)s2)cc1] |

TABLE 1-continued

| Analog # | IUPAC Chemical Name | Chemical Structure |
|---|---|---|
| 277 | [4-(2-{2-[3-(5-tert-Butyl-2-p-tolyl-2H-pyrazol-3-yl)-ureido]-thiazol-5-yl}-ethyl)-pyridin-2-yl]-carbamic acid benzyl ester | 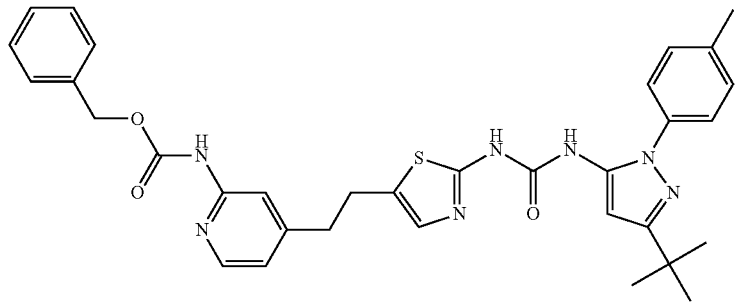 [SMILES: Cc1ccc(-n2nc(C(C)(C)C)cc2NC(=O)Nc2ncc(CCc3ccnc(NC(=O)OCc4ccccc4)c3)s2)cc1] |
| 281 | N-[4-[2-[2-[[5-tert-butyl-2-(p-tolyl)pyrazol-3-yl]carbamoylamino]thiazol-5-yl]ethyl]-2-pyridyl]-2-methoxy-aceamide | 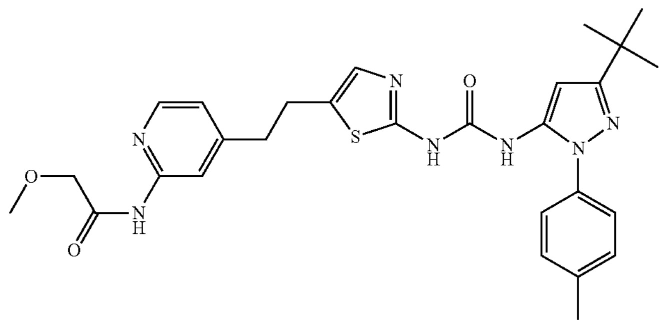 [SMILES: COCC(=O)Nc1cc(CCc2cnc(NC(=O)Nc3cc(C(C)(C)C)nn3-c3ccc(C)cc3)s2)ccn1] |
| 282 | N-[4-[2-[2-[[5-tert-butyl-2-(p-tolyl)pyrazol-3-yl]carbamoylamino]thiazol-5-yl]ethyl]-2-pyridyl]acetamide | 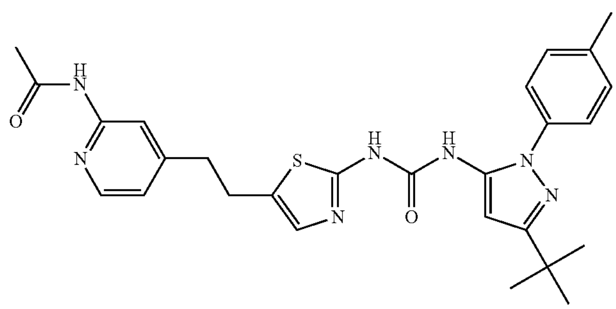 [SMILES: CC(=O)Nc1cc(CCc2cnc(NC(=O)Nc3cc(C(C)(C)C)nn3-c3ccc(C)cc3)s2)ccn1] |
| 283 | N-[4-[2-[2-[[5-tert-butyl-2-(p-tolyl)pyrazol-3-yl]carbamoylamino]thiazol-5-yl]ethyl]-2-pyridyl]-3-methoxy-propanamide | 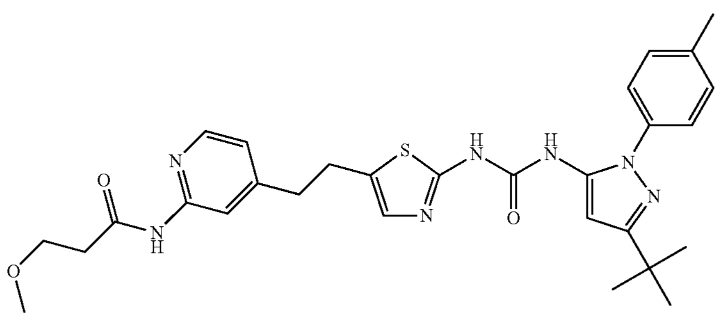 [SMILES: COCCC(=O)Nc1cc(CCc2cnc(NC(=O)Nc3cc(C(C)(C)C)nn3-c3ccc(C)cc3)s2)ccn1] |
| 284 | 1-[4-(2-{2-[3-(5-tert-Butyl-2-p-tolyl-2H-pyrazol-3-yl)-ureido]-thiazol-5-yl}-ethyl)-pyridin-2-yl]-3-ethyl-urea | 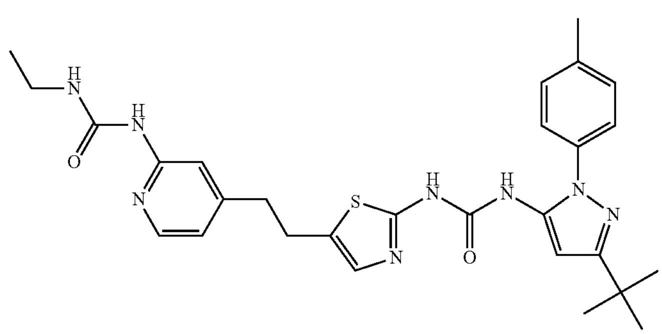 [SMILES: CCNC(=O)Nc1cc(CCc2cnc(NC(=O)Nc3cc(C(C)(C)C)nn3-c3ccc(C)cc3)s2)ccn1] |

TABLE 1-continued

| Analog # | IUPAC Chemical Name | Chemical Structure |
|---|---|---|
| 285 | [4-(2-{2-[3-(5-tert-Butyl-2-p-tolyl-2H-pyrazol-3-yl)-ureido]-thiazol-5-yl}-ethyl)-pyridin-2-yl]-carbamic acid methyl ester | 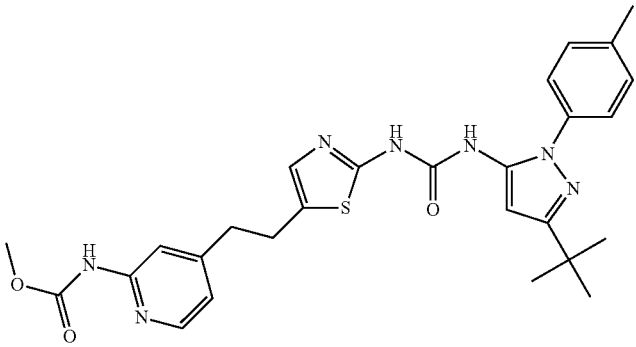 |
| 286 | [4-(2-{2-[3-(5-tert-Butyl-2-p-tolyl-2H-pyrazol-3-yl)-ureido]-thiazol-5-yl}-ethyl)-pyridin-2-yl]-carbamic acid ethyl ester | 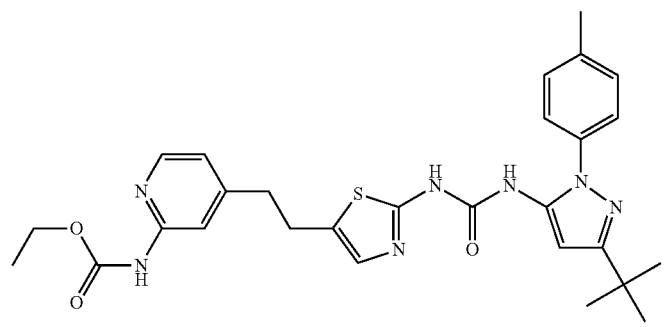 [SMILES: CCOC(=O)Nc1cc(CCc2cnc(NC(=O)Nc3cc(C(C)(C)C)nn3-c3ccc(C)cc3)s2)ccn1] |
| 287 | N-[4-(2-{2-[3-(5-tert-Butyl-2-p-tolyl-2H-pyrazol-3-yl)-ureido]-thiazol-5-yl}-ethyl)-pyridin-2-yl]-2-hydroxy-acetamide | 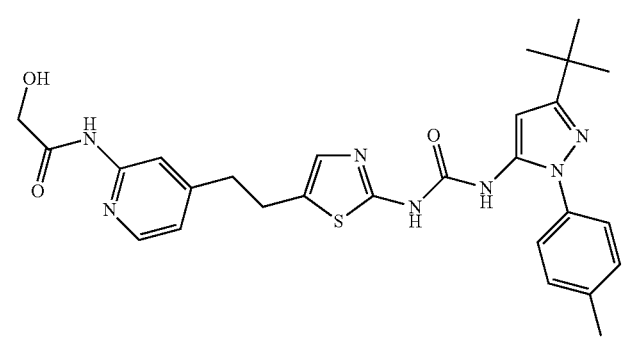 [SMILES: Cc1ccc(-n2nc(C(C)(C)C)cc2NC(=O)Nc2ncc(CCc3ccnc(NC(=O)CO)c3)s2)cc1] |
| 288 | Tetrahydro-pyran-4-carboxylic acid [4-(2-{2-[3-(5-tert-butyl-2-p-tolyl-2H-1-pyrazol-3-yl)-ureido]-thiazol-5-yl}-ethyl)-pyridin-2-yl]-amide | 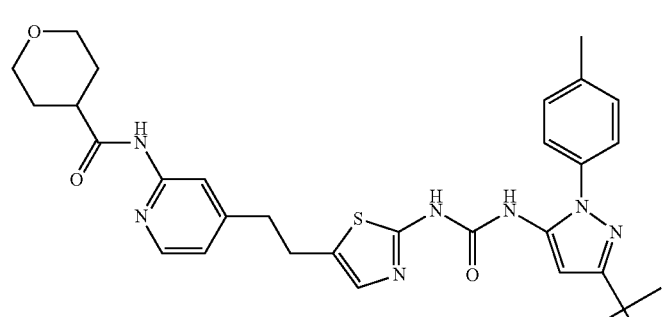 |

TABLE 1-continued

| Analog # | IUPAC Chemical Name | Chemical Structure |
|---|---|---|
| 302 | 1-[5-tert-Butyl-2-(4-fluoro-phenyl)-2H-pyrazol-3-yl]-3-[5-(2-pyridin-4-yl-ethyl)-thiazol-2-yl]-urea | 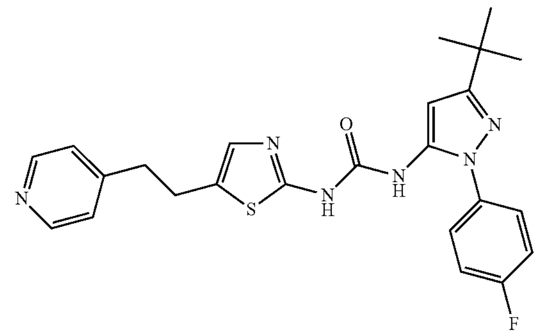 [SMILES: CC(C)(C)c1cc(NC(=O)Nc2ncc(CCc3ccncc3)s2)n(-c2ccc(F)cc2)n1] |
| 305 | 1-[5-tert-Butyl-2-(3-fluoro-phenyl)-2H-pyrazol-3-yl]-3-[5-(2-pyridin-4-yl-ethyl)-thiazol-2-yl]-urea | 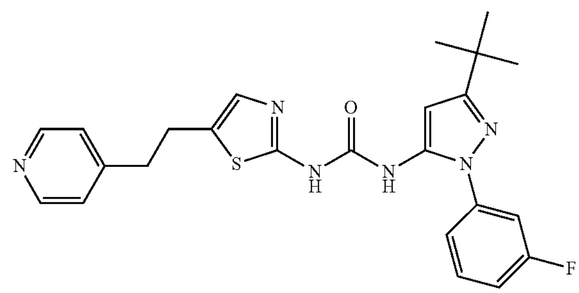 [SMILES: CC(C)(C)c1cc(NC(=O)Nc2ncc(CCc3ccncc3)s2)n(-c2cccc(F)c2)n1] |
| 311 | N-[4-(2-{2-[3-(5-tert-Butyl-2-p-tolyl-2H-pyrazol-3-yl)-ureido]-thiazol-5-yl}-ethyl)-pyridin-2-yl]-propionamide | 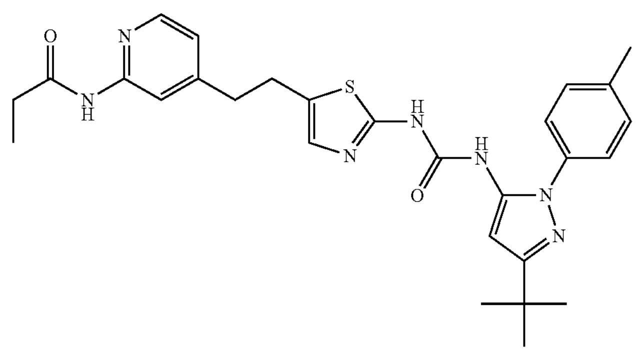 [SMILES: CCC(=O)Nc1cc(CCc2cnc(NC(=O)Nc3cc(C(C)(C)C)nn3-c3ccc(C)cc3)s2)ccn1] |
| 312 | 1-{5-[2-(2-Amino-pyridin-4-yl)-ethyl]-thiazol-2-yl}-3-[5-tert-butyl-2-(4-chloro-phenyl)-2H-pyrazol-3-yl]-urea | 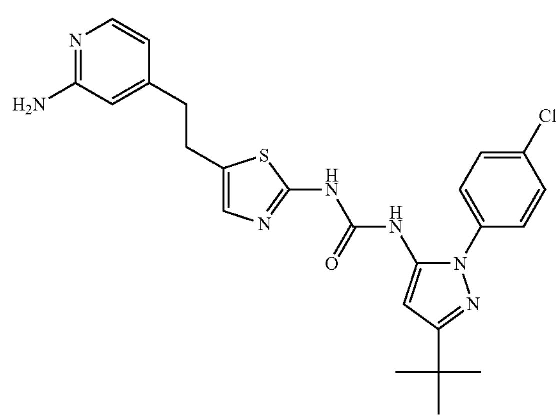 [SMILES: CC(C)(C)c1cc(NC(=O)Nc2ncc(CCc3ccnc(N)c3)s2)n(-c2ccc(Cl)cc2)n1] |

TABLE 1-continued

| Analog # | IUPAC Chemical Name | Chemical Structure |
|---|---|---|
| 313 | N-{4-[2-(2-{3-[5-tert-Butyl-2-(4-chloro-phenyl)-2H-pyrazol-3-yl]-ureido}-thiazol-5-yl)-ethyl]-pyridin-2-yl}-acetamide | 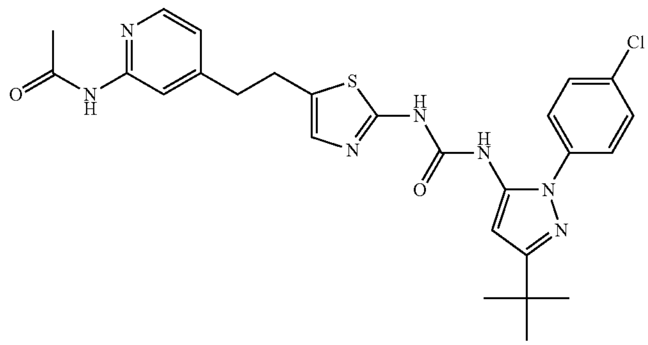 [SMILES: CC(=O)Nc1cc(CCc2cnc(NC(=O)Nc3cc(C(C)(C)C)nn3-c3ccc(Cl)cc3)s2)ccn1] |
| 314 | N-[4-(3-{3-[5-tert-Butyl-2-(4-chloro-phenyl)-2H-pyrazol-3-yl]-ureidomethylmethylsulfanyl}-propyl)-pyridin-2-yl]-2-hydroxy-acetamide | 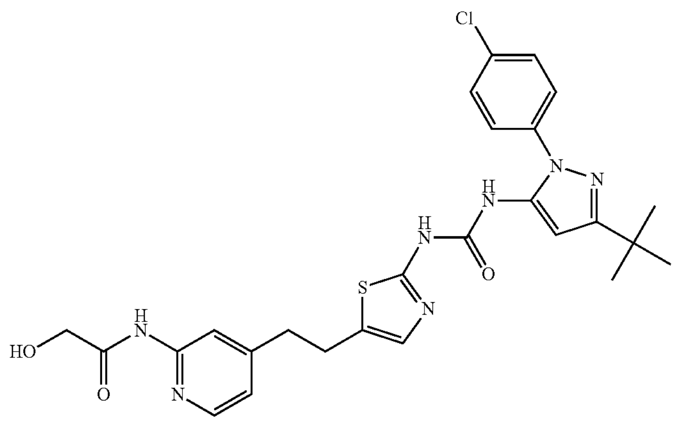 [SMILES: CC(C)(C)c1cc(NC(=O)Nc2ncc(CCc3ccnc(NC(=O)CO)c3)s2)n(-c2ccc(Cl)cc2)n1] |
| 319 | 1-{5-[2-(2-Amino-pyridin-yl)-ethyl]-thiazol-2-yl}-3-[5-tert-butyl-2-(3-fluoro-phenyl)-2H-pyrazol-3-yl]-urea | 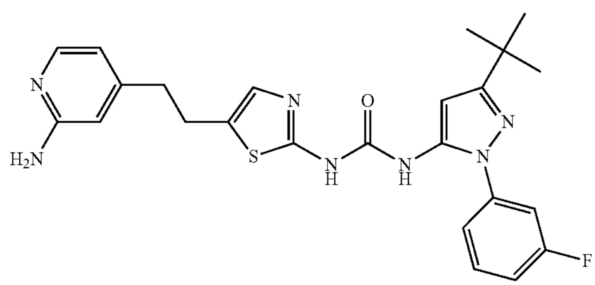 [SMILES: CC(C)(C)c1cc(NC(=O)Nc2ncc(CCc3ccnc(N)c3)s2)n(-c2cccc(F)c2)n1] |
| 320 | N-{4-[2-(2-{3-[5-tert-Butyl-2-(3-fluoro-phenyl)-2H-pyrazol-3-yl]-ureido}-thiazol-5-yl)-ethyl]-pyridin-2-yl}-acetamide | 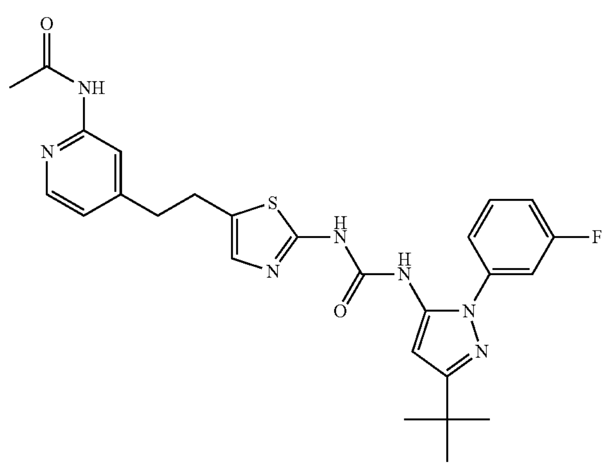 [SMILES: CC(=O)Nc1cc(CCc2cnc(NC(=O)Nc3cc(C(C)(C)C)nn3-c3cccc(F)c3)s2)ccn1] |

TABLE 1-continued

| Analog # | IUPAC Chemical Name | Chemical Structure |
|---|---|---|
| 321 | N-[4-[2-[2-[[5-tert-butyl-2-(3-fluoropholyl)pyrazol-3-yl]carbamoylamino]thiazol-5-yl]ethyl]-2-pyridyl]-2-hydroxy-acetamide | 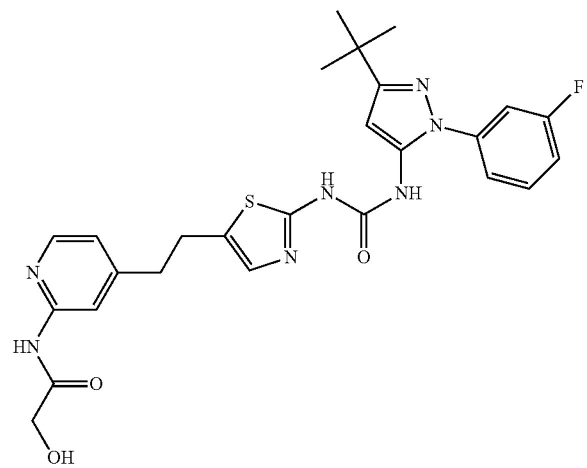 [SMILES: CC(C)(C)c1cc(NC(=O)Nc2ncc(CCc3ccnc(NC(=O)CO)c3)s2)n(-c2cccc(F)c2)n1] |
| 322 | 1-{5-[2-(2-Amino-pyridin-4-yl)-ethyl]-thiazol-2-yl}-3-(5-tert-butyl-2-cyclopropylmethyl-2H-pyrazol-3-yl)-urea | 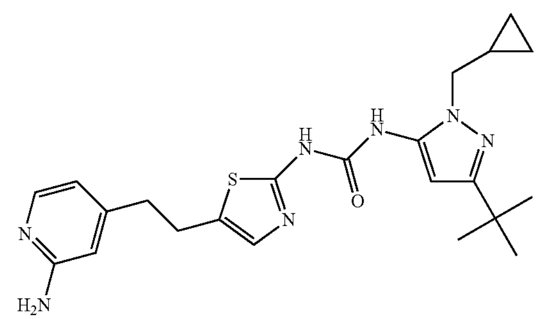 [SMILES: CC(C)(C)c1cc(NC(=O)Nc2ncc(CCc3ccnc(N)c3)s2)n(CC2CC2)n1] |
| 325 | N-[4-(2-{2-[3-(5-tert-Butyl-2-cyclopropylmethyl-2H-pyrazol-3-yl)-ureido]-thiazol-5-yl}-ethyl)-pyridin-2-yl]-acetamide | 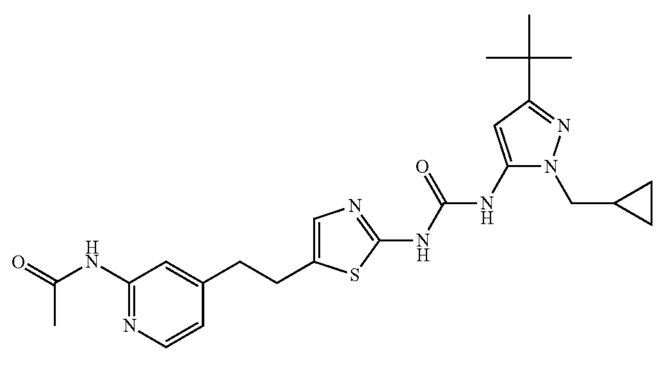 [SMILES: CC(=O)Nc1cc(CCc2cnc(NC(=O)Nc3cc(C(C)(C)C)nn3CC3CC3)s2)ccn1] |
| 326 | N-[4-(2-{2-[3-(5-tert-Butyl-2-cyclopropylmethyl-2H-pyrazol-3-yl)-ureido]-thiazol-5-yl}-ethyl)-pyridin-2-yl]-2-hydroxy-acetamide | 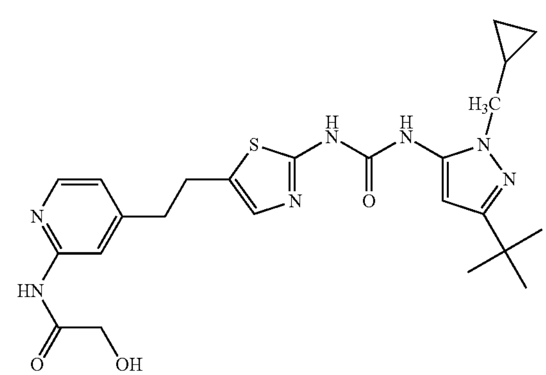 [SMILES: CC(C)(C)c1cc(NC(=O)Nc2ncc(CCc3ccnc(NC(=O)CO)c3)s2)n(CC2CC2)n1] |

TABLE 1-continued

| Analog # | IUPAC Chemical Name | Chemical Structure |
|---|---|---|
| 330 | N-[4-(2-{2-[3-(5-tert-Butyl-2-p-tolyl-2H-pyrazol-3-yl)-ureido]-thiazol-5-yl}-ethyl)-pyridin-2-yl]-isobutyramide | 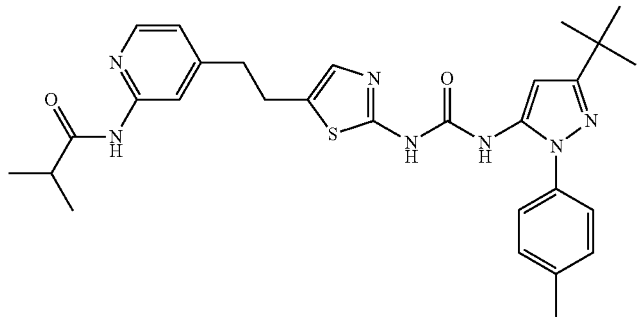 [SMILES: Cc1ccc(-n2nc(C(C)(C)C)cc2NC(=O)Nc2ncc(CCc3ccnc(NC(=O)C(C)C)c3)s2)cc1] |
| 331 | Cyclopropanecarboxylic acid [4-(2-{2-[3-(5-tert-butyl-2-p-tolyl-2H-pyrazol-3-yl)-ureido]-thiazol-5-yl}ethyl)-pyridin-2-yl]-amide | 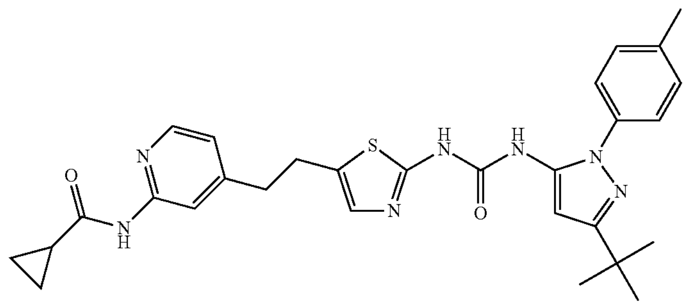 [SMILES: Cc1ccc(-n2nc(C(C)(C)C)cc2NC(=O)Nc2ncc(CCc3ccnc(NC(=O)C4CC4)c3)s2)cc1] |
| 332 | Cyclobutanecarboxylic acid [4-(2-{2-[3-(5-tert-butyl-2-p-tolyl-2H-pyrazol-3-yl)-ureido]-thiazol-5-yl}-ethyl)-pyridin-2-yl]-amide | 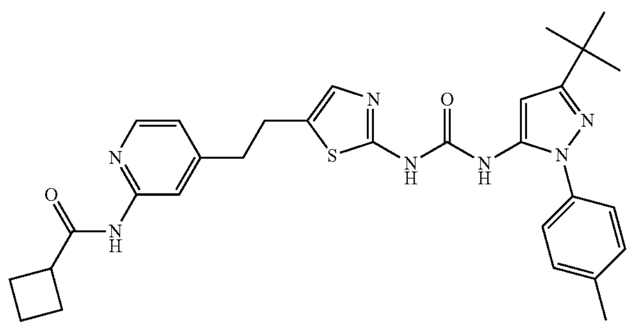 [SMILES: Cc1ccc(-n2nc(C(C)(C)C)cc2NC(=O)Nc2ncc(CCc3ccnc(NC(=O)C4CCC4)c3)s2)cc1] |
| 333 | N-[4-(2-{2-[3-(5-tert-Butyl-2-cyclopropylmethyl-2H-pyrazol-3-yl)-ureido]-thiazol-5-yl}-ethyl)-pyridin-2-yl]-amide | 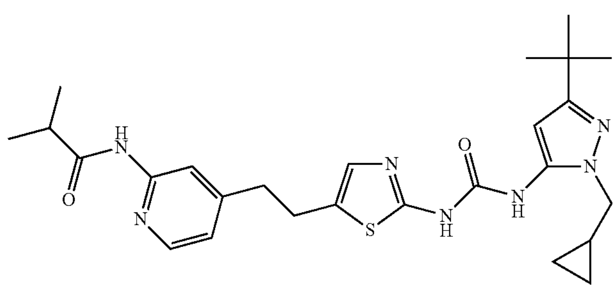 [SMILES: CC(C)C(=O)Nc1cc(CCc2cnc(NC(=O)Nc3cc(C(C)(C)C)nn3CC3CC3)s2)ccn1] |
| 334 | Cyclopropanecarboxylic acid [4-(2-{2-[3-(5-tert-butyl-2-cyclopropylmethyl-2H-pyrazol-3-yl)-ureido]-thiazol-5-yl}-ethyl)-pyridin-2-yl]-amide | 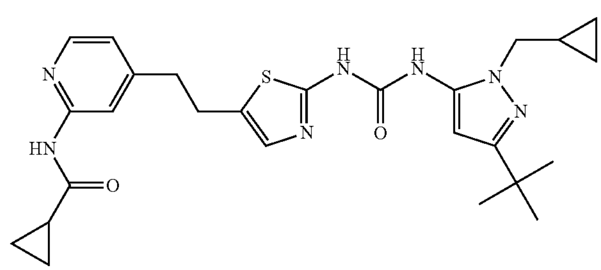 [SMILES: CC(C)(C)c1cc(NC(=O)Nc2ncc(CCc3ccnc(NC(=O)C4CC4)c3)s2)n(CC2CC2)n1] |

TABLE 1-continued

| Analog # | IUPAC Chemical Name | Chemical Structure |
|---|---|---|
| 335 | [4-(2-{2-[3-(5-tert-Butyl-2-methyl-2H-pyrazol-3-yl)-ureido]-thiazol-5-yl}-ethyl)-pyridin-2-yl]-carbamic acid ethyl ester | 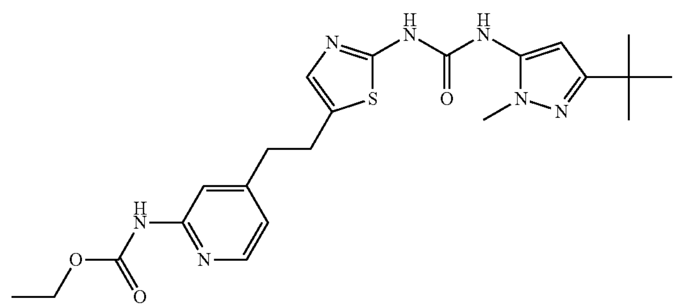 [SMILES: CCOC(=O)Nc1cc(CCc2cnc(NC(=O)Nc3cc(C(C)(C)C)nn3C)s2)ccn1] |
| 336 | [4-(2-{2-[3-(5-tert-Butyl-2-cyclopropylmethyl-2H-pyrazol-3-yl)-ureido]-thiazol-5-yl}-ethyl)-pyridin-2-yl]-carbamic acid ethyl ester | 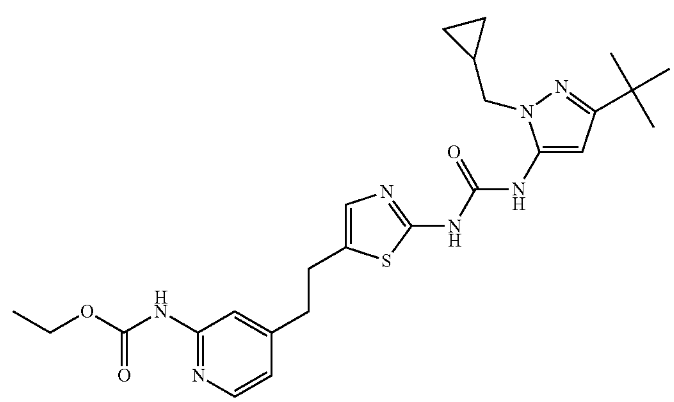 [SMILES: CCOC(=O)Nc1cc(CCc2cnc(NC(=O)Nc3cc(C(C)(C)C)nn3CC3CC3)s2)ccn1] |
| 337 | Pyrrolidine-1-carboxylic acid [4-(2-{2-[3-(5-tert-butyl-2-p-tolyl-2H-pyrazol-3-yl)-ureido]-thiazol-5-yl}-ethyl)-pyridin-2-yl]-amide | 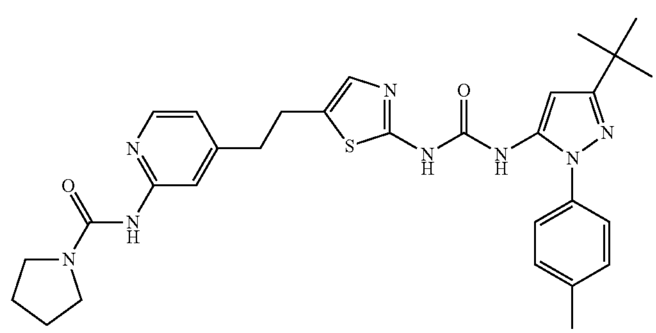 [SMILES: Cc1ccc(-n2nc(C(C)(C)C)cc2NC(=O)Nc2ncc(CCc3ccnc(NC(=O)N4CCCC4)c3)s2)cc1] |
| 339 | Cyclobutanecarboxylic acid [4-(2-{2-[3-(5-tert-butyl-2-cyclopropylmethyl-2H-pyrazol-3-yl)-ureido]-thiazol-5-yl}-ethyl)-pyridin-2-yl]-airdde | 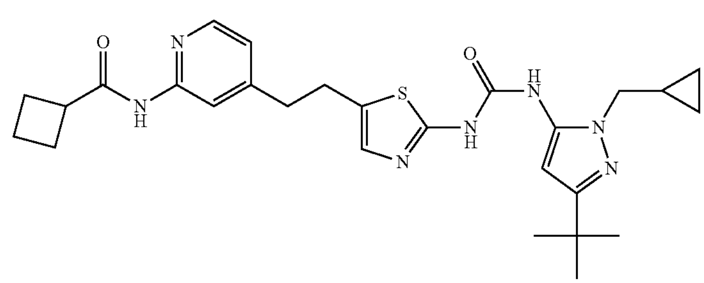 [SMILES: CC(C)(C)c1cc(NC(=O)Nc2ncc(CCc3ccnc(NC(=O)C4CCC4)c3)s2)n(CC2CC2)n1] |

TABLE 1-continued

| Analog # | IUPAC Chemical Name | Chemical Structure |
|---|---|---|
| 340 | 1-[4-(2-{2-[3-(5-tert-Butyl-2-cyclopropylmethyl-2H-pyrazol-3-yl)-uredo]-thiazol-5-yl}-ethyl)-pyridin-2-yl]-3-ethyl-urea | 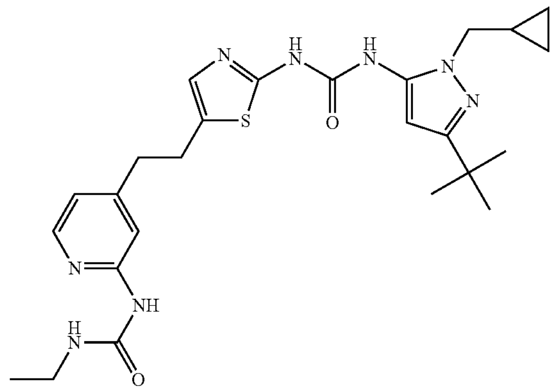 [SMILES: CCNC(=O)Nc1cc(CCc2cnc(NC(=O)Nc3cc(C(C)(C)C)nn3CC3CC3)s2)ccn1] |
| 341 | N-[4-(2-{2-[3-(5-tert-Butyl-2-cyclopropylmethyl-2H-pyrazol-3-yl)-ureido]-thiazol-5-yl}-ethyl)-pyridin-2-yl]-2-methoxy-acetamide | 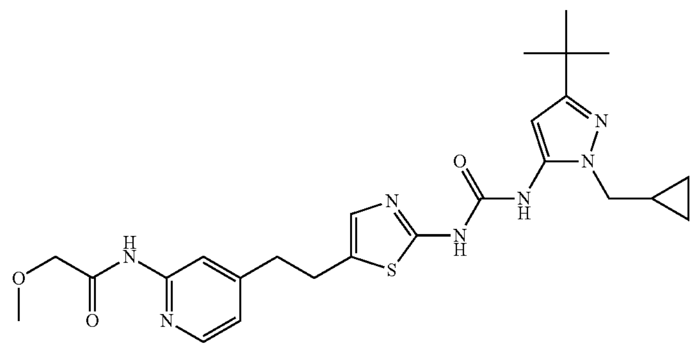 [SMILES: COCC(=O)Nc1cc(CCc2cnc(NC(=O)Nc3cc(C(C)(C)C)nn3CC3CC3)s2)ccn1] |
| 342 | N-[4-(2-{2-[3-(5-tert-Butyl-2-cyclopropylmethyl-2H-pyrazol-3-yl)-ureido]-thiazol-5-yl}-ethyl)-pyridin-2-yl]-3-methoxy-propionamide | 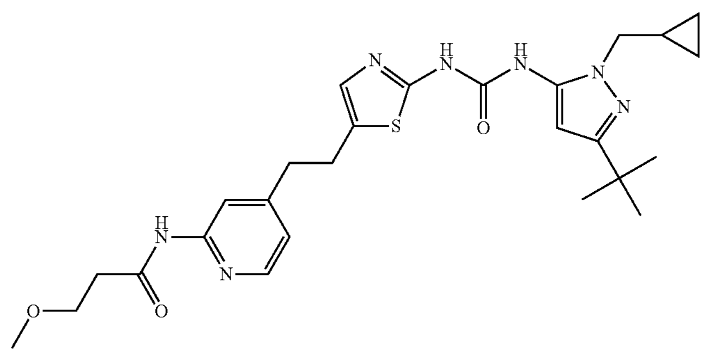 [SMILES: COCCC(=O)Nc1cc(CCc2cnc(NC(=O)Nc3cc(C(C)(C)C)nn3CC3CC3)s2)ccn1] |
| 343 | 1-{5-[2-(2-Amino-pyridin-4-yl)-ethyl]-thiazol-2-yl}-3-(5-tert-butyl-2-methyl-2H-pyrazol-3-yl)-urea | 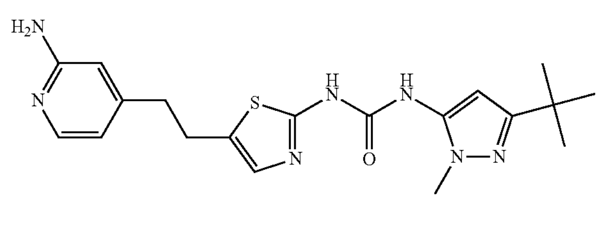 [SMILES: Cn1nc(C(C)(C)C)cc1NC(=O)Nc1ncc(CCc2ccnc(N)c2)s1] |
| 344 | N-[4-(2-{2-[3-(5-tert-Butyl-2-methyl-2H-pyrazol-3-yl)-ureido]-thiazol-5-yl}-ethyl)-pyridin-2-yl]-acetamide | 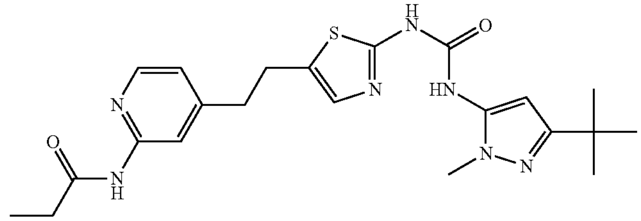 [SMILES: CCC(=O)Nc1cc(CCc2cnc(NC(=O)Nc3cc(C(C)(C)C)nn3C)s2)ccn1] |

TABLE 1-continued

| Analog # | IUPAC Chemical Name | Chemical Structure |
|---|---|---|
| 345 | Cyclopropanecarboxylic acid [4-(2-{2-[3-(5-tert-butyl-2-methyl-2H-pyrazol-3-yl)-ureido]-thiazol-5-yl}-ethyl)-pyridin-2-yl]-amide | 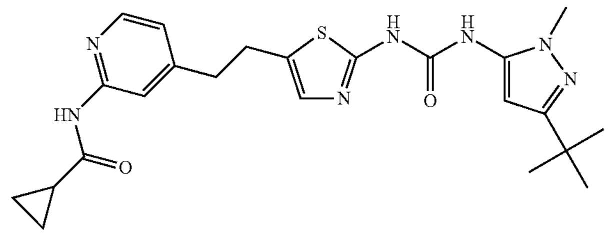 [SMILES: Cn1nc(C(C)(C)C)cc1NC(=O)Nc1ncc(CCc2ccnc(NC(=O)C3CC3)c2)s1] |
| 347 | N-[4-(2-{2-[3-(5-tert-Butyl-2H-pyrazol-3-yl)-ureido]-thiazol-5-yl}-ethyl)-pyridin-2-yl]-acetamide | 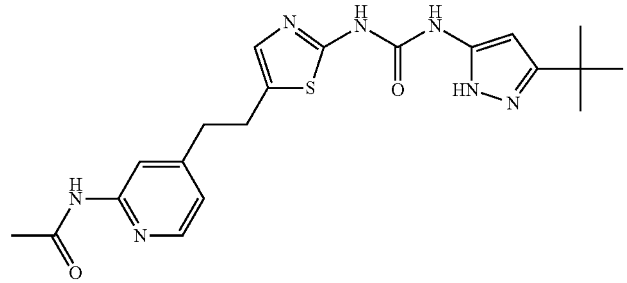 [SMILES: CC(=O)Nc1cc(CCc2cnc(NC(=O)Nc3cc(C(C)(C)C)n[nH]3)s2)ccn1] |
| 348 | N-[4-(2-{2-[3-(5-tert-Butyl-2-methyl-2H-pyrazol-3-yl)-ureido]-thiazol-5-yl}-ethyl)-pyridin-2-yl]-2-hydroxy-acetamide | 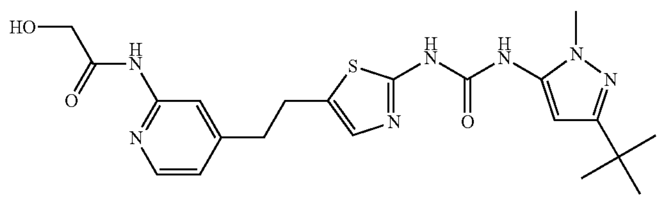 [SMILES: Cn1nc(C(C)(C)C)cc1NC(=O)Nc1ncc(CCc2ccnc(NC(=O)CO)c2)s1] |
| 349 | N-[4-(2-{2-[3-(5-tert-Butyl-2-methyl-2H-pyrazol-3-yl)-ureido]-thiazol-5-yl}-ethyl)-pyridin-2-yl]-isobutyramide | 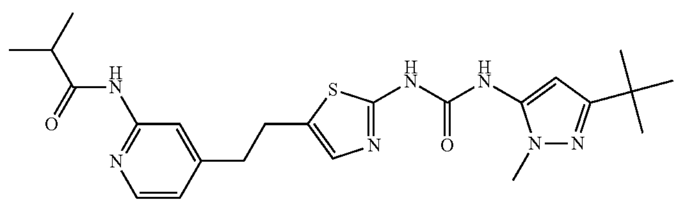 [SMILES: CC(C)C(=O)Nc1cc(CCc2cnc(NC(=O)Nc3cc(C(C)(C)C)nn3C)s2)ccn1] |
| 350 | N-[4-(2-{2-[3-(5-tert-Butyl-2-methyl-2H-pyrazol-3-yl)-ureido]-thiazol-5-yl}-ethyl)-pyridin-2-yl]-2-methoxy-acetamide | 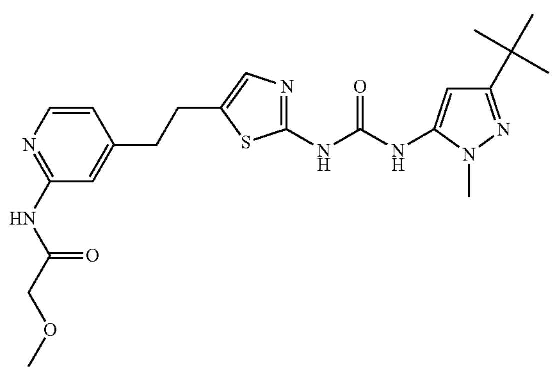 [SMILES: COCC(=O)Nc1cc(CCc2cnc(NC(=O)Nc3cc(C(C)(C)C)nn3C)s2)ccn1] |
| 351 | N-[4-(2-{2-[3-(5-tert-Butyl-2-methyl-2H-pyrazol-3-yl)-ureido]-thiazol-5-yl}-ethyl)-pyridin-2-yl]-methoxy-propionamide | 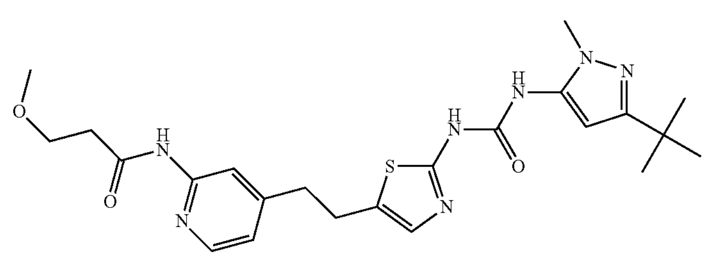 [SMILES: COCCC(=O)Nc1cc(CCc2cnc(NC(=O)Nc3cc(C(C)(C)C)nn3C)s2)ccn1] |

TABLE 1-continued

| Analog # | IUPAC Chemical Name | Chemical Structure |
|---|---|---|
| 352 | 1-[4-(2-{2-[3-(5-tert-Butyl-2-methyl-2H-pyrazol-3-yl)-ureido]-thiazol-5-yl}ethyl)-pyridin-2-yl]-3-ethyl-urea | 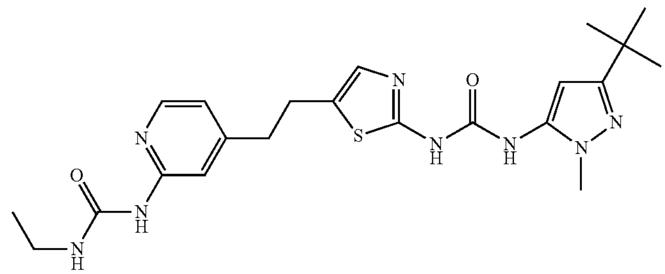 [SMILES: CCNC(=O)Nc1cc(CCc2cnc(NC(=O)Nc3cc(C(C)(C)C)nn3C)s2)ccn1] |
| 353 | Cyclobutanecarboxylic acid [4-(2-{2-[3-(5-tert-butyl-2-methyl-2H-pyrazol-3-yl)-ureido]-thiazol-5-yl}-ethyl)-pyridin-2-yl]-amide | 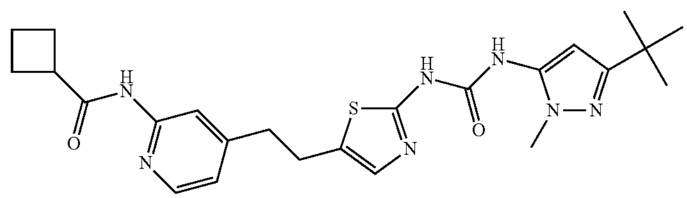 [SMILES: Cn1nc(C(C)(C)C)cc1NC(=O)Nc1ncc(CCc2ccnc(NC(=O)C3CCC3)c2)s1] |
| 354 | [4-(2-{2-[3-(5-tert-Butyl-2H-pyrazol-3-yl)-ureido]-thiazol-5-yl}-ethyl)-pyridin-2-yl]-carbamic acid ethyl ester | 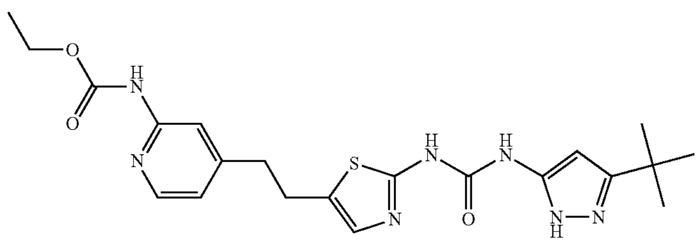 [SMILES: CCOC(=O)Nc1cc(CCc2cnc(NC(=O)Nc3cc(C(C)(C)C)n[nH]3)s2)ccn1] |
| 355 | [4-(2-{2-[3-(5-tert-Buty-2-isopropyl-2H-pyrazol-3-yl)-ureido]-thiazol-5-yl}-ethyl)-pyridin-2-yl]-carbamic acid ethyl ester | 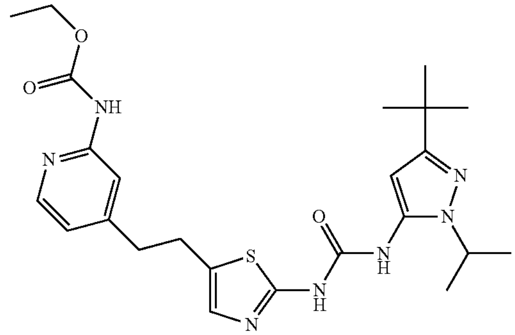 [SMILES: CCOC(=O)Nc1cc(CCc2cnc(NC(=O)Nc3cc(C(C)(C)C)nn3C(C)C)s2)ccn1] |
| 356 | Cyclopropanecarboxylic acid [4-(2-{2-[3-(3-tert-butyl-phenyl)-ureido]-thiazol-5-yl}-ethyl)-pyridin-2-yl]-amide | 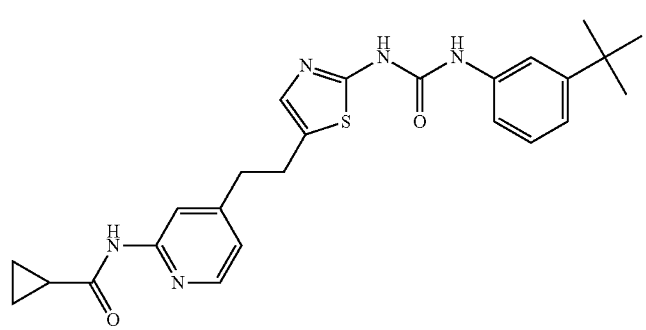 [SMILES: CC(C)(C)c1cccc(NC(=O)Nc2ncc(CCc3ccnc(NC(=O)C4CC4)c3)s2)c1] |

TABLE 1-continued

| Analog # | IUPAC Chemical Name | Chemical Structure |
|---|---|---|
| 357 | [4-(2-{2-[3-(2-Fluoro-5-trifluoromethyl-phenyl)-ureido]-thiazol-5yl}-ethyl)-pyridin-2-yl]-carbamic acid ethyl ester | 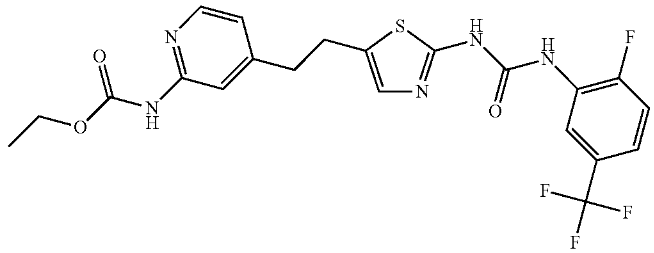 [SMILES: CCOC(=O)Nc1cc(CCc2cnc(NC(=O)Nc3cc(C(F)(F)F)ccc3F)s2)ccn1] |
| 363 | N-[4-(2-{2-[3-(2-Fluoro-5-trifluoromethyl-phenyl)-ureido]-thiazol-5-yl}-ethyl)-pyridin-2-yl]-acetamide | 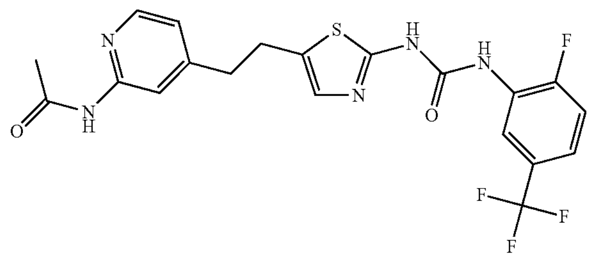 [SMILES: CC(=O)Nc1cc(CCc2cnc(NC(=O)Nc3cc(C(F)(F)F)ccc3F)s2)ccn1] |
| 364 | [4-(2-{2-[3-(5-tert-Butyl-isoxazol-3-yl)-ureido]-thiazol-5-yl}-ethyl)-pyridin-2-yl]-carbamic acid ethyl ester | 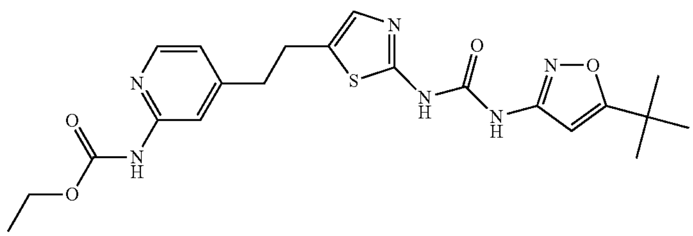 [SMILES: CCOC(=O)Nc1cc(CCc2cnc(NC(=O)Nc3cc(C(C)(C)C)on3)s2)ccn1] |
| 365 | 1-{5-[2-(2-Amine-pyridin-4-yl)-ethyl]-thiazol-2-yl}-3-(5-tert-butyl-isoxazol-3-yl)-urea | 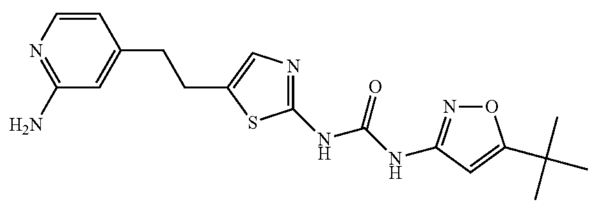 [SMILES: CC(C)(C)c1cc(NC(=O)Nc2ncc(CCc3ccnc(N)c3)s2)no1] |
| 366 | N-[4-(2-{2-[3-(5-tert-Butyl-isoxazol-3-yl)-ureido]-thiazol-5-yl}-ethyl)-pyridin-2-yl]-acetamide | 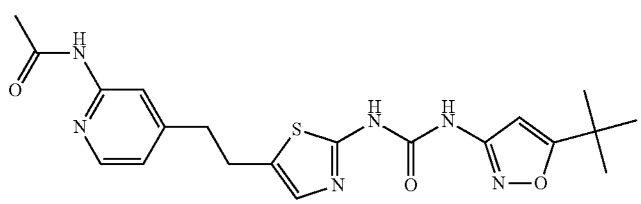 [SMILES: CC(=O)Nc1cc(CCc2cnc(NC(=O)Nc3cc(C(C)(C)C)on3)s2)ccn1] |
| 367 | 1-{5-[2-(2-Ainino-pyridin-4-yl)-ethyl]-thiazol-2-yl}-3-(5-tert-butyl-2H-pyrazol-3-yl)-urea | 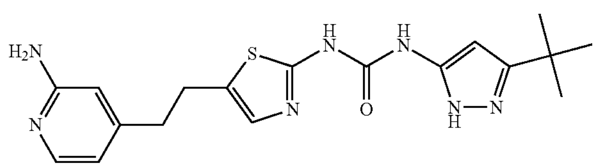 [SMILES: CC(C)(C)c1cc(NC(=O)Nc2ncc(CCc3ccnc(N)c3)s2)[nH]n1] |
| 368 | Cyclopropanecarboxylic acid [4-(2-{2-[3-(5-tert-butyl-2H-pyrazol-3-yl)-ureido]-thiazol-5-yl}-ethyl)-pyridin-2-yl]-amide | 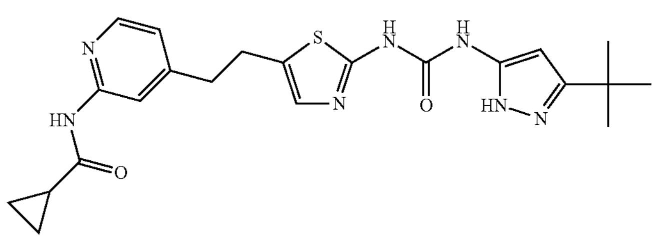 [SMILES: CC(C)(C)c1cc(NC(=O)Nc2ncc(CCc3ccnc(NC(=O)C4CC4)c3)s2)[nH]n1] |

TABLE 1-continued

| Analog # | IUPAC Chemical Name | Chemical Structure |
|---|---|---|
| 369 | Cyclopropanecarboxylic acid [4-(2-{2-[3-(5-tert-butyl-isoxazol-3-yl)-ureido]-thiazol-5-yl}-ethyl)-pyridin-2-yl]-amide | 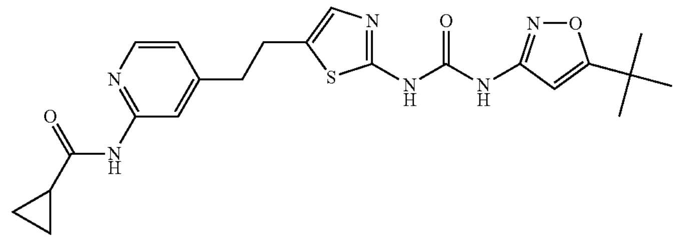 [SMILES: CC(C)(C)c1cc(NC(=O)Nc2ncc(CCc3ccnc(NC(=O)C4CC4)c3)s2)no1] |
| 380 | N-[4-(2-{2-[3-(5-tert-Butyl-2-chloro-phenyl)-ureido]-thiazol-5-yl}-ethyl)-pyridin-2-yl]-acetamide | 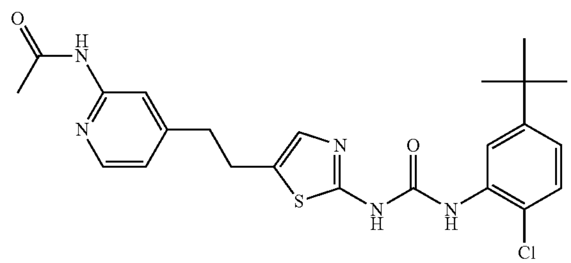 [SMILES: CC(=O)Nc1cc(CCc2cnc(NC(=O)Nc3cc(C(C)(C)C)ccc3Cl)s2)ccn1] |
| 381 | N-[4-(2-{2-[3-(5-tert-Butyl-2-isopropyl-2H-pyrazol-3-yl)-ureido]-thiazol-5-yl}-ethyl)-pyridin-2-yl]-acetamide | 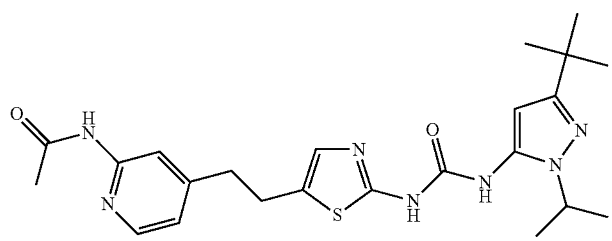 [SMILES: CC(=O)Nc1cc(CCc2cnc(NC(=O)Nc3cc(C(C)(C)C)nn3C(C)C)s2)ccn1] |
| 382 | N-[4-(2-{2-[3-tert-Butyl-isoxazol-5-yl)-ureido]-thiazol-5-yl}-ethyl)-pyridin-2-yl]-acetamide | 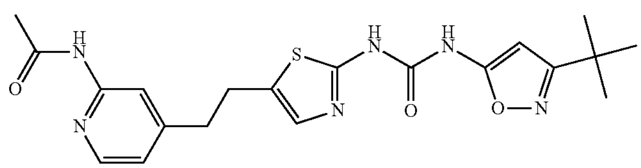 [SMILES: CC(=O)Nc1cc(CCc2cnc(NC(=O)Nc3cc(C(C)(C)C)no3)s2)ccn1] |
| 383 | N-[4-(2-{2-[3-(3-tert-Butyl-phenyl)-ureido]-thiazol-5-yl}-ethyl)-pyridin-2-yl]-acetamide | 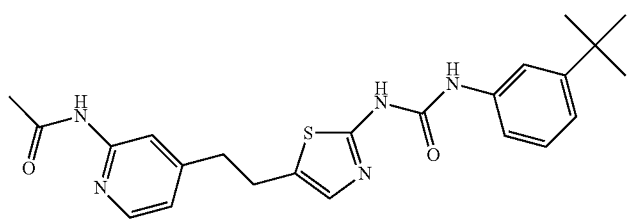 [SMILES: CC(=O)Nc1cc(CCc2cnc(NC(=O)Nc3cccc(C(C)(C)C)c3)s2)ccn1] |
| 384 | N-{4-[2-(2-{3-[5-tert-Butyl-2-(4-fluoro-phenyl)-2H-pyrazol-3-yl]-ureido}-thiazol-5-yl)-ethyl]-pyridin-2-yl}-acetamide | 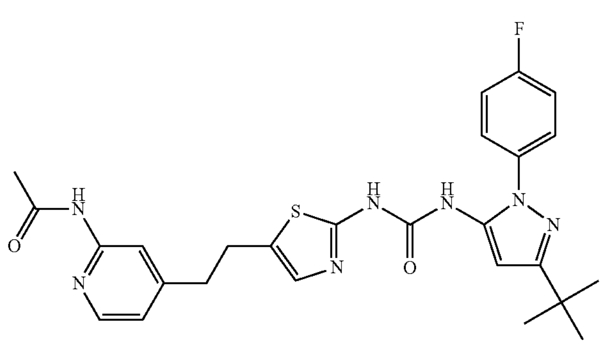 [SMILES: CC(=O)Nc1cc(CCc2cnc(NC(=O)Nc3cc(C(C)(C)C)nn3-c3ccc(F)cc3)s2)ccn1] |

TABLE 1-continued

| Analog # | IUPAC Chemical Name | Chemical Structure |
|---|---|---|
| 385 | N-{4-[2-(2-{3-[5-(3-Methyl-oxetan-3-yl)-2-p-tolyl-2H-pyrazol-3-yl]-ureido}-thiazo-5-yl)-ethyl]-pyridin-2-yl}-acetamide | 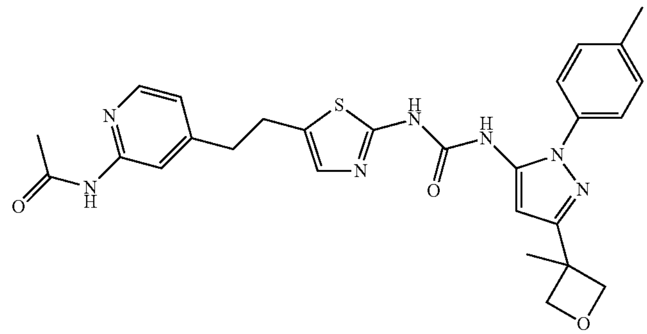 [SMILES: CC(=O)Nc1cc(CCc2cnc(NC(=O)Nc3cc(C4(C)COC4)nn3-c3ccc(C)cc3)s2)ccn1] |
| 386 | 1-(3-tert-Butyl-isoxazol-5-yl)-3-[5-(2-pyridin-4-yl-ethyl)-thiazol-2-yl]-urea | 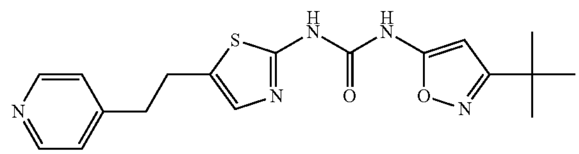 [SMILES: CC(C)(C)c1cc(NC(=O)Nc2ncc(CCc3ccncc3)s2)on1] |
| 387 | 1-(5-tert-Butyl-isoxazol-3-yl)-3-[5-(2-pyridin-4-yl-ethyl)-thiazol-2-yl]-urea | 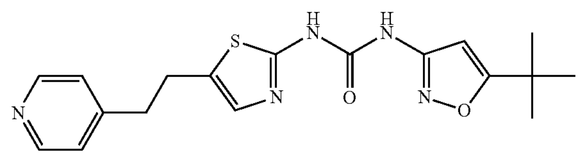 [SMILES: CC(C)(C)c1cc(NC(=O)Nc2ncc(CCc3ccncc3)s2)no1] |
| 388 | 1-(5-tert-Butyl-2-chloro-phenyl)-3-[5-(2-pyridin-4-yl-thiazol)-thiazol-2-yl]-urea | 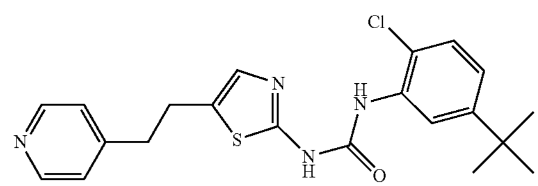 [SMILES: CC(C)(C)c1ccc(Cl)c(NC(=O)Nc2ncc(CCc3ccncc3)s2)c1] |
| 389 | 1-(5-tert-Butyl-2-isopropyl-2H-pyrazol-3-yl)-3-[5-(2-pyridin-4-yl-ethyl)-thiazol-2-yl]-urea | 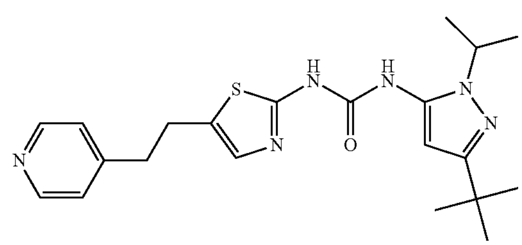 [SMILES: CC(C)n1nc(C(C)(C)C)cc1NC(=O)Nc1ncc(CCc2ccncc2)s1] |
| 390 | N-[4-[2-[2-[[5-tert-butyl-2-(4-chlorophenyl)pyrazol-3-yl]carbamoylamino]thiazol-5-yl]ethyl]-2-pyridyl]cyclopropanecarboxamide | 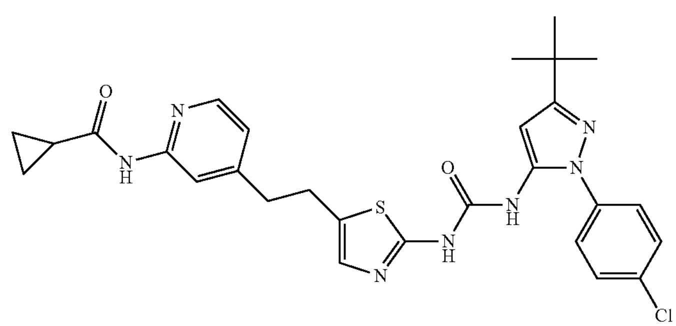 [SMILES: CC(C)(C)c1cc(NC(=O)Nc2ncc(CCc3ccnc(NC(=O)C4CC4)c3)s2)n(-c2ccc(Cl)cc2)n1] |

TABLE 1-continued

| Analog # | IUPAC Chemical Name | Chemical Structure |
|---|---|---|
| 398 | N-[4-(2-{2-[3-(5-Cyclopropyl-2-fluoro-phenyl)-ureido]-thiazol-5-yl}-ethyl)-pyridin-2-yl]-acetamide | 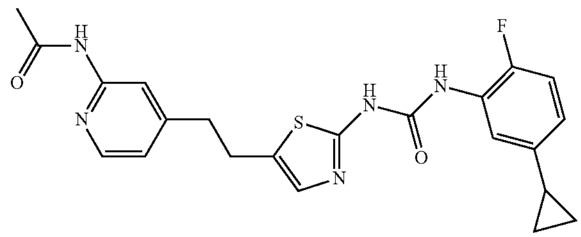 [SMILES: CC(=O)Nc1cc(CCc2cnc(NC(=O)Nc3cc(C4CC4)ccc3F)s2)ccn1] |
| 400 | N-[4-(2-{2-[3-(2-Fluoro-5-trimethylsilanyl-phenyl)-ureido]-thiazol-5-yl}-ethyl)-pyridin-2-yl]-acetamide | 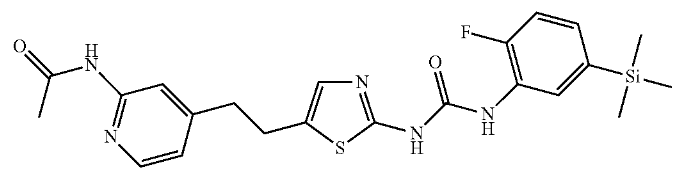 [SMILES: CC(=O)Nc1cc(CCc2cnc(NC(=O)Nc3cc([Si](C)(C)C)ccc3F)s2)ccn1] |
| 409 | N-{4-[2-(2-{3-[2-Fluoro-5-(1-methyl-cyclopropyl)-phenyl]-ureido}-thiazol-5-yl)-ethyl]-pyridin-2-yl}-acetamide | 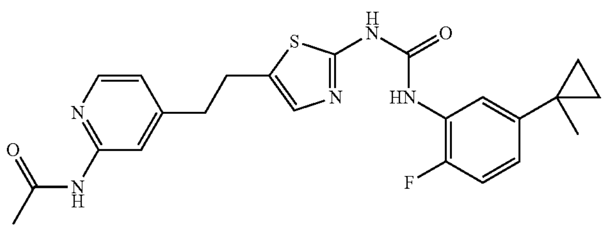 [SMILES: CC(=O)Nc1cc(CCc2cnc(NC(=O)Nc3cc(C4(C)CC4)ccc3F)s2)ccn1] |
| 410 | N-[4-(2-{2-[3-(2-Chloro-5-cyclopropyl-phenyl)-ureido]-thiazol-5-yl}-ethyl)-pyridin-2-yl]-acetamide | 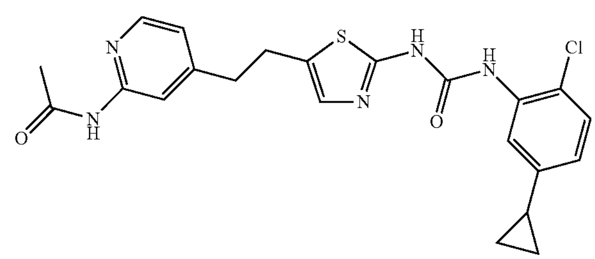 [SMILES: CC(=O)Nc1cc(CCc2cnc(NC(=O)Nc3cc(C4CC4)ccc3Cl)s2)ccn1] |
| 411 | N-[4-(2-{2-[3-(2-Fluoro-5-oxetan-3-yl-phenyl)-ureido]-thiazol-5-yl}-ethyl)-pyridin-2-yl]-acetamide | 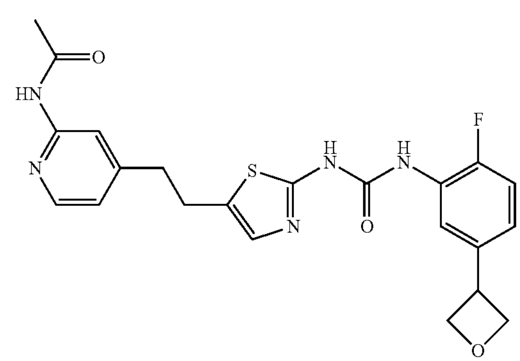 [SMILES: CC(=O)Nc1cc(CCc2cnc(NC(=O)Nc3cc(C4COC4)ccc3F)s2)ccn1] |

TABLE 1-continued

| Analog # | IUPAC Chemical Name | Chemical Structure |
|---|---|---|
| 315 | [4-(2-{4-[3-(5-tert-Butyl-2-p-tolyl-2H-pyrazol-3-yl)-ureido]-3-fluoro-phenyl}-ethyl)-pyridin-2-yl]-carbamic acid methyl ester | 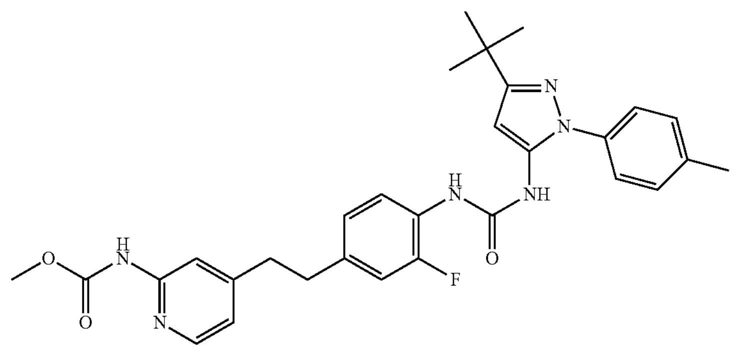 |
| 316 | [4-(2-{4-[3-(5-tet-Butyl-2-cyclopropylmethyl-2H-pyrazol-3-yl)-ureido]-3-fluoro-phenyl}-ethyl)-pyridin-2-yl]-carbamic acid methyl ester | 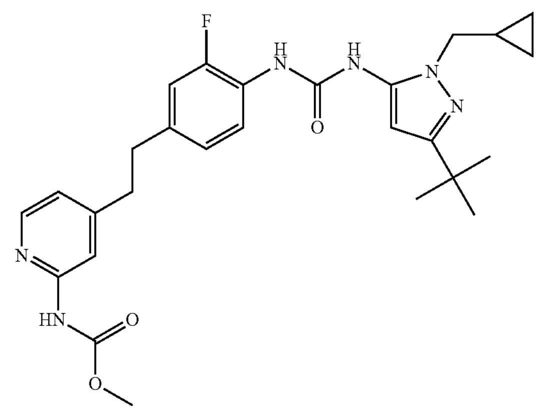 [SMILES: COC(=O)Nc1cc(CCc2ccc(NC(=O)Nc3cc(C(C)(C)C)nn3CC3CC3)c(F)c2)ccn1] |
| 317 | {4-[2-(4-{5-tert-Butyl-2-(4-fluoro-phenyl)-2H-pyrazol-3-yl]-ureido}-3-fluoro-phenyl)-ethyl]-pyridin-2-yl}-carbamic acid methyl ester | 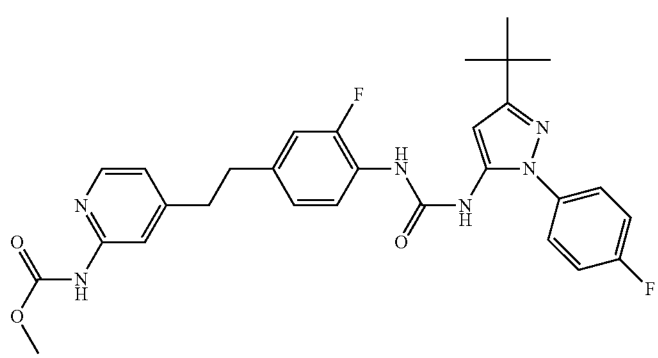 [SMILES: COC(=O)Nc1cc(CCc2ccc(NC(=O)Nc3cc(C(C)(C)C)nn3-c3ccc(F)cc3)c(F)c2)ccn1] |
| 318 | {4-[2-(4-{3-[5-tert-Butyl-2-(3-fluoro-phenyl)-2H-pyrazol-3-yl]-ureido}-3-fluoro-phenyl)-ethyl]-pyridin-2-yl}-carbamic acid methyl ester | 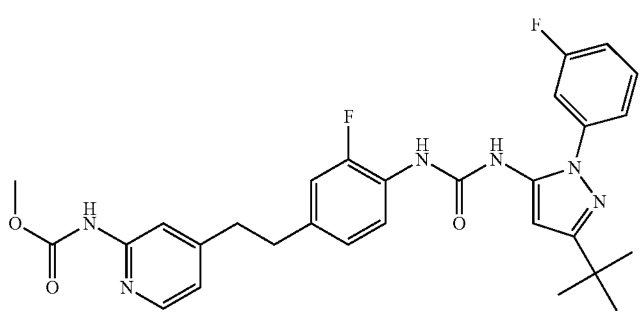 [SMILES: COC(=O)Nc1cc(CCc2ccc(NC(=O)Nc3cc(C(C)(C)C)nn3-c3cccc(F)c3)c(F)c2)ccn1] |

TABLE 1-continued

| Analog # | IUPAC Chemical Name | Chemical Structure |
|---|---|---|
| 329 | N-[4-(2-{4-[3-(5-tert-Butyl-2-p-tolyl-2H-pyrozol-3-yl)-ureido]-3-fluoro-phenyl}-ethyl)-pyridin-2-yl]-acetamide | 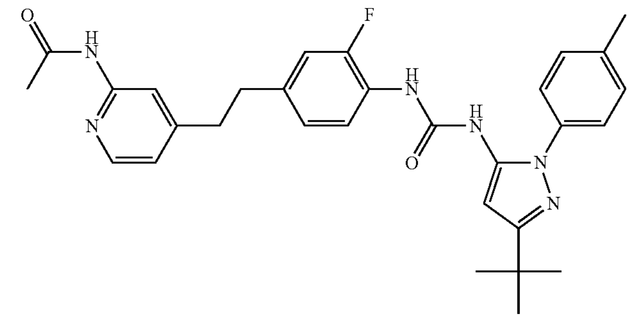 [SMILES: CC(=O)Nc1cc(CCc2ccc(NC(=O)Nc3cc(C(C)(C)C)nn3-c3ccc(C)cc3)c(F)c2)ccn1] |
| 358 | N-[4-(2-{4-[3-(5-tert-Butyl-isoxazol-3-yl)-ureido]-3-fluoro-phenyl}-ethyl)-pyridin-2-yl]-acetamide | 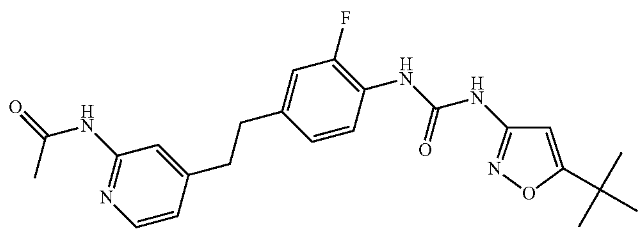 [SMILES: CC(=O)Nc1cc(CCc2ccc(NC(=O)Nc3cc(C(C)(C)C)on3)c(F)c2)ccn1] |
| 359 | N-[4-(2-{4-[3-(3-tert-Butyl-isoxazol-5-yl)-ureido]-3-fluoro-phenyl}-ethyl)-pyridin-2-yl]-acetamide | 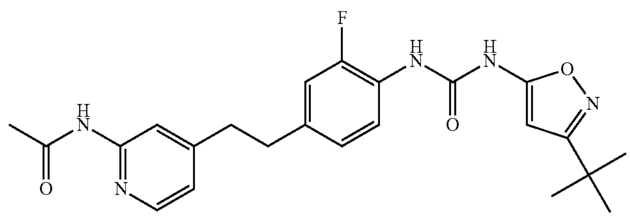 [SMILES: CC(=O)Nc1cc(CCc2ccc(NC(=O)Nc3cc(C(C)(C)C)no3)c(F)c2)ccn1] |
| 360 | N-[4-(2-{3-Fluoro-4-[3-(2-fluoro-5-trifluoromethyl-phenyl)-ureido]-phenyl}-ethyl)-pyridin-2-yl]-acetamide | 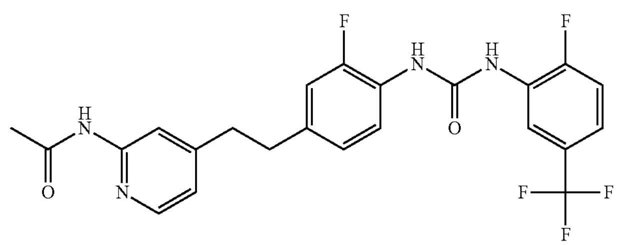 [SMILES: CC(=O)Nc1cc(CCc2ccc(NC(=O)Nc3cc(C(F)(F)F)ccc3F)c(F)c2)ccn1] |
| 361 | N-[4-(2-{4-[3-(5-tert-Butyl-2-methyl-2H-pyrazol-3-yl)-ureido]-3-fluoro-phenyl}-ethyl)-pyridin-2-yl]-acetamide | 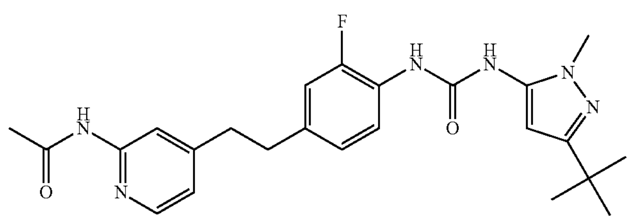 [SMILES: CC(=O)Nc1cc(CCc2ccc(NC(=O)Nc3cc(C(C)(C)C)nn3C)c(F)c2)ccn1] |
| 370 | N-[4-(2-{4-[3-(5-tert-Butyl-2-cyclopropylmethyl-2H-pyrazol-3-yl)-ureido]-3-fluoro-phenyl}-ethyl)-pyridin-2-yl]-acetamide | 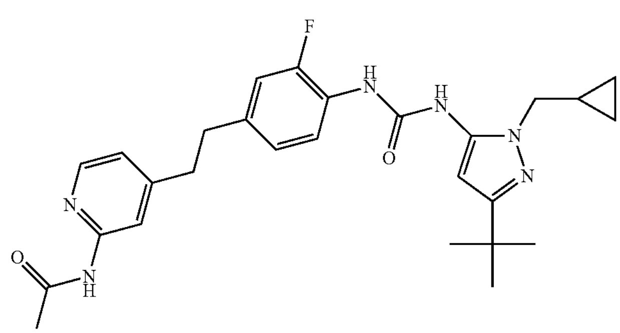 [SMILES: CC(=O)Nc1cc(CCc2ccc(NC(=O)Nc3cc(C(C)(C)C)nn3CC3CC3)c(F)c2)ccn1] |

TABLE 1-continued

| Analog # | IUPAC Chemical Name | Chemical Structure |
|---|---|---|
| 371 | N-[4-(2-{4-[3-(5-tert-Butyl-2-isopropyl-2H-pyrazol-3-yl)-ureido]-3-fluoro-phenyl}-ethyl)-pyridin-2-yl]-acetamide | 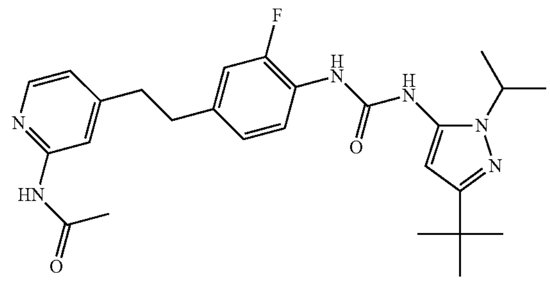 [SMILES: CC(=O)Nc1cc(CCc2ccc(NC(=O)Nc3cc(C(C)(C)C)nn3C(C)C)c(F)c2)ccn1] |
| 372 | Cyclopropanecarboxylic acid [4-(2-{4-[3-(5-tert-butyl-2-cyclopropylmethyl-2H-pyrazol-3-yl)-ureido]-3-fluoro-phenyl}-ethyl)-pyridin-2-yl]-amide | 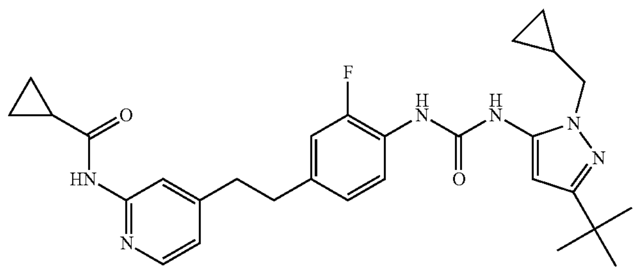 [SMILES: CC(C)(C)c1cc(NC(=O)Nc2ccc(CCc3ccnc(NC(=O)C4CC4)c3)cc2F)n(CC2CC2)n1] |
| 373 | Cyclopropanecarboxylic acid [4-(2-{4-[3-(5-tert-butyl-2-methyl-2H-pyrazol-3-yl)-ureido]-3-fluoro-phenyl}-ethyl)-pyridin-2-yl]-amide | 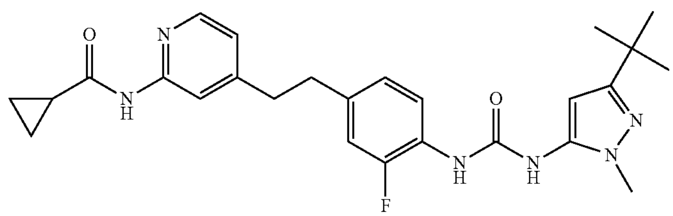 [SMILES: Cn1nc(C(C)(C)C)cc1NC(=O)Nc1ccc(CCc2ccnc(NC(=O)C3CC3)c2)cc1F] |
| 374 | Cycloproprinecarboxylic acid [4-(2-{4-[3-(3-tert-butyl-isoxazol-5-yl)-ureido]-3-fluoro-phenyl}-ethyl)-pyridin-2-yl]-amide | 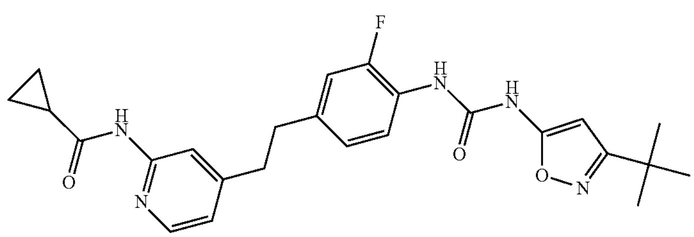 [SMILES: CC(C)(C)c1cc(NC(=O)Nc2ccc(CCc3ccnc(NC(=O)C4CC4)c3)cc2F)on1] |
| 375 | Cyclopropanecarboxylic acid [4-(2-{4-[3-(5-tert-butyl-2-isopropyl-2H-pyrazol-3-yl)-ureido]-3-fluoro-phenyl}-ethyl)-pyridin-2-yl]-amide | 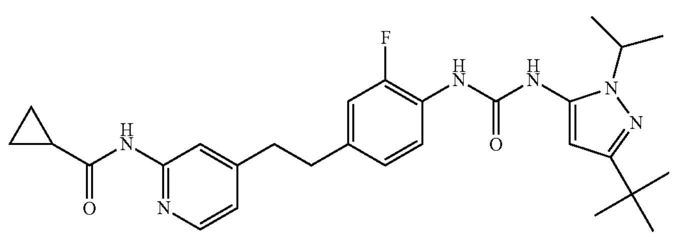 [SMILES: CC(C)n1nc(C(C)(C)C)cc1NC(=O)Nc1ccc(CCc2ccnc(NC(=O)C3CC3)c2)cc1F] |
| 376 | Cyclopropancearboxylic acid [4-(2-{4-[3-(3-tert-butyl-phenyl)-ureido]-3-fluoro-phenyl}-ethyl)-pyridin-2-yl]-amide | 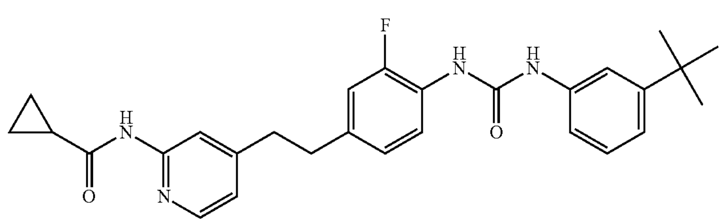 [SMILES: CC(C)(C)c1cccc(NC(=O)Nc2ccc(CCc3ccnc(NC(=O)C4CC4)c3)cc2F)c1] |

TABLE 1-continued

| Analog # | IUPAC Chemical Name | Chemical Structure |
|---|---|---|
| 377 | N-[4-(2-{4-[3-(3-tert-Butyl-phenyl)-ureido]-3-fluoro-phenyl}-ethyl)-pyridin-2-yl]-acetamide | 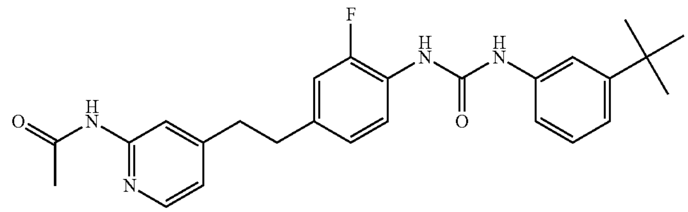 [SMILES: CC(=O)Nc1cc(CCc2ccc(NC(=O)Nc3cccc(C(C)(C)C)c3)c(F)c2)ccn1] |
| 378 | Cyclopropanecarboxylic acid [4-(2-{4-[3-(5-tert-butyl-isoxazol-3-yl)-ureido]-3-fluoro-phenyl}-ethyl)-pyridin-2-yl]-amide | 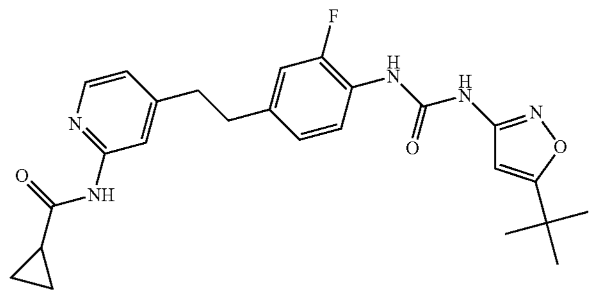 [SMILES: CC(C)(C)c1cc(NC(=O)Nc2ccc(CCc3ccnc(NC(=O)C4CC4)c3)cc2F)no1] |
| 379 | N-{4-[2-(4-{3-[5-tert-Butyl-2-(4-fluoro-phenyl)-2H-pyrazol-3-yl]-ureido}-3-fluoro-phenyl)-ethyl]-pyridin-2-yl}-acetamide | 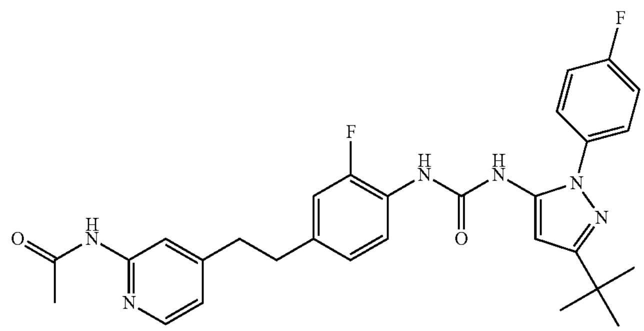 [SMILES: CC(=O)Nc1cc(CCc2ccc(NC(=O)Nc3cc(C(C)(C)C)nn3-c3ccc(F)cc3)c(F)c2)ccn1] |
| 402 | N-(4-{4-[3-(5-tert-Butyl-2-p-tolyl-2H-pyrazol-3-yl)-ureido]-3-fluoro-phenoxymethyl}-pyridin-2-yl)-acetamide | 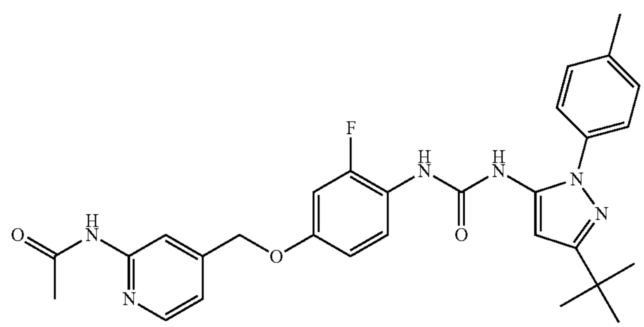 [SMILES: CC(=O)Nc1cc(COc2ccc(NC(=O)Nc3cc(C(C)(C)C)nn3-c3ccc(C)cc3)c(F)c2)ccn1] |
| 403 | N-(4-{4-[3-(5-Cyclopropyl-2-fluoro-phenyl)-ureido]-3-fluoro-phenoxymethyl}-pyridin-2-yl)-acetamide | 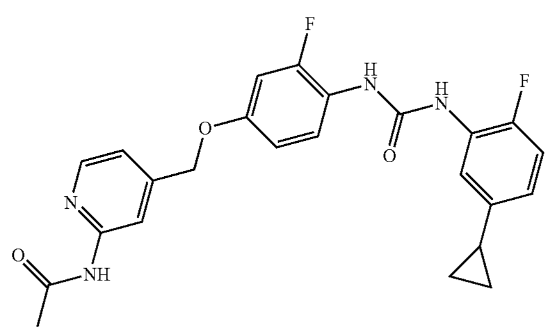 [SMILES: CC(=O)Nc1cc(COc2ccc(NC(=O)Nc3cc(C4CC4)ccc3F)c(F)c2)ccn1] |

TABLE 1-continued

| Analog # | IUPAC Chemical Name | Chemical Structure |
|---|---|---|
| 404 | N-[4-(3-Fluoro-4-{3-[2-fluro-5-(1-methyl-cyclopropyl)-phenyl]-ureido}-phenoxymethyl)-pyridin-2-yl]-acetamide | 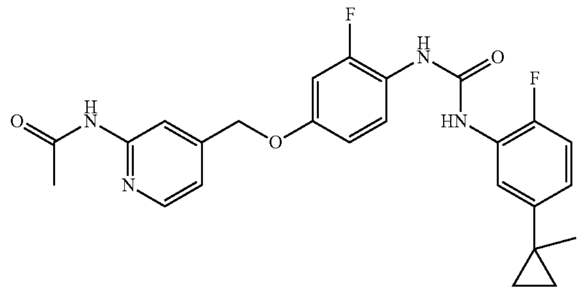 [SMILES: CC(=O)Nc1cc(COc2ccc(NC(=O)Nc3cc(C4(C)CC4)ccc3F)c(F)c2)ccn1] |
| 405 | N-(4-{3-fluoro-4-[3-(2-fluoro-trimethylsilanyl-phenyl)-ureido]-phenoxymethyl}-pyridin-2-yl)-acetamide | 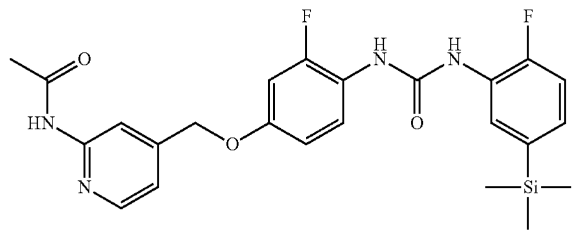 [SMILES: CC(=O)Nc1cc(COc2ccc(NC(=O)Nc3cc([Si](C)(C)C)ccc3F)c(F)c2)ccn1] |
| 406 | N-(4-{4-[3-(2-Chloro-5-cyclopropyl-phenyl)-ureido]-3-fluoro-phenoxymethyl}-pyridin-2-yl)-acetamide | 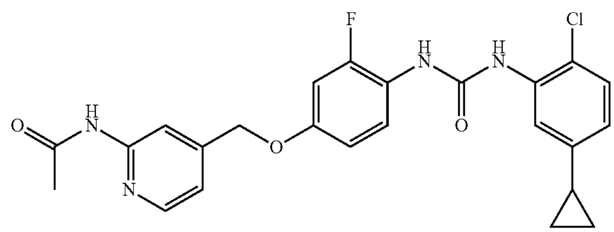 [SMILES: CC(=O)Nc1cc(COc2ccc(NC(=O)Nc3cc(C4CC4)ccc3Cl)c(F)c2)ccn1] |
| 413 | N-(4-{4-[3-(5-tert-Butyl-2-cyclopropylmethyl-2H-pyrazol-3-yl)-ureido]-3-fluoro-phenoxymethyl}-pyridin-2-yl)-acetamide | 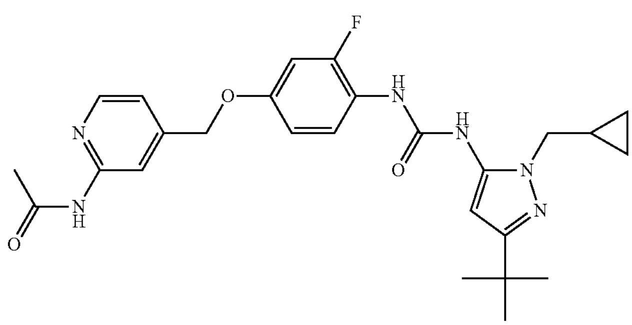 [SMILES: CC(=O)Nc1cc(COc2ccc(NC(=O)Nc3cc(C(C)(C)C)nn3CC3CC3)c(F)c2)ccn1] |
| 414 | N-(4-{4-[3-(5-tert-Butyl-2-chloro-phenyl)-ureido]-3-fluoro-phenoxymethyl}-pyridin-2-yl)-acetamide | 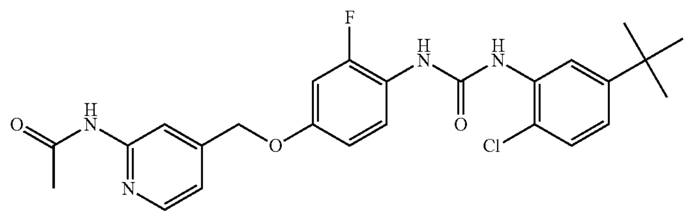 [SMILES: CC(=O)Nc1cc(COc2ccc(NC(=O)Nc3cc(C(C)(C)C)ccc3Cl)c(F)c2)ccn1] |

TABLE 1-continued

| Analog # | IUPAC Chemical Name | Chemical Structure |
|---|---|---|
| 259 | 2-Methoxy-N-[4-(4-{3-[5-(3-methyl-oxetan-3-yl)-2-p-tolyl-2H-pyrazol-3-yl]-ureido}-phenoxy)-pyridin-2-yl]-acetamide | 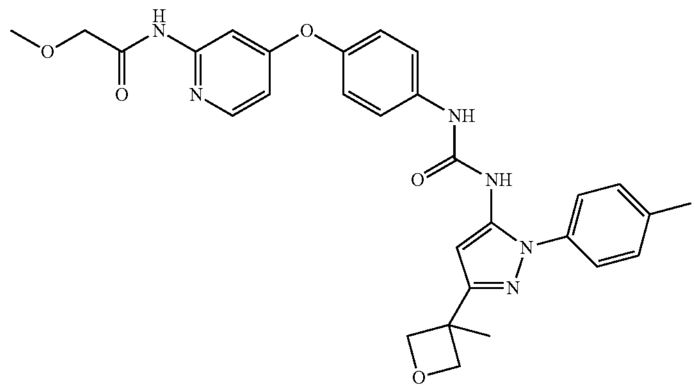 |
| 260 | 2-Methoxy-N-[4-(4-{3-[5-(3-methyl-thietan-3-yl)-2-p-tolyl-2H-pyrazol-3-yl]-ureido}-phenoxy)-pyridin-2-yl]-acetamide | 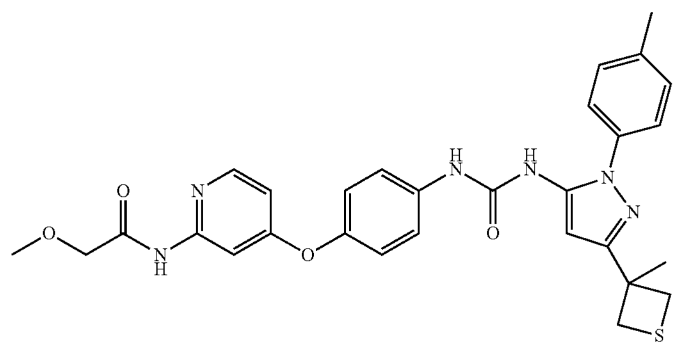 [SMILES: COCC(=O)Nc1cc(Oc2ccc(NC(=O)Nc3cc(C4(C)CSC4)nn3-c3ccc(C)cc3)cc2)ccn1] |
| 261 | [4-(4-{3-[5-(3-Methyl-oxetan-3-yl)-2-p-tolyl-2H-pyrazol-3-yl]-ureido}-phenoxy)-pyridin-2-yl]-carbainic acid methyl ester | 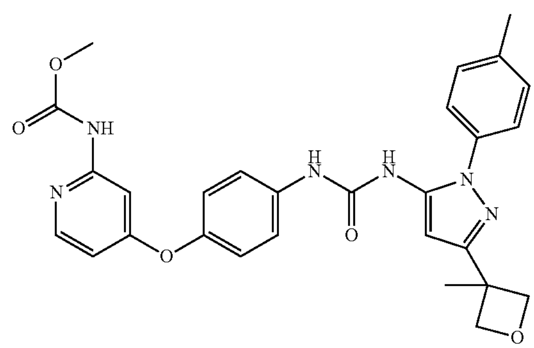 [SMILES: COC(=O)Nc1cc(Oc2ccc(NC(=O)Nc3cc(C4(C)COC4)nn3-c3ccc(C)cc3)cc2)ccn1] |
| 262 | [4-(4-{3-[5-(3-Methyl-thietan-3-yl)-2-p-tolyl-2H-pyrazol-3-yl]-ureido}-phenoxy)-pyridin-2-yl]-carbamic acid methyl ester | 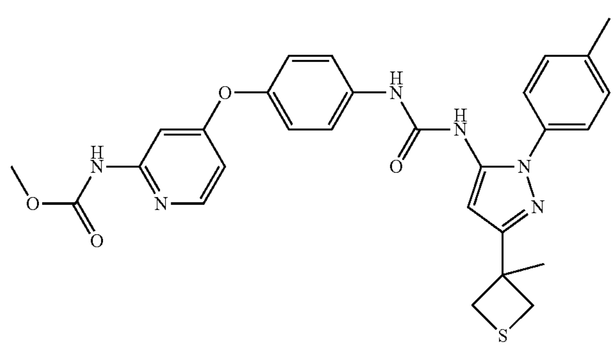 |

TABLE 1-continued

| Analog # | IUPAC Chemical Name | Chemical Structure |
|---|---|---|
| 267 | N-[4-[3-fluoro-4-[[5-(3-methyloxetan-3-yl)-2-(p-tolyl)pyrazol-3-yl]carbamoylamino]phenoxy]-2-pyridyl]-2-methoxy-acetamide | 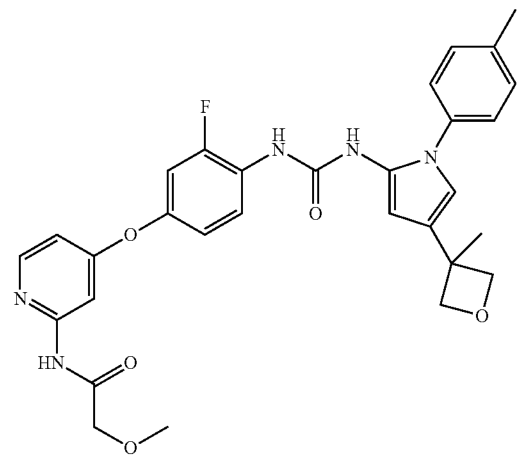 [SMILES: COCC(=O)Nc1cc(Oc2ccc(NC(=O)Nc3cc(C4(C)COC4)cn3-c3ccc(C)cc3)c(F)c2)ccn1] |
| 268 | N-[4-(3-fluoro-4-{3-[5-(3-methyl-thietan-3-yl)-2-p-tolyl-2H-pyrazol-3-yl]-ureido}-phenoxy)-pyridin-2-yl]-2-methoxy-acetamide | 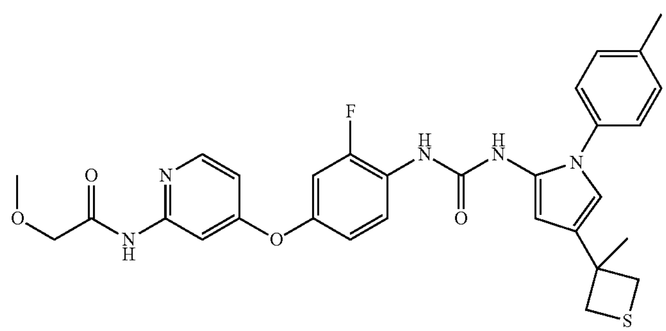 |
| 279 | 1-[2-Fluoro-4-(pyridin-4-yloxy)-phenyl]-3-[5-(2-hydroxy-1,1-dimethyl-ethyl)-2-p-tolyl-2H-pyrazol-3-yl]-urea | 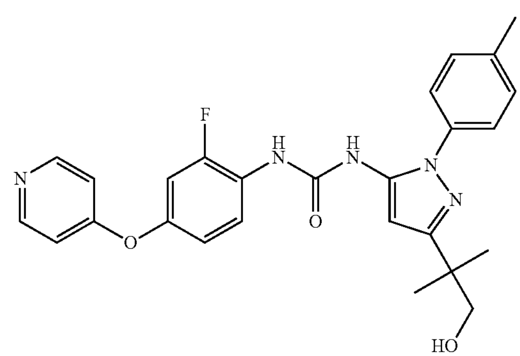 [SMILES: Cc1ccc(-n2nc(C(C)(C)CO)cc2NC(=O)Nc2ccc(Oc3ccncc3)cc2F)cc1] |
| 280 | 1-[5-(2-Hydroxy-1,1-dimethyl-ethyl)-2-p-tolyl-2H-pyrazol-3-yl]-3-[4-(pyridin-4-yloxy)-phenyl]-urea | 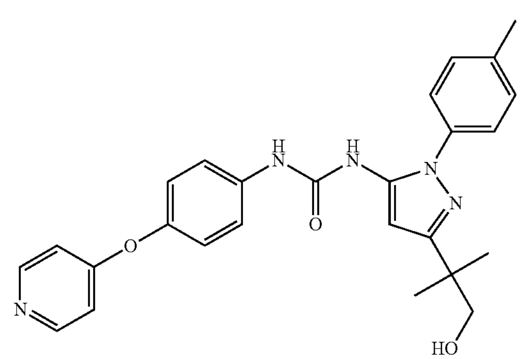 [SMILES: Cc1ccc(-n2nc(C(C)(C)CO)cc2NC(=O)Nc2ccc(Oc3ccncc3)cc2)cc1] |

TABLE 1-continued

| Analog # | IUPAC Chemical Name | Chemical Structure |
|---|---|---|
| 300 | 1-(5-tert-Butyl-2-p-tolyl-2H-pyrazol-3-yl)-3-[2-fluoro-4-(3-methyl-pyridin-4-yloxy)-phenyl]-urea | 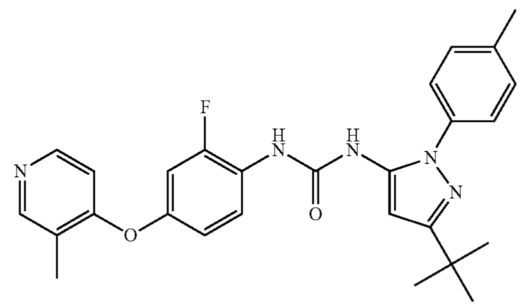 [SMILES: Cc1ccc(-n2nc(C(C)(C)C)cc2NC(=O)Nc2ccc(Oc3ccncc3C)cc2F)cc1] |
| 303 | 1-[5-tert-Butyl-2-(4-fluoro-phenyl)-2H-pyrazol-3-yl]-3-[2-fluoro-4-(pyridin-4-yloxy)-phenyl]-urea | 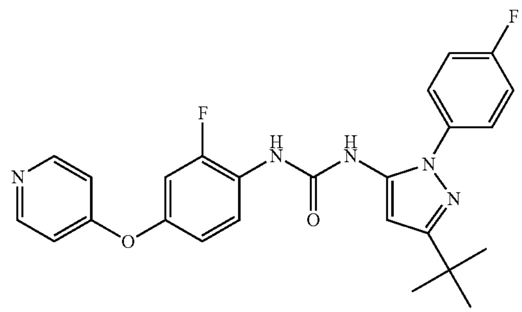 [SMILES: CC(C)(C)c1cc(NC(=O)Nc2ccc(Oc3ccncc3)cc2F)n(-c2ccc(F)cc2)n1] |
| 304 | 1-[4-(2-Amino-pyridin-4-yloxy)-2-fluoro-phenyl]-3-[5-tert-butyl-2-(3-fluoro-phenyl)-2H-pyrazol-3-yl]-urea | 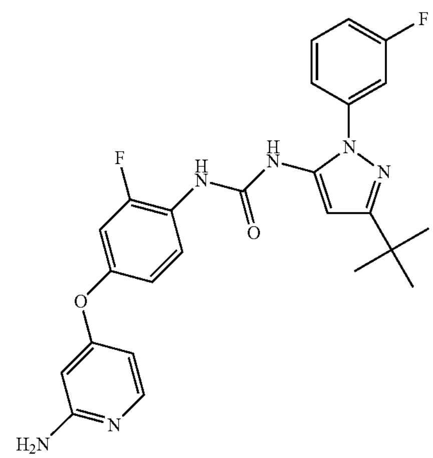 [SMILES: CC(C)(C)c1cc(NC(=O)Nc2ccc(Oc3ccnc(N)c3)cc2F)n(-c2cccc(F)c2)n1] |
| 306 | 1-[5-tert-but yl-2-(3-fluorophenyl)pyrazol-3-yl]-3-[2-fluoro-4-(4-pyridyloxy)phenyl]urea | 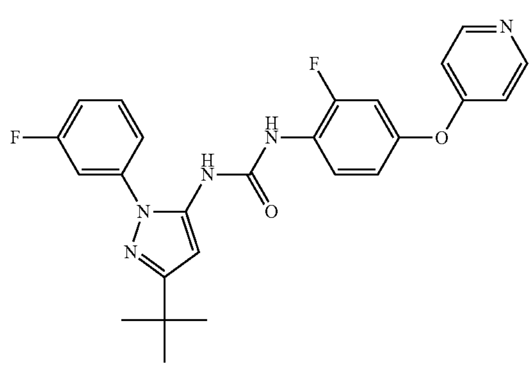 [SMILES: CC(C)(C)c1cc(NC(=O)Nc2ccc(Oc3ccncc3)cc2F)n(-c2cccc(F)c2)n1] |

TABLE 1-continued

| Analog # | IUPAC Chemical Name | Chemical Structure |
|---|---|---|
| 310 | 1-(5-tert-Butyl-2-cyclopropylmethyl-2H-pyrazol-yl)-3-[2-fluoro-4-(pyridin-4-yloxy)-phenyl]-urea | 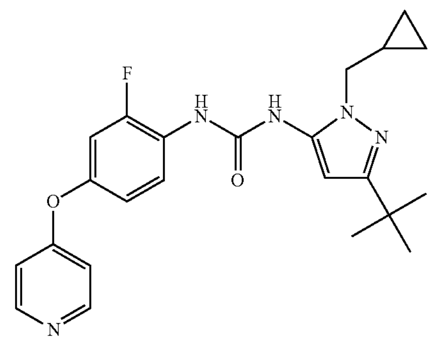 [SMILES: CC(C)(C)c1cc(NC(=O)Nc2ccc(Oc3ccncc3)cc2F)n(CC2CC2)n1] |
| 391 | N-(4-{4-[3-(5-tert-Butyl-2-methyl-2H-pyrazol-3-yl)-ureido]-3-fluoro-phenoxy}-pyridin-2-yl)-acetamide | 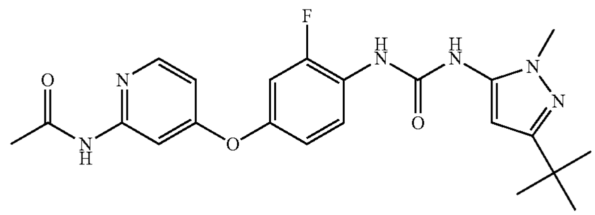 [SMILES: CC(=O)Nc1cc(Oc2ccc(NC(=O)Nc3cc(C(C)(C)C)nn3C)c(F)c2)ccn1] |
| 392 | N-(4-{4-[3-(5-tert-Butyl-2-isopropyl-2H-pyrazol-3-yl)-ureido]-3-fluoro-phenoxy}-pyridin-2-yl)-acetamide | 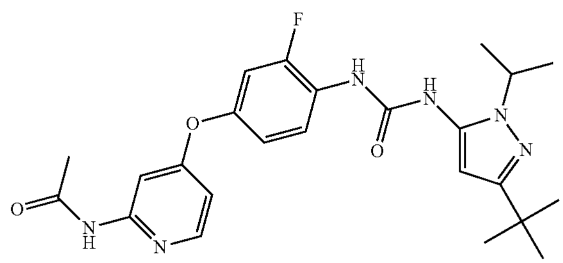 [SMILES: CC(=O)Nc1cc(Oc2ccc(NC(=O)Nc3cc(C(C)(C)C)nn3C(C)C)c(F)c2)ccn1] |
| 393 | N-(4-{4-[3-(5-tert-Butyl-2-cyclopropylmethyl-2H-pyrazol-3-yl)-ureido]-3-fluoro-phenoxy}-pyridin-2-yl)-acetamide | 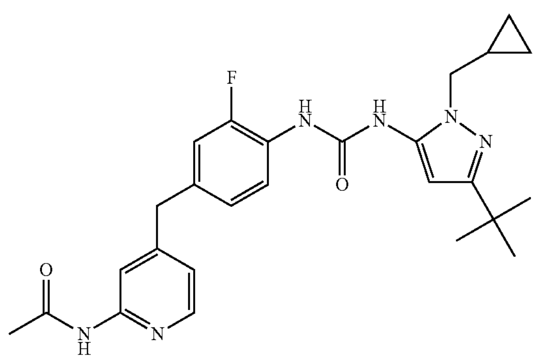 [SMILES: CC(=O)Nc1cc(Cc2ccc(NC(=O)Nc3cc(C(C)(C)C)nn3CC3CC3)c(F)c2)ccn1] |
| 394 | N-(4-{4-[3-(5-tert-Butyl-isoxazol-3-yl)-ureido]-3-fluoro-phenoxy}-pyridin-2-yl)-acetamide | 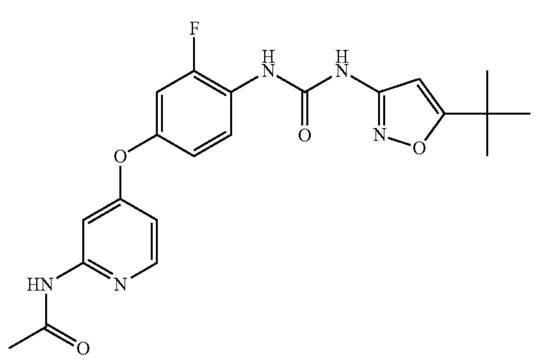 [SMILES: CC(=O)Nc1cc(Oc2ccc(NC(=O)Nc3cc(C(C)(C)C)on3)c(F)c2)ccn1] |

TABLE 1-continued

| Analog # | IUPAC Chemical Name | Chemical Structure |
|---|---|---|
| 395 | N-(4-{4-[3-(3-tert-Butyl-isoxazol-5-yl)-ureido]-3-fluoro-phenoxy}-pyridin-2-yl)-acetamide | 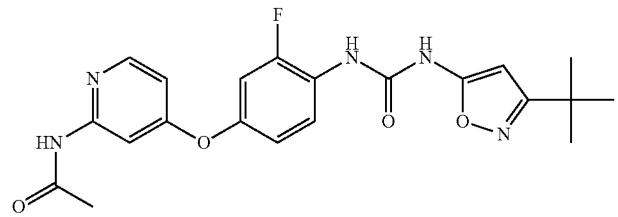 [SMILES: CC(=O)Nc1cc(Oc2ccc(NC(=O)Nc3cc(C(C)(C)C)no3)c(F)c2)ccn1] |
| 396 | N-(4-{4-[3-(5-tert-Butyl-3-chloro-phenyl)-ureido]-3-fluoro-phenoxy}-pyridin-2-yl)-acetamide | 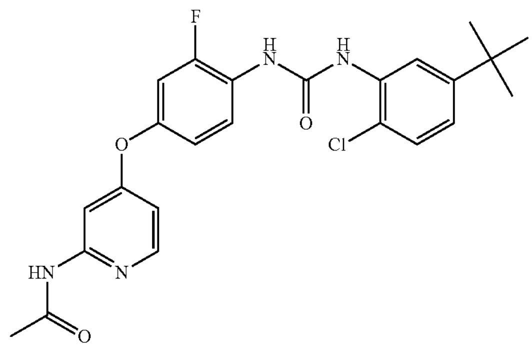 [SMILES: CC(=O)Nc1cc(Oc2ccc(NC(=O)Nc3cc(C(C)(C)C)ccc3Cl)c(F)c2)ccn1] |
| 397 | N-(4-{4-[3-(5-Cyclopropyl-2-fluoro-pheny)-ureido]-3-fluoro-phenoxy}-pyridin-2-yl)-actamde | 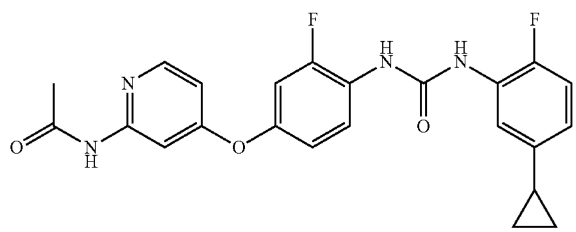 [SMILES: CC(=O)Nc1cc(Oc2ccc(NC(=O)Nc3cc(C4CC4)ccc3F)c(F)c2)ccn1] |
| 399 | N-(4-{3-Fluoro-4-[3-(2-fluoro-5-trimethylsilanyl-phenyl)-ureido]-phenoxy}-pyridin-2-yl)-acetamide | 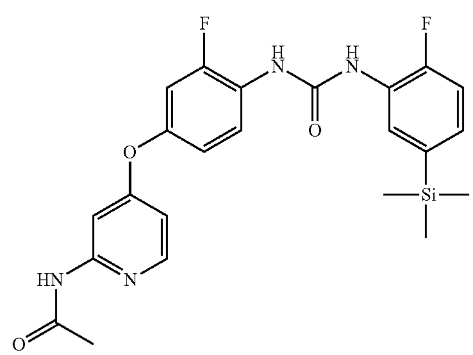 [SMILES: CC(=O)Nc1cc(Oc2ccc(NC(=O)Nc3cc([Si](C)(C)C)ccc3F)c(F)c2)ccn1] |
| 407 | N-[4-(3-fluro-4-{3-[2-fluoro-5-(1-methyl-cyclopropyl)-phenyl]-ureido}-phenoxy)-pyridin-2-yl]-acetamide | 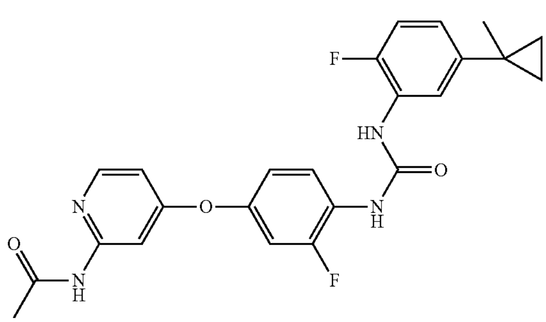 [SMILES: CC(=O)Nc1cc(Oc2ccc(NC(=O)Nc3cc(C4(C)CC4)ccc3F)c(F)c2)ccn1] |

TABLE 1-continued

| Analog # | IUPAC Chemical Name | Chemical Structure |
|---|---|---|
| 412 | N-(4-{3-Fluoro-4-[3-(2-fluoro-5-oxetan-3-yl-phenyl)-ureido]-phenoxy}-pyridin-2-yl)-acetamide | 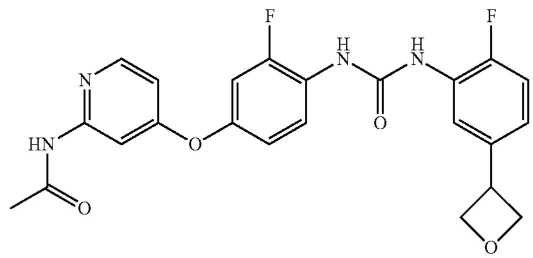 [SMILES: CC(=O)Nc1cc(Oc2ccc(NC(=O)Nc3cc(C4COC4)ccc3F)c(F)c2)ccn1] |
| 423 | N-(4-{4-[3-(2-Chloro-5-cyclopropyl-phenyl)-ureido]-3-fluoro-phenoxy}-pyridin-2-yl)-acetamide | 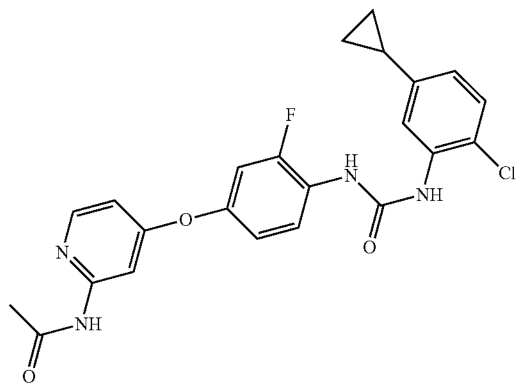 [SMILES: CC(=O)Nc1cc(Oc2ccc(NC(=O)Nc3cc(C4CC4)ccc3Cl)c(F)c2)ccn1] |
| 424 | N-(4-{4-[3-(5-Cyclopropyl-2-fluoro-phenyl)-ureido]-3-fluoro-phenoxy}-pyridin-2-yl)-2-hydroxy-acetamide | 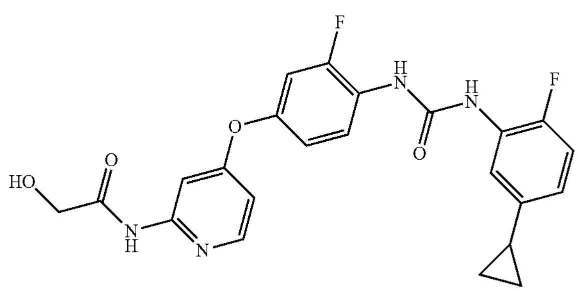 [SMILES: O=C(CO)Nc1cc(Oc2ccc(NC(=O)Nc3cc(C4CC4)ccc3F)c(F)c2)ccn1] |
| 425 | N-(4-{4-[3-(5-Cyclopropyl-2-fluoro-phenyl)-ureido]-3-fluoro-phenoxy}-pyridin-2-yl)-3 methoxypropionamide | 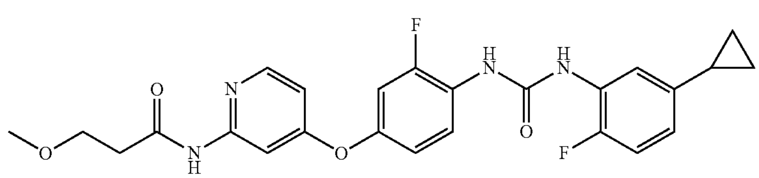 [SMILES: COCCC(=O)Nc1cc(Oc2ccc(NC(=O)Nc3cc(C4CC4)ccc3F)c(F)c2)ccn1] |
| 426 | N-(4-{4-[3-(5-tert-Butyl-2-chloro-phenyl)-ureido]-3-fluoro-phenoxy}-pyridin-2-yl)-2-hydroxy-acetamide | 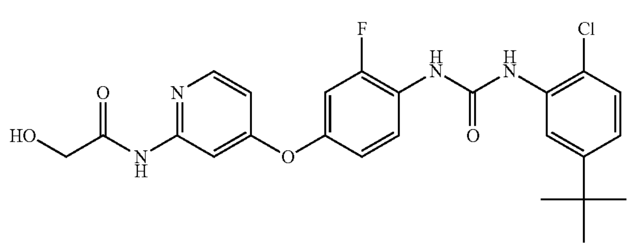 [SMILES: CC(C)(C)c1ccc(Cl)c(NC(=O)Nc2ccc(Oc3ccnc(NC(=O)CO)c3)cc2F)c1] |

TABLE 1-continued

| Analog # | IUPAC Chemical Name | Chemical Structure |
|---|---|---|
| 427 | N-(4-{4-[3-(5-tert-Butyl-2-chloro-phenyl)-ureido]-3-fluoro-phenoxy}-pyridin-2-yl)-3-methoxy-propionamide | 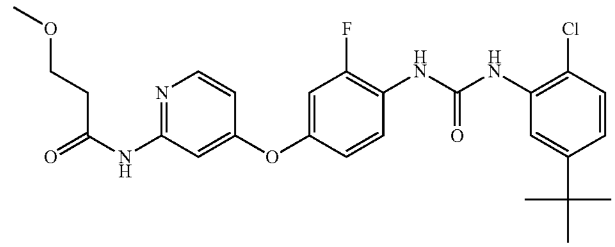 [SMILES: COCCC(=O)Nc1cc(Oc2ccc(NC(=O)Nc3cc(C(C)(C)C)ccc3Cl)c(F)c2)ccn1] |
| 428 | 1-[4-(2-Amino-pyridin-4-yloxy)-2-fluoro-phenyl]-3-(5-tert-butyl-2-chloro-phenyl)-urea | 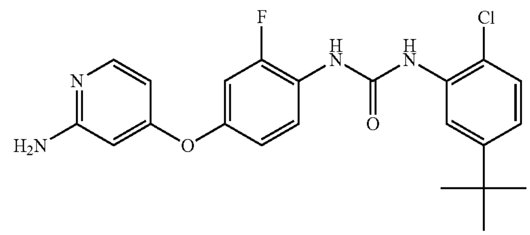 [SMILES: CC(C)(C)c1ccc(Cl)c(NC(=O)Nc2ccc(Oc3ccnc(N)c3)cc2F)c1] |
| 408 | 1-[4-(4-{3-[2-Chloro-5-(tert-butyl)phenyl]ureido}-3-fluorophenoxy)-2-pyridylamino]-1-ethanone | 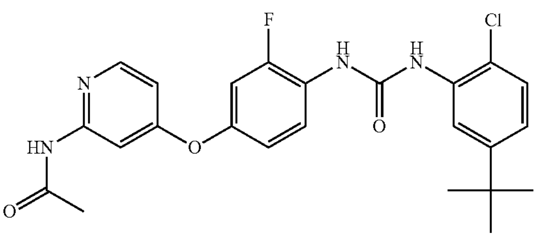 [SMILES: CC(=O)Nc1cc(Oc2ccc(NC(=O)Nc3cc(C(C)(C)C)ccc3Cl)c(F)c2)ccn1] |

TABLE 2

| Compound # | Formula Type | MAPK13 inhibition* | MAPK14 IC$_{50}$** |
|---|---|---|---|
| 340 | I | +++ | >10,000 |
| 354 | I | +++ | >10,000 |
| 364 | I | +++ | >10,000 |
| 398 | I | +++ | >10,000 |
| 400 | I | +++ | >10,000 |
| 355 | I | +++ | 8445 |
| 356 | I | +++ | 6407 |
| 343 | I | +++ | 2464 |
| 352 | I | +++ | 2255 |
| 383 | I | +++ | 1785 |
| 380 | I | +++ | 1735 |
| 385 | I | +++ | 1608 |
| 322 | I | +++ | 1568 |
| 350 | I | +++ | 1504 |
| 284 | I | +++ | 1132 |
| 348 | I | +++ | 1076 |
| 336 | I | +++ | 1031 |
| 286 | I | +++ | 780 |
| 347 | I | +++ | 720 |
| 341 | I | +++ | 704 |
| 381 | I | +++ | 692 |
| 326 | I | +++ | 676 |
| 351 | I | +++ | 611 |
| 285 | I | +++ | 527 |
| 335 | I | +++ | 514 |
| 339 | I | +++ | 477 |
| 369 | I | +++ | 453 |
| 344 | I | +++ | 414 |
| 273 | I | +++ | 313 |
| 342 | I | +++ | 312 |
| 334 | I | +++ | 299 |
| 390 | I | +++ | 294 |
| 353 | I | +++ | 294 |
| 349 | I | +++ | 270 |
| 345 | I | +++ | 267 |
| 287 | I | +++ | 262 |
| 366 | I | +++ | 251 |
| 337 | I | +++ | 243 |
| 382 | I | +++ | 236 |
| 281 | I | +++ | 232 |
| 368 | I | +++ | 225 |
| 325 | I | +++ | 221 |
| 319 | I | +++ | 210 |
| 331 | I | +++ | 202 |
| 330 | I | +++ | 201 |
| 333 | I | +++ | 200 |
| 332 | I | +++ | 193 |
| 314 | I | +++ | 181 |
| 311 | I | +++ | 148 |
| 283 | I | +++ | 139 |
| 282 | I | +++ | 129 |
| 288 | I | +++ | 114 |
| 384 | I | +++ | 90 |
| 399 | III | +++ | 83 |
| 300 | III | +++ | 67 |
| 321 | I | +++ | 67 |
| 397 | III | +++ | 62 |
| 313 | I | +++ | 52 |
| 268 | III | +++ | 40 |
| 426 | I | +++ | 40 |
| 262 | III | +++ | 37 |
| 304 | III | +++ | 36 |
| 424 | III | +++ | 28 |
| 423 | III | +++ | 24 |
| 303 | III | +++ | 23 |
| 427 | I | +++ | 21 |
| 267 | III | +++ | 19 |
| 320 | I | +++ | 18 |

TABLE 2-continued

| Compound # | Formula Type | MAPK13 inhibition* | MAPK14 IC$_{50}$** |
|---|---|---|---|
| 306 | III | +++ | 17 |
| 259 | III | +++ | 15 |
| 392 | III | +++ | 12 |
| 261 | III | +++ | 11 |
| 260 | III | +++ | 11 |
| 329 | II | +++ | 7 |
| 393 | III | +++ | 7 |
| 396 | III | +++ | 7 |
| 425 | III | +++ | 7 |
| 310 | III | +++ | 6 |
| 391 | III | +++ | 6 |
| 402 | II | +++ | 5 |
| 394 | III | +++ | 5 |
| 395 | III | +++ | 4 |
| 277 | I | ++ | >10,000 |
| 367 | I | ++ | >10,000 |
| 387 | I | ++ | 9380 |
| 365 | I | ++ | 2100 |
| 271 | I | ++ | 1358 |
| 386 | I | ++ | 962 |
| 312 | I | ++ | 925 |
| 316 | II | ++ | 919 |
| 373 | II | ++ | 775 |
| 302 | I | ++ | 470 |
| 270 | I | ++ | 419 |
| 305 | I | ++ | 245 |
| 379 | II | ++ | 122 |
| 280 | III | ++ | 94 |
| 279 | III | ++ | 64 |
| 405 | II | ++ | 51 |
| 413 | II | ++ | 37 |
| 414 | II | ++ | 31 |
| 357 | I | + | >10,000 |
| 388 | I | + | >10,000 |
| 360 | II | + | >10,000 |
| 376 | II | + | 18260 |
| 377 | II | + | 8310 |
| 389 | I | + | 3147 |
| 372 | II | + | 1999 |
| 371 | II | + | 1874 |
| 378 | II | + | 1702 |
| 375 | II | + | 1377 |
| 358 | II | + | 1117 |
| 374 | II | + | 1075 |
| 370 | II | + | 1068 |
| 361 | II | + | 476 |
| 359 | II | + | 307 |
| 315 | II | + | 171 |
| 428 | I | + | 95 |
| 363 | I | | not tested |
| 409 | I | | |
| 410 | I | | |
| 411 | I | | |
| 317 | II | | |
| 318 | II | | |
| 403 | II | | |
| 404 | II | | |
| 406 | II | | |
| 407 | III | | |
| 408 | III | | |
| 412 | III | | |

*+++: <250 nM; ++: 250-1000 nM, +: >1000 nM)
**for selectivity
*** compared to vehicle control In some embodiments, the present teachings include uses of the compounds.

In some configurations, the present teachings include methods of treating a cancer in a subject in need thereof. The cancer can be, for example, a breast cancer. In various configurations, the methods can comprise administering to a subject in need a therapeutically effective amount of a MAPK13 inhibitor of the present teachings. In some configurations, the methods can comprise administering to a subject in need a therapeutically effective amount of an inhibitor of MAPK13 and at least one other MAPK of the present teachings, such as, without limitation, an inhibitor of MAPK13 and MAPK14.

In some configurations, examples of inhibitors of MAPK13 that can be used to treat cancer can include compounds 340, 354, 364, 398, 400, 355, 356, 343, 352, 383, 380, 385, 322, 350, 284, 348 and 336.

In some configurations, examples of inhibitors of MAPK13 and MAPK14 that can be used to treat cancer can include compounds 286, 347, 341, 381, 326, 351, 285, 335, 339, 369, 344, 273, 342, 334, 390, 353, 349, 345, 287, 366, 337, 382, 281, 368, 325, 319, 331, 330, 333.332, 314.311, 283, 282, 288, 384, 399, 300.321, 397, 313, 268, 426, 262, 304.424, 423, 303, 427, 267, 320, 306, 259, 392, 261, 260, 329, 393, 396, 425, 310, 391, 402, 394 and 395.

In some configurations, examples of inhibitors of MAPK13 and MAPK14 that can be used to treat cancer can include compounds 260, 329, 393, 396, 425, 310, 391, 402, 394, and 395.

In some aspects, a method of treating cancer can include administering, to a subject in need, a therapeutically effective amount of compound 282

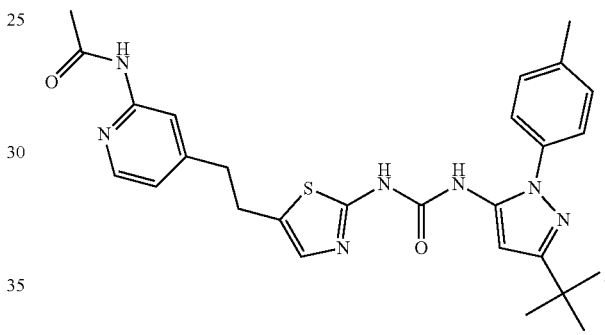

In some aspects, a method of treating cancer can include administering, to a subject in need, a therapeutically effective amount of compound 396

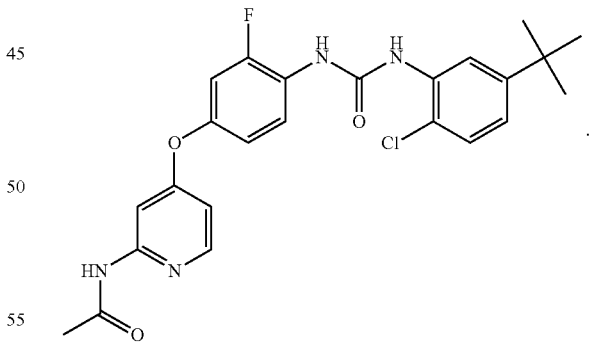

In various configurations, the present teachings include the use of any compound disclosed herein for the treatment of cancer. In some aspects, any compound disclosed herein can be used as an anti-cancer therapeutic. In some aspects, any compound disclosed herein can be used the manufacture of a medicament for the treatment of cancer.

In some configurations, the present teachings include methods of treating a respiratory disease in a subject in need thereof. In various aspects, these methods include administering to a subject in need thereof a therapeutically effective amount of a MAPK13 inhibitor disclosed herein. In various aspects, these methods include administering to a subject in need thereof a therapeutically effective amount of an inhibitor of MAPK13 and at least one other MAPK, such as, in non-limiting example, a combined inhibitor of MAPK13 and MAPK14.

Non-limiting examples of MAPK13 inhibitors of the present teachings that can be used for treating a respiratory disease include compounds 340, 354, 364, 398, 400, 355, 356, 343, 352, 383, 380, 385, 322, 350, 284, 348 and 336.

Non-limiting examples of an inhibitor of MAPK13 and MAPK14 include compounds 286, 347, 341, 381, 326, 351, 285, 335, 339, 369, 344, 273, 342, 334, 390, 353, 349, 345, 287, 366, 337, 382, 281, 368, 325, 319, 331, 330, 333, 332, 314, 311, 283, 282, 288, 384, 399, 300, 321, 397, 313, 268, 426, 262, 304, 424, 423, 303, 427, 267, 320, 306, 259, 392, 261, 260, 329, 393, 396, 425, 310, 391, 402, 394 and 395.

Non-limiting examples of an inhibitor of MAPK13 and MAPK14 include compounds 260, 329, 393, 396, 425, 310, 391, 402, 394, and 395.

In some aspects a method of treating a respiratory disease in a subject in need thereof can comprise administering to a subject in need thereof a therapeutically effective amount of compound 282

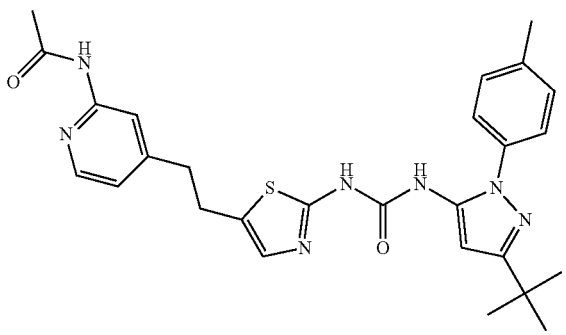

In some aspects a method of treating a respiratory disease in a subject in need thereof can comprise administering to a subject in need thereof a therapeutically effective amount of compound 3%

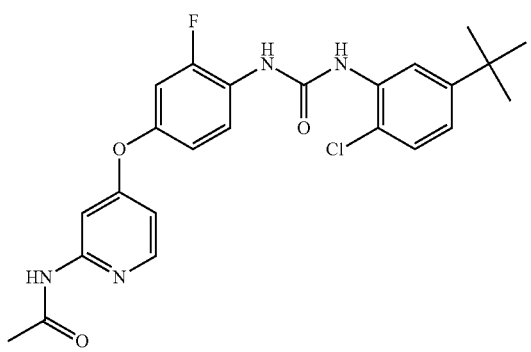

In various aspects, the respiratory disease can be, without limitation, asthma, rhinitis, sinusitis, COPD, pulmonary fibrosis and a combination thereof.

In some aspects, a compound of the present teachings can be used for the manufacture of a medicament for the treatment of a respiratory disease.

BRIEF DESCRIPTION OF THE DRAWINGS

Those of skill in the art will understand that the drawings, described below, are for illustrative purposes only. The drawings are not intended to limit the scope of the present teachings in any way.

FIG. 1a illustrates MAPK11-14 mRNA level in normal versus tumor tissue for indicated types of cancer.

FIG. 1b illustrates survival rates for breast cancer versus rectal adenocarcinoma patients with low versus high expression of MAPK13 mRNA in tpm.

FIG. 1c illustrates corresponding survival rates in patients with breast cancer with low versus high expression of MAPK14 mRNA.

FIG. 1d illustrates corresponding survival rates in patients with cancer relative to MAPK11-14 mRNA expression.

FIG. 2a illustrates the effect of hit compounds with a significant effect on MDA-MB-231 cell number FIG. 2b illustrates a dose-response for the most active compounds from screen described in (a)

FIG. 3a illustrates that Compound 43 (BIRB-796) represents the starting point for scaffold hopping to compounds such as Compound 282 to decrease MAPK13 $IC_{50}$.

FIG. 3b illustrates structures of Compound 43 and 282 bound to MAPK13, illustrating functional targets and DFG-out binding mode.

FIG. 3c illustrates biolayer interferometry (BLI) analysis for slow on-off binding of Compound 282 to MAPK13.

FIG. 3d illustrates level of indicated kinase activities remaining after incubation with Compounds 43 and 282 (100 nM) assessed with a custom-kinase panel relevant to cell-based phosphokinase antibody arrays and cancer biology.

FIG. 4a presents a scheme for protocol for compound treatment of breast cancer cell lines in culture.

FIG. 4b illustrates a time-course study on the effect on cell number for MAPK14 inhibitor Compound 43 and MAPK13 inhibitor Compound 282 (100 nM) for indicated cell-lines.

FIG. 4c illustrates a corresponding dose-response (1-1000 nM for 3 d for conditions in (a).

FIG. 4d illustrates flow cytometry analysis by PI staining of DNA content using the FlowJo Dean-Jett-Fox (DJF) modeling algorithm to define cell cycle phases for indicated cell lines with vehicle versus Compound 282 (30 nM).

FIG. 4e illustrates quantification of data from (d).

FIG. 4f illustrates flow cytometry analysis by BrdU staining for conditions in (d).

FIG. 4g illustrates quantification of data from (f).

FIG. 4h illustrates levels for cells remaining attached in PMA-treated cell lines with vehicle versus Compound 282 (300 nM).

FIG. 4i illustrates levels of cell migrating across membrane in Boyden chambers. Values represent mean±s.e.m. *$P<0.01$.

FIG. 5a illustrates a protocol scheme for treatment.

FIG. 5b illustrates body weights for NOD-SCID mice with MDA-MB-231 cell-line xenograft (Xg) and treatment with vehicle versus Compound 282 (20 mg/kg i.p. twice per d for 14-31 d after Xg implantation.

FIG. 5C illustrates tumor size for conditions in (a).

FIG. 6a illustrates that Compound 43 (BIRB-7%) represents the starting point for scaffold hopping to Compound 354 and Compound 3% to improve potency against MAPK13.

FIG. 6b illustrates structure for Compound 43 (by modeling) bound to MAPK13 (by x-ray crystallography) illustrating target regions for drug design and DFG-out binding mode.

FIG. 6c illustrates structural basis for Compound 3% interactions for MAPK13 with hydrogen-bond and hydrophobic interactions.

FIG. 6d illustrates biolayer interferometry (BLI) analysis for slow on-off binding of Compound 396 to MAPK13.

FIG. 6e illustrates a screen for kinase inhibition for Compounds 43 and 396 (0.1 IM).

FIG. 7a illustrates a protocol scheme for primary-culture of human tracheobronchial epithelial cells (hTECs) under ALI conditions and treatment with or without IL-13 and MAPK13 inhibitor. FIG. 7b illustrates levels of MUC5AC in apical cell supernatants of hTECs cultured with or without IL-13 (50 ng/ml).

FIG. 7c illustrates MUC5AC levels for conditions in (a,b) with MAPK14-selective VX-745, MAPKI3-selective Compounds 354 and 398, MAPK13/14-selective Compounds 3% and 397), or vehicle control.

FIG. 7d illustrates values for transepithelial electrical resistance (TEER) and cell viability (using resazurin assay) for Compound 3% for conditions in (c). For (b,c,d), values represent mean±s.e.m. for one cell donor. Results are representative of 3 individual donors.

FIG. 7e illustrates a Western blot of hTECs after control (Ctl) or APK gene knockdown using indicated CRISPR/Cas9 lentivirus vectors.

FIG. 7f illustrates levels of MUC5AC in apical cell supernatants of hTECs cultured with or without IL-13 (50 ng/ml) using MAPK gene knockdown conditions in (e) with or without treatment with Compound 3% (100 nM) for 21 d.

FIG. 8a illustrates a pharmacokinetic (PK) analysis of Compound 3% in mini-pigs with plasma concentrations determined after oral dose of 2 mg/kg.

FIG. 8b illustrates protocol scheme for IL-13 challenge of right lung segments on Study Days 0 and 14 with BAL sample of right and left lung on indicated Study Days and either vehicle or compound treatment on Study Days 12-17.

FIG. 8c illustrates levels of MUC5AC and CLCA1 in BAL fluid for scheme in (b) using vehicle control (left column) or Compound 3% (C-396) at 2 mg/kg orally twice per day (right column).

FIG. 8d illustrates corresponding eosinophil counts in BAL for conditions in (c).

FIG. 8e illustrates MUC5AC and CLCA1 levels in BAL fluid after Sendai virus (SeV) infection of right lung segments on Study Day 0 and either vehicle or C-396 treatment on Study Days −2 to 21.

FIG. 9a illustrates a pharmacokinetic (PK) analysis of Compound 3% in mice, rats, and dogs with plasma concentrations determined after oral dose of 2 mg/kg.

FIG. 9b illustrates a protocol scheme for respiratory virus infection with Sendai virus (SeV) on Study Day 0 ($1 \times 10^5$ pfu intranasally) and vehicle or Compound 3% (C-396) treatment (2 mg/kg intraperitoneally twice per day) on indicated study days with sample analysis of lung tissue at 21 d after infection.

FIG. 9c illustrates body weights for each condition at 0-21 d after infection with SeV or control SeV-UV.

FIG. 9d illustrates levels of indicated mRNA in lung tissue for scheme in (a).

DETAILED DESCRIPTION

Figure 1:
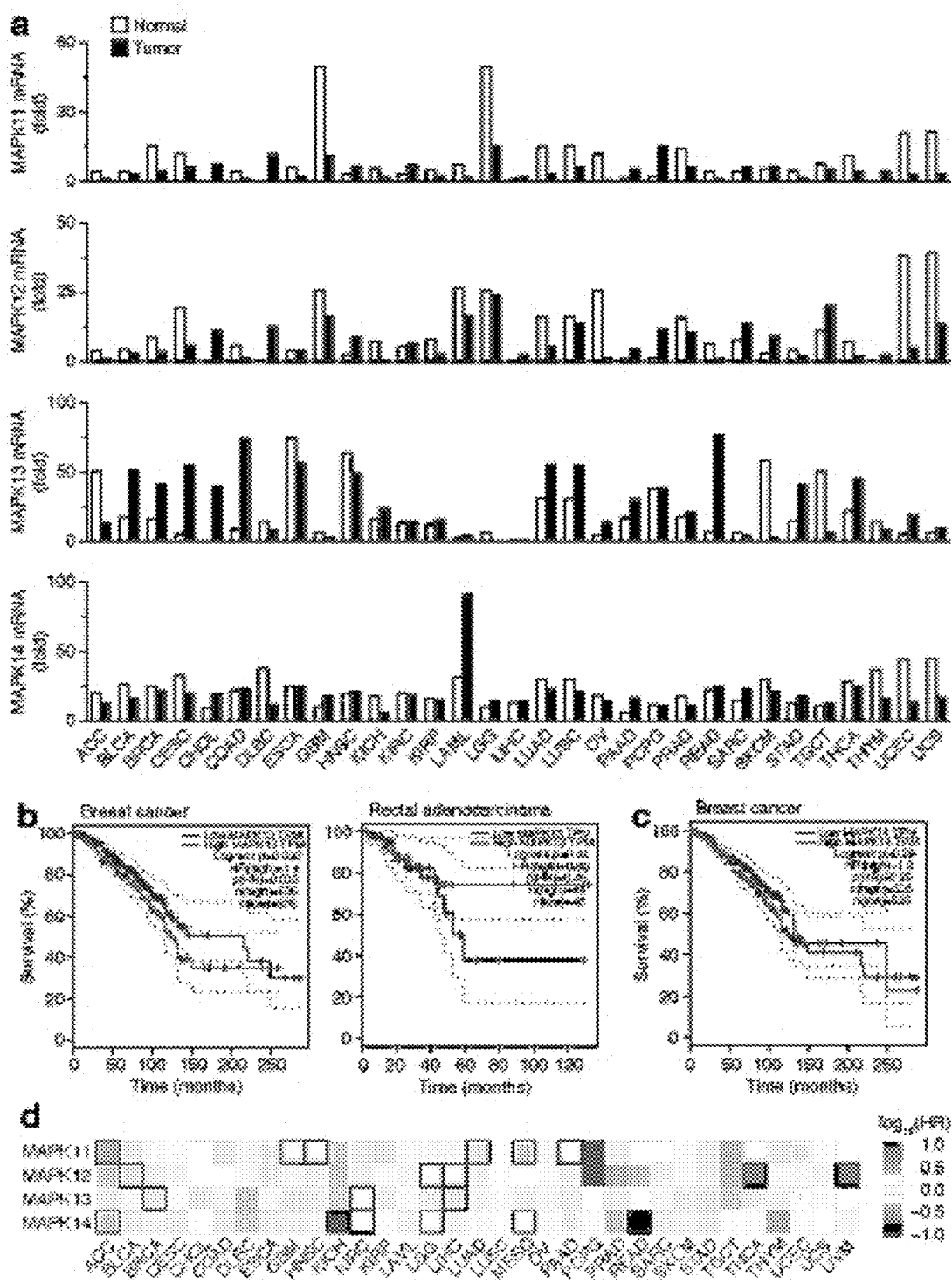
FIG. 1 illustrates that MAPK11-14 gene expression is linked to cancers and breast cancer survival.

The present disclosure is based, at least in part, on the discoveries that novel generation of MAPK13 inhibitors and combined MAPK13-other-kinase (e.g., combined MAPK13-MAPK14 or combined MAPK13-MAPK12) inhibitors have enhanced selectivity, potency and effectiveness regarding MAPK13 and combined MAPK13-other-kinase (e.g., combined MAPK13-MAPK14 or combined MAPK13-MAPK12) inhibitors in controlling respiratory mucus production disease often manifested by respiratory inflammation and mucus production and breast cancer often manifested by cancer cell growth proliferation and invasion.

Described herein are compositions for blocking mucus production and inflammation in respiratory diseases, including asthma, rhinitis, sinusitis, chronic obstructive pulmonary disease (COPD), and pulmonary fibrosis, and in respiratory infections or reactions to other environmental stimuli, and in other disorders of excess mucus secretion at other tissue sites, including breast and gastrointestinal tract.

Described herein are compositions for blocking or preventing cancer, including progression due to epithelial cell growth and migration in carcinomas such as breast cancer.

A MAPK13 inhibiting agent or combined MAPK13-other-kinase (e.g., combined MAPK13-MAPK14 or combined MAPK13-MAPK12) inhibiting agent can be an agent or compound that acts as both a MAPK13 inhibitor and as an inhibitor for another kinase such as MAPK14 or MAPK12. In other words, the MAPK13 inhibiting agent can have MAPK13 inhibiting activity and another kinase (e.g., MAPK14 or MAPK12) inhibiting activity. An example of a MAPK13-MAPK14-MAPK12 inhibitor is compound 3%. A MAPK13-MAPK14 inhibitor can block mucus production and inflammation. An example of a MAPK13-MAPK12 inhibitor is compound 282. A MAPK13-MAPK12 inhibitor can block cancer cell proliferation and invasiveness.

Alternatively, a MAPK13 inhibiting agent can be combined with one or more MAPK13 inhibiting agents or one or more inhibiting agents for another kinase such as MAPK14 or an unrelated kinase to provide an additive effect on respiratory disease or cancer or other inflammatory or fibrotic or degenerative disease. Such diseases include arthritis, diabetes, and dementia based on existing literature. In the present teachings, compounds are disclosed that have activity as inhibitors of mitogen-activated protein kinases (MAPKs). A compound of the present teachings can be highly specific for an individual MAPK, e.g., MAPK13, or can inhibit multiple MAPKs, e.g., MAPK13 and MAPK14.

The present teachings also include pharmaceutically acceptable salts, solvates, polymorphs, tautomers and stereoisomer of disclosed compounds.

The disclosed compounds have therapeutic uses in the treatment of various diseases, such as, for example, respiratory diseases and cancer.

The present teachings also include methods of synthesizing the compounds, and methods of assaying the compounds for biochemical or biological activity.

The term "prodrug" is used in its broadest sense and encompasses compounds that are converted in vivo to the compounds of the present teachings. Such prodrug compounds include, for example, compounds comprising an ester in place of a free hydroxy group, or an N-oxide in place of ring Nitrogen. Examples of ester prodrugs include alkyl esters, phosphate esters and esters formed from amino acids, such as valine.

The term "pharmaceutically acceptable ester" includes biologically acceptable esters of a compound of the present teachings such as sulphonic, phosphonic and carboxylic acid derivatives.

The present teachings include pharmaceutical compositions. In some embodiments, a pharmaceutical composition can comprise any of the compounds, pharmaceutically acceptable salts solvates, polymorphs, tautomers and stereoisomer thereof described herein, and a pharmaceutically acceptable excipient. An excipient of the present teachings can be any excipient known to skilled artisans, such as, without limitation, an excipient described in Rowe, R. C., et al., Handbook of Pharmaceutical Excipients, Fourth Edition, Pharmaceutical Press, 2003. A pharmaceutical composition of the present teachings can include a MAPK inhibitor disclosed herein and an excipient such as, but not limited to, a cyclodextrin, a PEG, a non-ionic surfactant, or an oil.

Pharmaceutical compositions of the present teachings can be prepared by procedures known in the art. For example, the compounds can be formulated into tablets, capsules, powders, suspensions, solutions for parenteral administration including intravenous, intramuscular, and subcutaneous administration, and into solutions for application onto patches for transdermal application with common and conventional carriers, binders, diluents, and excipients. In various configurations, powder particle size can be within the range of 0.1-50 microns. In various configurations, powder particle size can be 1-5 microns. In various configurations, a powder composition can be administered directly to the lung. In various configurations, a composition can be administered using a dry powder inhaler (DPI) apparatus.

Inert pharmaceutically acceptable carriers useful to form pharmaceutical formulations in accordance with the present teachings include starch, mannitol, calcium sulfate, dicalcium phosphate, magnesium stearate, silicic derivatives, and/or sugars such as sucrose, lactose, and glucose. Binding agents can include carboxymethyl cellulose and other cellulose derivatives, gelatin, natural and synthetic gums including alginates such as sodium alginate, polyethylene glycol, waxes and the like. Diluents useful in the present teachings can include a suitable oil, saline, sugar solutions such as aqueous dextrose or aqueous glucose, and glycols such as polyethylene or polypropylene glycol. Other excipients can include lubricants such as sodium oleate, sodium acetate, sodium stearate, sodium chloride, sodium benzoate, talc, and magnesium stearate, and the like; disintegrating agents including agar, calcium carbonate, sodium bicarbonate, starch, xanthan gum, and the like; and adsorptive carriers such as bentonite and kaolin. Coloring and flavoring agents can also be added to a pharmaceutical formulation.

Methods

Methods and compositions described herein utilize laboratory techniques well known to skilled artisans, and guidance can be found in laboratory manuals such as Sambrook and Russel (2006), Condensed Protocols from Molecular Cloning: A Laboratory Manual, Cold Spring Harbor Laboratory Press, ISBN 0879697717; Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Ausubel, F. M., et al., ed., Current Protocols in Molecular Biology, Wiley Interscience, 2003; Nagy, A., et al., Manipulating the Mouse Embryo: A Laboratory Manual (Third Edition), Cold Spring Harbor Laboratory Press, Cold Spring Harbor. N.Y., 2003; Hedrickson et al., Organic Chemistry 3rd edition. McGraw Hill, New York, 1970; Carruthers, W., and Coldham, I., Modern Methods of Organic Synthesis (4th Edition), Cambridge University Press, Cambridge. U.K., 2004; Graham Solomons T. W., et al., Organic Chemistry 9th edition, Wiley, John & Sons, Incorporated, 2007. Unless indicated otherwise, chemical descriptions and names follow standards of the International Union of Pure and Applied Chemistry (TUPAC), set forth in publications such as "Compendium of Chemical Terminology Gold Book" version 2.3.3. published by IUPAC in 2014. In addition, radicals on organic compounds can be further optionally substituted with one or more groups, which can be independently selected from the group consisting of halogen, cyano, hydroxyl. $C_{1-8}$alkyl ether; $C_{1-8}$alkyl hydroxyl; amine; $C_{1-8}$carboxylic acid; $C_{1-8}$ carboxyl; $C_{1-8}$alkyl amide, $C_{1-8}$alkyl urea, $C_{1-8}$alkyl carbamate, $C_{1-8}$alkyl (e.g., straight chain or branched), optionally containing unsaturation (e.g., alkene or alkyne); a $C_{2-8}$cycloalkyl optionally containing unsaturation or one oxygen or nitrogen atom; straight chain or branched $C_{1-8}$alkyl amine; heterocyclyl; heterocyclic amine; heterocyclic ether, morpholinyl; piperazinyl; pyrrolidinyl, aryl comprising a phenyl; heteroaryl containing from 1 to 4 N, O, or S atoms; unsubstituted phenyl ring; substituted phenyl ring; unsubstituted heterocyclyl; and substituted heterocyclyl, wherein the unsubstituted phenyl ring or substituted phenyl ring or heteroaryl ring can be optionally substituted with one or more groups independently selected from the group consisting of halogen; cyano; hydroxyl; amide; urea; carbamate; $C_{1-8}$alkyl ether, $C_{1-8}$alkyl amide; $C_{1-8}$alkyl urea; $C_{1-8}$alkyl carbamate; $C_{1-8}$alkyl hydroxyl; amine; $C_{1-8}$ carboxylic acid; $C_{1-8}$carboxyl; straight chain or branched $C_{1-8}$alkyl, optionally containing unsaturation (e.g., alkene or alkyne); straight chain or branched $C_{1-8}$alkyl amine, optionally containing unsaturation; a $C_{1-8}$cycloalkyl optionally containing unsaturation or one oxygen or nitrogen atom; straight chain or branched $C_{1-8}$alkyl amine; heterocyclyl; heterocyclic amine; aryl comprising a phenyl; and heteroaryl containing from 1 to 4 N, O, or S atoms; and the unsubstituted heterocyclyl or substituted heterocyclyl can be optionally substituted with one or more groups independently selected from the group consisting of halogen; cyano; hydroxyl; $C_{1-8}$alkyl ether; $C_{1-8}$alkyl hydroxyl; amine; $C_{1-8}$carboxylic acid; $C_{1-8}$-carboxyl; straight chain or branched $C_{1-8}$alkyl, optionally containing unsaturation; straight chain or branched $C_{1-8}$alkyl amine, optionally containing unsaturation; a $C_{2-10}$cycloalkyl optionally containing unsaturation or one oxygen or nitrogen atom; morpholinyl; piperazinyl; heterocyclyl; straight chain or branched $C_{1-8}$alkyl amine; heterocyclic amine; and aryl comprising a phenyl; and heteroaryl containing from 1 to 4 N, O, or S atoms. Any of the above can be further optionally substituted.

As used herein, the singular forms "a", "an" and "the" are intended to include the plural forms as well, unless the context indicates otherwise. Methods of administration of pharmaceuticals and dosage regimes can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. Non-limiting examples of administration methods include oral, i.v., i.m., inhaled, and aerosol. In some configurations, a MAPK inhibitor of the present teachings can be administered in a solution which can be administered by well-established means such as, without limitation, oral administration or by injection; or in a powder, which can be ingested orally or inhaled.

Administration

Without limitation, a MAPK inhibitor of the present teachings can be administered in a dosage range which can be determined using well known methods. A dosage range for administering a MAPK inhibitor of the present teachings can be, for example and without limitation, 5-5000 mg, and can be administered, for example, once per day, twice per day, three times per day, or four times per day.

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

A therapeutically effective amount of a MAPK13 inhibiting agent (or combination MAPK13 and other kinase inhibiting agent) can be administered at least once per week, at least one per day, at least twice a day, or at least 3 times per day.

Screening

Also provided are methods for screening.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 MW, or less than about 1000 MW, or less than about 800 MW) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl, heteroaryl, or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 550 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Salts

In various embodiments, a pharmaceutically acceptable salt of the present teachings can include acid addition salts, base addition salts, and the salts of quaternary amines and pyridiniums. An acid addition salts can be formed from a compound of the present teachings and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums can include, for example, chloride, bromide, iodide, sulfate, phosphate, methansulfonate, citrate, acetate, malonate, fumarate, sulfamate, or tartrate. A base addition salts can include but are not limited to salts such as sodium, potassium, calcium, lithium, magnesium, ammonium and alkylammonium. In some configurations, a salt of a MAPK inhibitor of the present teachings can be, for example and without limitation, a hydrochloride salt, a hydrobromide salt, a tosylate salt, a mesylate salt, a sulfate salt, a bisulfate salt, a fumarate salt, or a maleate salt. Also, basic nitrogen-containing groups can be quaternised with such agents as lower alkyl halides, such as methyl, ethyl, propyl, and butyl chlorides, bromides and iodides; dialkyl sulfates like dimethyl and diethyl sulfate; and others. A salt of the present teachings can be made by methods well-known to skilled artisans for example by treating the compound with an appropriate acid or base in the presence of a suitable solvent. I In some embodiments, a compound of the present teachings can be in crystalline form and/or as a solvate (e.g. hydrate). The term "solvate" as used herein refers to a complex of variable stoichiometry formed by a solute (such as a compound of the present teachings) and a solvent that does not interfere with the biological activity of the solute. Solvents can be, for example, water, ethanol or acetic acid. Methods of solvation are generally known within the art.

Synthesis of Compounds

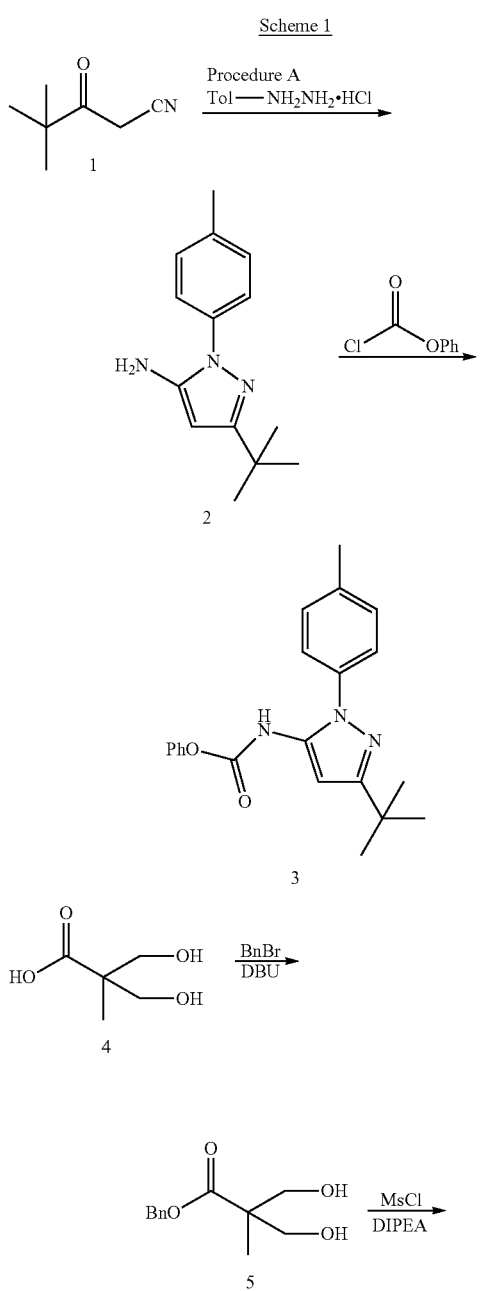

Scheme 1

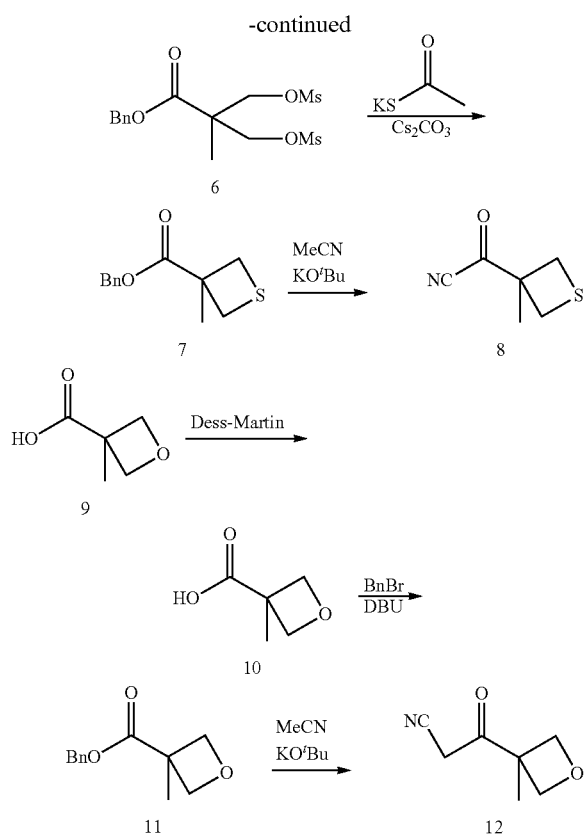

Procedure A.

5-tert-Butyl-2-p-tolyl-2H-pyrazol-3-ylamine (2). Pivaloylacetonitrile (1) (1.9 g, 15.1 mMol) was placed in a flask with tolylhydrazine hydrochloride (2.4 g, 15.1 mMol) in ethanol (19 mL) and the solution was heated to reflux for 1.5 hr. The solution was concentrated in vacuo until only a small amount of ethanol remained whereupon it was triturated with hexane, allowing it to stir for 1 hr before filtration of the white solid. Pyrazole 2 was isolated as its hydrochloride salt (3.6 g, 1.35 mMol) and was determined to be pure by LC-MS analysis (M+H=230.1).

Procedure B.

(5-tert-Butyl-2-p-tolyl-2H-pyrazol-3-yl)-carbamic acid phenyl ester (3). Pyrazole 2 (1.0 g, 4.4 mMol), diisopropylethylamine (684 mg, 5.3 mMol), and DCM (9 mL) were cooled to −10° C. and phenyl chloroformate (750 mg, 4.8 mMol) was added in a single portion. The solution was allowed to warm to 0° C. and stir for 30 min. The solution was partitioned between ether and aqueous sodium bicarbonate and the ether layer was washed with brine. The organic fraction was dried over anhydrous sodium sulfate and the solvent removed in vacuo. [Alternatively, for less reactive intermediates, the reaction with phenyl chloroformate was performed in DCM solvent in the presence of DIPEA as base.] After workup the residue purified using silica gel chromatography eluting with ethyl acetate (5%-50%)/hexane. Solvent removal afforded the carbamate (3) as a brittle foam (1.46 g) which provided a single peak by LC-MS analysis (M+H=350.3). $^1$H NMR (400 MHz, CDCl$_3$) δ: 7.40-7.38 (m, 3H), 7.34 (dd, J=8.4, Hz, 2H), 7.25 (tt, J=7.6 Hz, 2H), 7.12 (d, J=6.6 Hz, 2H) 6.95 (br s, 1H), 6.5 (s, 1H), 2.43 (s, 3H), 1.36 (s, 9H).

3-Hydroxy-2-hydroxymethyl-2-methyl-propionic acid benzyl ester (5). Commercially available diol 4 (50 g) and acetonitrile (650 ml) were cooled in an ice-bath and DBU (56.75 g) added. Benzyl bromide (61.85 g) was added over 30 min and the solution was allowed to warm to room temperature and stir for 24 hr. The solvent was removed in vacuo and the residue diluted with water (600 ml) and stirred in an ice-bath to cause crystallization of the benzyl ester, which was filtered and washed with cold water and then dried by pulling air through the solid. This material was suspended in ether and filtered, washing with ether to obtain pure benzyl ester 5 (52.8 g). A second fraction of benzyl ester was obtained by combining the washings, adding DCM (600 ml) and aqueous 2N hydrochloric acid (100 ml) and extracting. The organic layer was washed with water and then saturated sodium bicarbonate and brine. After drying over sodium sulfate the solvent was removed in vacuo to afford benzyl ester 5 as a solid (25.6 g). LC-MS retention time=3.338 min (M+H=225.2).

3-Methanesulfonyloxy-2-methanesulfonyloxymethyl-2-methyl-propionic acid benzyl ester (6). Benzyl ester 5 (131 g) was placed in a flask with DCM (1000 mi) and DIPEA (170.5 g) and cooled in an ice-bath. Methanesulfonyl chloride (140.7 g) was added slowly and the reaction stirred for 30 min. The solution was extracted with water, aqueous 2N hydrochloric acid, water (2-), saturated aqueous sodium bicarbonate, and brine. Drying over sodium sulfate and solvent removal in vacuo afforded 208.8 g of dimesylate 6 as a viscous liquid in greater than 95% purity. LC-MS retention time=4.486 min (no M+H peak); TLC Rf=0.55 (ethyl acetate/hexane; 1:1).

3-Methyl-thietane-3-carboxylic acid benzyl ester (7). Dimesylate 6 (120.2 g) was placed in a flask fitted with an mechanical stirrer with DMF (1000 ml) and cesium carbonate (154 g) and stirred while cooling in an ice-bath. Potassium thioacetate (36.1 g) was added in portions while maintaining a nitrogen atmosphere and the mixture heated to 60° C. The reaction was maintained overnight while monitoring using HPLC for completion (30 hr). Ice water was added to the mixture followed by ether and the mixture was partitioned, and the organic layer was washed with water (5×) and then dried over sodium sulfate. Solvent removal afforded 73 g of a brown oil that was purified by silica gel chromatography, eluting with a gradient comprised of 2% to 8% ethyl acetate in hexane to obtain 24 g of thiooxetane 7. LC-MS retention time=5.08 min (M+H=223.0); TLC Rf=0.78 (ethyl acetate hexane; 1:9).

3-(3-Methyl-thietan-3-yl)-3-oxo-propionitrile (8). Potassium t-butoxide (3.78 g) and dry THF (15 ml) were placed into a flask and cooled in an ice-bath. Dry acetonitrile (1.01 g) was added and then thiooxetane 7 (5 g) dissolved in THF (10 ml) was rapidly added with efficient stirring. After 30 min the reaction was complete. Aqueous 2N hydrochloric acid was added and the solution was extracted with ether. The layers were partitioned and the organic layer dried over sodium sulfate and the solvent removed at 50 torr to obtain 5.5 g of a yellow oil which was purified using silica gel chromatography, eluting with a gradient comprised of 0% to 50% ethyl acetate in hexane. Keto-nitrile 8 was obtained as an oil (3.41 g). TLC Rf=0.8 (ethyl acetate/hexane; 1:1).

3-Methyl-oxetane-3-carboxylic acid benzyl ester (11). Commercially available oxetane 9 (17.7 g), (diacetoxyiodo) benzene (111.7 g), acetonitrile (200 ml), and water (200 ml) were cooled in an ice-bath. TEMPO (5.42 g) was added and the solution was stirred overnight at room temperature. The solution was cooled in an ice bath and solid sodium hydroxide (38 g) was added and stirred until dissolved and the solution was washed with ether (2×). The aqueous layer was cooled in an ice-bath and acidified with 12 N hydrochloric acid to pH 3 and then extracted with ether (3×500 ml). The solvent was removed in vacuo to afford the carboxylic acid (10) as a liquid (14 g). Carboxylic acid 10 (9 g) was dissolved in acetonitrile (180 ml) and cooled in an ice-bath. DBU (13 g) was added followed by slow addition of benzyl bromide (14 g) and the solution stirred overnight at room temperature. The solvent was removed in vacuo to reduce volume by one-half and then the residue was partitioned between ether and aqueous 1N hydrochloric acid. The organic layer was washed with water (2×) and dried over sodium sulfate. Solvent removal afforded a brown oil (14.8 g) that was purified using silica gel chromatography, eluting with a gradient comprising 0% to 30% ethyl acetate in hexane. Benzyl ester 11 was obtained (9.7 g). LC-MS retention time=4.25 min (M+H not observed); TLC Rf=0.35 (ethyl acetatehexane; 1:9).

3-(3-Methyl-oxetan-3-yl)-3-oxo-propionitrile (12). Solid potassium t-butoxide (7.9 g) was placed in a dry flask with THF (35 ml) and cooled in an ice-bath. Dry acetonitrile (2.0 g) was added followed by benzyl ester 11 (9.7 g) in THF (15 m). The reaction was followed using LC-MS to determine completion and then and aqueous 2N hydrochloric acid was added. The reaction was extracted with DCM (2×150 ml) and the organic layer washed with water and then brine and dried over sodium sulfate. Solvent removal afforded 9.4 g of a pale yellow oil that was purified using silica gel chromatography, eluting with a gradient comprised of 5% to 90% ethyl acetate in hexane to obtain 12 as a pale yellow oil (4.68 g).

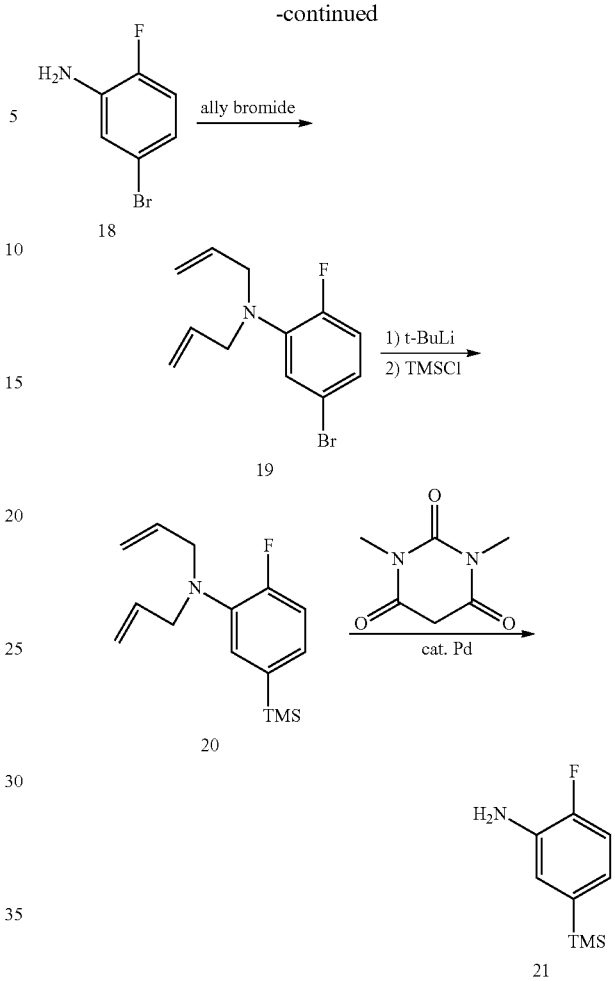

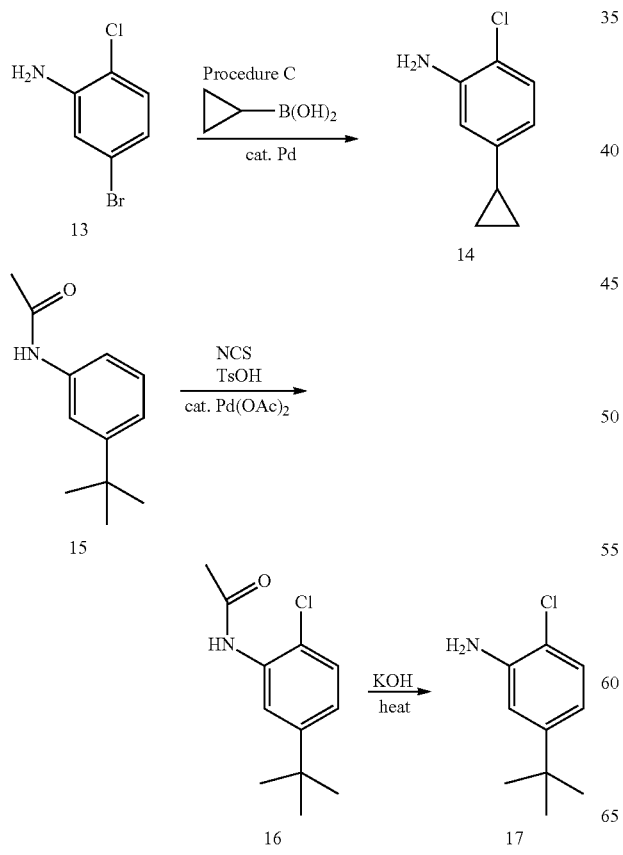

Procedure C.

2-Chloro-5-cyclopropyl-phenylamine (14). 5-Bromo-2-chloro-phenylamine (20.9 g, 101.5 mMol) was placed in a flask with cyclopropylboronic acid (11.3 g, 132 mMol), potassium carbonate (75 g, 355 mMol), palladium acetate (1.37 g, 11.34 mMol), and tricyclohexylphosphine (3.41 g, 12.1 mMol). The flask was flushed with nitrogen and toluene (280 mL) and water (70 mL) added with stirring. The slurry was heated to 80° C. and stirred overnight. After cooling, the mixture was filtered through diatomaceous earth and extracted with ether and water. The organic layer was washed 2× with water and dried over sodium sulfate and the solvent removed in vacuo to afford a dark liquid. This was purified using silica gel chromatography, eluting with DCM/hexane (7:93). Solvent removal afforded the title compound as a waxy solid (7.2 g). LC-MS retention time=4.33 min (M+H=168.1); TLC Rf=0.35 (ethyl acetate/hexane; 5:95)

N-(5-tert-Butyl-2-chloro-phenyl)-acetamide (16). N-3-tert-Butyl-phenyl)-acetamide (15)(28 g, 146 mMol) was placed in a round bottom flask fitted with an overhead stirrer. To this was added N-chlorosuccinimide (20.3 g, 152 mMol), p-toluenesulfonic acid hydrate (13.9 g, 73 mMol), palladium acetate (1.64 g, 7.32 mMol), and toluene (450 mL). The slurry was stirred overnight after which it was diluted with DCM (50 mL) and filtered through diatomaceous earth. The filtrate was washed with 10% aqueous sodium thiosulfate, water (2×), aqueous sodium bicarbonate (2×), and brine, and then dried over sodium sulfate. Solvent removal afforded a yellow-brown solid which was dissolved in hot hexane containing ~4% DCM and allowed to cool while stirring. The product precipitated as a white solid which was isolated by filtration and then rinsed with more hexane. A second crop was obtained and the solids combined and dried in vacuo to afford 13.3 g of 16 as a white solid. LC-MS retention time=4.479 min (M+H=226.1).

5-tert-Butyl-2-chloro-phenylamine (17). Amide 16 (29.4 g, 130.7 mMol) and potassium hydroxide (43.9 g, 784 mMol) were combined in a flask and water (130 mL) and ethanol (390 mL) added and the mixture refluxed overnight. The solvent was removed in vacuo and the residue extracted with ether and water. The ether layer was washed with water 3× followed by brine, then dried over sodium sulfate and the solvent removed in vacuo to afford a yellow liquid. This was dissolved in ether/hexane (1:1) and filtered through a short plug (50 mL) of silica gel. Solvent removal afforded 24 g of almost pure 17. This was dissolved in an xs of hydrogen chloride in methanol, followed by removal of the volatiles in vacuo to obtain a solid, which was dissolved in hot methanol (55 mL) and stirred while adding ether (220 mL). The thick powder slurry was eventually cooled to 0° C. and filtered, rinsing with ether. A second crop was also obtained and these were combined and the white solids were dried overnight at 45' in vacuo to afford 50 g of pure 17. LC-MS retention time=4.83 min (M+H=184.1); TLC Rf=0.35 (ethyl acetate/hexane: 10:90).

Scheme 3

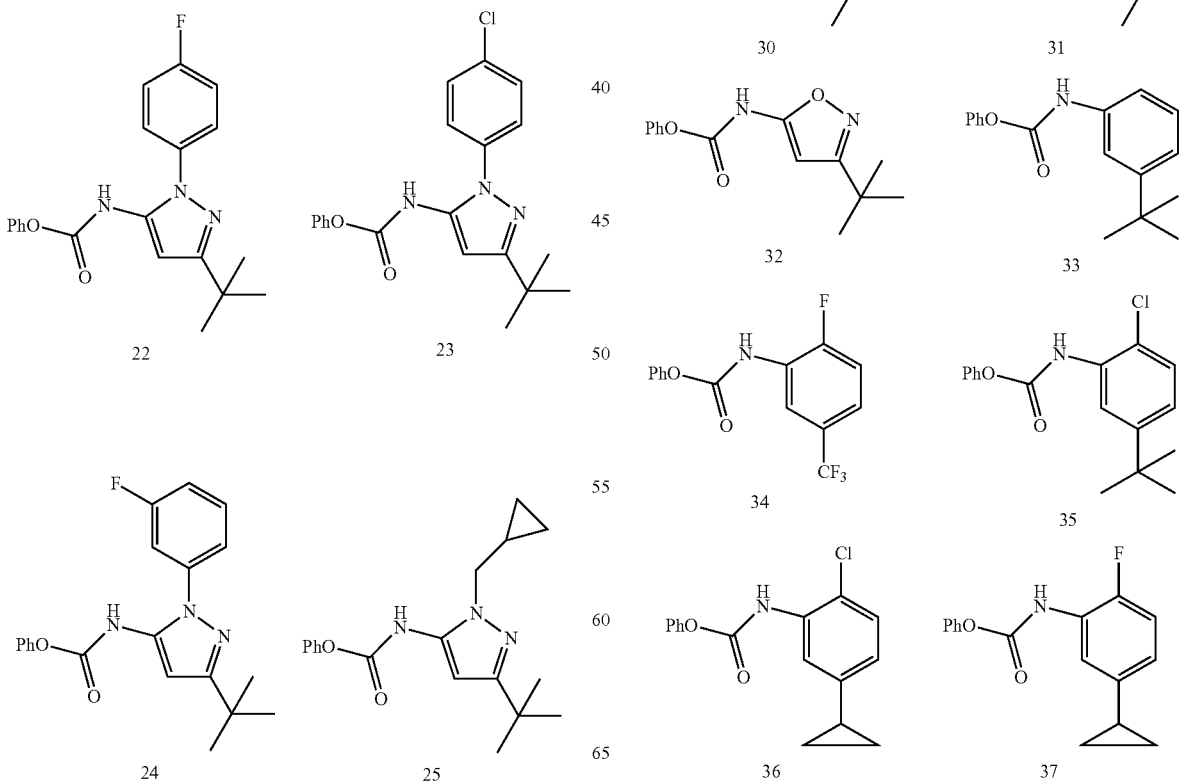

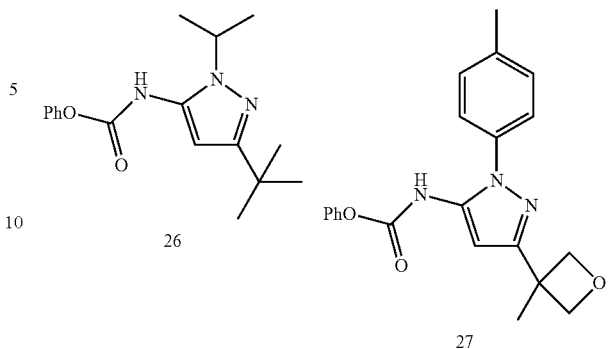

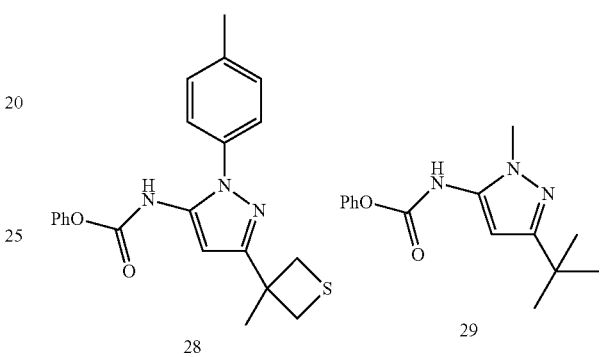

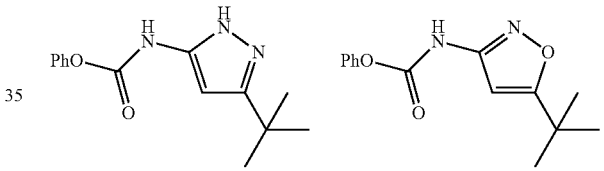

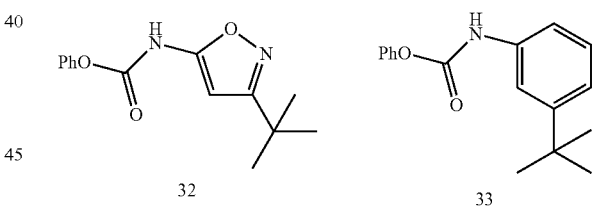

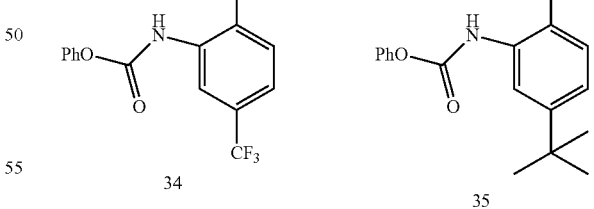

109
-continued
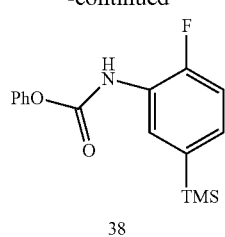
38
Scheme 4
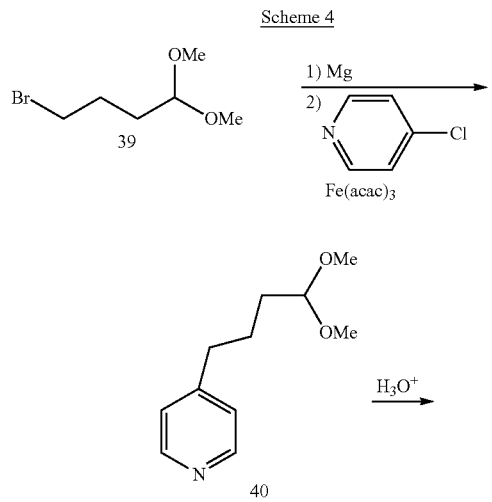
110
-continued
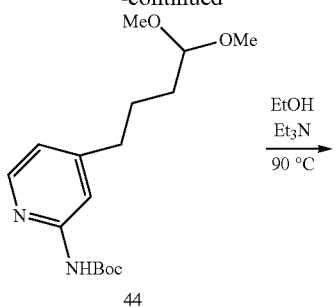
44
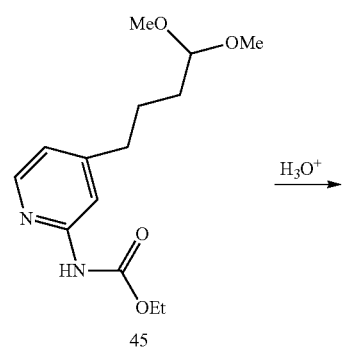
45
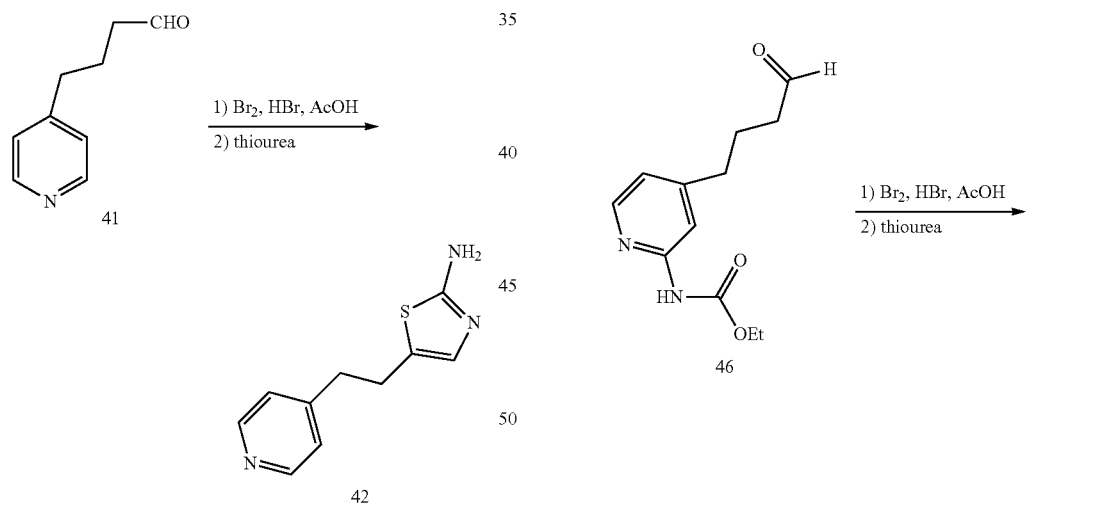
46
47
Scheme 5
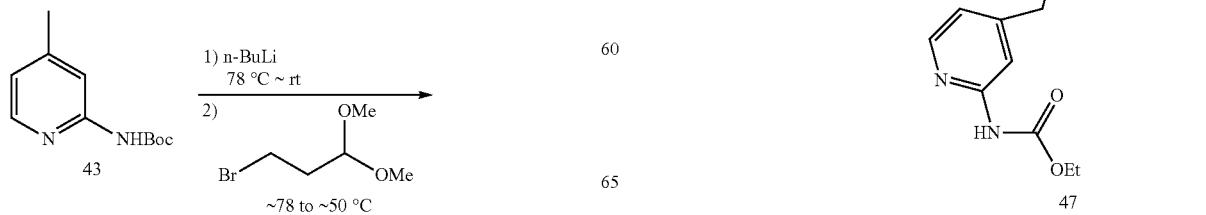

Scheme 6
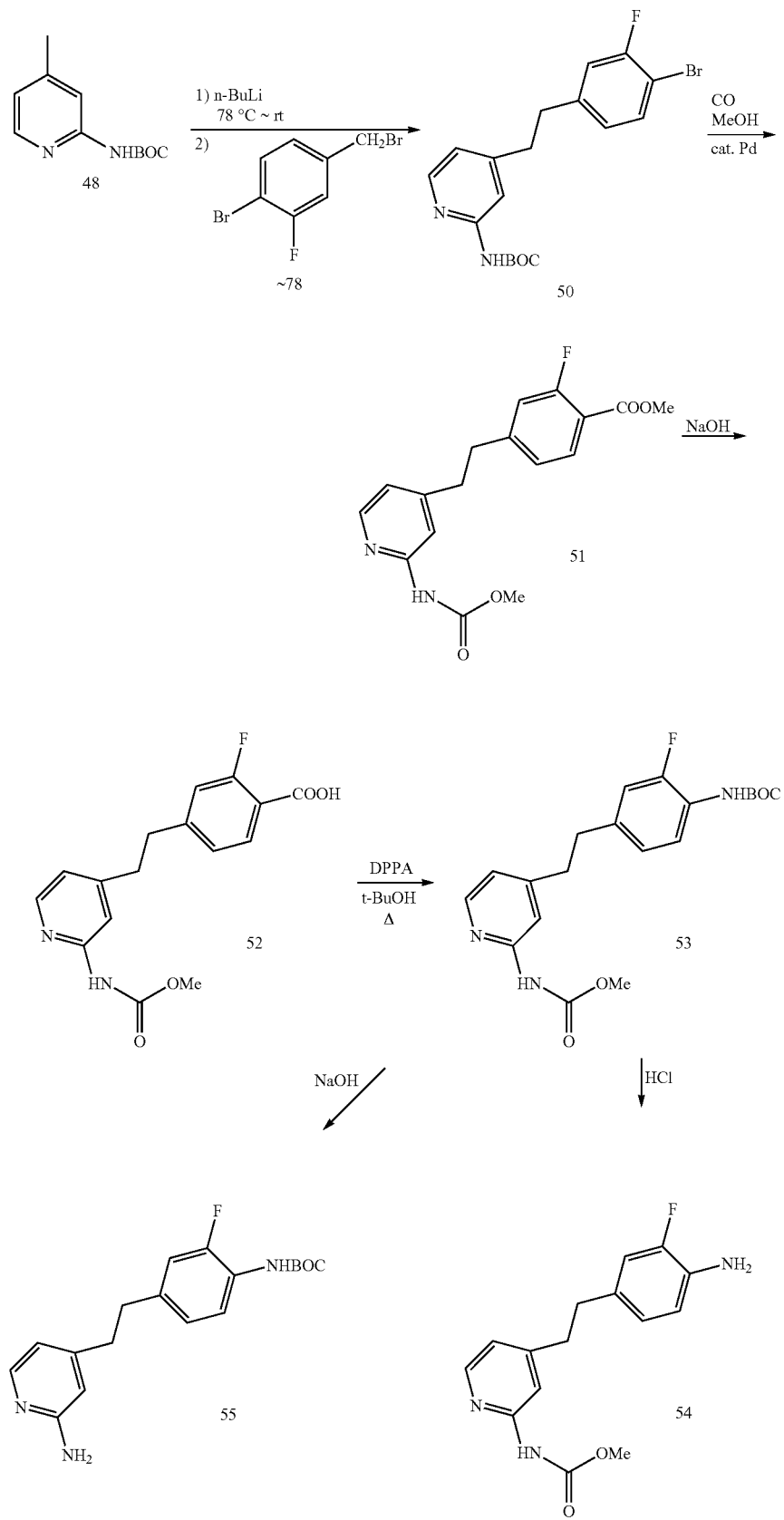

Scheme 7
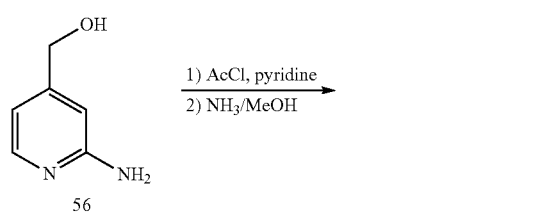
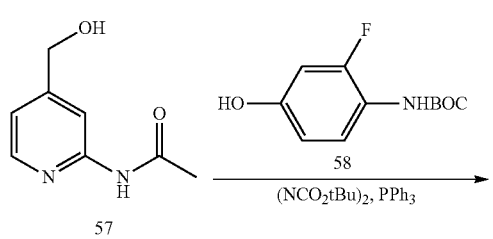
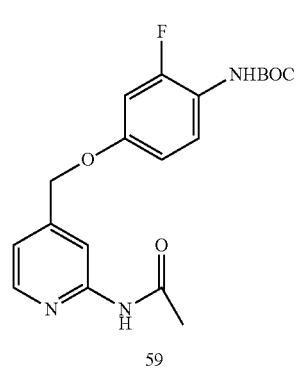
Scheme 8
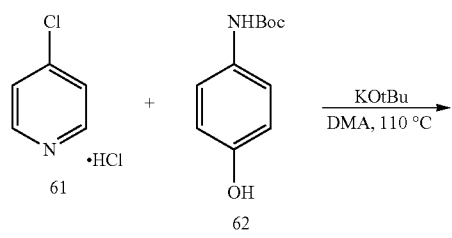
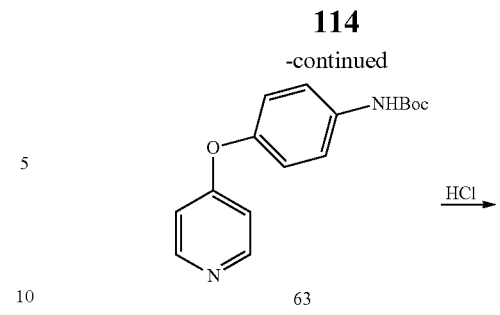
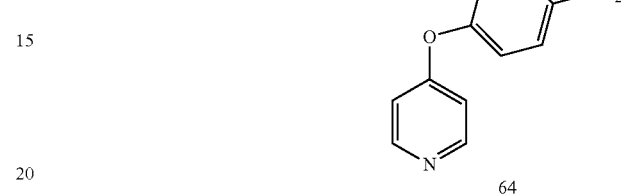
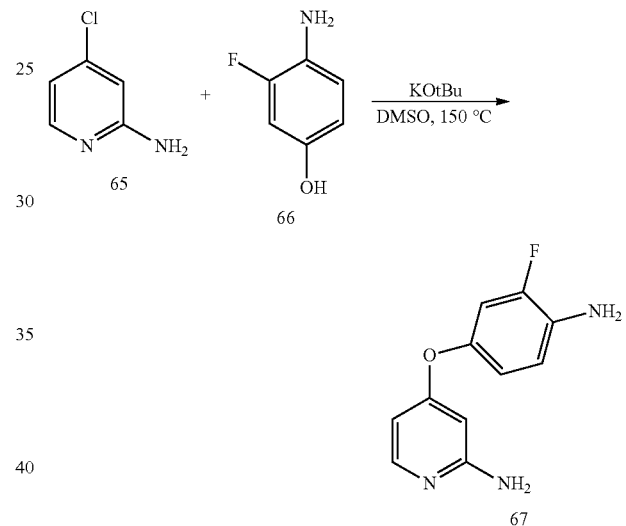
Scheme 9: Synthesis of Formula I Compounds
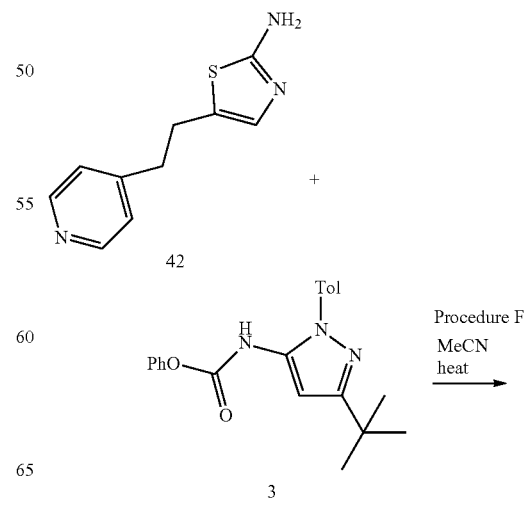

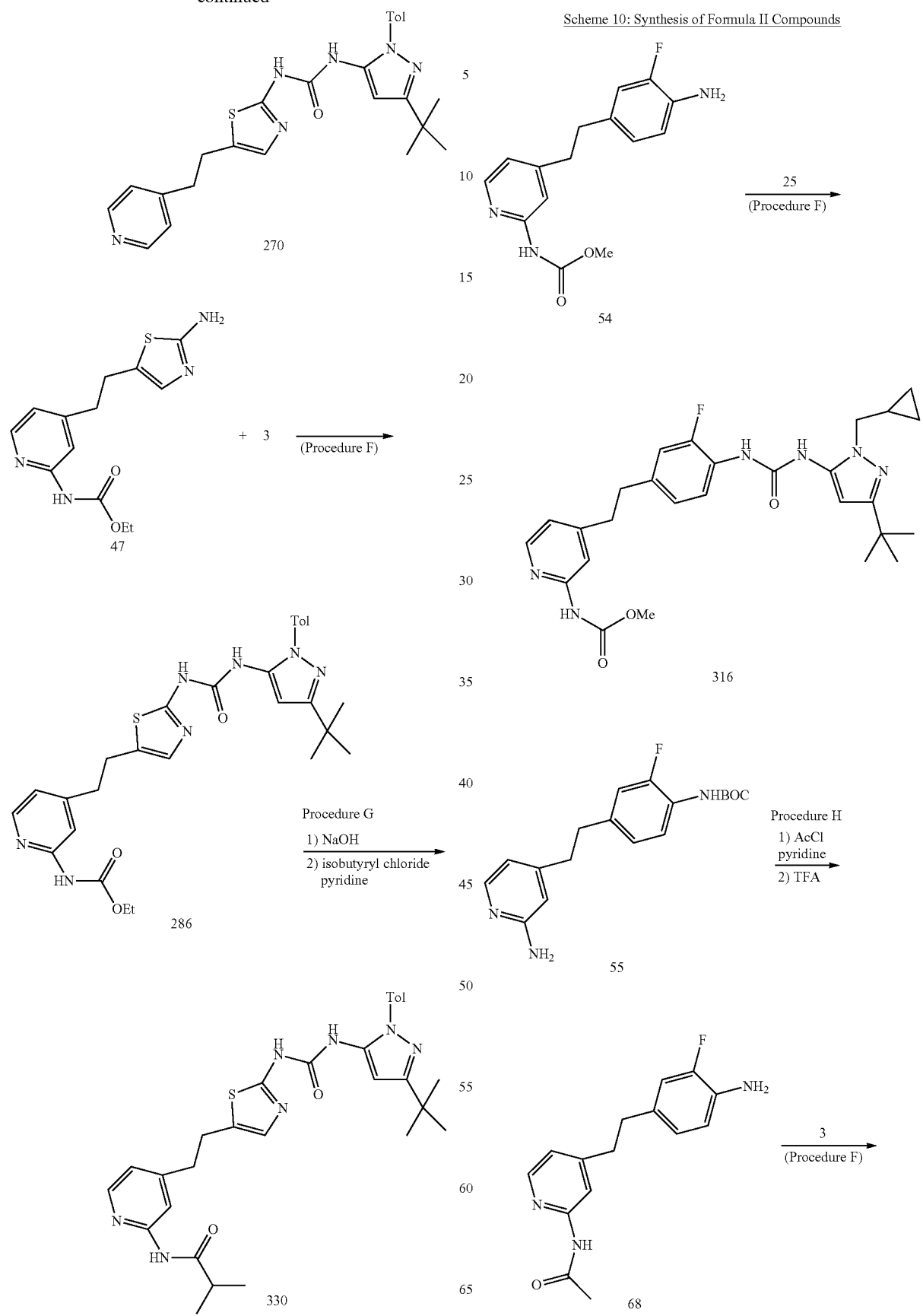

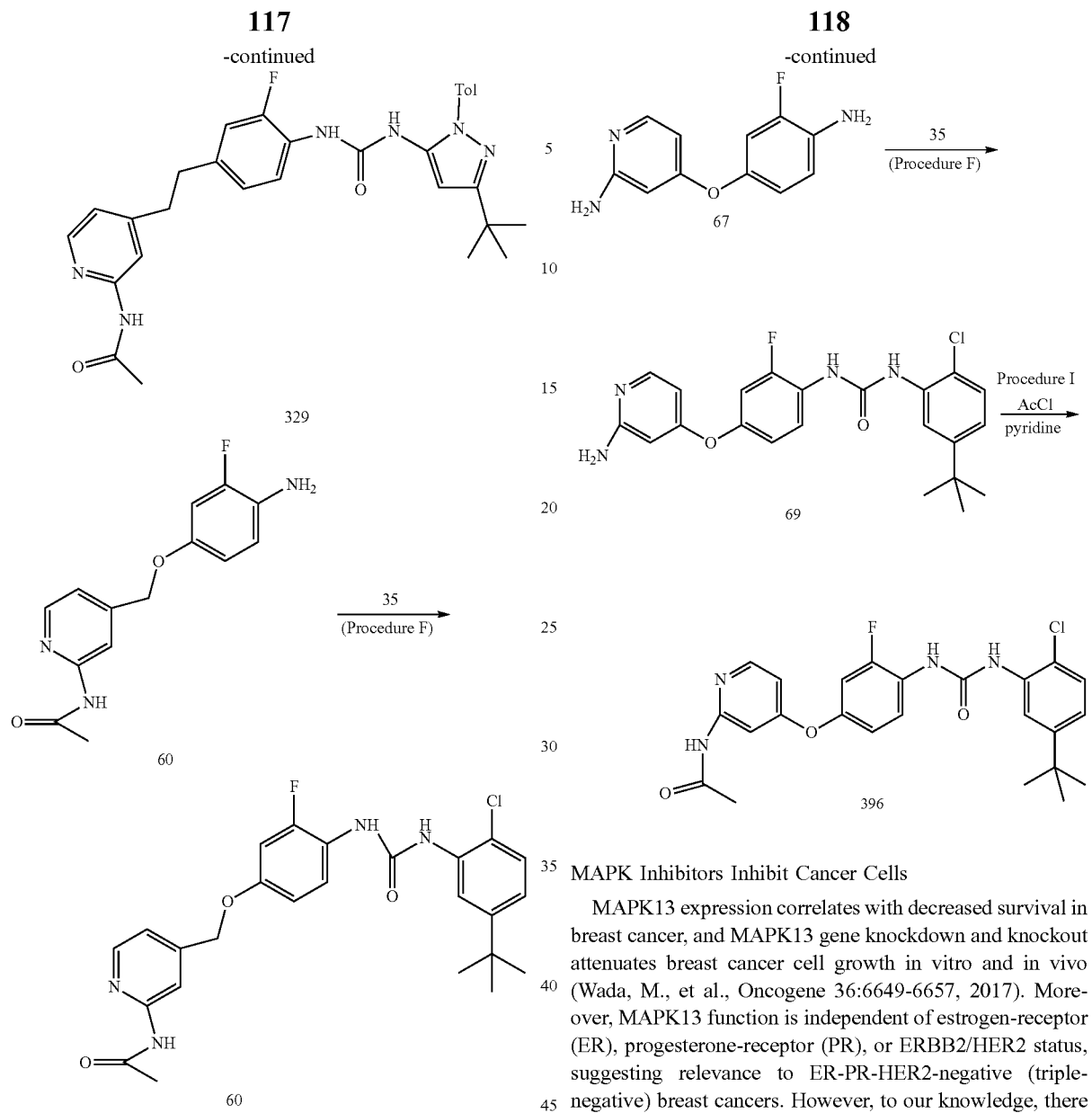

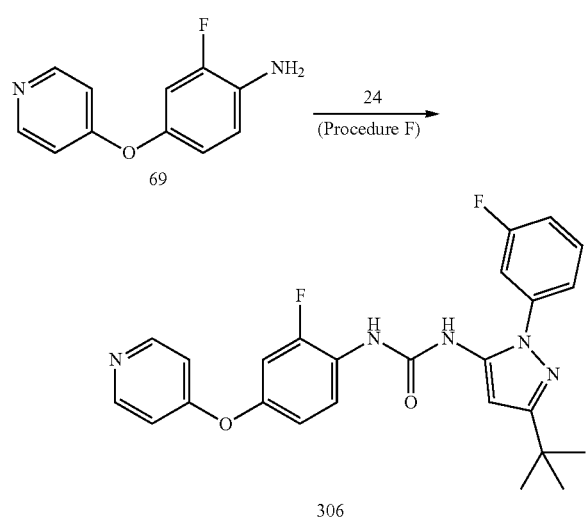

Scheme 11. Synthesis of Formula III Compounds

MAPK Inhibitors Inhibit Cancer Cells

MAPK13 expression correlates with decreased survival in breast cancer, and MAPK13 gene knockdown and knockout attenuates breast cancer cell growth in vitro and in vivo (Wada, M., et al., Oncogene 36:6649-6657, 2017). Moreover, MAPK13 function is independent of estrogen-receptor (ER), progesterone-receptor (PR), or ERBB2/HER2 status, suggesting relevance to ER-PR-HER2-negative (triple-negative) breast cancers. However, to our knowledge, there were no MAPK13 inhibitors available to test this application (O'Callaghan, C., et al., Int. J. Cell Biol. 2014:1-12).

The inventors are defining a new signal transduction pathway that regulates the formation and function of secretory (mucin-producing) epithelial cells in airway and breast tissues (FIG. 1). Key elements of this pathway include IL-13-driven expression and activation of MAPK13 that is required for epithelial progenitor cell differentiation towards mucous cells (typical of airway disease) (Tyner, J. W., et al., J. Clin. Invest. 116:309-321; Kim, E. Y., et al., Nat. Med. 14:633-640, PMCID: PMC2575848; Alevy, Y., et al., J. Clin. Invest. 122:4555-4568, PMCID: PMC3533556; Byers, D. E., et al., J. Clin. Invest. 123:3967-3982, PMCID: PMC3754239) and epithelial stem cell proliferation (typical of carcinoma). These observations fit with the role of the type 2 immune response in airway disease with mucous cell metaplasia/hyperplasia (Holtzman. M. J., et al., Nat. Rev. Immunol. 14:686-698. PMCID; PMC4782595) and breast cancer with uncontrolled epithelial cell proliferation and invasion (Aspord, C., et al., J. Exp. Med. 204:1037-1047, 2007; Venmar, K. T., et al., Cancer Res. 74:4329-4340, 2010; Park, M. H., et al., Ann Surg Oncol 24:3780-3787, 2017; Gaggianesi, M., et al., Cancer Res. 77:3268-3279, 2017; Miska, J. et al., J. Exp. Med. 215:841-858, 2018; Suzuki, A., et al., Cytokine 75:79-88, 2015), thereby reconciling why two distinct types of disease might be linked with a common control mechanism. Moreover, MAPK13 activation is often localized to basal-like progenitor-stem cells, raising the issue of relevance to basal-like triple-negative breast cancer cells. However, definition of biological significance for MAPK13 function has heretofore been difficult because of the lack of an available small-molecule kinase inhibitor (SMK) for MAPK13. As developed in the next section, we took the unusual step of building on our biological discoveries to construct a full-spectrum drug discovery program aimed at generating and developing the first MAPK13 inhibitor. We now find that our newest inhibitors are active in airway progenitor epithelial cells to control mucus production and breast cancer cells to control cell proliferation.

The inventors have developed inhibitors that block mucous cell formation safely in vitro (with a cell-based IC50=10 pM) and in vivo (with an orally-dosed pig model). In doing that work, we discovered MAPK13 control of cell proliferation that extended to other types of secretory epithelial cells, notably breast cancer cells. Our data fits with observations that MAPK13 expression correlates with poor prognosis in breast cancer (FIG. 1), and MAPK13 gene-knockdown decreases proliferation and invasiveness of breast cancer cells in culture while MAPK13 gene-knockout decreases growth and metastasis of breast cancer in MMTV-PyMT transgenic mice (Wada, M., et al., Oncogene 36:6649-6657, 2017).

FIG. 1 illustrates that MAPK11-14 gene expression is linked to cancers and breast cancer survival. (a) MAPK11-14 mRNA level in normal versus tumor tissue for indicated types of cancer. (b) Survival rates for breast cancer versus rectal adenocarcinoma patients with low versus high expression of MAPK13 mRNA in tpm. (c) Corresponding survival rates in patients with breast cancer with low versus high expression of MAPK14 mRNA. (d) Corresponding survival rates in patients with cancer relative to MAPK11-14 mRNA expression. Boxes with black frame indicate $P<0.05$. Analysis from GEPIA database at http://gepia.cancer-pku.cn.

The inventors have identified a type 2 immune signaling pathway that requires MAPK13 function, and we proceeded to develop MAPK13 inhibitors that effectively attenuated TL-13-driven transition of airway progenitor epithelial cells towards mucous cell metaplasia/hyperplasia (Tyner, J. W., et al., J. Clin. Invest. 116:309-321; Kim, E. Y., et al., Nat. Med. 14:633-640, PMCID: PMC2575848; Alevy, Y., et al., J. Clin. Invest, 122:4555-4568, PMCID: PMC3533556; Byers, D. E., et al., J. Clin. Invest. 123:3967-3982. PMCD; PMC3754239, Patel, A. C., et al., Genomics 25:502-513, 2006; Wu, K., et al., J. Exp. Med. 212:681-697, 2015 PMCID: PMC4419356; Gerovac, B. J, et al., Am. J. Respir. Crit. Care Med. 2018).

The inventors investigated potential MAPK13 inhibitors with increased potency and selectivity compared to known inhibitors. They established a comprehensive structure-based drug design program encompassing full structural (X-ray crystallography), computational (in silico docking), biochemical (enzymology), kinetic (biolayer interferometry), thermodynamic (ITC), and functional characterization of new MAPK13 inhibitors. The initial strategy was based on scaffold hopping from a MAPK14 inhibitor (Compound 43, also known as BIRB-796), where replacing the bulky naphthalene moiety with the narrower thiazole allowed for a better fit into the more restricted MAPK13 pocket for binding ATP (FIG. 2a,b), extending our earlier descriptions of initial compound generation (Alevy, Y., et al., J. Clin. Invest. 122:4555-4568, PMCID: PMC3533556; Byers, D. E., et al., J. Clin. Invest. 123:3967-3982, PMCID: PMC3754239). Co-crystal structures showed that the compounds with this change, such as Compound 89, continue to bind to MAPK13 with the desired DFG-out binding mode that inhibits drug release and thereby results in prolonged engagement and increased efficacy (FIG. 2a,b). Subsequent analogs such as Compound 282 incorporated changes particularly in the hinge-binding region to generate structures with the goal of promoting potency and selectivity for a drug with characteristics suitable for oral dosing. In particular, Compound 282 forms potential hydrogen bonds between acetamide-NH and M110 in the hinge region in addition to urea-O with D168 in the DFG region, urea-NH with E72 in the alpha-C-helix, and pyrazol-NH with D168-0 as well as three sets of hydrophobic interactions as keys to structure-function for drug design.

Under this strategy, the inventors generated a total of 396 chemical analogs to date. Each of these analogs were checked for physical chemical characteristics based on molecular weight, Lipinski's Rule of 5, partition coefficient (log P), and topological polar surface area (tPSA). Acceptable analogs were assessed for IC50 in MAPK13 and MAPK14 enzyme assays, using inhibition of the closely related MAPK14 as a surrogate for specificity against the broader kinome.

In addition, the compounds were tested for inhibition of IL-13-stimulated mucus formation in primary-culture human and porcine airway epithelial cells as part of our search for blockade of mucous cell metaplasia. In this system, compounds also were assessed for evidence of toxicity based on cell integrity using transepithelial electrical resistance and on cell metabolism using resazurin assay at 21 d of compound treatment. These approaches resulted in a panel of 33 compounds as potent, selective, and nontoxic MAPK13 inhibitors in addition to three compounds with selective MAPK14 inhibition to serve as controls. The therapeutic index for these compounds in the airway epithelial cell assay system, which we define as therapeutic ratio=IC50/lowest concentration exhibiting any decrease in TEER or increase in resazurin value) was always greater than 1000 and generally >10,000. This project has progressed to identify a lead compound that fully blocks IL-13-stimulated mucous cell metaplasia with oral dosing in pigs.

Figure 2:
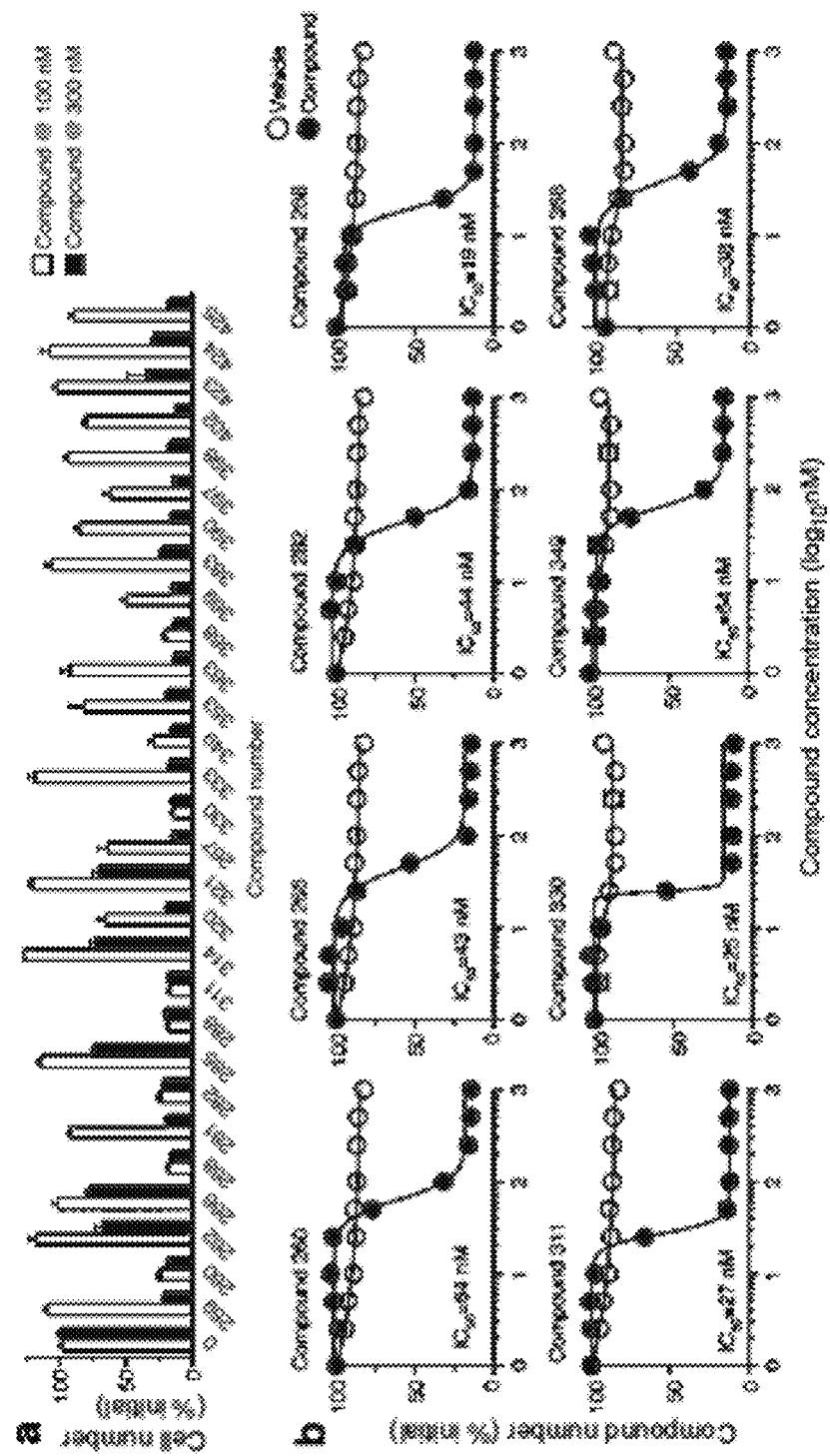
FIG. 2 illustrates initial identification of compounds that effectively control breast cancer cell growth.

FIG. 2 illustrates Initial identification of compounds that effectively control breast cancer cell growth. (a) Effect of hit compounds (n=13) with a significant effect on MDA-MB-231 cell number out of a compound library (n=428) screened for activity at concentrations of 100 and 300 nM for 3 d. Values represent mean±s.e.m. (b) Dose-response (1-1000 nM for 3 d) for the most active compounds (n=8) from screen described in (a).

Second, the inventors initiated studies of luminal A, ER-positive, HER2-negative MCF-7 and basal-like triple-negative MDA-MB-231 breast cancer cell lines and found that both lines expresses MAPK13 based on immunostaining (FIG. 3a), consistent with PCR-based assays of MAPK13 mRNA levels (Chen, L., Cancer Res. 69:8853-8861, 2009). In addition, we showed that selective and potent MAPK13 inhibitors markedly blocked cell proliferation of these lines based on a DNA-content assay (FIG. 3b,c and Table 3), with Compound 282 as the most effective in assays of cell-based growth-inhibition ($GI_{50}$=44 nM) and MAPK13 enzyme-based inhibition (IC50=9 nM). By contrast, selective and potent MAPK14 inhibitors such as Compound 43 caused no decrease in breast cancer cell proliferation (FIG. 3b,c and Table 3), suggesting that MAPK14 blockade is not sufficient to control breast cancer. The findings were therefore consistent with our proposal that MAPK3 inhibition is more relevant to control of epithelial cell proliferation in the setting of type 2 immune responses. Neither MAPK13 nor MAPK14 inhibitor compounds (up to 1 µM) exhibited any evidence of cytotoxicity in cell culture. The inventors also found that IL-13 stimulation of airway epithelial cells resulted in relatively selective and marked activation of MAPK13 and ERK2 using phosphokinase-antibody arrays for MAPK and RTK activation and that IL-13 stimulation of MDA-MB-231 cells caused significant increases in cell proliferation. These results indicate MAPK13-ERK2 is a candidate pathway for regulating airway and perhaps breast epithelial cell proliferation, the latter even without IL-13.

TABLE 3

Characteristics of hit compounds for blocking MAPK13 and MAPK14 enzyme activity and MCF-7 and MDA-MB-231 cell proliferation in culture.

| Compound No. | MAPK13 $IC_{50}$ (nM) | MAPK14 $IC_{50}^1$ (nM) | MCF-7 $IC_{50}$ (nM) | MDA-MB-231 $IC_{50}^1$ (nM) |
|---|---|---|---|---|
| 43 | 500 | 5 | >1000 | >1000 |
| 282 | 9 | 129 | 44 | 45 |
| 283 | 8 | 139 | 85 | 71 |
| 331 | 11 | 202 | 87 | 79 |
| 332 | 18 | 193 | 65 | 92 |
| 391 | 6 | 6 | 99 | 78 |
| 394 | 9 | 5 | 65 | 121 |
| 395 | 11 | 4 | 88 | 76 |

Figure 3:
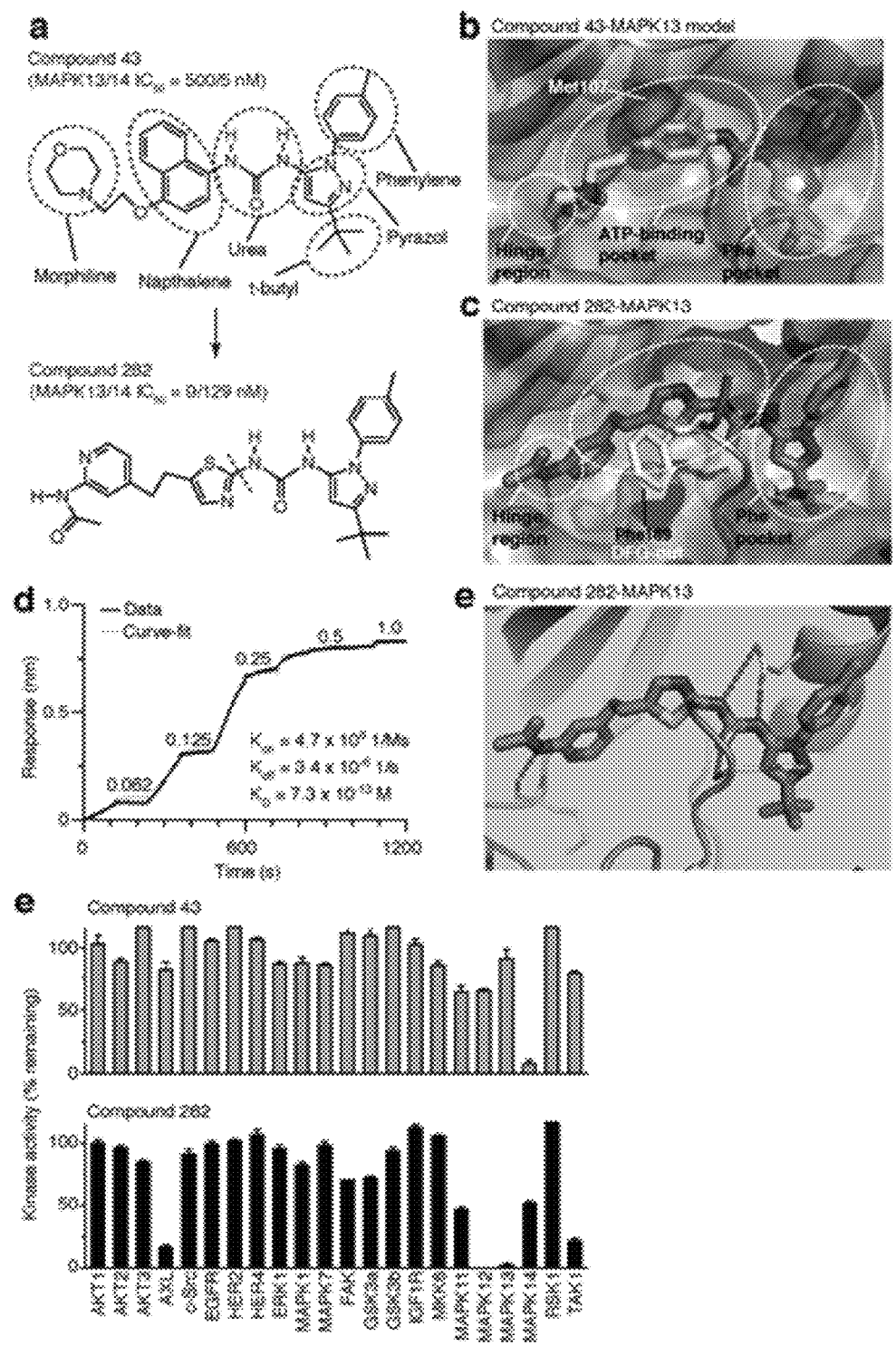
FIG. 3 illustrates that Compound 282 exhibits favorable binding and selectivity.

$^1IC_{50}$ = compound concentration for 50% decrease in cell number at 3 d in culture FIG. 3 illustrates the inventor's design plan for Compound 282 that exhibits favorable binding and selectivity. (a) Compound 43 (BIRB-796) represents the starting point for scaffold hopping to compounds such as Compound 282 (with modifications in magenta) to decrease MAPK13 IC50. (b) Structures of Compound 43 and 282 bound to MAPK13 illustrating functional targets and DFG-out binding mode. (c) Biolayer interferometry (BLI) analysis for slow on-off binding of Compound 282 to MAPK13. (d) Level of indicated kinase activities remaining after incubation with Compounds 43 and 282 (100 nM) assessed with a custom-kinase panel relevant to cell-based phosphokinase antibody arrays and cancer biology.

Figure 4:
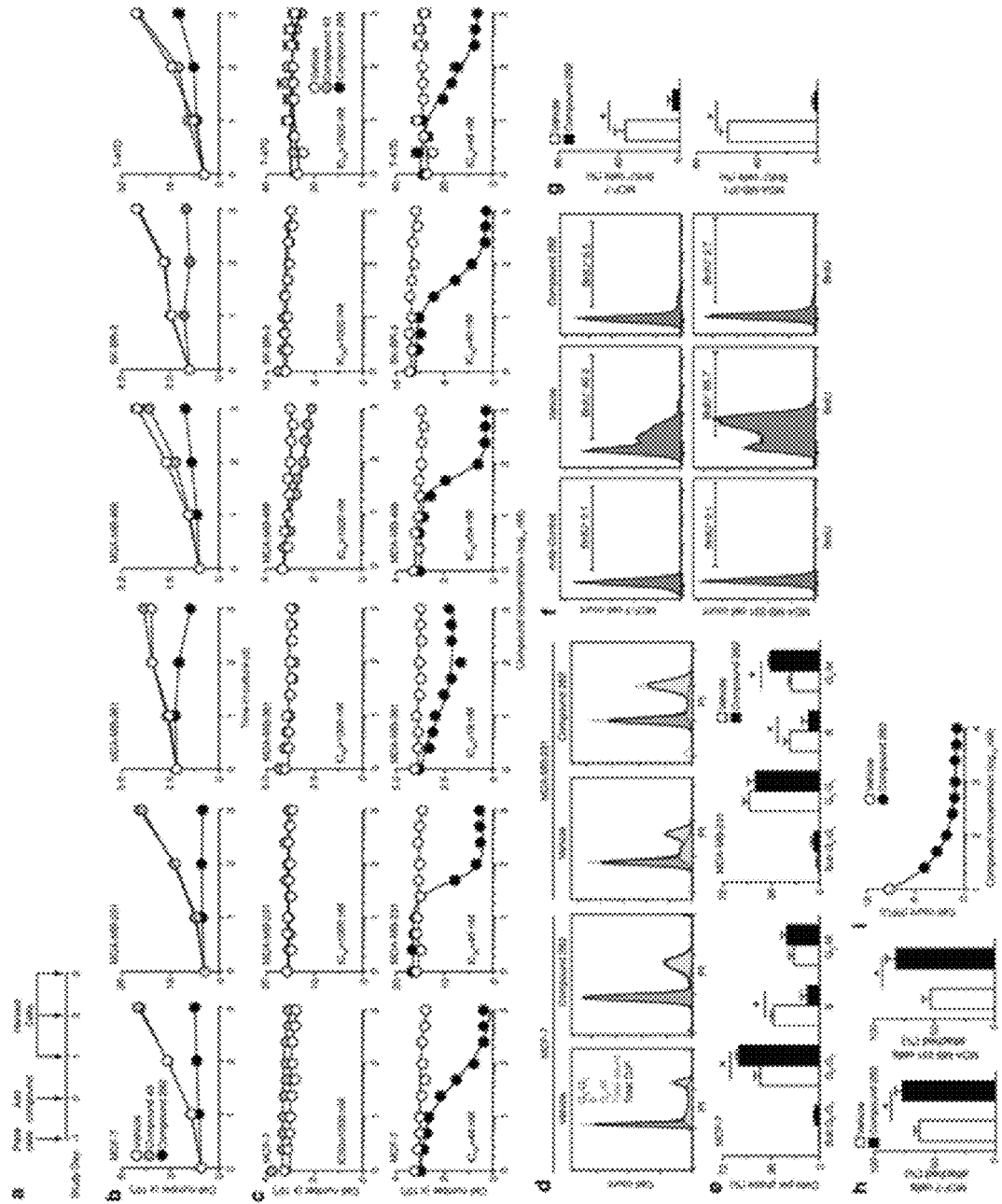
FIG. 4 illustrates that Compound 282 blocks breast cancer cell proliferation and invasiveness in vitro.

The inventors also tested Compound 282 against the same MAPK and RTK substrates present on the phosphokinase-antibody array and other kinases relevant to breast cancer (e.g., focal adhesion kinase). FIG. 4 illustrates that compound 282 blocks breast cancer cell proliferation and invasiveness in vitro. (a) Scheme for protocol for compound treatment of breast cancer cell lines in culture. (b) Time-course for MAPK14 inhibitor Compound 43 and MAPK13 inhibitor Compound 282 (100 nM) effect on cell number for indicated cell-lines. Values represent mean±s.e.m. (c) Corresponding dose-response (1-1000 nM for 3 d) for conditions in (a). Values represent mean±s.e.m. (d) Flow cytometry analysis by PI staining of DNA content using the FlowJo Dean-Jett-Fox (DJF) modeling algorithm to define cell cycle phases for indicated cell lines with vehicle versus Compound 282 (300 nM). (e) Quantification of data from (d). (f) Flow cytometry analysis by BrdU staining for conditions in (d). (g) Quantification of data from (f). Values=mean±s.e.m. *P<0.01. (h) Levels for cells remaining attached in PMA-treated cell lines with vehicle versus Compound 282 (300 nM). (i) Levels of cell migrating across membrane in Boyden chambers. Values represent mean±s.e.m. *P<0.01. The results show that Compound 282 exhibited a high degree of selectivity for MAPK13 inhibitory activity (FIG. 4), consistent with a primary role for MAPK13 function in breast cancer.

Figure 5:
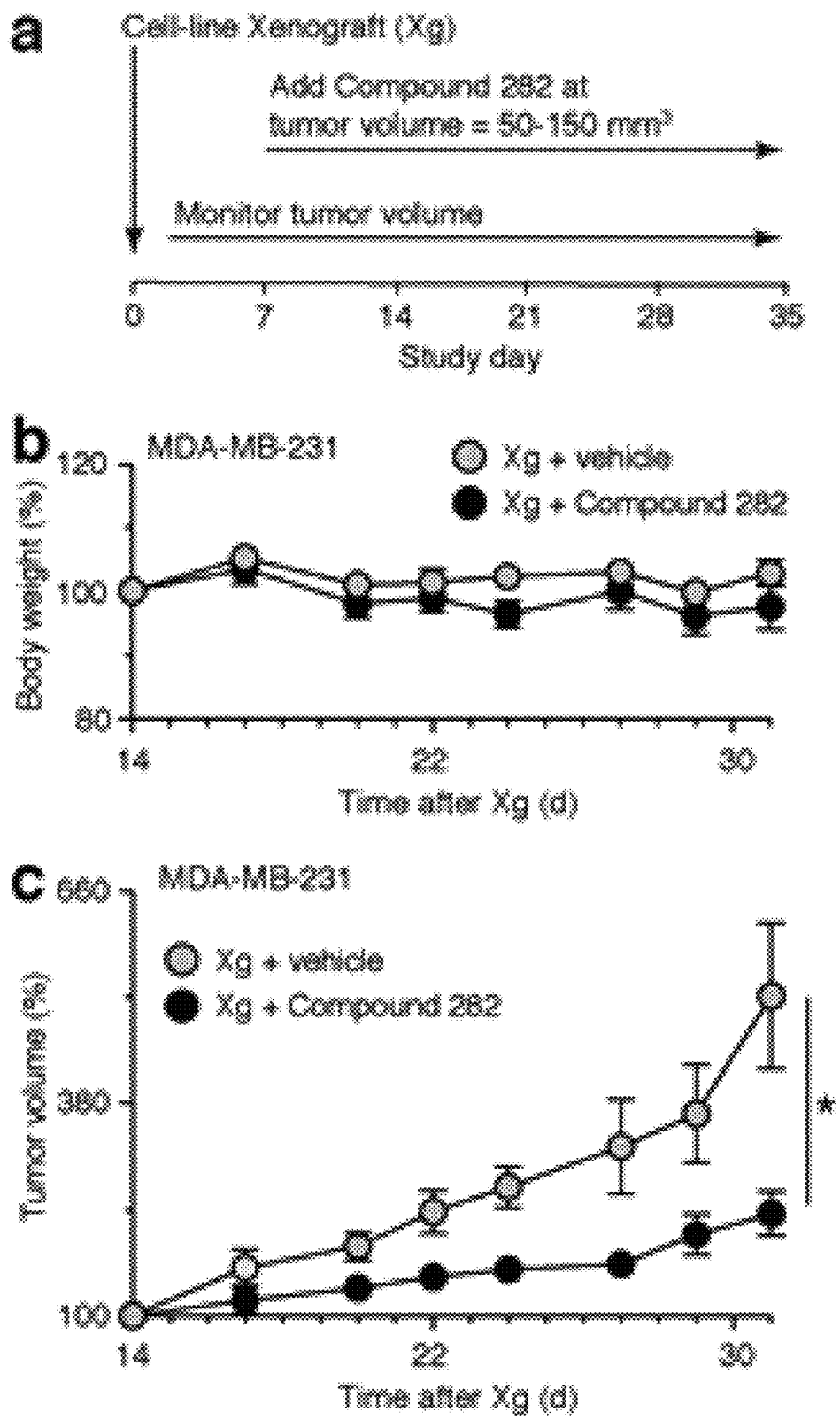
FIG. 5 illustrates that Compound 282 blocks breast cancer growth in vivo.

Third, the inventors pursued additional development of Compound 282 as a lead candidate for breast cancer, finding first that Compound 282 exhibited acceptable results in rat, pig, and human liver microsomal stability assays and CACO-2 cell permeability assays. Moreover, Compound 282 possesses acceptable characteristics for oral dosing based on PK analysis of intravenous dosing at 0.5 mg/kg and oral dosing at 2 mg/kg in rats (FIG. 5). At this oral dose, Compound 282 achieves plasma concentrations ($C_{max}$=0.8 µM) that exceed the levels required for full control of cancer cell growth in culture. FIG. 5 illustrates that compound 282 blocks breast cancer growth in vivo. (a) Body weights for NOD-SCID mice with MDA-MB-231 cell-line xenograft (Xg) and treatment with vehicle versus Compound 282 (20 mg/kg i.p. twice per d for 14-31 d after Xg implantation. (b) Tumor size for conditions in (a). Values mean±s.e.m. *P<0.01 (n=8 mice per group). These results thereby support Compound 282 as the best performing of our chemical analogs and provide for at least one back-up lead (Compound 331) with similarly acceptable attributes for function (Table 3) and ADME and PK characteristics. No toxicity was observed in the in vivo PK experiments for any of the MAPK13 inhibitor compounds or in mucus blocking experiments that have tested doses as high as 20 mg/kg given orally twice per day for 7 d.

MAPK Inhibitors can be Used to Treat Respiratory Diseases

Chronic respiratory diseases such as asthma and COPD have emerged as leading causes of morbidity and mortality in the U.S. and worldwide. Moreover, there is growing recognition that serious forms of these diseases are linked to inflammatory mucus obstruction of the airways (Hogg. J. C. et al., N. Eng. J. Med. 350, 2645-2653 (2004); Hogg, J. C. et al. Am J Respir Crit Care Med 176, 454-459, doi:200612-17720C [pii] 10.1164/rccm.200612-17720C [doi](2007); Kuyper, L. M. et al. Am J Med 15, 6-11 (2003); Groneberg. D. A. et al.; Histopathology 40, 367-373 (2002)). However, there are no specific and effective therapies to attenuate airway mucus production.

The inventors identified a novel pathway for mucus production that includes IL-13 activation of mitogen-activated protein kinase 13 (MAPK13) and downstream induction of mucin MUC5AC and its mucin granule companion CLCA1 as signatures of mucous cell metaplasia and mucus formation (Alevy, Y. et al., J. Clin. Invest. 122, 4555-4568 (2012); Patel, A. C. et al., Physiol. Genomics 25, 502-513 (2006)). This combination of events was defined in airway epithelial cell culture and viral-infection mouse models but was also detected in patients with excess mucus production due to COPD and asthma (Alevy, Y. et al., J. Clin. Invest. 122, 45554568 (2012); Byers, D. E. et al. J. Clin. Invest. 123, 3967-3982 (2013)). However, to the inventors' knowledge, no specific, potent, and safe MAPK13 inhibitors are yet available. The inventors have discovered and developed small-molecule MAPK13 inhibitors to block inflammatory mucus production in respiratory airway disease and further define the role of MAPK13 in regulating epithelial stem cell and mucous cell function.

Structure-Based Drug Design Yields Potent MAPK13 Inhibitors

Determination of MAPK13 structure suggested that a well-characterized MAPK14 inhibitor (BIRB-796; Compound 43 in our series) could be modified to create a new MAPK13 inhibitor (FIG. 6a). The inventors have identified compounds that are potent inhibitors of MAPK13 versus MAPK14, MAPK14 versus MAPK13, and both MAPK13 and MAPK14 (Tables 4-6), with particularly favorable values represented by Compound 354 for MAPK 13 versus MAPK14 inhibition and Compound 396 for combined MAPK13 and MAPK14 (MAPK13-14) inhibition (FIG. 6a). Structure determinations of analog-MAPK13 co-crystals confirmed DFG-out binding mode (FIG. 6c) that predicts slow dissociation kinetics and consequent high potency and long duration of action. Indeed, we detected extremely slow on- and off-rates (hours) for Compound 396 based on bio-layer interferometry (FIG. 6d), similar to Compound 43 binding to MAPK14. In addition, an initial kinome screen for relevant airway epithelial cell targets showed that Compound 396 exhibited selective inhibition of MAPK13-14 and closely related MAPK11-12 (FIG. 6e), and a subsequent broader screen showed that only 4% of 400 kinases with >90% inhibition at 0.1 µM. Together, the results identified Compound 396 as an ideal lead candidate based on enzyme inhibition, binding, kinetics, and kinome selectivity, and fit with a strategy to block MAPK13-14 for down-regulation of both alternative type 2 and conventional immune responses that drive inflammatory airway disease.

Figures 1, 6:
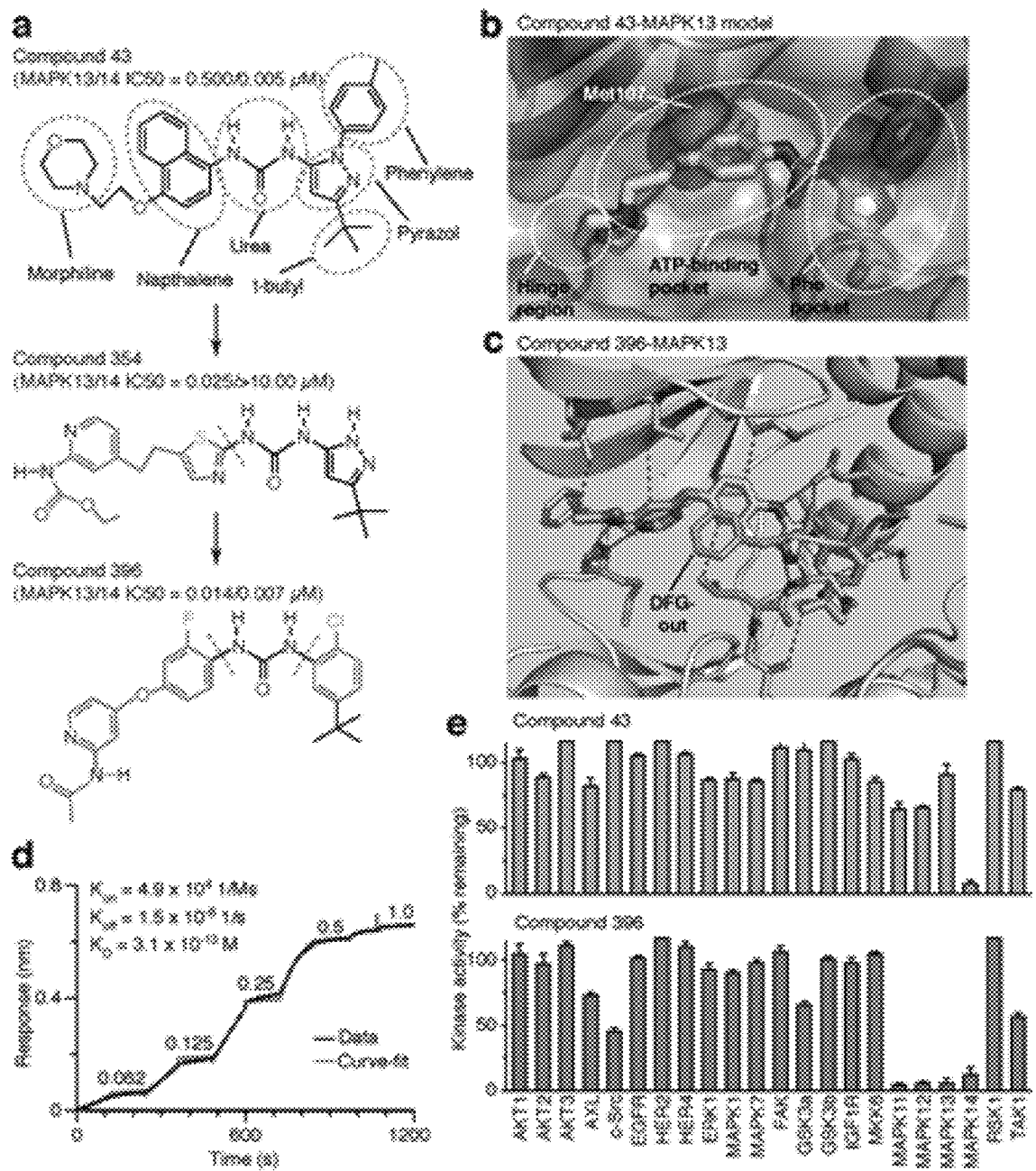
FIG. 6 illustrates structure-based drug design for identifying small-molecule MAPK13 inhibitors.

In FIG. 6, Structure-based drug design identifies a small-molecule MAPK13 inhibitor. (a) Compound 43 (BIRB-796) represents the starting point for scaffold hopping to Compound 354 and Compound 3% to improve potency against MAPK13 (changes indicated in magenta). (b) Structure for Compound 43 (by modeling) bound to MAPK13 (by x-ray crystallography) illustrating target regions for drug design and DFG-out binding mode. (c) Structural basis for Compound 3% interactions for MAPK13 with hydrogen-bond and hydrophobic interactions indicated with red-dashed lines. (d) Biolayer interferometry (BLI) analysis for slow on-off binding of Compound 396 to MAPK13. (e) Screen for kinase inhibition for Compounds 43 and 396 (0.1 µM). Values represent mean±s.e.m.

MAPK13 Inhibitors Block Mucus Formation in Human Airway Epithelial Cells

Compound 3% (and other analogs) were also assessed for inhibition of inflammatory mucus production using human tracheobronchial epithelial cells (hTECs) under air-liquid interface primary-culture conditions with IL-13-dependent induction of MUC5AC mucin formation (FIG. 7a,b). This analysis identified MAPK13 inhibitors with high potency (IC50<0.1 nM for MUC5AC blockade) and low toxicity (cell therapeutic index (CTI)>1,000) where CTI=ratio of IC50 to the lowest compound concentration to decrease monolayer integrity (using trans-epithelial electrical resistance, TEER) or cell metabolism (using resazurin assay) (Table 7). Moreover, MAPK14 inhibitors such as Compound 401 (VX-745) 22 showed no significant inhibition of MUC5AC production, whereas MAPK13 inhibitors such as Compound 354 and 398 and combined MAPK13-14 inhibitors such as Compound 3% and 397 achieved marked attenuation of MUC5AC production at concentrations that caused no cell toxicity (FIG. 7c). Similar results were found for comparable cultures of porcine tracheobronchial epithelial cells (pTECs) (Table 8). For Compound 396, IC50 values ranged from 0.05-0.009 among three human donors but were no different for IL-13 versus IL-4 stimulation of hTECs (data not shown), thereby demonstrating blockade against both of these cytokines at least via the Type II IL-4R (IL-13R). Initial data suggests that lower IC50 values for mucus compared to enzyme inhibition may be due to increased intracellular concentrations of these compounds with multiday treatment (data not shown), consistent with slow-on-off kinetics.

Figures 2, 7:
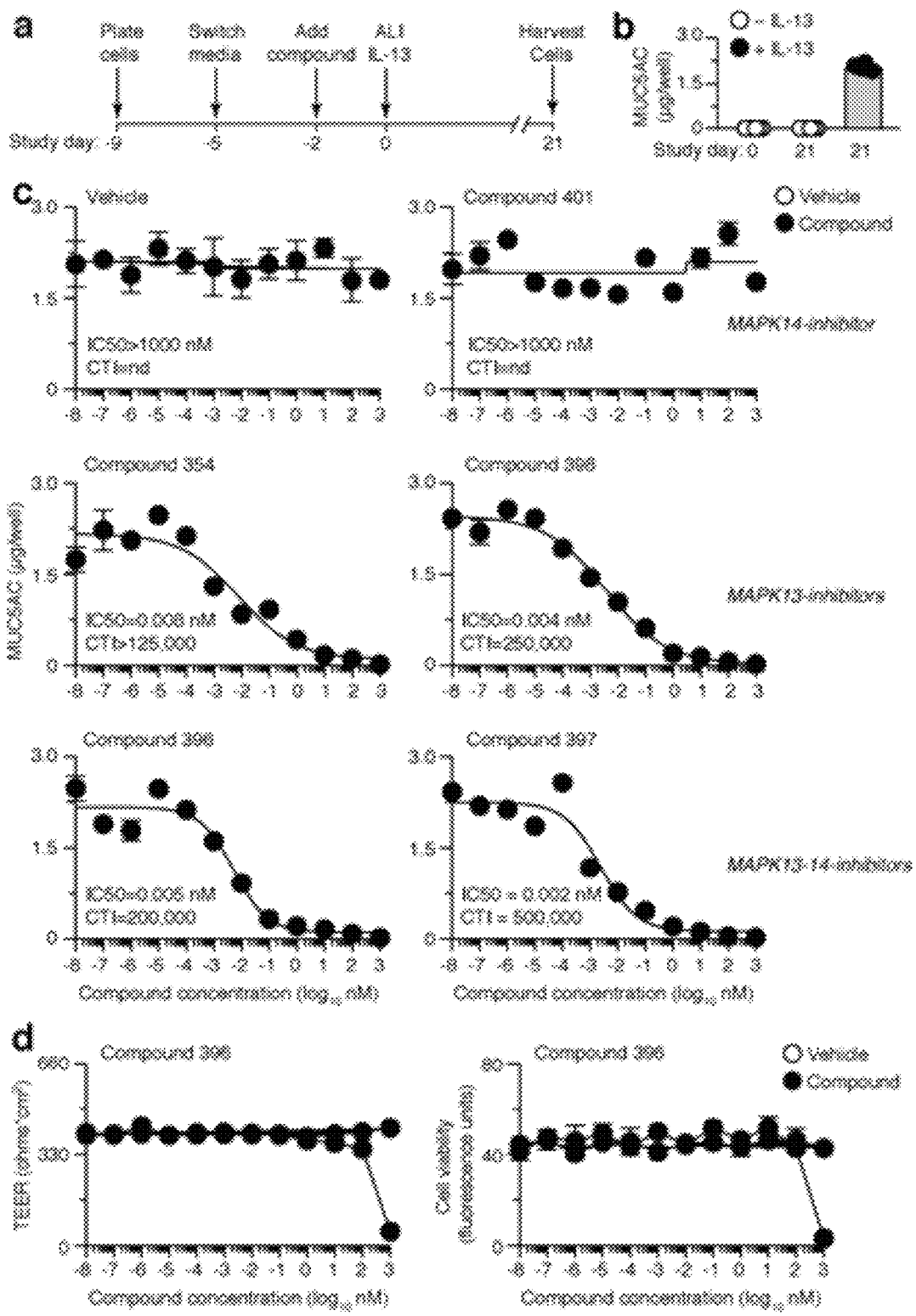
FIG. 7 illustrates that MAPK13 inhibitors block mucus production in human airway epithelial cells.

In FIG. 7, MAPK13 inhibitors block mucus production in human airway epithelial cells. (a) Protocol scheme for primary-culture of human tracheobronchial epithelial cells (hTECs) under ALI conditions and treatment with or without IL-13 and MAPK13 inhibitor. (b) Levels of MUC5AC in apical cell supernatants of hTECs cultured with or without IL-13 (50 ng/ml). (c) MUC5AC levels for conditions in (a,b) with MAPK14-selective VX-745, MAPK13-selective Compounds 354 and 398, MAPK1314-selective Compounds 396 and 397), or vehicle control. (d) Values for transepithelial electrical resistance (TEER) and cell viability (using resazurin assay) for Compound 396 for conditions in (c). For (b,c,d), values represent mean±s.e.m. for one cell donor. Results are representative of 3 individual donors. (e) Western blot of hTECs after control (Ct) or MAPK gene knockdown using indicated CRISPR/Cas9 lentivirus vectors. (f) Levels of MUC5AC in apical cell supernatants of hTECs cultured with or without IL-13 (50 ng/ml) using MAPK gene knockdown conditions in (e) with or without treatment with Compound 396 (10 nM) for 21 d. Values represent mean±s.e.m. * P<0.05.

TABLE 7

Compound efficacy for blocking MUC5AC mucin formation in IL-13-stimulated hTEC cultures

| Compound # | MUC5AC $IC_{50}$ (Nm) | Cell Therapeutic Ratio |
| --- | --- | --- |
| 282 | 0.019 | 52,631 |
| 354 | 0.008 | 125,000 |
| 396 | 0.005 | 200,000 |
| 397 | 0.002 | 500,000 |
| 398 | 0.004 | 250,000 |
| 399 | 0.004 | 250,000 |
| 400 | 0.003 | 333,333 |
| 401 | >1000 | >1 |

[1]$IC_{50}$ = compound concentration that causes 50% decrease in MUC5AC level from IL-13 versus no IL-13 treatment at 21 d in culture.
[2]Ratio of $IC_{50}$ for MUC5AC inhibition to initial concentration exhibiting any decrease in TEER or resazurin assay value.

TABLE 8

Compound efficacy for blocking MUC5AC mucin formation in IL-13-stimulated pTEC cultures.

| Compound # | MUC5AC $IC_{50}$ (nM)[1] | Cell Therapeutic Ratio[2] |
| --- | --- | --- |
| 43 | Pending | Pending |
| 282 | 0.022 | 45,454 |
| 354 | 0.289 | >3,460 |
| 396 | 0.420 | 2,381 |
| 397 | 1.000 | 1,000 |
| 398 | 0.281 | >3,558 |
| 399 | 0.263 | 3,802 |
| 400 | 0.010 | >10,000 |
| 401 | >1000 | >1 |

[1]$IC_{50}$ = compound concentration that causes 50% decrease in MUC5AC level from IL-13 versus no IL-13 treatment at 21 d in culture.
[2]Ratio of $IC_{50}$ for MUC5AC inhibition to initial concentration exhibiting any decrease in TEER or resazurin assay value.

Compound 396 Blocks Airway Mucus Production in Pigs

The inventors extended their studies of MAPK13 inhibitors to studies of excess mucus production in vivo. To refine compound selection, the candidate compounds from enzyme-based and cell-based inhibition experiments were subjected to analysis of in vitro ADMET and physical chemistry attributes and then in vivo pharmacokinetic (PK) characteristics. ADMET studies of liver microsome stability (for rat, mini-pig, dog, and human) and Caco-2 cell permeability as well as physical chemical attributes indicated favorable characteristics for a subset of compounds that again included Compound 396 (Tables 9, 10). Further testing demonstrated extremely favorable PK characteristics for Compound 396 (Tables 11, 12), with dosing at 2 mg/kg achieving plasma concentrations (>100 nM) for at least 8 h (FIG. 8a) that inhibit mucus production in hTEC and pTEC cultures (FIG. 7c). Additional PK analysis showed favorable characteristics of Compound 396 in rat and dog with intravenous (i.v.) and oral dosing as well as mouse with i.v., oral, and intraperitoneal (i.p.) dosing (FIG. 6).

Figure 8:
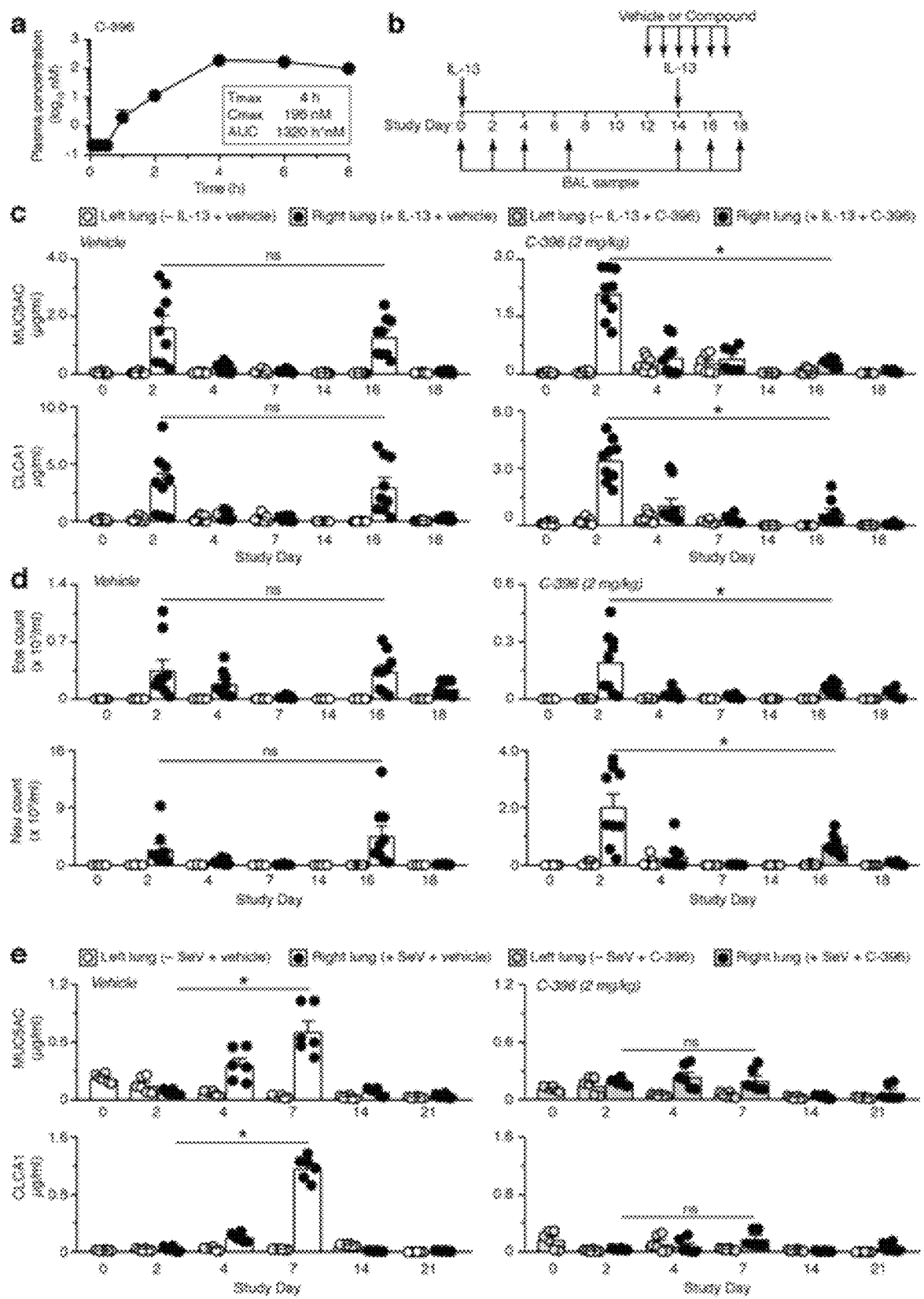
FIG. 8 illustrates that Compound 3% blocks airway inflammation and mucus production in IL-13-challenge and SeV-infection pig models.

In FIG. 8, Compound 396 blocks airway inflammation and mucus production in IL-13-challenge and SeV-infection pig modela. (a) Pharmacokinetic (PK) analysis of Compound 396 in mini-pigs with plasma concentrations determined after oral dose of 2 mg/kg. (b) Protocol scheme for IL-13 challenge of right lung segments on Study Days 0 and 14 with BAL sample of right and left lung on indicated Study Days and either vehicle or compound treatment on Study Days 12-17. (c) Levels of MUC5AC and CLCA1 in BAL fluid for scheme in (b) using vehicle control (left column) or Compound 396 (C-396) at 2 mg-kg orally twice per day (right column). (d) Corresponding eosinophil counts in BAL for conditions in (c). (e) MUC5AC and CLCA1 levels in BAL fluid after Sendai virus (SeV) infection of right lung segments on Study Day 0 and either vehicle or C-396 treatment on Study Days −2 to 21. For (c,d), each plot represents values for 3 lung segments for 3 pigs, and for (e), 3 segments for 2 pigs. *P<0.01. Values represent mean±s.e.m.

Based on these combined results. Compound 3% was selected for blockade of mucus production in pigs in vivo. For this purpose, we developed a model of airway inflammation and mucus production whereby Yucatan mini-pigs undergo cytokine challenge using recombinant porcine IL-13 delivered to specific right lung segments (in caudal and accessory lobes) via flexible fiber-optic bronchoscopy on two separate occasions (Study Days 0 and 14) with response monitored in bronchoalveolar lavage (BAL) samples (FIG. 8b). This approach demonstrated that IL-13-challenge caused reproducible increases in MUC5AC and its mucin granule companion CLCA1 with no difference between the first and second challenge and therefore no effect of vehicle treatment on the second challenge (FIG. 8c, left column). In contrast, these markers of mucus production were significantly decreased by treatment with Compound 396 at 2 mg/kg given orally twice per day for the second challenge (FIG. 8c, right column). In addition to decreases in mucus production, treatment with Compound 3% also significantly attenuated the influx of eosinophils and neutrophils into the airspace (FIG. 8d), consistent with blockade of IL-13 induction of chemokine production. Anti-mucus and anti-inflammatory effects were decreased at 0.2 mg/kg and were preserved at 20 mg/kg dosing (FIG. 7). No adverse effects (e.g., change in animal behavior, appetite, body weight, vital signs, gastrointestinal and urinary function, and complete blood count) were observed at any of these doses of the compound.

The inventors next determined whether Compound 3% might also block mucus production in response to respiratory viral infection in the pig model. For these experiments, pigs were infected with Sendai virus (SeV), which is a natural pathogen in this species. Indeed, infection with SeV via bronchoscopy resulted in at least $1\times10^4$-fold increases in viral titer for 7 d and a consequent increase in MUC5AC and CLCA1 levels in BAL samples (FIG. 8e). Moreover, the post-viral increases in MUC5AC and CLCA1 were significantly attenuated by treatment with Compound 3% at 2 mg/kg orally twice per day (FIG. 8e). Treatment did not cause any change in viral titer and did not result in any detectable side effects (as noted above) despite more prolonged dosing (23 d).

Compound 3% Blocks Airway Mucus Production in Mice

The inventors investigated whether Compound 396 can provide therapeutic benefit in a second preclinical species, particularly in mice where we established a model of chronic inflammatory mucus production after SeV infection. As noted above, delivery of Compound 3% with i.p. administration of 2 mg/kg resulted in plasma concentrations that block MAPK13 activity in enzyme assay and mucus production in airway epithelial cell culture (Tables 4-8 and FIG. 7c). Accordingly, the inventors developed a protocol to determine the effect of Compound 3% at 2 mg/kg given i.p. twice daily either 2 d before or 10 d after SeV infection followed by analysis of lung tissue samples (FIG. 9a). Neither dosing regimen caused any detectable effect on behavior or weight in uninfected mice or any change in clinical signs or weight loss that develop after SeV infection (FIG. 9b). Despite similar acute infectious illness, the usual increases in Muc5ac and Clea1 mRNA were fully blocked in mice treated with Compound 396 starting 2 d before infection compared to vehicle control (FIG. 9c). Moreover, these endpoints were also significantly attenuated even when treatment was delayed until 10 d after SeV infection (FIG. 9c). Treatment also significantly decreased the induction of Aqp3. Krt5, and Trp63 mRNA, which are markers of basal-ESCs in this model (FIG. 9c), consistent with an effect of MAPK13 inhibition on ESC expansion that begins at 8 d and peaks at 12 d after infection and is restricted to a specific basal-ESC subset based on single-cell RNA-sequencing (scRNA-seq). These findings suggest that MAPK13 inhibition corrects ESC reprogramming to prevent the downstream type 2 immune response. Indeed, initial data suggests that Compound 3% treatment (either starting at −2 d or 10 d after infection) blocks induction of 1133, 1113, and Arg1 mRNA expression (FIG. 9c), which are markers of the type 2 immune response in this model. Thus, similar to the pig model, Compound 396 markedly attenuates inflammation and mucus production and other key aspects of the epithelial and type 2 immune response underlying airway disease, including ESC reprogramming to more fully and permanently correct the susceptibility to inflammatory mucus production.

Figure 9:
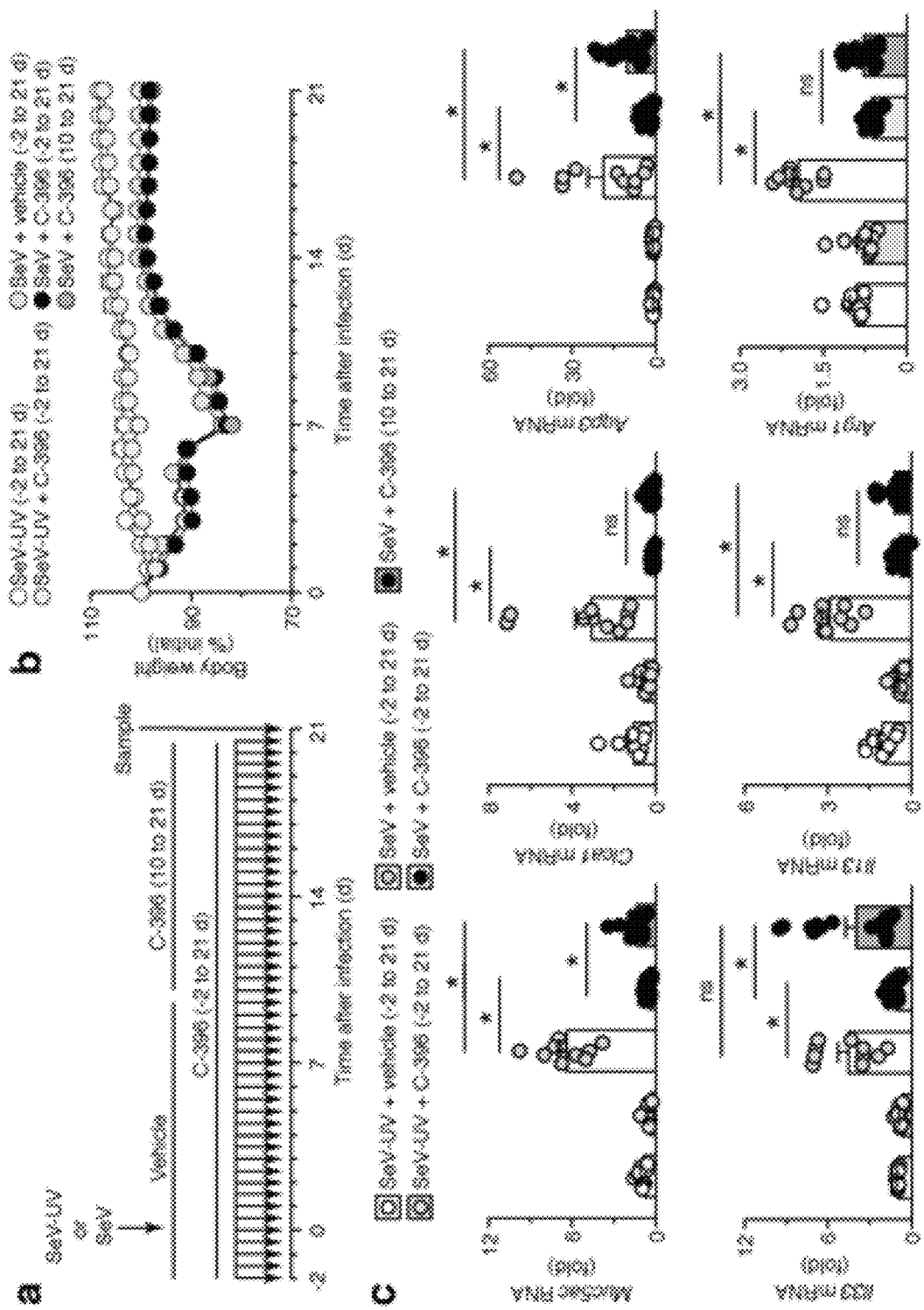
FIG. 9 illustrates that Compound 3% blocks airway inflammation and mucus production in respiratory-virus-infection mouse model.

In FIG. 9, Compound 396 blocks airway inflammation and mucus production in respiratory-virus-infection mouse model. (a) Pharmacokinetic (PK) analysis of Compound 396 in mice, rats, and dogs with plasma concentrations determined after oral dose of 2 mg/kg. (b) Protocol scheme for respiratory virus infection with Sendai virus (SeV) on Study Day 0 ($1\times105$ pfu intranasally) and vehicle or Compound 396 (C-396) treatment (2 mg/kg intraperitoneally twice per day) on indicated study days with sample analysis of lung tissue at 21 d after infection. (c) Body weights for each condition at 0-21 d after infection with SeV or control SeV-UV. (d) Levels of indicated mRNA in lung tissue for scheme in (a). Each plot represents values from 10 mice. *P<0.01. Values represent mean±s.e.m.

Figure 10:
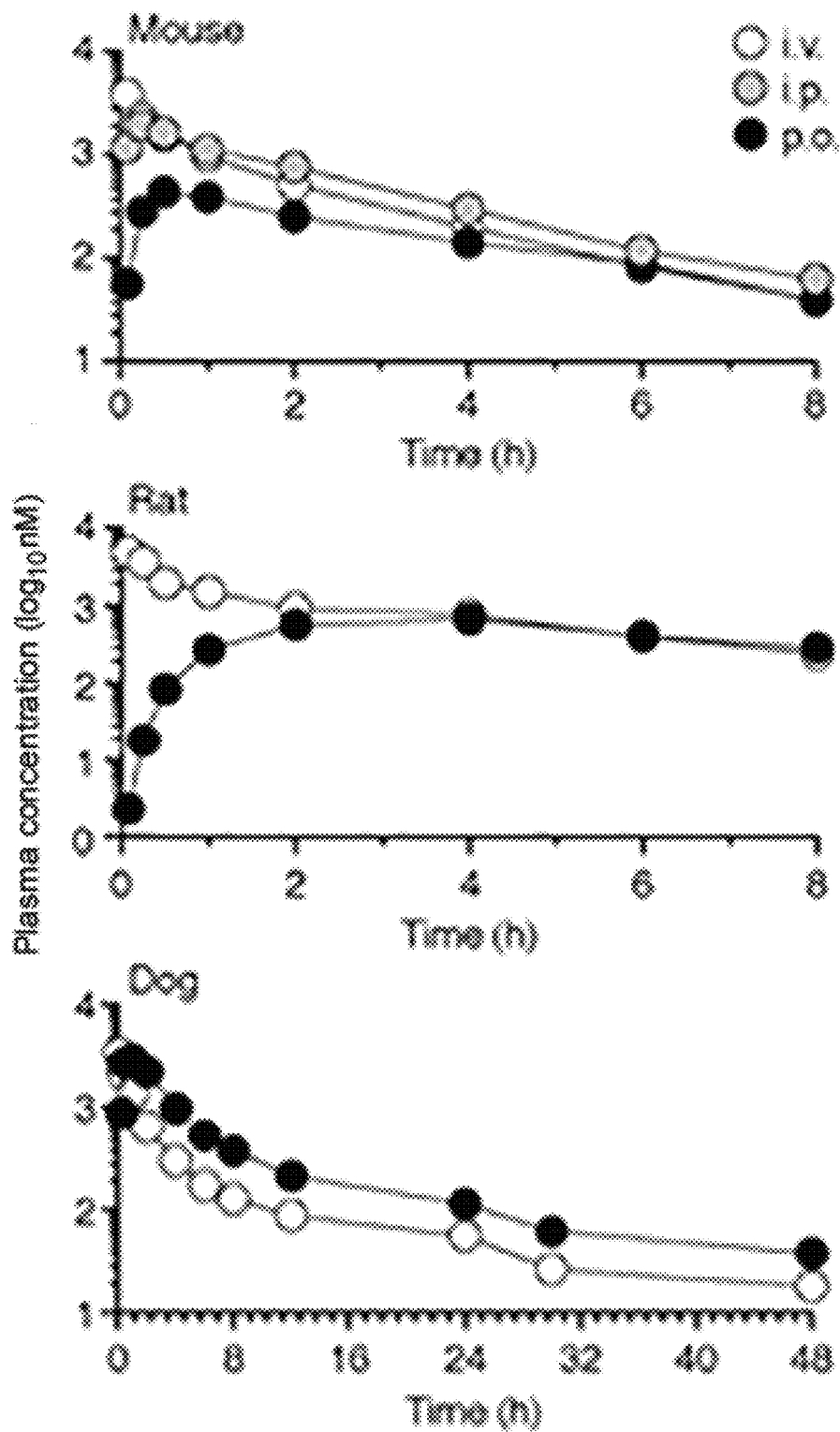
FIG. 10 presents a pharmacokinetic (PK) analysis of Compound 3% in mice, rats, and dogs.

FIG. 10 presents a Pharmacokinetic (PK) analysis of Compound 396 in mice, rats, and dogs. Plasma concentrations were determined after intravenous, intraperitoneal, or oral dosing (2 mg/kg).

Figure 11:
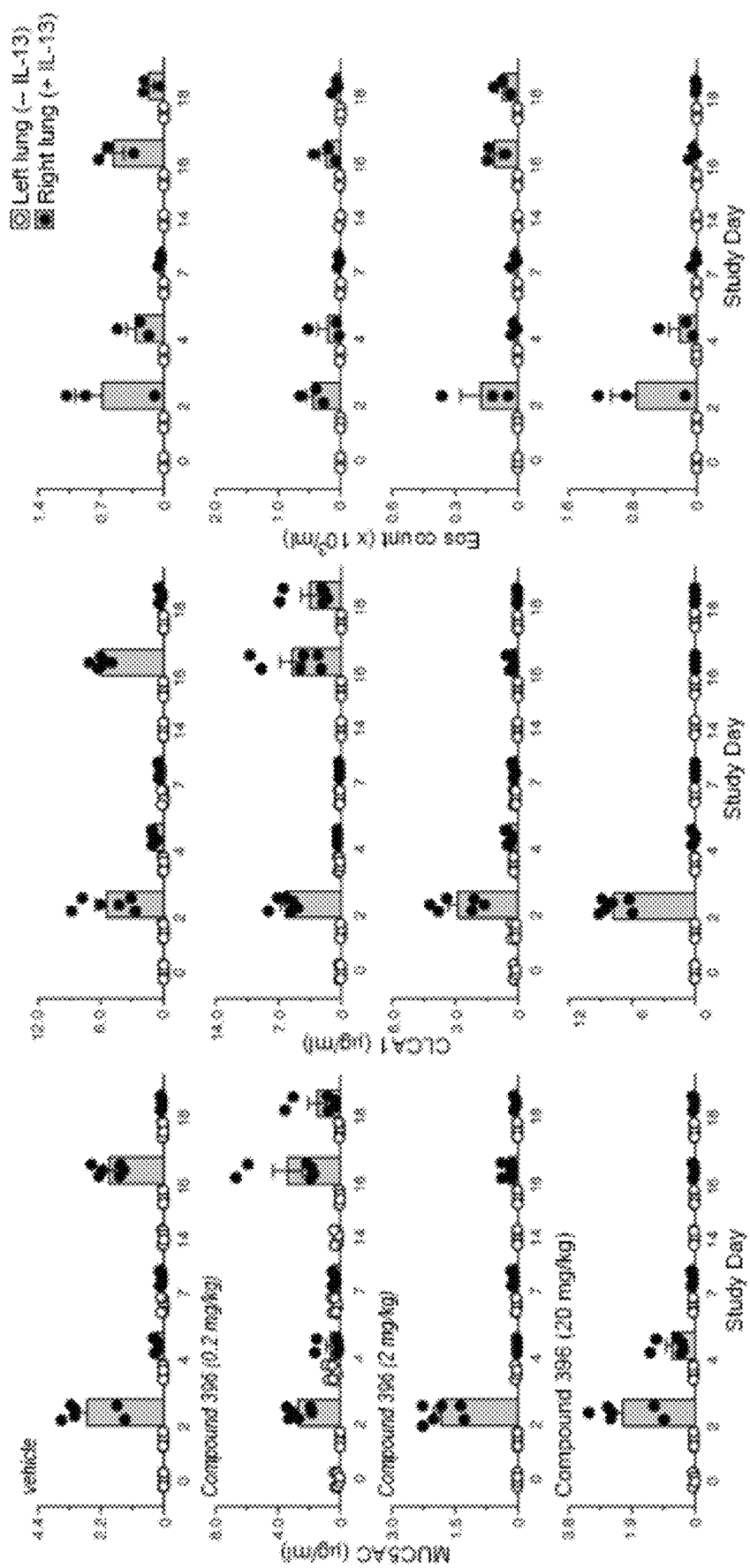
FIG. 11 illustrates that Compound 3% blocks airway inflammation and mucus production with dose-dependency in an IL-13-challenge pig model.

FIG. 11 shows that Compound 396 blocks airway inflammation and mucus production with dose-dependency in an IL-13-challenge pig model. Protocol scheme for IL-13 challenge of right lung segments on Study Days 0 and 14 with BAL sample of right and left lung on indicated Study Days and either vehicle or compound treatment on Study Days 12-17 is the same as FIG. 3. Levels of MUC5AC in BAL fluid during treatment with vehicle control (left column) or Compound 396 (C-396) at 0.2-20 mg/kg orally twice per day (right column).

Methods

MAPK13 inhibitors. MAPK13 inhibitors were developed as part of an analog series generated with a scaffold hopping strategy as introduced previously. Compounds were reconstituted in DMSO vehicle for cell experiments done in vitro and as a micronized dry powder with lactose carrier for experiments done in vivo. For each preparation, compound purity was verified using LC-MS and NMR. X-ray crystallography and biolayer interferometry were performed as described previously (Huang, P. et al. Lab Chip 15, 3125-3131 (2015)).

Epithelial cell culture. Human tracheal and bronchial epithelial cells (hTECs) were isolated by enzymatic digestion, seeded onto permeable filter supports, and grown as described previously. For the present experiments, cells were cultured in 24-well Transwell plates (6.5-mm diameter inserts, 0.4 µm pore size) from Corning (Corning, N.Y.) with UNC BEGM medium supplemented with Primocin (100 µg/ml, (InvivoGen, San Diego, Calif.), retinoic acid ($1 \times 10^{-8}$ M, Sigma. St. Louis, Mo.) with or without human IL-13 (10 ng/ml, Peprotech, Rocky Hill, N.J.) under submerged conditions for 2 d and then air-liquid interface conditions for 21 d. Cells were also cultured in the presence or absence of inhibitors or vehicle that were added 2 d before addition of IL-13 and were re-added with each medium change/IL-13 treatment (twice per week). Transepithelial electrical resistance (TEER) and resazurin cell metabolism assay (Promega CellTiter Blue) were performed as described previously (Alevy, Y., et al., J. Clin. Invest. 122:4555-4568, PMCID: PMC3533556; Patel. D. A., et al., PloS ONE 7, e36594 (2012)). To assess mucus secretion (versus production), IL-13 was withdrawn from the medium for 2 d, the apical cell surface was washed with DPBS as described previously 33, and either methacholine (20 µM), histamine (20 µM), or ATPgS (100 µM) were added to the apical compartment for 30 min at 37° C. before analysis of apical cell supernatant. All conditions were performed as 3-4 replicates.

ELISA and western blotting. For ELISA, samples were assayed in triplicate on 96-well white half-area flat-bottom ELISA plates (Phenix Research products, Candler, N.C.) after incubation at 37° C. overnight. The assay for MUC5AC was performed using biotin-conjugated mouse anti-MUC5AC mAb as described previously (Alevy, Y., et al., J. Clin. Invest. 122:4555-4568, PMCID: PMC3533556). The assay for N-CLCA1-N was performed using rabbit anti-human CLCA1 (amino acid 33-63) antibody (Abgent) and HRP-conjugated goat anti-rabbit IgG antibody (Santa Cruz Biotechnology). The assay for C-CLCA1 was performed using mouse anti-human CLCA1 mAb (clone 7D6) (1) and HRP-conjugated goat anti-mouse IgG (Life Technologies). All assay reactions were developed using the GLO substrate kit (R&D Company, Minneapolis, Minn.) and quantified by comparison to a standard curve with recombinant proteins. Western blotting for C-CLCA1 was performed using mouse anti-human CLCA1 mAb (clone 7D6) and for N-CLCA1 using mouse anti-human CLCA1 mAb (clone 8D3) generated as described previously 9.

Immunostaining. Cells were fixed, permeabilized, and treated for epitope retrieval and lung sections were incubated with citrate-based Antigen Unmasking Solution for antigen retrieval as described previously (Alevy, Y., et al., J. Clin. Invest. 122:4555-4568, PMCID; PMC3533556). Immunostaining was performed using mouse anti-MUC5AC biotin-conjugated mAb (clone 45M1, Thermo Fisher Scientific) detected with Alexa-555-conjugated streptavidin (Life Technologies), rabbit anti-human N-CLCA1 (amino acids 33-63) antibody (Abgent) detected with Alexa 488-conjugated goat anti-rabbit secondary antibody. All slides were also counterstained Prolong Gold with DAPI (Life Technologies) and then imaged by confocal or conventional microscopy.

Real-time quantitative PCR assay. RNA was purified from lung homogenates and cells using Trizol (Invitrogen) and was converted to cDNA using a High-Capacity cDNA Archive kit (Life Technologies). Target mRNA was quantified by real-time PCR assay using specific fluorogenic probes and primer sets and the Fast Universal PCR Master Mix system (Applied Biosystems). Samples were assayed with the 7300HT Fast Real-Time PCR System and analyzed using Fast System Software (Applied Biosystems). All real-time PCR data was normalized to the level of GAPDH mRNA to correct for variation between samples. Values were expressed as fold-change based on the delta-delta Ct method as described previously 10.

LC-MS-based PK assay. Samples were analyzed on an Agilent 6460 QQQ mass spectrometer in the positive ion mode coupled to an Agilent 1290 LCMS. Samples were injected onto a Synergi (Phenomenex, Torrence, Calif.) 4u Polar RP 80A column (250 v2 mm×4 um) using a flow rate of 0.25 ml/min. The gradient used was as follows: Solvent A 0.1% formic acid was held constant for 1 min at 80% and solvent B (90% acetonitrile in 0.1% formic acid was held constant at 20% for 1 min. Solvent B was increased to 95% by 10 min and then held constant for 3 minutes and then back to 20% by 15 min. The column was allowed to equilibrate for 5 min before starting the next run. The capillary voltage was set to 3500 and the gas temp was set to 300. The gas flow, nebulizer, sheath gas heater and sheath gas flow were set to 5 L/min, 45 psi, 250 and 11 respectively. The fragmentor was set to 80V. The scan range was 75-600 Da. MRM mode identification was performed with collision gas energy of 10V for the following MS/MS transitions (precursor m/z/product m/z): compound 89, 469/256 and 469.214; compound 270, 461/256 and 461/206.

Pig model. Male and female Yucatan pigs (21-25 kg and 7-8 weeks of age) were obtained from Sinclair Research (Columbia, Mo.) and housed in environmentally controlled animal care facilities. Pigs were acclimated for 1 week before experiments. Animal husbandry and experimental procedures were approved by the Animal Studies Committees of Washington University School of Medicine in accordance with the guidelines from the National Institutes of Health. Pigs were anesthetized using tiletamine/zolasepam (Telazol, 4.4 mg/kg), ketamine (2.2 mg-kg) and xylazine (2.2 mg/kg) administered intramuscularly, intubated with a 6.5-7.0-mm ID endotracheal tube, and maintained under 2-3% isoflurane anesthesia. Pigs were mechanically ventilated using a Drager anesthesia workstation for each challenge procedure. Segmental cytokine challenge was performed on Study Days 0 and 14 using recombinant porcine TL-13 (0.25 mg in 6 ml of PBS) with 2 ml delivered to each of three subsegments (right caudal and accessory lobes) via a fiber-optic bronchoscope (Olympus Model LF-2, 3.8-mm OD). Pigs were maintained with reverse Trendelenberg position for 30 min to prevent drainage from the right lung before anesthesia was discontinued. The subsequent response to IL-13 challenge was monitored in bronchoalveolar lavage (BAL) fluid and cells at Study Days 2, 4, 7, 14, 16, and 18. Controls included samples from three unchallenged subsegments (left caudal lobes) on Study Day 0 and each of the other Study Day sampling times. BAL was performed by instillation and aspiration of 10-ml aliquots of PBS into left and right anterior lung segments. In some experiments, lungs were removed for tissue analysis on Study Days 2 or 16. For treatment, pigs were dosed orally with Compound 396 (0.2-20 mg/kg twice per day) in 10 ml of Ensure nutrition shake or with an equivalent amount of Ensure alone on Study Days 12-17. BAL and tissue samples were processed for ELISA, cell count, staining, and real-time qPCR assay as described above. For respiratory virus infection, Sendai virus (SeV) was delivered in the same manner via bronchoscopy using $1.3 \times 10^7$ pfu in 1 ml of PBS) with 0.7 ml delivered to each of three subsegments and BAL performed with 6-ml aliquots of PBS in each segment.

Mouse model. Male and female wild-type C57BL/6J mice (000664) mice were obtained from The Jackson Laboratory. All mice were maintained and co-housed in a barrier facility using cages fitted with micro-isolator lids. Animal husbandry and experimental procedures were approved by the Animal Studies Committees of Washington University School of Medicine in accordance with the guidelines from the National Institutes of Health. SeV was obtained from ATCC (Sendai/52 Fushimi strain, ATCC VR-105) and prepared and titered by plaque-forming assay and qPCR assay as described previously Kim, E. Y. et al., Nat. Med. 14, 633-640 (2008). Mice were infected with SeV ($5 \times 10^5$ viruses based on qPCR assay for viral RNA equivalent to $1 \times 10^5$ PFU based on plaque-forming assay for infectious virus) or EV-D68 ($1.5 \times 10^8$ viruses equivalent to $0.5 \times 10^5$ ePFU) as described previously (Zhang, Y. et al., Immunol. 202, 2332-2347 (2019)). Dosing was performing intranasally using SeV in 30 µl of PBS or an equivalent amount of UV-inactivated virus or PBS alone under ketamine/xylazine anesthesia at 6-9 wk of age. Results from male and female mice were pooled since no significant differences were found between sexes as reported initially (van Nunen, M. C. J. & van der Veen. J., Arch Gesamte Virusforsch 22, 388-397 (1967)), and confirmed and confirmed recently (Zhang, Y. et al., Immunol. 202, 2332-2347 (2019)) and in the present experiments (data not shown). Mouse lungs were frozen at −70° C. for homogenization in PBS with a cell disrupter (Mini-Beadbeater-96, Biospec Products) followed by viral plaque-forming assay to track PFU level normalized to gm of lung tissue (recognizing that one mouse lung weighs approximately 100 mg). Viral titers for stock solutions and lung infections were monitored by PCR assay using primers defined previously (Zhang, Y. et al., Immunol. 202, 2332-2347 (2019)).

FACS. Single cell suspensions were generated from minced lung tissue that was subjected to collagenase (Liberase Blendzyme III, Roche), hyaluronidase (Sigma), and DNAse I (grade II, Roche) digestion for 45 min at 37° C. as described previously (Byers, D. E. et al., J. Clin. Invest. 123, 3967-3982 (2013)). Following FcR blockade, lung cell suspensions were incubated with labeled antibodies and were sorted using a Moflo (DAKO-Cytomation) high-speed cell sorter. Nonviable cells were excluded from analysis by AAD staining. NKT cells were immunostained using APC-conjugated PBS-57-loaded mouse CD1d tetramer conjugated provided by the NIH Tetramer Core Facility and PE-conjugated anti-porcine CD3ε mAb as described previously (Kim. E. Y. et al., Nat. Med. 14, 633-640 (2008); Renukaradhya, G. J. et al., J. Clin. Immunol. 31, 228-239 (2011)). Lung monocytes were immunostained using FITC-conjugated anti-porcine CD14 mAb from AbD Serotec as described previously for porcine PBMCs (Fairbain, L. et al. J. Immunol. 190, 6389-6396 (2013)) and enhanced using anti-PE/Cy7-conjugated anti-human CD-66b mAb from eBiosciences, Flow cytometry results were plotted and analyzed using FlowJo10 software (TreeStar).

Statistical analysis. Unless otherwise stated, all data are presented as mean±SEM, and two-tailed unpaired Student's t test was used to assess statistical significance between means. In all cases, significance threshold was set at $p<0.05$. All values are representative of at least three experiments.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Generation of Novel MAPK13 Inhibitors

We generated new chemical analogs derived from our patented chemical scaffold in a manner that was not described in our initial patent (U.S. Pat. No. 9,187,470). These compounds were found to be more effective inhibitors of MAPK13 at low nM concentrations using an in vitro enzyme activity assay with MAPK13. Some of these compounds were also found to be more selective based relative inhibition of MAPK14 in the same type of assay. We also generated combined MAPK13-other-kinase (e.g., combined MAPK13-MAPK14 and MAPK13-MAPK12) inhibitors to gain additional benefit for anti-inflammatory and anti-cancer activities. In addition, we performed PK analysis of our most promising compounds using oral dosing in rat and pig and demonstrated favorable characteristics for oral dosing in humans. We have also obtained similarly favorable data using in vitro ADMET assays for microsomal stability and Caco-2 cell permeability.

Example 2: Effectiveness of Novel MAPK13 Inhibitors

We administered our MAPK13 and combined MAPK13-other-kinase (e.g., combined MAPK13-MAPK14) inhibitors to primary-culture human and porcine airway epithelial cells and showed inhibition of IL-13-stimulated mucus production at pM concentrations without evidence of cell toxicity up to µM concentrations. In addition, we have demonstrated effectiveness for blocking inflammatory mucus production without toxicity in a pig and mouse in vivo models. In addition, we have administered these inhibitors to breast cancer cell lines (including hormone-negative and HER2-negative lines) in culture and achieved blockade of cell growth without toxicity using nM concentrations of compounds. We have also demonstrated effectiveness for blocking tumor growth in a mouse in vivo model of hormone-negative-HER2-negative breast cancer.

All publications, patents, patent applications, and other references cited in this application are incorporated herein by reference, each in its entirety for all purposes to the same extent as if each individual publication, patent, patent application or other reference was specifically and individually indicated to be incorporated by reference in its entirely for all purposes. Citation of a reference herein shall not be construed as an admission that such is prior art to the present disclosure.

What is claimed is:

1. A compound of Formula I

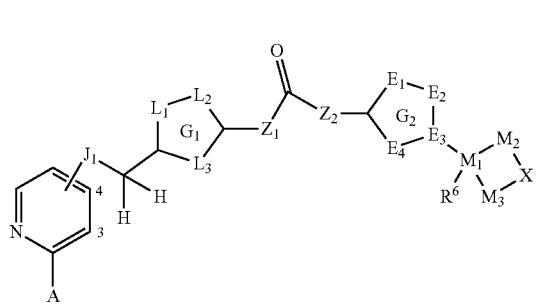

(I)

or a pharmaceutically acceptable salt or solvate thereof, wherein:
A is hydrogen or —NH(CO)R²;
R² is selected from the group consisting of alkyl, cycloalkyl, cycloalkylalkyl, OR³ and NR⁴R⁴;
R³ is selected from the group consisting of alkyl, cycloalkyl and cycloalkylalkyl;
each R⁴ is independently selected from the group consisting of H, alkyl, cycloalkyl and cycloalkylalkyl;
$J_1$ is —CH₂— and is substituted at position 4 on the pyridine;
$G_1$ is thiazole wherein $L_1$ is CH, $L_2$ is N and $L_3$ is S;
$Z_1$ and $Z_2$ are each NH;
$G_2$ is pyrazole, isoxazole, or phenyl;
$E_1$ is CH or CR¹ when $G_2$ is phenyl, or $E_1$ is NR¹ when $G_2$ is pyrazole, or $E_1$ is N or O when $G_2$ is isoxazole;
wherein R¹ is selected from the group consisting of H, $C_{1-8}$ alkyl, cycloalkyl, cycloalkylalkyl, and halogen;
$E_2$ is N when $G_2$ is pyrazole, $E_2$ is N or O when $G_2$ is isoxazole, or $E_2$ is CH—CH when $G_2$ is phenyl;
$E_3$ is C when $G_2$ is pyrazole, isoxazole, or phenyl;
$E_4$ is CH when $G_2$ is pyrazole, isoxazole, or phenyl; and
$M_1$ is selected from the group consisting of C and Si;
wherein if $M_1$ is Si, each of $M_2$ and $M_3$ is methyl, R⁶ is methyl, and X is absent;
wherein if $M_1$ is C, each of $M_2$ and $M_3$ is selected from the group consisting of $CH_3$ and $CH_2$, R⁶ is selected from the group consisting of H and $C_{1-8}$ alkyl, and X is selected from the group consisting of $CH_2$, O and S, or is absent;
wherein if $M_1$ is C and X is $CH_2$, O or S, then $M_1$, $M_2$, $M_3$ and X together form a 4-member ring.

2. The compound or a pharmaceutically acceptable salt or solvate thereof of claim 1, wherein the compound is

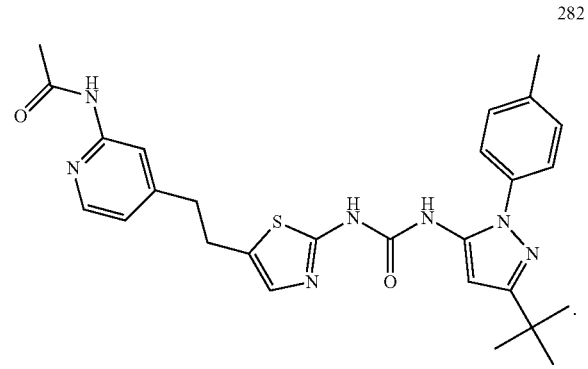 [SMILES: CC(=O)Nc1cc(CCc2cnc(NC(=O)Nc3cc(C(C)(C)C)nn3-c3ccc(C)cc3)s2)ccn1]

3. The compound or a pharmaceutically acceptable salt or solvate thereof of claim 1, wherein the compound is

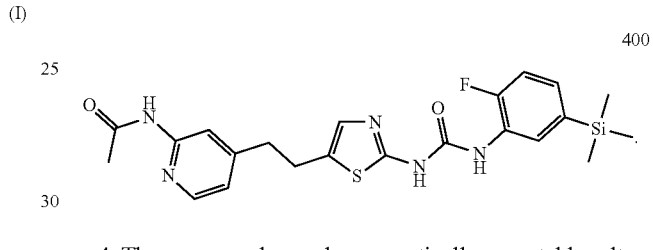

4. The compound or a pharmaceutically acceptable salt or solvate thereof of claim 1, wherein the compound is

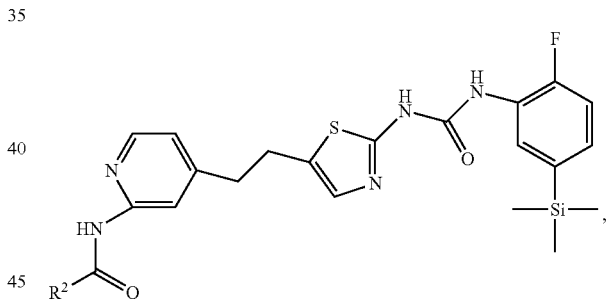

R² is cycloalkyl.

5. The compound or a pharmaceutically acceptable salt or solvate thereof of claim 4, wherein R² is cyclopropyl.

6. The compound or a pharmaceutically acceptable salt or solvate thereof of claim 1, wherein the compound is

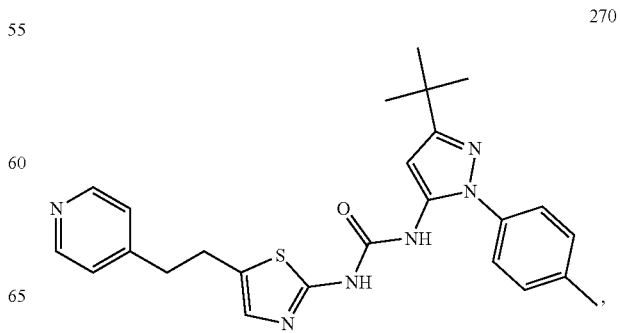

271 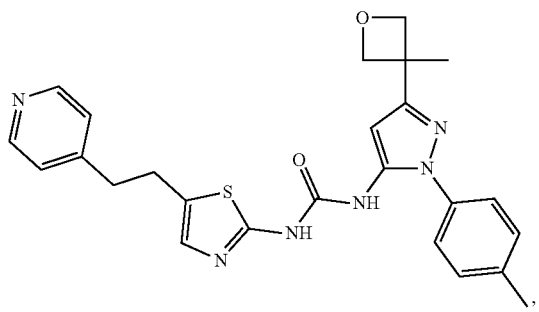
282 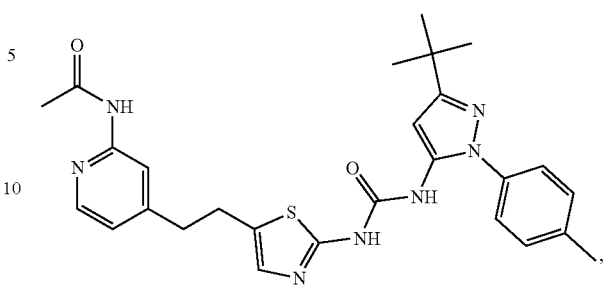
272 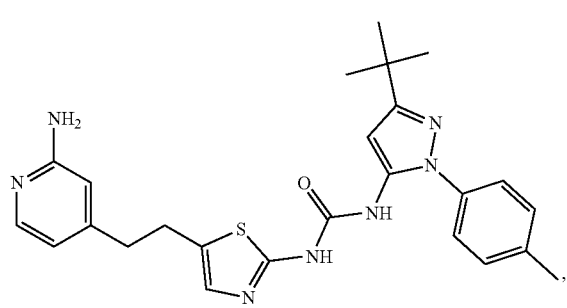
283 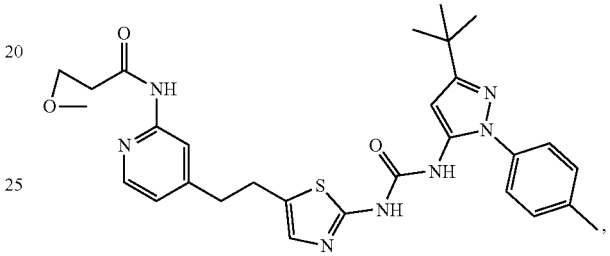
273 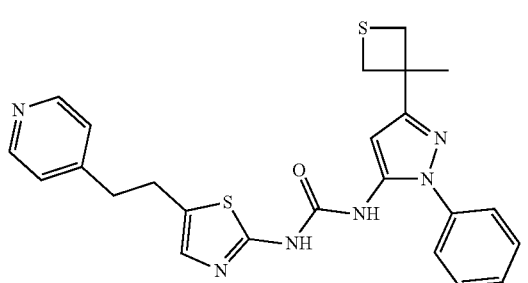
284 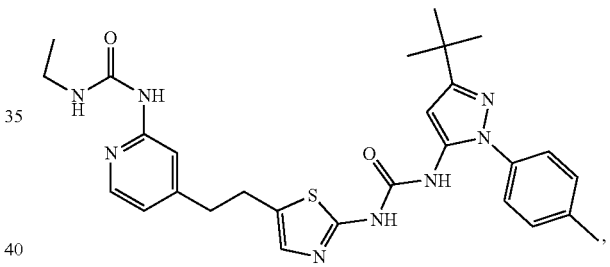
277 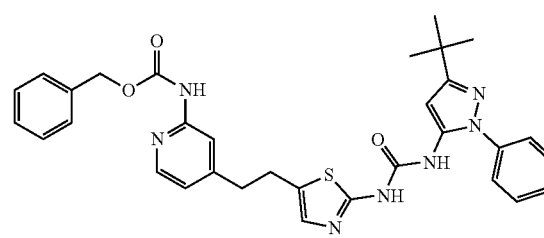
285 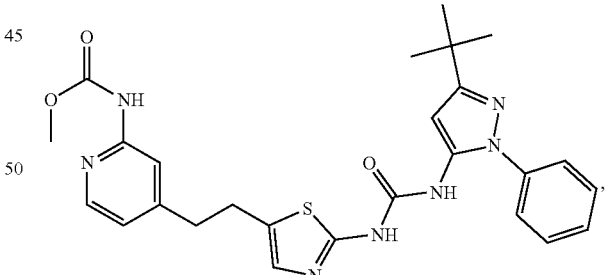
281 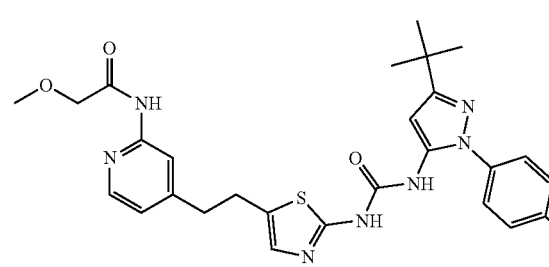
286 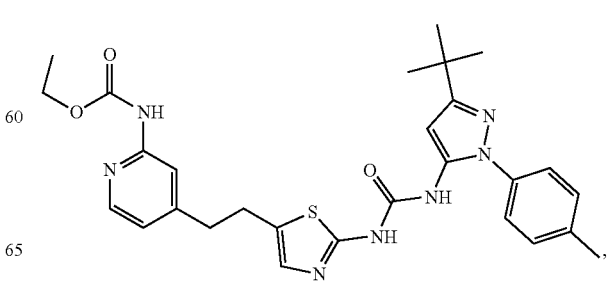

287
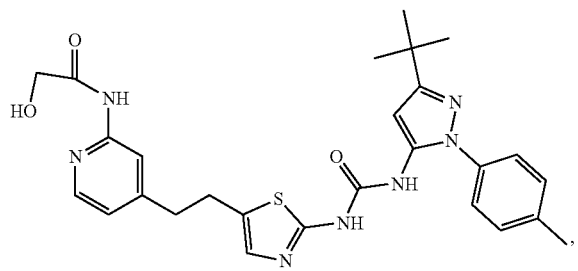
288
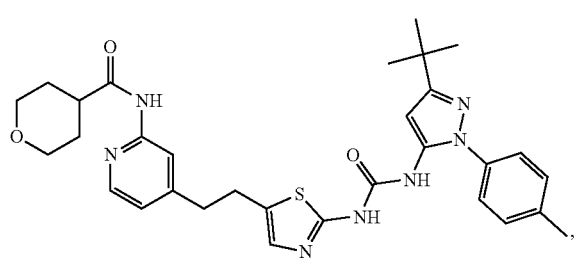
302
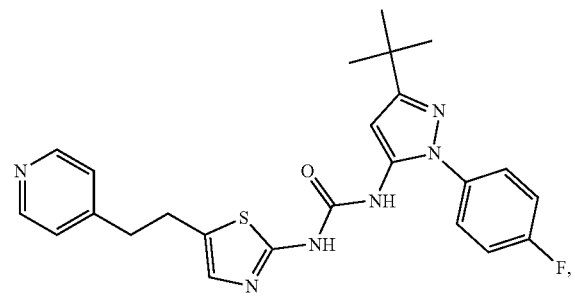
305
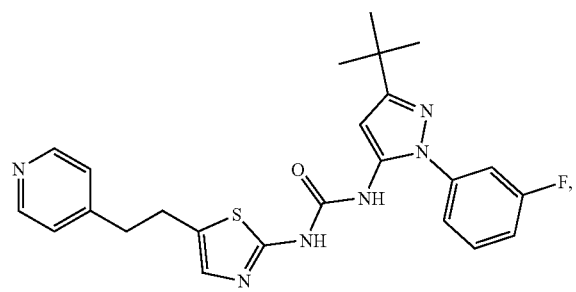
311
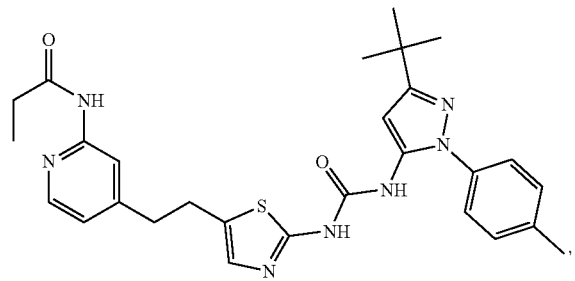
312
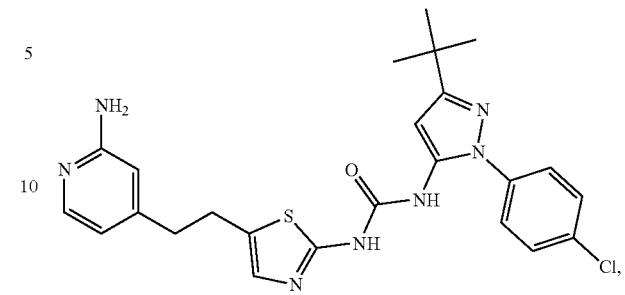
313
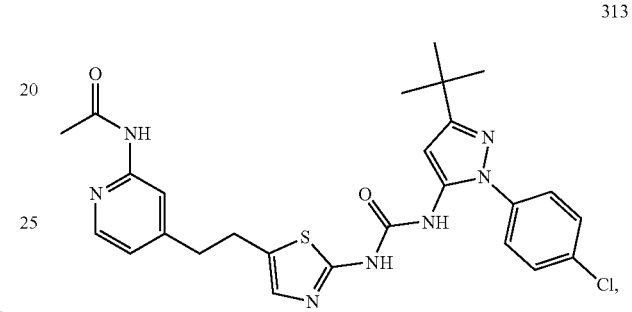
314
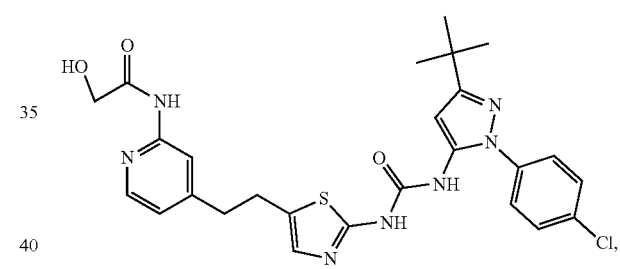
319
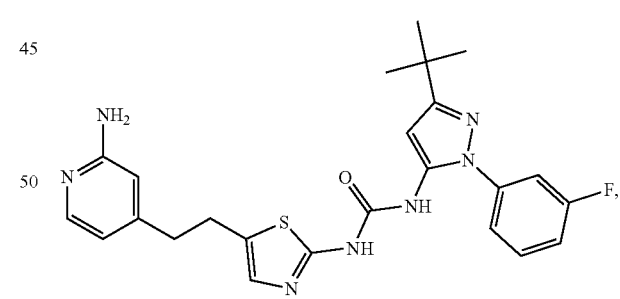
320
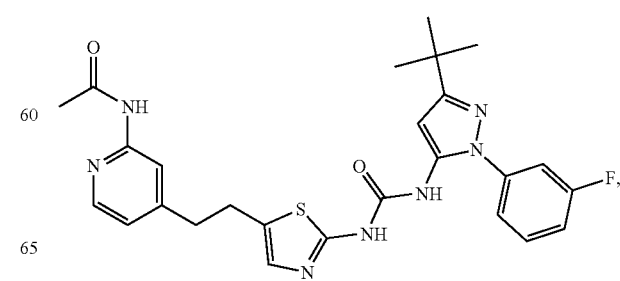

137
-continued
321
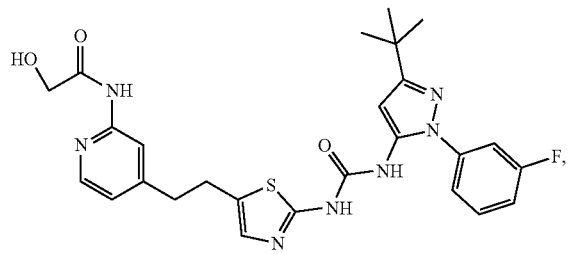
322
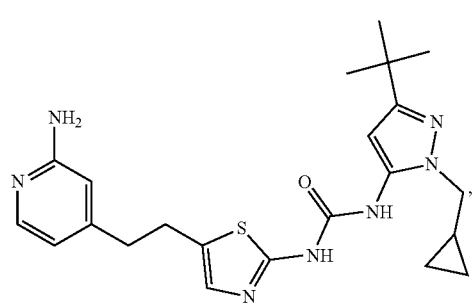
325
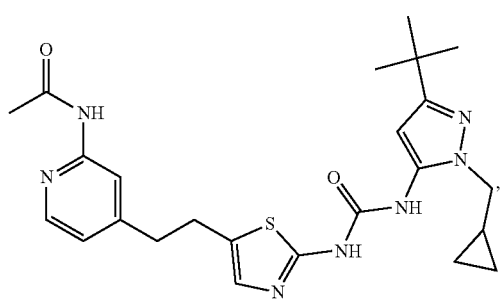
326
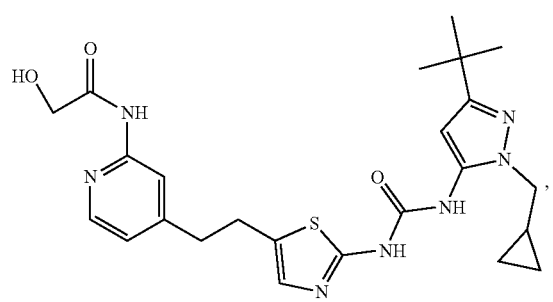
330
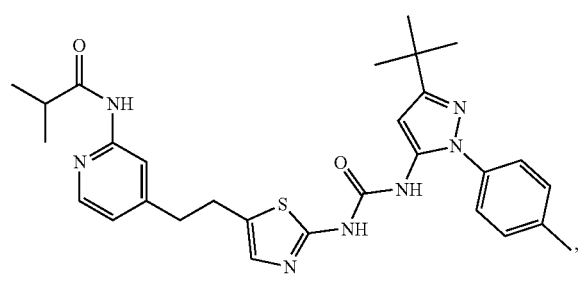
138
-continued
331
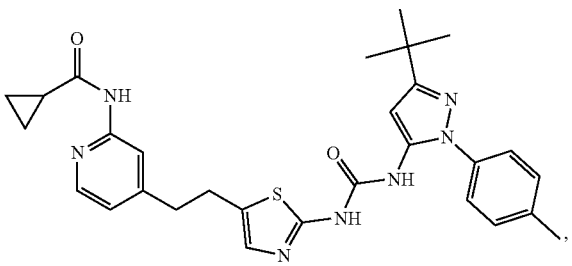
332
333
334
335
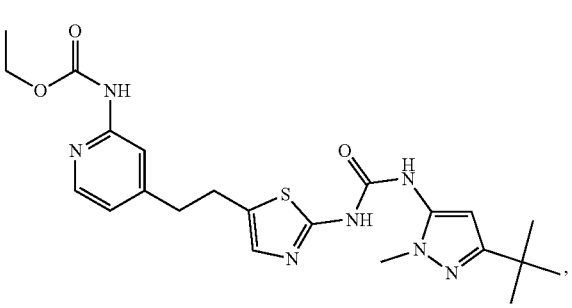

336
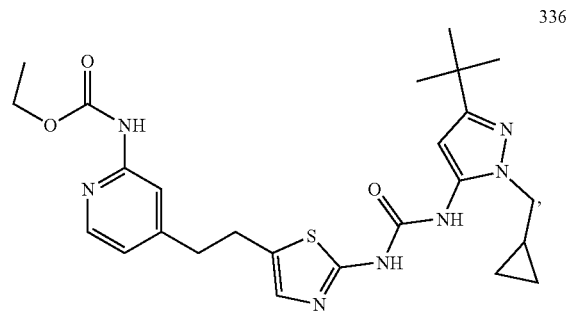
337
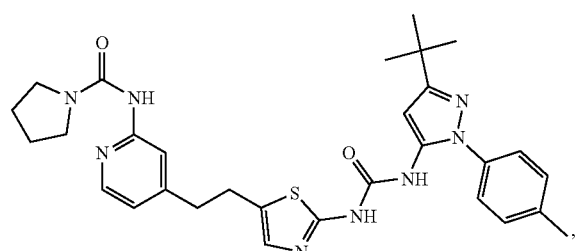
339
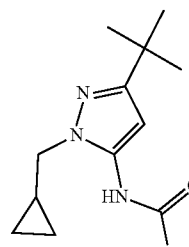
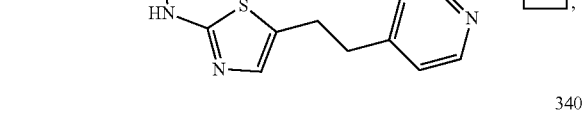
340
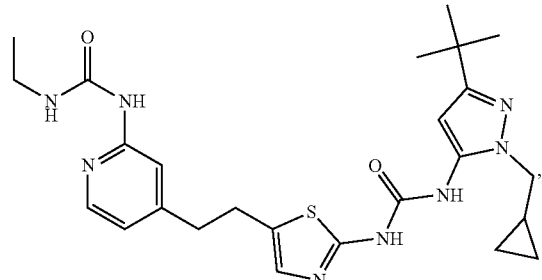
341
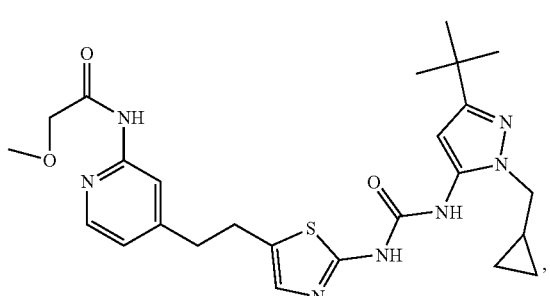
342
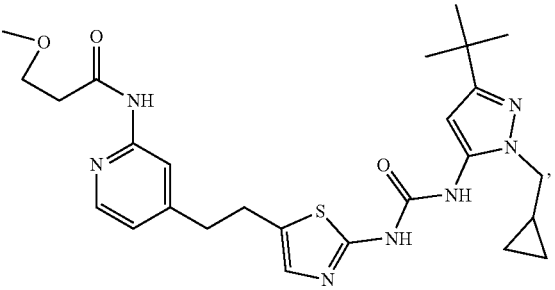
343
344
345
347
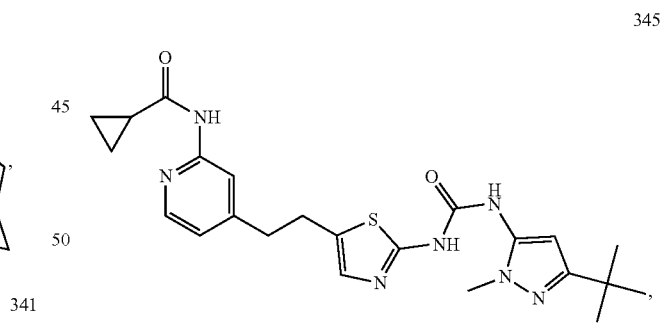
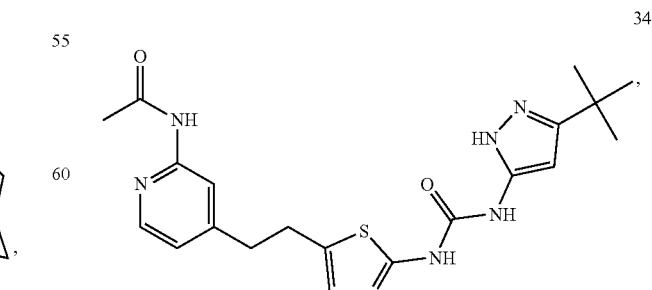

348
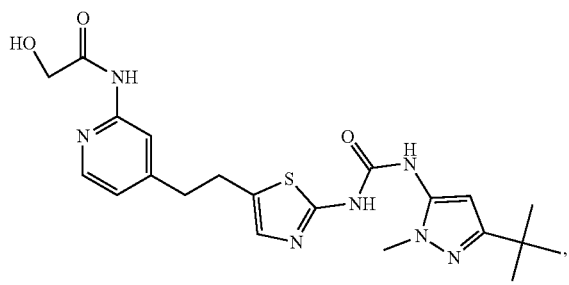
349
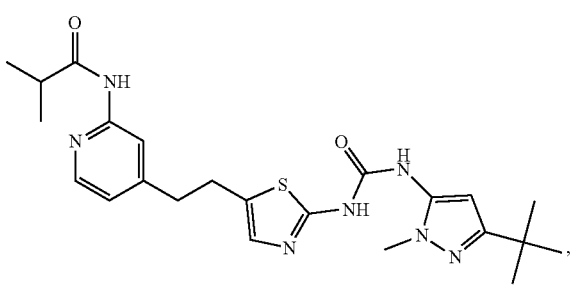
350
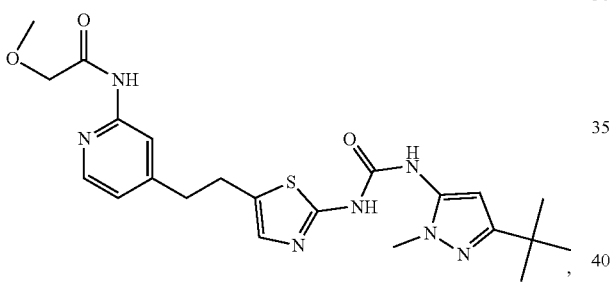
351
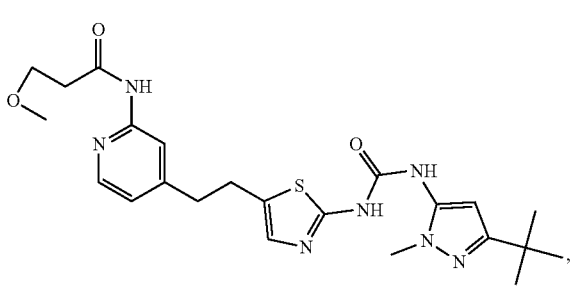
352
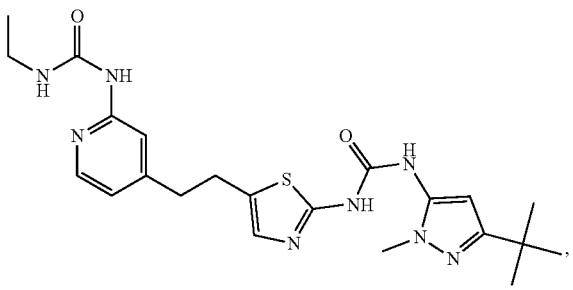
353
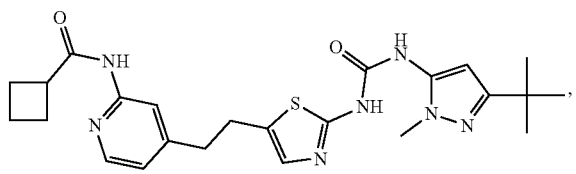
354
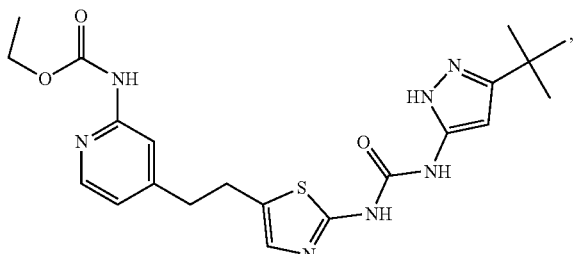
355
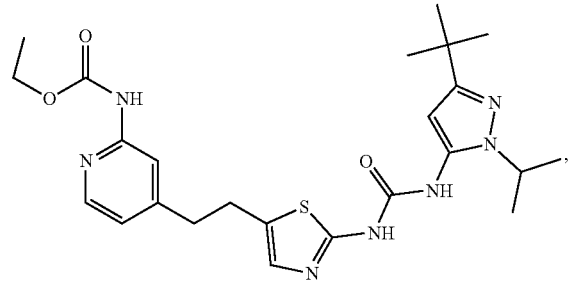
367
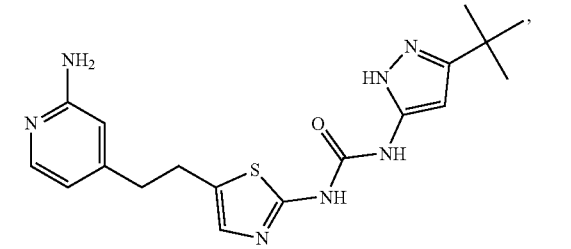
368
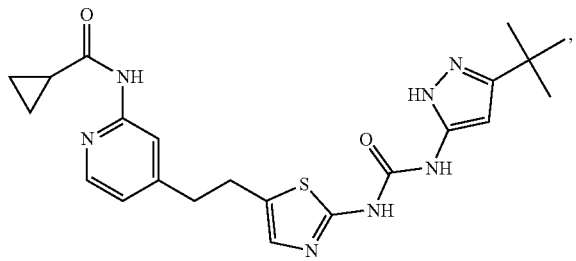

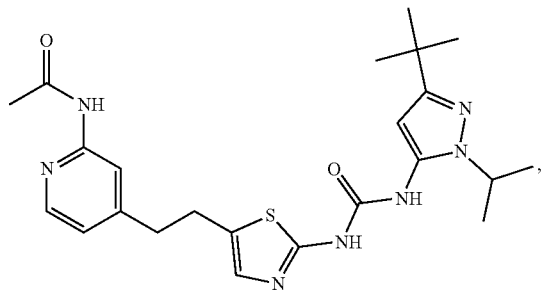
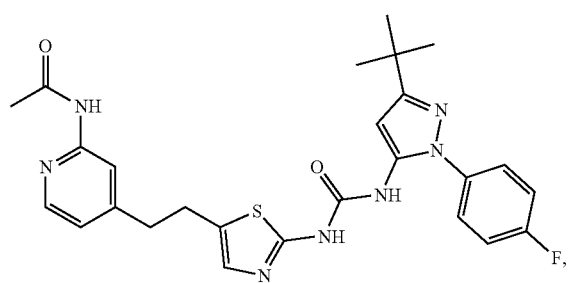
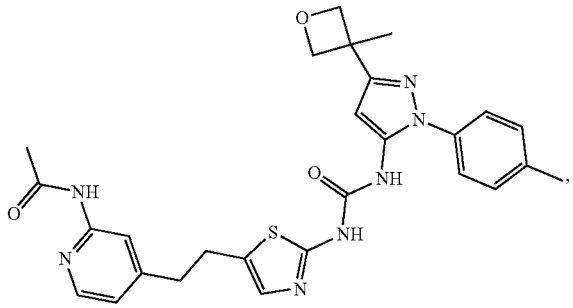
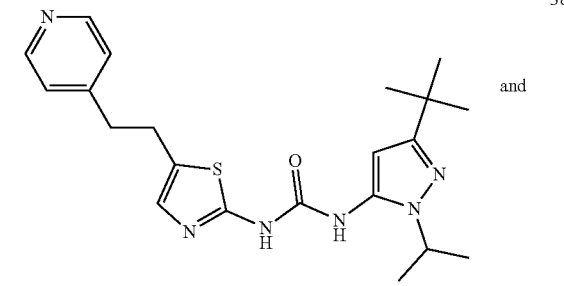
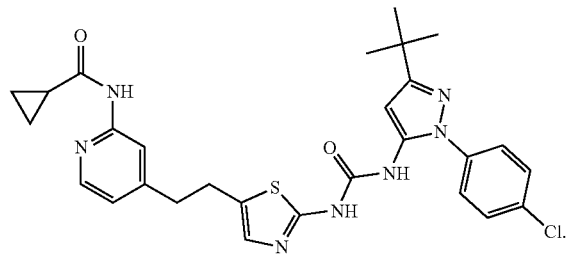

365
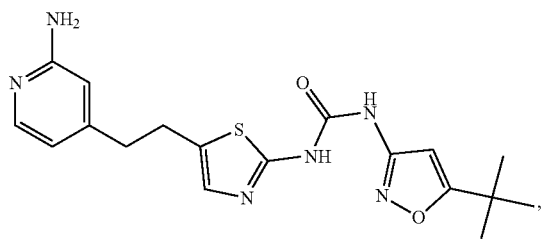
387
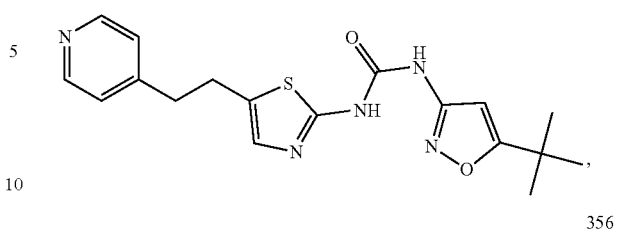
366
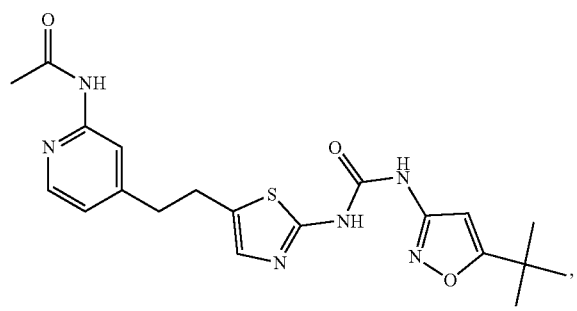
356
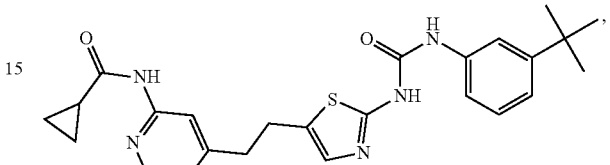
357
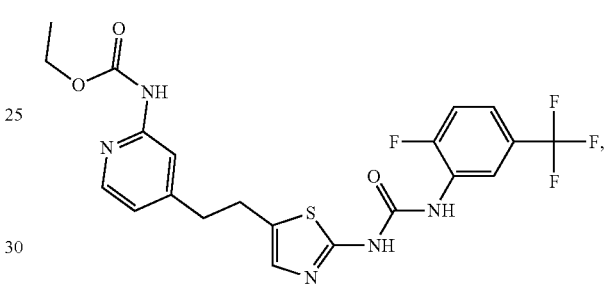
369
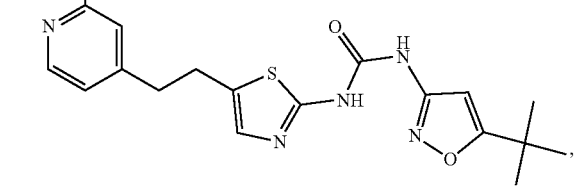
363
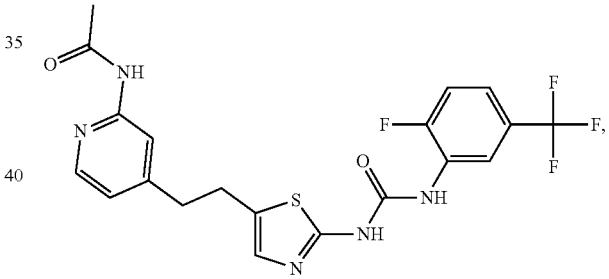
382
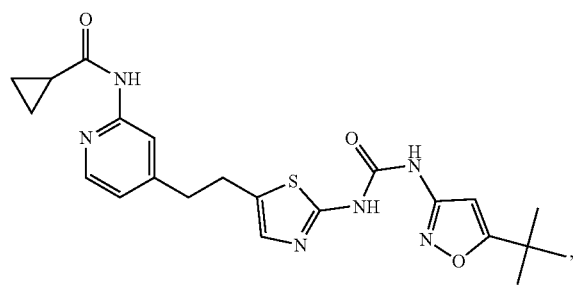
380
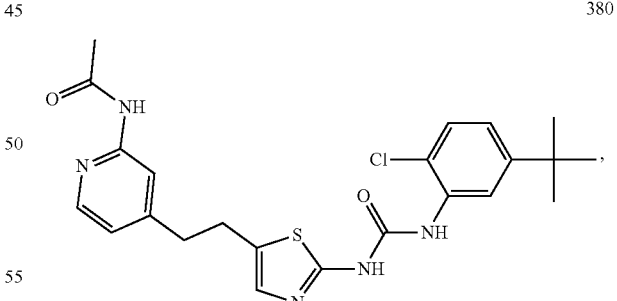
386
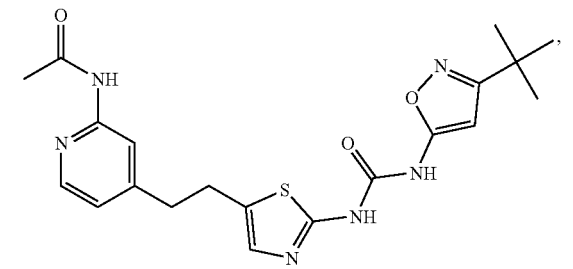
383
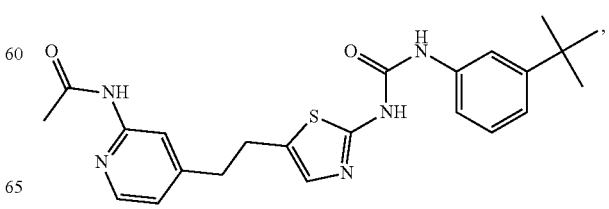
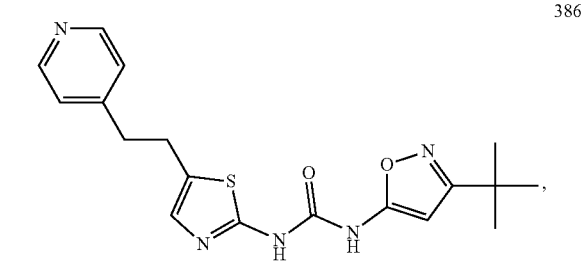

388
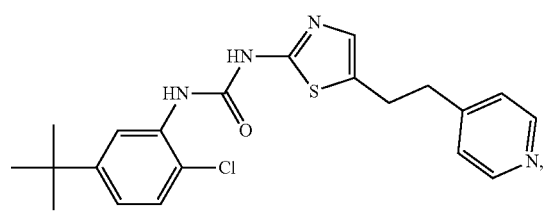
398
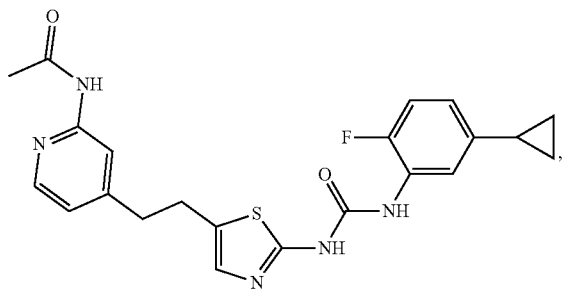
400
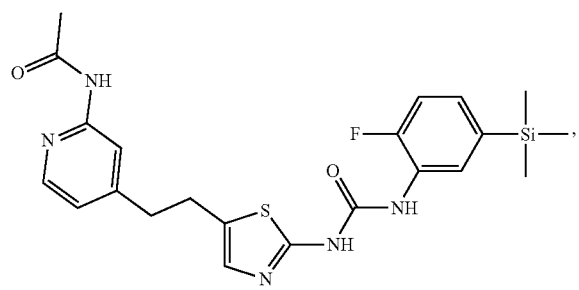
409
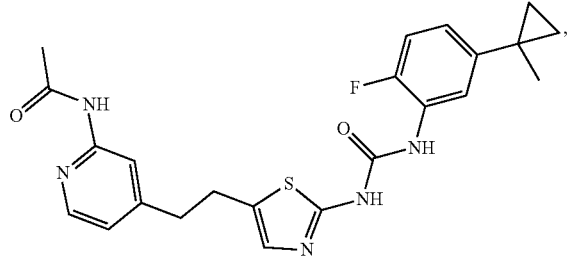
410
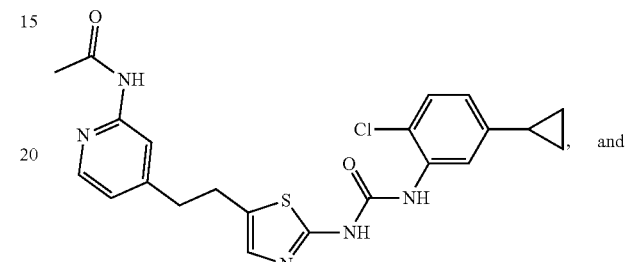
411
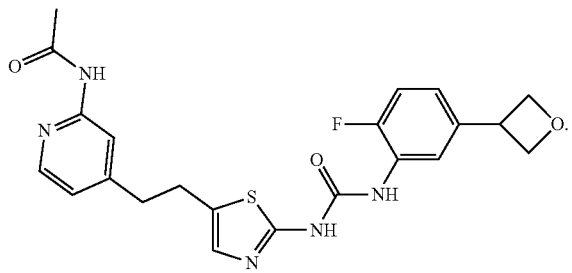
* * * * *